United States Patent
Wright et al.

(10) Patent No.: US 11,155,573 B2
(45) Date of Patent: Oct. 26, 2021

(54) BILE SALT HYDROLASE PROBE AND METHOD OF MAKING AND USING THE SAME

(71) Applicant: Battelle Memorial Institute, Richland, WA (US)

(72) Inventors: Aaron T. Wright, Richland, WA (US); Kristoffer R. Brandvold, Richland, WA (US); Susan Ramos-Hunter, Kennewick, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 16/159,429

(22) Filed: Oct. 12, 2018

(65) Prior Publication Data
US 2019/0112330 A1 Apr. 18, 2019

Related U.S. Application Data

(60) Provisional application No. 62/571,941, filed on Oct. 13, 2017.

(51) Int. Cl.
| | |
|---|---|
| *G01N 33/92* | (2006.01) |
| *C07J 41/00* | (2006.01) |
| *C07J 9/00* | (2006.01) |
| *C07J 43/00* | (2006.01) |
| *C12Q 1/34* | (2006.01) |

(52) U.S. Cl.
CPC .......... *C07J 41/0066* (2013.01); *C07J 9/005* (2013.01); *C07J 43/00* (2013.01); *C12Q 1/34* (2013.01); *G01N 33/92* (2013.01); *C12Y 301/02026* (2013.01)

(58) Field of Classification Search
CPC combination set(s) only.
See application file for complete search history.

(56) References Cited

U.S. PATENT DOCUMENTS

| | | |
|---|---|---|
| 7,736,911 B2 | 6/2010 | Zhang et al. |
| 2011/0020837 A1 | 1/2011 | Haberkant et al. |

FOREIGN PATENT DOCUMENTS

| | | |
|---|---|---|
| EP | 2 482 077 | 8/2012 |
| WO | WO 2001/77684 | 10/2001 |
| WO | WO 2004/033397 | 4/2004 |
| WO | WO 2014/031498 | 2/2014 |
| WO | WO 2017/221270 | 12/2017 |

OTHER PUBLICATIONS

Sun, J. et al., Tetrahedron Letters 2016, vol. 57, pp. 2125-2128.*
Kirby, L. et al., Lipids, 1995, vol. 30, pp. 863-867.*
Kirby et al., "Continuous Spectrophotometric Assay of Conjugated Bile Acid Hydrolase," *Lipids*, 30(9): 863-867, Sep. 1995.
Sun et al., "Biological and deoxycholic acid-coumarin conjugates: photo-switchable structures and self-assembly morphology," *Tetrahedron Letters*, 57(19): 2125-2128, Apr. 2016.
Kumar et al., "Design, synthesis, and physico-chemical interactions of bile acid derived dimeric phospholipid amphiphiles with model membranes," *Journal of Colloid and Interface Science*, vol. 448, pp. 398-406, Feb. 7, 2015.
Davis et al., "Nuclear magnetic resonance identification of the taurine conjugate of 3α,6β,7β-trihydroxy-5β,22-cholen-24-oic acid (tauro-$\Delta^{22}$-β-muricholate) in the serum of female rats treated with α-naphthylisothiocyanate," *Journal of Lipid Research*, vol. 34, pp. 651-662, May 1993.
Invitation to Pay Additional fees issued by International Searching Authority dated Feb. 8, 2019, for International Application No. PCT/US2018/055666.
Bottcher et al., "β-Lactams and β-lactones as activity-based probes in chemical biology," *MedChemComm.*, No. 3, pp. 408-417, Jan. 4, 2012.
Chauvigne-Hines et al., "Suite of Activity-Based Probes for Cellulose-Degrading Enzymes," *J. Am. Chem. Soc.*, vol. 134, pp. 20521-20532, Nov. 24, 2012.
Dai et al., "A practical strategy to design and develop an isoform-specific fluorescent probe for a target enzyme: CYP1A1 as a case study," *Chem. Sci.*, vol. 8, pp. 2795-2803, Sep. 5, 2016.
Examination Report issued for European Application No. 18826838.7 dated Mar. 25, 2021.
Examination Report issued for European Application No. 18800783.5 dated Apr. 30, 2021.
Hirose et al., "Review: Recent development of two chitinase inhibitors, Argifin and Argadin, produced by soil microorganisms," *Proc. Jpn. Acad. Ser. B*, 86(2): 85-102, Feb. 2010.
Hong et al., "Live-cell stimulated raman scattering imaging of alkyne-tagged biomolecules," *Angew. Chem. Int. Ed.*, 53(23): 5827-5831, 2014.
Hsu et al., "Development of Activity-Based Probes for Imaging Human α-L-Fucosidases in Cells," *J. Org. Chem.*, vol. 80, pp. 8458-8463, Aug. 4, 2015.
International Search Report and Written Opinion issued for International Application No. PCT/IB2018/058935 dated Jun. 27, 2019.
International Search Report and Written Opinion issued for International Application No. PCT/IB2018/059536 dated Apr. 9, 2019.
Invitation to Pay Additional Fees issued by International Searching Authority dated Feb. 12, 2019, for International Application No. PCT/US2018/051230.
Invitation to Pay Additional Fees issued by International Searching Authority dated Jan. 16, 2019, for International Application No. PCT/US2018/054242.

(Continued)

Primary Examiner — Heidi Reese
(74) Attorney, Agent, or Firm — Klarquist Sparkman, LLP

(57) ABSTRACT

Probe embodiments for targeting, identifying, and isolating enzymes exhibiting BSH activity as well as devices and kits that use the probes are described herein. Methods of making and using the probes, devices, and kits are also described. In some embodiments, probes, devices, and kits for targeting, identifying, and isolating enzymes in a biological sample are disclosed. In some embodiments, compositions and methods of treatment using the probes, devices, and kits disclosed herein are described.

20 Claims, 21 Drawing Sheets

(56) References Cited

OTHER PUBLICATIONS

Liu et al., "Exploring the binding proteins of glycolipids with bifunctional chemical probes," *Angew. Chem. Int. Ed.*, 55(46): 14330-14334, Nov. 7, 2016.
Lockhart et al., "Screening-based discovery of *Aspergillus fumigatus* plant-type chitinase inhibitors," *FEBS Letters*, No. 588, pp. 3282-3290, Jul. 22, 2014.
Lu et al., "Design of a Mechanism-Based Probe for Neuraminidase to Capture Influenza Viruses," *Angew. Chem. Int. Ed.*, vol. 44, pp. 6888-6892, 2005.
Lumba et al., "A β-galactosidase probe for the detection of cellular senescence by mass cytometry," *Org. Biomol. Chem.*, 15(30): 6388-6392, May 19, 2017.
Sadler et al., "Activity-based protein profiling of microbes," *Current Opinion in Chemical Biology*, vol. 24, pp. 139-144, Dec. 19, 2014.
Stoddard et al., "Activity-based probes for isoenzyme- and site-specific functional characterization of glutathione S-transferases," *J. Am. Chem. Soc.*, 139(45): 16032-16035, Oct. 25, 2017.
Verhelst et al., "Probing Functional Tyrosines," *Chemistry & Biology*, 20(4): 541-548, Apr. 18, 2013.
Wright et al., "A suite of activity-based probes for human cytochrome P450 enzymes," *J. Am. Chem. Soc.*, 131(30):10692-10700, Aug. 5, 2009.
Wright et al., "Chemical Proteomic Probes for Profiling Cytochrome P450 Activities and Drug Interactions in Vivo," *Chemistry & Biology*, vol. 14., pp. 1043-1051, Sep. 2007.
Wu et al., "Activity-based probes for functional interrogation of retaining β-glucuonidases," *Nat. Chem. Biol.*, 13(8): 867-873, Jun. 5, 2017.

\* cited by examiner a CA-AMCA
b AMCA

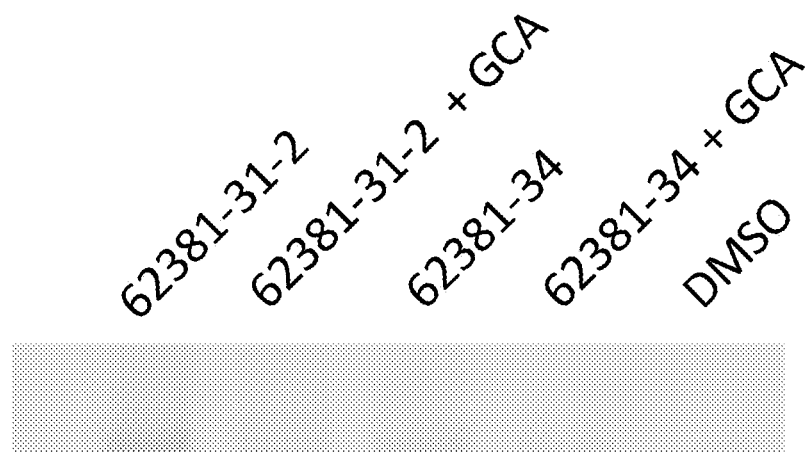
Probes: 100 µM
GCA: 2.5 mM
FIG. 18A
[62381-31-2] (µM)
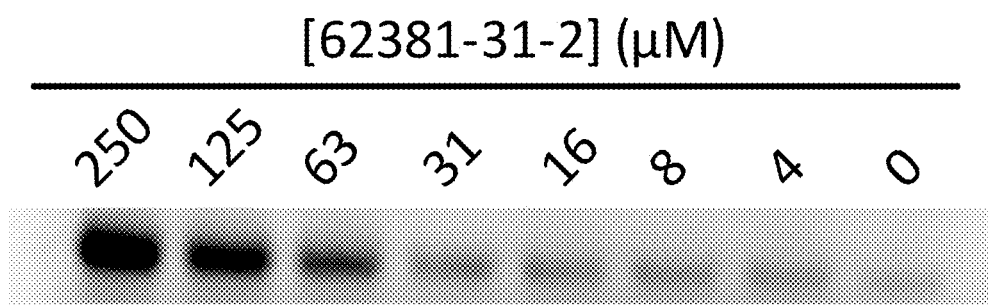
[62381-34] (µM)
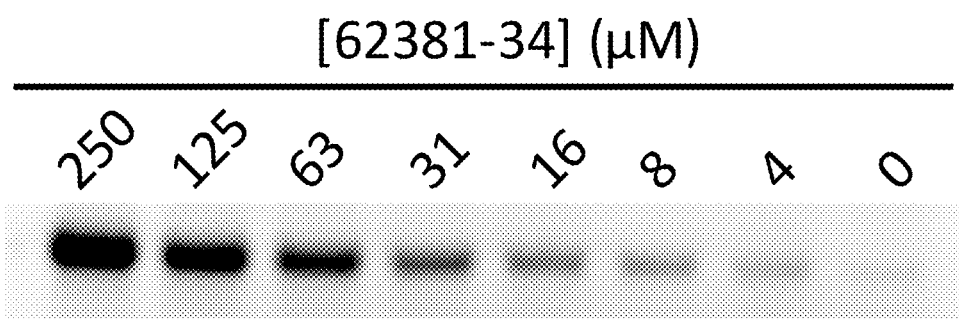
FIG. 18B

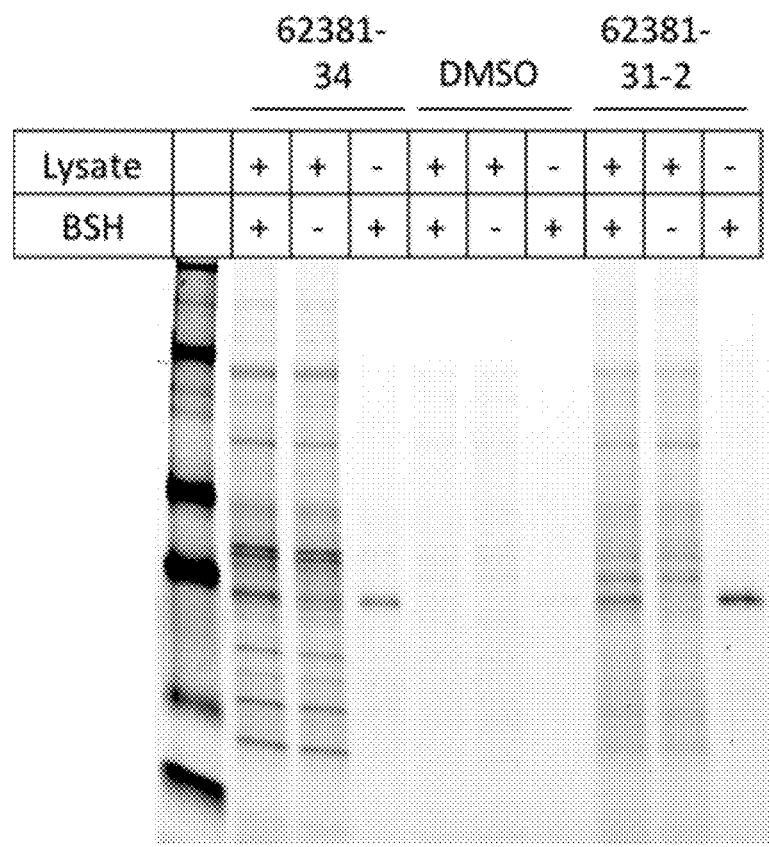
FIG. 19
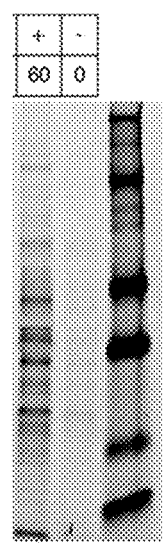 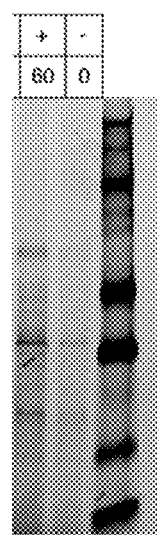
FIG. 20A   FIG. 20B

BILE SALT HYDROLASE PROBE AND METHOD OF MAKING AND USING THE SAME

CROSS REFERENCE TO RELATED APPLICATION

This application claims the benefit of the earlier priority date of U.S. Provisional Patent Application No. 62/571,941, filed on Oct. 13, 2017; this prior application is incorporated by reference herein in its entirety.

ACKNOWLEDGMENT OF GOVERNMENT SUPPORT

This invention was made with government support under DE-AC0576RL01830 awarded by the U.S. Department of Energy. The government has certain rights in the invention.

FIELD

The present disclosure is directed to probes for identifying bile salt hydrolase activity and methods of making and using the same.

BACKGROUND

The gut microbiome has a role in determining host health, including impacts on nutrient absorption and chemical signaling to the host. There are currently few approaches that inform on the microbial taxa involved, and the specific cellular machinery (enzymes) that they employ to carry out these processes. The complex mixture of microbes in the gut can have a major impact on host health. A prominent example of microbiome-host interaction is chemical microbial modification of the host's bile acid pool. Certain microbes are capable of modulating the hydrophobicity of the bile acid pool through the activity of bile salt hydrolases. Bile salt hydrolases (BSH) catalyze the hydrolysis of bile salts to free bile acids and amino acids. The result of BSH activity is a net change in the physicochemical properties of the bile acid pool, ultimately making it more hydrophobic, and therefore making fatty gut contents more prone to excretion. Increasing BSH activity is postulated to be an effective strategy for treating obesity and hypercholesterolemia. Also, BSH activity also is known to be linked to liver and colorectal cancer. Currently, the bioassays for characterizing bile salt hydrolase activity are time-consuming or have poor sensitivity. New techniques and probes for identifying, characterizing, and enriching enzymes that exhibit bile salt hydrolase activity are needed in the art.

SUMMARY

Disclosed herein are embodiments of a probe capable of identifying analytes that exhibit bile salt hydrolase activity. In some embodiments, the probe has a structure according to any or all of the formulas disclosed herein. Representative probe species also are disclosed. Also disclosed herein are embodiments of a method of using the probes, which comprises exposing a subject or a sample to a probe embodiment for a time sufficient to allow the probe to bind to an enzyme capable of hydrolyzing a bile salt to thereby form a probe-enzyme conjugate; and analyzing the subject or the sample using a detection technique sufficient to identify a detectable signal produced by reaction between the probe and the enzyme. Method embodiments of treating or preventing a disease associated with bile salt hydrolase activity also are disclosed. In some embodiments, the method can comprise any one or more of the following steps: (i) labeling at least one enzyme capable of hydrolyzing a bile salt with a probe embodiment of the present disclosure to provide at least one labeled enzyme; (ii) determining the presence of the at least one labeled enzyme in a sample by detecting a detectable signal; (iii) sorting or isolating the at least one labeled enzyme or microbes comprising the at least one labeled enzyme; (iv) identifying the microbes comprising the at least one labeled enzyme; (v) selecting a physical environment for altering the bile salt hydrolase activity of the at least one enzyme; and/or (vi) altering bile salt hydrolase activity in the selected physical environment to thereby treat the disease or condition by enriching the selected physical environment with identified microbes; reducing the amount of identified microbes in the selected physical environment; or reducing the bile salt hydrolase activity in the selected physical environment.

Also disclosed herein are embodiments of a kit comprising a probe embodiment and a substrate, wherein the probe is covalently bound to the substrate.

The foregoing and other objects and features of the present disclosure will become more apparent from the following detailed description, which proceeds with reference to the accompanying figures.

BRIEF DESCRIPTION OF THE DRAWINGS

FIG. 4A shows that CA-AMCA (150 µM) was added to buffered solutions with varying concentrations of BSH and increasing the concentration of BSH resulted in increased rates of CA-AMCA hydrolysis as assessed by monitoring product formation using a fluorimeter; and FIG. 4B shows that the increase in fluorescence observed by adding CA-AMCA (150 µM) to BSH is attenuated by addition of authentic substrate, glycocholic acid (GCA) (10 mM), or cysteine-reactive iodoacetamide (IAA) (12 mM), but not DMSO.

FIG. 10B was obtained by adding CA-AMCA (150 µM) to buffered solutions containing varying amounts of intact *L. plantarum* cells; the rates of CA-AMCA turnover are dependent on cell density.

FIGS. 18A and 18B show dose responses for labeling purified BSH with representative probe embodiments disclosed herein, and competition with native substrate.

FIG. 19 shows probe labeling of BSH in *Escherichia coli* bacterial lysate.

FIGS. 20A and 20B shows probe labeling of BSH in *Lactobacillus plantarum* (FIG. 20A is from the lysate and FIG. 20B is from in vivo labeling).

DETAILED DESCRIPTION

I. Overview of Terms

Figure 1A:
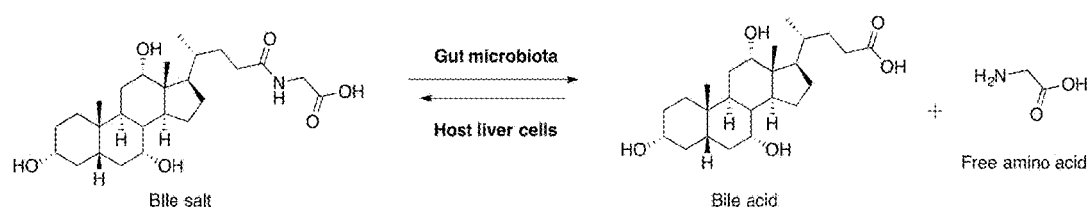
FIGS. 1A and 1B are schematic illustrations of bile salt hydrolase activity on a bile salt (FIG. 1A) and a representative probe embodiment disclosed herein (FIG. 1B).

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

Compounds disclosed herein may contain one or more asymmetric elements such as stereogenic centers, chiral exes and the like, for example asymmetric carbon atoms, so that the chemical conjugates can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In these situations, the single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them. In structures where no specific stereochemistry is illustrated, it is understood that all stereoisomers and/or diastereomers are contemplated. Representative structures will set stereoisomers and/or diastereomers are provided herein and constitute representative examples of the generic formulas; however, such examples are not exclusive and the other form(s) also are contemplated, such as by the inclusion of a general structure having no specific stereochemistry illustrated.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. Additionally, certain structures illustrated herein may include a wavy line ("⁓") going through a solid bond (e.g.,

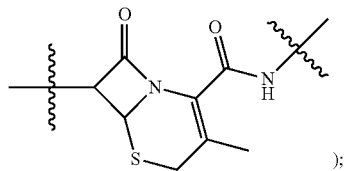 [SMILES: *NC(=O)C1=C(C)CSC2C(*)C(=O)N12]

);

the wavy line in this context is used to indicate a bond disconnection.

All forms (for example solvates, optical isomers, enantiomeric forms, polymorphs, free compound and salts) of a probe may be employed either alone or in combination.

To facilitate review of the various embodiments of the disclosure, the following explanations of specific terms are provided. Certain functional group terms include a "-" symbol at the beginning of the functional group formula; this symbol is not a part of the functional group, but instead denotes how the functional group connects to the formulas described herein. For example, a functional group with a formula "—OC(O)R$^b$" is attached to an atom of the functionalized compound by the oxygen atom of the functional group that is next to the "-" symbol.

Acyloxy: —OC(O)R$^b$, wherein R$^b$ is selected from hydrogen, aliphatic, aryl, heteroaliphatic, aliphatic-aryl, heteroaryl, aliphatic-heteroaryl, heteroaliphatic-aryl, heteroaliphatic-heteroaryl, and any combination thereof.

Administer: As used herein, administering a composition to a subject means to give, apply or bring the composition into contact with the subject. Administration can be accomplished by any of a number of routes, such as, for example, topical, oral, rectal, vaginal, transdermal, subcutaneous, intramuscular, intraperitoneal, intravenous, intrathecal, and intradermal.

Aldehyde: —C(O)H.

Aliphatic: A hydrocarbon group having at least one carbon atom to 50 carbon atoms ($C_{1-50}$), such as one to 25 carbon atoms ($C_{1-25}$), or one to ten carbon atoms ($C_{1-10}$), and which includes alkanes (or alkyl), alkenes (or alkenyl), alkynes (or alkynyl), including cyclic versions thereof, and further including straight- and branched-chain arrangements, and all stereo and position isomers as well.

Aliphatic-aromatic: An aromatic group that is or can be coupled to a probe disclosed herein, wherein the aromatic group is or becomes coupled through an aliphatic group.

Aliphatic-aryl: An aryl group that is or can be coupled to a probe disclosed herein, wherein the aryl group is or becomes coupled through an aliphatic group.

Aliphatic-heteroaromatic: A heteroaromatic group that is or can be coupled to a probe disclosed herein, wherein the heteroaromatic group is or becomes coupled through an aliphatic group.

Aliphatic-heteroaryl: A heteroaryl group that is or can be coupled to a probe disclosed herein, wherein the heteroaryl group is or becomes coupled through an aliphatic group.

Alkenyl: An unsaturated monovalent hydrocarbon having at least two carbon atoms to 50 carbon atoms ($C_{2-50}$), such as two to 25 carbon atoms ($C_{2-25}$), or two to ten carbon atoms ($C_{2-10}$), and at least one carbon-carbon double bond, wherein the unsaturated monovalent hydrocarbon can be derived from removing one hydrogen atom from one carbon atom of a parent alkene. An alkenyl group can be branched, straight-chain, cyclic (for example, cycloalkenyl), cis, or trans (for example, E or Z).

Alkoxy: —O-aliphatic, such as —O-alkyl, —O-alkenyl, or —O-alkynyl, with exemplary embodiments including, but not limited to, methoxy, ethoxy, n-propoxy, isopropoxy, n-butoxy, t-butoxy, sec-butoxy, n-pentoxy.

Alkyl: A saturated monovalent hydrocarbon having at least one carbon atom to 50 carbon atoms ($C_{1-50}$), such as one to 25 carbon atoms ($C_{1-25}$), or one to ten carbon atoms ($C_{1-10}$), wherein the saturated monovalent hydrocarbon can be derived from removing one hydrogen atom from one carbon atom of a parent compound (for example, alkane). An alkyl group can be branched, straight-chain, or cyclic (for example, cycloalkyl).

Alkynyl: An unsaturated monovalent hydrocarbon having at least two carbon atoms to 50 carbon atoms ($C_{2-50}$), such as two to 25 carbon atoms ($C_{2-25}$), or two to ten carbon atoms ($C_{2-10}$), and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (for example, cycloalkynyl).

Alkylaryl/Alkenylaryl/Alkynylaryl: An aryl group that is or can be coupled to a probe disclosed herein, wherein the aryl group is or becomes coupled through an alkyl, alkenyl, or alkynyl group, respectively.

Alkylheteroaryl/Alkenylheteroaryl/Alkynylheteroaryl: A heteroaryl group that is or can be coupled to a probe disclosed herein, wherein the heteroaryl group is or becomes coupled through an alkyl, alkenyl, or alkynyl group, respectively.

Amide: —C(O)NR$^b$R$^c$ wherein each of R$^b$ and R$^c$ independently is selected from hydrogen, aliphatic, aryl, heteroaliphatic, aliphatic-aryl, heteroaryl, aliphatic-heteroaryl, heteroaliphatic-aryl, heteroaliphatic-heteroaryl, and any combination thereof.

Amine: —NR$^b$R$^c$, wherein each of R$^b$ and R$^c$ independently is selected from hydrogen, aliphatic, aryl, heteroaliphatic, aliphatic-aryl, heteroaryl, aliphatic-heteroaryl, heteroaliphatic-aryl, heteroaliphatic-heteroaryl, and any combination thereof.

Anchor Moiety: A functional group that can be used to attach a probe embodiment to a surface of a substrate component. In some embodiments, the anchor moiety can be a clickable functional group, an activated ester (e.g., NHS-ester), a carboxylic acid, a halide, or an alkyl halide.

Aromatic: A cyclic, conjugated group or moiety of, unless specified otherwise, from 5 to 15 ring atoms having a single ring (for example, phenyl, pyridinyl, or pyrazolyl) or multiple condensed rings in which at least one ring is aromatic (for example, naphthyl, indolyl, or pyrazolopyridinyl); that is, at least one ring, and optionally multiple condensed rings, have a continuous, delocalized π-electron system. Typically, the number of out of plane π-electrons corresponds to the Hückel rule (4n+2). The point of attachment to the parent structure typically is through an aromatic portion of the condensed ring system. For example,

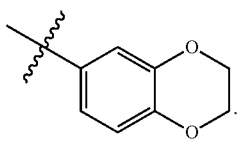 [SMILES: *c1ccc2c(c1)OCCO2]

However, in certain examples, context or express disclosure may indicate that the point of attachment is through a non-aromatic portion of the condensed ring system. For example,

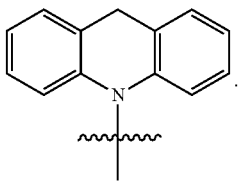 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (for example, S, O, N, P, or Si), such as in a heteroaryl group or moiety.

Aryl: An aromatic carbocyclic group comprising at least five carbon atoms to 15 carbon atoms ($C_5$-$C_{15}$), such as five to ten carbon atoms ($C_5$-$C_{10}$), having a single ring or multiple condensed rings, which condensed rings can or may not be aromatic provided that the point of attachment to a remaining position of the compounds disclosed herein is through an atom of the aromatic carbocyclic group. Aryl groups may be substituted with one or more groups other than hydrogen, such as aliphatic, heteroaliphatic, aryl, heteroaryl, other functional groups, or any combination thereof. In some embodiments, the aryl ring is selected from, but not limited to, phenyl, naphthyl, anthracenyl, indenyl, azulenyl, fluorenyl, tetracyanoanthaquinodimethyl, and the like.

Benzyl carbonyl: —C(O)Ph.

Bile Acids: Small organic compounds found in bile that can affect its net physicochemical properties (e.g., by aiding in digestion and absorption of fats and nutrients as well as disposal of drug and metabolites; Han et al., *Mol. Endocrinol.*, 24(6): 1151-1164, 2010, the relevant portion of which is incorporated herein by reference). Using cholesterol as a starting material, bile acids are steroid acids produced in the liver through a multi-step biosynthetic pathway regulated by cholesterol 7α-hydroxylase. Humans produce two primary bile acids, cholic and chenodeoxycholic acid (e.g., see Chiang, *Journal of Lipid Research*, 50:1955-1966, 2009, the relevant portion of which is incorporated herein by reference), which differ by one hydroxyl group but can exert different biological effects. After synthesis in the liver, bile acids are conjugated to glycine or taurine to yield bile salt products, which significantly modulate hydrophilicity. After synthesis, bile salts are stored in the gall bladder and are eventually released into the duodenum to aid in digestion. Bile acids can act as surfactants, which increase solubility of hydrophobic molecules, such as fatty acids, aiding in digestion. Bile acids also act as selective chemical signals (e.g., signaling molecules) that bind human nuclear receptors, such as FXR (e.g., see Joyce et al., *Proceedings of the National Academy of Sciences*, 111:7421-7426, 2014, the relevant portion of which is incorporated herein by reference), vitamin D receptor (e.g., see Makishima et al., *Science*, 296:1313-1316, 2002, the relevant portion of which is incorporated herein by reference), small heterodimer partner (NR0B2), and surface receptors, such as TGR5 (e.g., see Maruyama, *Biochemical and biophysical research communications*, 298:714-719, 2002; Kawamata, *The Journal of biological chemistry*, 278:9435-9440, 2003, both of which are incorporated herein by reference in their entireties), regulate signaling pathways, and play a role in lipid, glucose, drug, and energy metabolism. Binding of bile salts by host receptors can provide information on the state of the bile acid pool and regulate the first step in of bile salt synthesis from cholesterol along with other processes, including bile acid, cholesterol, lipid and carbohydrate metabolism as well as inflammation, fibrosis, and carcinogenesis. Microbial metabolism in the gut can result in modified secondary bile acids, which include deoxycholic, ursodeoxycholic, and lithocholic acid (e.g., see Ridlon et al., *Journal of Lipid Research*, 47:241-259, 2006, the relevant portion of which is incorporated herein by reference).

Bile Salt Hydrolase (BSH): An enzyme that catalyzes the hydrolysis of bile salts into bile acids and amino acids (e.g., glycine and taurine), a process that is also known as deconjugation. For example, bile salt hydrolases can act as cysteine hydrolases that promote the reaction, such as through a catalytic triad, which can include an N-terminal cysteine. BSH deconjugation can produce a net change in the physicochemical properties of a bile acid pool, ultimately increasing the hydrophobicity, in which nonpolar/fatty gut contents become more prone to excretion. In some examples, altering BSH activity (e.g., increasing or decreasing BSH activity) may be useful for treating disease (e.g., obesity and hypercholesterolemia, such as by increasing BSH activity, by which cholesterol pools can become depleted to compensate for the production of fresh bile where bile acids are excreted in excess endogenously (Joyce et al., *Proceedings of the National Academy of Sciences*, 111:7421-7426, 2014, the relevant portion of which is incorporated herein by reference). BSH activity is often observed in common probiotics (Begley et al., *Applied and Environmental Microbiology*, 72, 1729-1738, 2006, the relevant portion of which is incorporated herein by reference). Enzymatic hydrolysis of bile salts by BSH can display standard Michaelis-Menten kinetics and can include a nucleophilic cysteine that attacks the amide bond, forming a covalent enzyme-bile acid complex, which is hydrolyzed, allowing the hydrolase to participate in another catalytic cycle. BSH inhibitors can include, for example, antibiotic growth promoters, carnosic acid, $FeSO_4$, $CoCl_2$, $NaSeO_3$, $NaIO_4$, retinol, and linolenic acid, $KIO_3$, $NaHIO_3$, $NaIO_4$, $CuSO_4$, $CuCl_2$, $ZnSO_4$, $ZnCl_2$, menadione, riboflavin, gossypetin, caffeic acid phenethyl ester [CAPE], epicatechin monogallate, purpurogallin, oxytetracycline, demeclocycline hydrochloride, methacycline hydrochloride, doxycycline hydrochloride, roxarsone, or lincomycin (e.g., Smith et al., PLoS One, 9(1): e85344, 2014; Lin et al., Pathogens, 3(4): 947-956, 2014; Katie Smith, Identification of bile salt hydrolase inhibitors, the promising alternative to antibiotic growth promoters to enhance animal production, Master's Thesis, University of Tennessee, 2013, trace.tennessee.edu, all of which are incorporated herein by reference in their entireties).

Bile Salt Hydrolase Activity: The ability to hydrolyze an amide bond present in a bile salt (or a probe embodiment of the present disclosure). In particular embodiments, the amide bond of a bile salt conjugates an amino acid to a sterol moiety.

Bile Salts: Amphipathic agents that can form micelles, such as taurocholate, glycocholate, taurodeoxycholate, and glycodeoxycholate (e.g., see US Pat. Pub. No. 2009/0074895, the relevant portion of which is incorporated herein by reference). Bile salts can also be referred to as conjugated bile acids (e.g., bile acids conjugated to amino acids, such as glycine or taurine).

Carboxyl: —$C(O)OR^b$, wherein $R^b$ is aliphatic, aryl, heteroaliphatic, aliphatic-aryl, heteroaryl, aliphatic-heteroaryl, heteroaliphatic-aryl, heteroaliphatic-heteroaryl, hydrogen, and any combination thereof.

Click Chemistry: Chemical synthetic methods for making compounds using reagents that can be joined together using efficient reagent conditions and that can be performed in benign solvents or solvents that can be removed or extracted using facile methods, such as evaporation, extraction, or distillation. A representative example of click chemistry is a reaction that couples an azide and an alkyne to form a triazole.

Clickable Functional Group: A functional group that can be used in a click chemistry reaction to form a product. In some embodiments, the clickable functional group is an azide or an alkyne.

Colon Cancer (Colorectal Cancer): A cancer of the colon (e.g., large intestine), including adenocarcinoma, gastrointestinal stromal tumors (GIST), lymphoma, carcinoids, turcot syndrome, peutz-jeghers syndrome (PJS), familial colorectal cancer (FCC), juvenile polyposis coli, or stage I, II, III, or IV colon cancer. Colon cancer can be hereditary or nonhereditary and can begin as small, noncancerous clumps of cells (polyps, such as adenomatous polyps), which can become colon cancer. Examples of colon cancer symptoms include bowel changes, rectal bleeding (or blood in stool), persistent abdominal discomfort, a feeling that the bowel does not empty, weakness, fatigue, and unexplained weight loss. Diagnosis techniques can include colonoscopy and/or blood tests (e.g., for carcinoembryonic antigen [CEA]). Treatment can include surgery, chemotherapy or drug therapy, immunotherapy, or palliative care. In some examples, the colon cancer is related to BSH, for example, overactive BSH or an overabundance of deconjugated bile salts (e.g., Ridlon et al., J Lipid Res., 47(2):241-59, 2006, incorporated herein by reference in its entirety).

Detectable Moiety (or DM): A functional group or a molecule that is capable of producing a signal that can be visually and/or instrumentally detected. In particular disclosed embodiments, the detectable moiety provides the ability to visualize or detect, using an appropriate detection method, an enzyme because the reporting moiety becomes covalently attached to the enzyme.

Detectable Moiety Precursor (or pDM): A functional group that is capable of being converted to a detectable moiety by coupling with a functional group or molecule capable of producing a signal that can be visually and/or instrumentally detected.

Diabetes Mellitus: A group of metabolic diseases in which a subject has high blood sugar, either because the pancreas does not produce enough insulin, or because cells do not respond to the insulin that is produced. Type 1 diabetes results from the body's failure to produce insulin. This form has also been called "insulin-dependent diabetes mellitus" (IDDM) or "juvenile diabetes". Type 1 diabetes mellitus is characterized by loss of the insulin-producing 1-cells, leading to insulin deficiency. This type can be further classified as immune-mediated or idiopathic. Type 2 diabetes results from insulin resistance, a condition in which cells fail to use insulin properly, sometimes combined with an absolute insulin deficiency. Type 2 diabetes is also called "non-insulin-dependent diabetes mellitus" (NIDDM) or "adult-onset diabetes." In some examples, the diabetes, such as type 2 diabetes, is related to BSH activity (e.g., Labbe et al., *PLoS One*, 9(12):e115175, 2014, the relevant portion of which is incorporated herein by reference). The defective responsiveness of body tissues to insulin is believed to involve the insulin receptor. Diabetes mellitus is characterized by recurrent or persistent hyperglycemia, and can be diagnosed by demonstrating any one of:

a. Fasting plasma glucose level≥7.0 mmol/l (126 mg/dl);

b. Plasma glucose≥11.1 mmol/l (200 mg/dL) two hours after a 75 g oral glucose load as in a glucose tolerance test;

c. Symptoms of hyperglycemia and casual plasma glucose≥11.1 mmol/l (200 mg/dl);

d. Glycated hemoglobin (Hb A1C)≥6.5%.

In some examples, the diabetes is related to BSH activity, such as an imbalance in primary and secondary bile acids, for example, underactive or inactive BSH or insufficient deconjugation of bile acids.

Dysbiosis: A microbial imbalance or maladaptation on or inside the body, such as an impaired microbiota (e.g., of human or animal gut, skin, lung, oral, ocular, mouth, vaginal, and uterine environment). Dysbiosis is most commonly reported as a condition in the intestine, particularly as small intestinal bacterial overgrowth (SIBO) or small intestinal fungal overgrowth (SIFO). Microbes and microbial colonies in and one the body are often beneficial (e.g., microbes or microbe colonies with BSH activity or drug- or xenobiotic-metabolizing activity). Therefore, a disruption or disturbance of the balance (e.g., a chronic imbalance) can have pathological consequences, for example, periodontal disease, inflammatory bowel disease, chronic fatigue syndrome, obesity, cancer, bacterial vaginosis, and colitis are associated with dysbiosis. In some examples, the dysbiosis is related to BSH activity, such as an imbalance in primary and secondary bile acids, for example, underactive or inactive BSH or insufficient deconjugation of bile acids (e.g., Kakiyama et al., *J. Hepatol.*, 58(5):949-955, 2013, the relevant portion of which is incorporated herein by reference).

Ester: —C(O)OR$^b$, wherein R$^b$ is selected from hydrogen, aliphatic, aryl, heteroaliphatic, aliphatic-aryl, heteroaryl, aliphatic-heteroaryl, heteroaliphatic-aryl, heteroaliphatic-heteroaryl, or any combination thereof.

Farnesoid X-Activated Receptor (FXR): Also known as retinoid X receptor-interacting protein 14 (RIP14); RXR-interacting protein 14; bile acid receptor (BAR); and nuclear receptor subfamily 1, group H, member 4 (NR1H4; e.g., OMIM 603826), FXR is a transcription factor and nuclear receptor that binds bile acids, such as chenodeoxycholic acid. FXR plays a role in regulating gut microbiota, bile acid, lipid, and glucose metabolism as well as interorgan communication and, thus, is a therapeutic target for liver and metabolic disease.

Includes FXR nucleic acid molecules and proteins. FXR sequences are publicly available. For example, GenBank® Accession Nos. HQ709175.1, NM_021745.1, and BC015261.1 disclose exemplary human, rat, and mouse FXR nucleotide sequences, respectively, and GenBank® Accession Nos. BAH02290.1, AAC52205.1, and NP_001157172.1 disclose exemplary human, rat, and mouse FXR protein sequences, respectively, all of which are incorporated by reference in their entireties. One of ordinary skill in the art can identify additional FXR nucleic acid and protein sequences, including FXR variants that retain FXR biological activity (such as regulating gut microbiota, bile acid, lipid, and glucose metabolism).

Gallstones: Hardened digestive fluid or stones that form from bile components in the gallbladder. Symptoms include pain in and around the center or upper right abdomen, shoulder blades, or right shoulder; nausea; vomiting; fever; chills; and yellowing of eyes and skin. Gallstones can include cholesterol or pigment gallstones. In some examples, the gallstones are associated with BSH, for example, overactive BSH or an overabundance of deconjugated bile salts (e.g., Ridlon et al., J Lipid Res., 47(2):241-59, 2006, incorporated herein by reference in its entirety). In some examples, the gallstones are cholesterol gallstones.

Genomics: The study of genome structure, function, evolutions, mapping, and editing (e.g., Sims et al., *Nat. Rev. Genet.*, 15(2):121-32, 2014, the relevant portion of which is incorporated herein by reference), such as through whole genome and/or whole exome sequencing (WGS and WES, respectively); sequencing for single nucleotide variants, insertions, and/or deletions (indels), copy number variations; RNA sequencing (e.g., RNA-seq or whole transcriptome shotgun sequencing), such as 16S sequencing; assaying interactions between nucleic acids and ligands and/or macromolecules (e.g., molecules typically with a mass of at least 2 kDa, such as nucleic acids with at least 10 nucleotides, polynucleotides, polypeptides, proteins, enzymes, and complexes with plurality of macromolecules); and metagenomics (e.g., Sharma and Lal, *Indian J. Microbiol.*, 57(1): 23-38, 2017, incorporated herein by reference). Typical genomics assays include sequencing and sequence assembly and annotation, such as using de novo techniques, for example, shotgun sequencing or PCR, or next generation techniques (e.g., "next gen" or high-throughput), for example, real-time single-molecule, ion torrent, pyro, synthesis, combinatorial probe anchor, ligation (e.g., oligonucleotide ligation and detection or SOLiD), nanopore or Sanger sequencing; chromatin or cross-linking immunoprecipitation (e.g., ChI and CLIP, respectively); and bioinformatics and computational biology.

Halogen: An atom selected from fluoro, chloro, bromo, or iodo.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group. Exemplary heteroaliphatic groups include, but are not limited to, aliphatic groups comprising an ether, a thioether, an ester, an amine, a carboxy, a carbonyl, or an amide.

Heteroaliphatic-aromatic: An aromatic group that is or can be coupled to a probe disclosed herein, wherein the aromatic group is or becomes coupled through a heteroaliphatic group.

Heteroaliphatic-aryl: An aryl group that is or can be coupled to a probe disclosed herein, wherein the aryl group is or becomes coupled through a heteroaliphatic group.

Heteroalkyl/Heteroalkenyl/Heteroalkynyl: An alkyl, alkenyl, or alkynyl group (which can be branched, straight-chain, or cyclic) comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroaromatic: An aromatic group comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroaryl: An aryl group comprising at least one heteroatom to six heteroatoms, such as one to four heteroatoms, which can be selected from, but not limited to oxygen, nitrogen, sulfur, selenium, phosphorous, and oxidized forms thereof within the ring. Such heteroaryl groups can have a single ring or two or more fused rings, which fused rings may or may not be aromatic and/or contain a heteroatom, provided that the point of attachment is through an atom of the aromatic heteroaryl group. In some embodiments, the heteroaryl ring is selected from, but not limited to, pyridinyl, quinolinyl, quinazolinyl, quinoxalinyl, benzoquinolinyl, benzoquinoxalinyl, benzoquinazolinyl, indolyl, indolinyl, benzofuranyl, benzothiophenyl, benzimidizolyl, purinyl, carbazolyl, acridinyl, phenazinyl, and the like.

Heteroaliphatic-heteroaromatic: A heteroaromatic group that is or can be coupled to a probe disclosed herein, wherein the heteroaromatic group is or becomes coupled through a heteroaliphatic group.

Hypercholesterolemia: Also known as high cholesterol, hypercholesterolemia is high levels of cholesterol in the blood and includes genetic and acquired hypercholesterolemia (e.g., Ibrahim and Jialal, *Hypercholesterolemia*, StatPearls Publishing, 2018, ncbi.nlm.nih.gov, the relevant portion of which is incorporated herein by reference). In some examples, hypercholesterolemia features include LDL cholesterol greater than 190 mg/dL, greater than 160 mg/dL with one cardiovascular risk factor, or greater than 130 mg/dL with two cardiovascular risk factors, where exemplary risk factors include age for males 45 years or older and females 55 years or older, a positive family history of premature atherosclerotic cardiovascular disease at younger than 55 years in males and younger than 65 years in females, hypertension, diabetes, smoking, and low HDL cholesterol levels, such as less than 40 mg/dl in males and less than 55 mg/dl in female. In some examples, the hypercholesterolemia is related to BSH activity, such as an imbalance in primary and secondary bile acids, for example, underactive or inactive BSH or insufficient deconjugation of bile acids.

Inhibiting or Treating a Disease: Inhibiting the full development of a disease or condition, for example, in a subject who is at risk for a disease, such as obesity and/or hypercolesterolemia. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Irritable Bowel Disease (IBD): IBD involves inflammation of the small and large intestine and includes Crohn's disease and ulcerative colitis. Crohn's disease affects the small intestine and large intestine, as well as the mouth, esophagus, stomach and the anus, whereas ulcerative colitis primarily affects the colon and the rectum. Symptoms include abdominal pain, vomiting, diarrhea, rectal bleeding, severe internal cramps/muscle spasms in the region of the pelvis and weight loss. Anemia is the most prevalent extraintestinal complication of inflammatory bowel disease. Additional complaints or diseases related to IBD include arthritis, pyoderma gangrenosum, primary sclerosing cholangitis, non-thyroidal illness syndrome (NTIS), deep vein thrombosis (DVT), and bronchiolitis obliterans organizing pneumonia (BOOP). Diagnosis is generally by assessment of inflammatory markers in stool followed by colonoscopy with biopsy of pathological lesions. In some examples, the IBD is related to BSH activity, such as an imbalance in primary and secondary bile acids, for example, underactive or inactive BSH or insufficient deconjugation of bile acids.

Ketone: —C(O)$R^b$, wherein $R^b$ is selected from aliphatic, aryl, heteroaliphatic, aliphatic-aryl, heteroaryl, aliphatic-heteroaryl, heteroaliphatic-aryl, heteroaliphatic-heteroaryl and any combination thereof.

Liver Cancer: A cancer of the liver, including primary liver and secondary liver cancer. In primary liver cancer, the cancer originates in the liver, but in secondary liver cancer (i.e., metastatic liver cancer), the cancer has metastasized into the liver from another originating site in the body. Examples of primary liver cancer include hepatocellular carcinoma (i.e., hepatocellular cancer), intrahepatic cholangiocarcinoma (i.e., bile duct cancer), angiosarcoma, hemangiosarcoma, and hepatoblastoma. In some examples, the liver cancer is related to obesity (e.g., Ridlon et al., *Curr. Opin. Gastroenterol.*, 30(3):332-338, 2014, the relevant portion of which is incorporated herein by reference). In some examples, the colon cancer is related to BSH, for example, overactive BSH or an overabundance of deconjugated bile salts.

Metabolism: Biochemical construction and destruction, such as metabolism regulating nutrition and energy. In some examples, metabolism includes microbial metabolism that occurs in the environment (for example, the surroundings of plants, animals, humans, or microbes, which can include internal environment of plants, animals, humans, and microbes), such as metabolism of xenobiotics, pharmaceutical drugs or biologicals, carbon, nitrogen, sulfur, phosphate, reducing equivalents, and energy (e.g., Nakamura and Whited, *Curr. Opin. Biotechnol.*, 14(5):454-9, 2003, the relevant portion of which is incorporated herein by reference). In some examples, metabolism includes a specific metabolic function (e.g., enzymatic activity and/or metabolite uptake or sensing). In some examples, metabolism can be altered, such as through enriching or reducing microbes (for example, bacteria, archaea, or fungi) in an environment involved in metabolism or altering the amount of or expression of one or more proteins involved in metabolism (for example, enriching or reducing microbes involved in at least one specific metabolic function or altering the amount of or expression of one or more proteins involved in at least one specific metabolic function). In some examples, metabolism involves energy (for example, energy production or conversion), nutrients (for example, nutrient production or conversion), xenobiotics (for example, xenobiotic conversion or catabolism), or regulation of intracellular or extracellular processes (for example, internal or external to plants, animals, humans, or microbes). Thus, altering metabolism can alter energy, nutrients, xenobiotics, or regulation of intracellular or extracellular processes.

In some examples, the metabolism is drug or xenobiotic metabolism (e.g., breakdown of drugs or xenobiotics by living organisms). In some examples, such as in humans, drug metabolism can include three phases. In phase I, enzymes (e.g., cytochrome P450 oxidase) add reactive or polar groups onto a drug or xenobiotic. In phase II, modified drugs or xenobiotics can then be conjugated to polar compounds (e.g., methyl, sulfate, acetyl, glucuronic acid, glutathione, and glycine groups), for example, by transferase enzymes (e.g., methyltransferase, sulfotransferase, N-acetyltransferases, bile acid-coA:amino acid N-acyltransferases, UDP-glucuronosyltransferases, glutathione S-transferases, XM-ligase, and glycine N-acyltransferase). In phase III, the conjugated drugs or xenobiotics may be further processed and are then pumped out of cells by efflux transporters. In some examples of drug or xenobiotic metabolism, lipophilic compounds can be converted into hydrophilic products that are more readily excreted. In some examples, drug or xenobiotic metabolism can affect pharmacodynamics or drug clearance. In some examples, insufficient or excessive drug or xenobiotic metabolism can lead to therapeutic failure or side effects.

Microbe: Microorganism or microscopic organism, including all unicellular organisms and microbes that live as a single cell or in a colony of cells. Examples of microbes include bacteria, archaea, algae, fungi, protozoa, and viruses. In some examples, microbes are present in another organism, such as a plant, animal, or human (for example, as part of a microbiome within an animal or a human, such as a gut microbiome in an animal or a human). In specific examples, the microbes can include *L. plantarum*, bacteriodetes, or firmucutes.

Obesity: A disease state characterized by a body mass index (BMI) of 30 or greater. Obesity is associated with other diseases, such as type 2 diabetes, high blood pressure, heart disease and strokes, certain types of cancer, sleep apnea, osteoarthritis, fatty liver disease, kidney disease, pregnancy problems (for example, high blood sugar during pregnancy, high blood pressure, and increased risk for cesarean delivery). In some examples, the obesity is related or at least in part related to the presence, absence, or abundance of microbes or enzymes (e.g., microbial enzymes), such as microbes or enzymes with at least one specific metabolic function (e.g., BSH activity). In some examples, the obesity is related to an imbalance in primary and secondary bile acids, for example, underactive or inactive BSH or insufficient deconjugation of bile acids.

Pharmaceutical Agent or Drug: A chemical compound or composition capable of inducing a desired therapeutic or prophylactic effect when properly administered to a subject.

Pharmaceutically Acceptable Carriers: The pharmaceutically acceptable carriers useful in this disclosure are conventional. *Remington's Pharmaceutical Sciences* (E. W. Martin, Mack Publishing Co., Easton, Pa., 18th Edition, 1990, the relevant portion of which is incorporated herein by reference) describes compositions and formulations suitable for pharmaceutical delivery of pharmaceutical agents or drugs. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol, or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH-buffering agents, and the like, for example, sodium acetate or sorbitan monolaurate.

Proteomics: A study of proteins, for example, a large- or small-scale study, such as using techniques for separating, identifying, and analyzing proteins (for example, analyzing intermolecular or intramolecular interactions, such as protein structure, protein-protein interactions, or protein-ligand interactions; Lee, *Trends Biotechnol.*, 19(6):217-22, 2001, the relevant portion of which is incorporated herein by reference). Many tools are available for proteomic analysis, for example, mass spectrometry (for example, using hard or soft ionization techniques, including matrix-assisted laser desorption/ionization or electrospray ionization, for example, with mass analyzers, such as time of flight, quadrupole filter, or ion trapping, as well as other techniques, such as liquid chromatography, capillary electrophoresis, tandem mass spectrometry, or fragmentation techniques, for example, collision-induced dissociation); electrophoresis (for example, 1 D- or 2D-gel electrophoresis or western blotting), immunological assays (for example, immunological microarray assays or enzyme-linked immunosorbent assays, ELISAs), protein microarray assays (for example, functional protein or target protein array assays), chromatography (for example, affinity, size-exclusion, ion-exchange, or reverse-phase), tools for analyzing protein structure or electrochemistry (for example, x-ray crystallography or nuclear magnetic resonance), computational or bioinformatics tools (for example, protein identification, structure, or interaction modeling tools), or any combination thereof. In some embodiments, mass spectrometry (MS), such as liquid chromatography MS (LC-MS), is used.

Sample: A specimen to be used for analysis. Any type of sample can be used, including a sample obtained from a subject, such as a sample from a physical environment (e.g., intestine (such as the small intestine, large intestine, or rectum), stomach, liver, gall bladder, fecal matter, blood or fraction thereof (e.g., serum or plasma), urine, ejaculate, saliva, tissue biopsy, surgical specimen, and autopsy material), or a sample obtained from a bioreactor, soil, or an aqueous environment. In some examples, samples are used directly in the methods provided herein. In some examples, samples are manipulated prior to analysis using the disclosed methods, such as through concentrating, filtering, centrifuging, diluting, desalting, denaturing, reducing, alkylating, proteolyzing, or combinations thereof. In some examples, components of the samples are isolated or purified prior to analysis using the disclosed methods, such as isolating cells, proteins, and/or nucleic acid molecules from the samples. In some examples, the sample includes microbial proteins.

Subject: As used herein, the term "subject" refers to animals and includes, without limitation, mammals, such as humans, domestic animals (e.g., dogs or cats), farm animals (e.g., cows, horses, or pigs), non-human primates, and laboratory animals (mice, rats, hamsters, guinea pigs, pigs, rabbits, dogs, or monkeys). Other exemplary subjects include fish, amphibians, reptiles, and birds (such as chickens and turkeys). Subjects can serve as a source of samples analyzed using the disclosed methods and devices.

Takeda G Protein-Coupled Bile Acid Receptor (TGR5): Also known as BG37, G Protein-Coupled Bile Acid Receptor 1 (GPBAR1), G-Protein Coupled Receptor 19 (GPCR19), and Membrane-Type Receptor For Bile Acids (M-BAR; e.g., OMIM No. 610147), TGR5 suppresses macrophage functions and regulates energy homeostasis and metabolism by bile acids and plays a role in diseases, including metabolic disorders (e.g., obesity), liver disease (e.g., non-alcoholic fatty liver disease), hypercholesterolemia, and atherosclerosis.

Includes TGR5 nucleic acid molecules and proteins. TGR5 sequences are publicly available. For example, GenBank® Accession Nos. AB089307.1, AB089310.1, and AB089308.1 disclose exemplary human, rat, and mouse TGR5 nucleotide sequences, respectively, and GenBank® Accession Nos. NP_001308879.1, NP_808797.1, and NP_778150.1 disclose exemplary human, rat, and mouse TGR5 protein sequences, respectively, all of which are incorporated by reference herein in their entireties. One of ordinary skill in the art can identify additional TGR5 nucleic acid and protein sequences, including TGR5 variants that retain TGR5 biological activity (such as regulating energy homeostasis and metabolism).

Therapeutic Agent: Used in a generic sense, it includes treating agents, prophylactic agents, and replacement agents.

Therapeutically Effective Amount: A quantity of an agent sufficient to achieve a desired effect in a subject being treated. For instance, this can be an amount necessary to treat a disease or condition in a subject, a dose sufficient to prevent advancement or to cause regression of a disease or condition, or an amount that is capable of relieving symptoms caused by a disease or condition. In one example, the amount is sufficient to prevent advancement or to cause regression of a disease or condition. In another example, the amount is sufficient to inhibit a sign or symptom of a disease or condition.

An effective amount of an agent can be administered systemically or locally. In addition, an effective amount can be administered in a single dose or in several doses, for example, daily, during a course of treatment. However, the effective amount will be dependent on the preparation applied, the subject being treated, the severity and type of the affliction, and the manner of administration of the compound.

Vitamin D Receptor (VDR): Also known as 1,25-Dihydroxyvitamin D3 Receptor; Vitamin D Hormone Receptor;

Calcitriol Receptor; and Nuclear Receptor Subfamily 1, Group I, Member 1 (NR1|1; e.g., OMIM No. 601769), VDR binds bile acids in addition to vitamin D and other ligands. Further, VDR regulates bile acid production, calcium and phosphate homeostasis, cell proliferation and differentiation, and the immune and nervous systems, and it aids in protecting against cardiovascular disease, diabetes, and cancer.

Includes VDR nucleic acid molecules and proteins. VDR sequences are publicly available. For example, GenBank® Accession Nos. J03258.1, NM_017058.1, and D31969.1 disclose exemplary human, rat, and mouse VDR nucleotide sequences, respectively, and GenBank® Accession Nos. BAA83389.1, EDL87095.1, and BAA06737.1 disclose exemplary human, rat, and mouse VDR protein sequences, respectively, all of which are incorporated by reference herein in their entireties. One of ordinary skill in the art can identify additional VDR nucleic acid and protein sequences, including VDR variants that retain VDR biological activity (such as regulating bile acid production).

The descriptions provided above are not intended to include impermissible substitution patterns (for example, methyl substituted with 5 different groups, and the like). Such impermissible substitution patterns are recognized by a person of ordinary skill in the art. In formulas and specific compounds disclosed herein, a hydrogen atom is present and completes any formal valency requirements (but may not necessarily be illustrated) wherever a functional group or other atom is not illustrated. For example, a phenyl ring that is drawn as

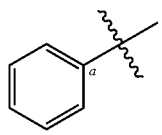 [SMILES: *c1ccccc1]

comprises a hydrogen atom attached to each carbon atom of the phenyl ring other than the "a" carbon, even though such hydrogen atoms are not illustrated.

Any functional group disclosed herein and/or defined above can be substituted or unsubstituted, unless otherwise indicated herein.

II. Introduction

The animal gut accommodates a complex mixture of microbes that greatly influence host health, with effects including alteration of nutrient absorption, creation of chemical signals that modulate host physiology, and protection against pathogens. A major route through which the gut microbiome affects the host is through chemical transformations of xeno- and endobiotics. The capacity for certain types of chemical transformations depends on the identity and abundance of the individual microbes within the gut microbiome, which can vary dramatically between individuals, and are influenced by factors including diet, age, geographic location, and even season. The metabolic activity of the gut microbiome can positively affect host health through increasing the nutritional value that can be extracted from food, as in the case of digestion of complex polysaccharides. The gut microbiome can also create chemical metabolites, such as short chain fatty acids, which induce signal transduction pathways in the host that reduce susceptibility to disease. Alternatively, chemical modification of host-produced metabolites by the gut microbiota can be detrimental, as some metabolites are associated with increased incidence of cancer. A clearer understanding of gut microbiome metabolism is needed to increase host resilience and decrease susceptibility to disease.

An example of a microbiota-host interaction is the microbial modification of the host's bile fluid. Animals produce bile to aid in the digestion of hydrophobic nutrients through increasing solubility. Bile acids, which are small organic compounds that are a primary component of bile, have a large effect on the net physicochemical properties of this fluid. Bile acids are produced in the liver through a multi-step biosynthetic pathway, which uses cholesterol as a starting material. Humans produce two primary bile acids, cholic and chenodeoxycholic acid, which differ by the presence of one hydroxyl group, but can have distinct biological effects. After synthesis in the liver, bile acids are subsequently conjugated to glycine or taurine to yield bile salts, which significantly increases the hydrophilicity of the molecule. After synthesis in the liver, bile salts are stored in the gall bladder, and are released into the duodenum to facilitate digestion, and are eventually reabsorbed for later use.

Although bile acids clearly influence digestion, these molecules are no longer thought of as simple surfactants that increase solubility of hydrophobic nutrients, but are now also appreciated to be selective chemical signals that bind human nuclear receptors in the intestine such as FXR and the vitamin D receptor, and surface receptors such as TGR5. Binding of bile salts by host receptors provides information on the state of the bile acid pool, and negatively regulates the first step in the synthesis of bile salts from cholesterol. Bile acid receptors also feed into signaling pathways that regulate other processes, including glucose and energy homeostasis.

Microbial metabolism in the gut produces modified, secondary bile acids including deoxycholic, ursodeoxycholic, and lithocholic acid, which can have disparate biological effects relative to each other and the primary bile acids. Bile salts must be de-conjugated from glycine/taurine in order for the microbiota to modify primary bile acids. De-conjugation of bile salts results from the activity of microbial bile salt hydrolases (BSHs), which hydrolyze the amide bond between the bile acid and glycine/taurine (FIG. 1A) using a nucleophilic cysteine. Because of its role in preparing bile acids for further microbial modification, BSH can be thought of as the gatekeeper for secondary bile acid formation. The result of BSH de-conjugation activity is a net change in the physicochemical properties of the bile acid pool, which ultimately makes it more hydrophobic. BSH de-conjugation is also strongly correlated with excretion of bile acids. Increasing BSH activity has been suggested to be an effective strategy for treating obesity and hypercholesterolemia, because if bile acids are excreted in excess, endogenously produced cholesterol pools will be depleted to compensate for the production of fresh bile. BSH activity has been proposed to be responsible for the beneficial health effects of several common probiotics.

Enzymatic hydrolysis of bile salts by BSH generally relies on an N-terminal nucleophilic cysteine that attacks the amide bond of a bile salt to free the amino acid and form an intermediate covalent enzyme-bile acid complex, which is subsequently hydrolyzed, and leaves the cysteine free to participate in another catalytic cycle. Current methods for quantification of BSH activity rely on multi-step detection of free amines (amino acid product), HPLC purification, or through spectrophotometric detection of precipitated products. These methods all suffer from respective drawbacks. Detection of free amines, as in ninhydrin-based assays, is not practical when analyzing complex samples (e.g. cell lysates or stool) that contain many nucleophilic amines that would cause assay interference. HPLC methods suffer from lengthy experiment times and low-throughput data generation. Few of the current methods are useful for analyzing BSH activity in fecal samples, which are most relevant to a clinical setting. Additionally, there are currently no methods that can be applied in in vivo bacterial cultures, which significantly limits the types of questions that researchers can ask about the biology of BSH.

Figure 1B:
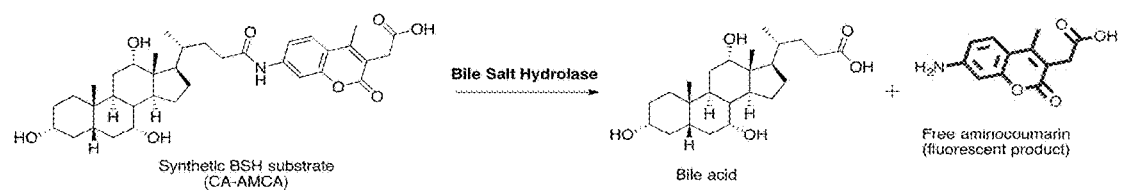

Disclosed herein are embodiments of a probe and method embodiments of using the probe to identify and characterize enzyme species that exhibit activity similar to BSH. The disclosed probe embodiments are designed to covalently bind to enzymes exhibiting BSH activity and/or react with such enzymes and provide a detectable signal so that these enzymes can be identified, isolated, and characterized. FIG. 1B shows an embodiment wherein a probe reacts with a BSH so as to displace a detectable moiety from the probe. And, the taxa in the gut that are involved with such enzymes can be determined. Also disclosed are embodiments of assay methods that can be used with the disclosed probe embodiments. In one embodiment, a continuous fluorescence-based BSH assay is described. As the disclosed probe embodiments and method embodiments can be used to determine which microbes in the gut are capable of BSH activity, they can be used to provide insight into how activity differs in healthy and diseased individuals. There is currently no approach that allows for comprehensive determination of the enzymes in the gut microbiome that are capable of bile salt hydrolase activity. The disclosed probe embodiments and method embodiments use unique chemistries and reactivities that have not been applied to BSH detection and/or isolation.

III. Probe Embodiments

Disclosed herein are embodiments of a probe that can be used to target, identify, and isolate enzymes exhibiting BSH activity. In particular disclosed embodiments, the probe comprises a detectable moiety ("DM") or a detectable moiety precursor ("pDM"). The pDM group can be used to append a detectable moiety to the probe. Some embodiments of the probe can comprise a linker group that couples the detectable moiety (or the detectable moiety precursor) to the probe. In embodiments comprising a linker, the probe can further comprise a photoactivatable moiety or an anchor moiety that is covalently attached to the linker. The photoactivatable moiety is capable of forming a covalent bond with an enzyme after being activated by an energy source (for example, a light source, such as a light source that provides light at wavelengths ranging from 10 nm to 400 nm, or from 10 nm to 370 nm, or from 10 nm to 365 nm). The anchor moiety is a functional group that can be used to attach a probe embodiment to a surface of a substrate. Other embodiments of the probe do not comprise a linker and instead have a detectable moiety (or a detectable moiety precursor) directly attached to the probe.

Probe embodiments described herein can have a structure satisfying Formula I. In particular disclosed embodiments, the probe can have a structure having the stereochemistry shown in Formulas IA-ID, wherein any combination of stereoisomers for $R^1$-$R^3$ is contemplated.

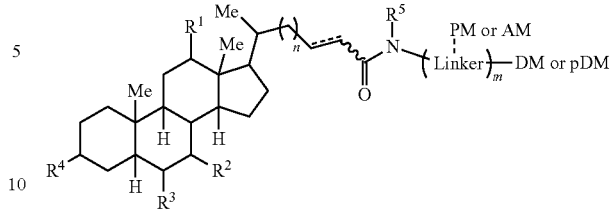

Formula I

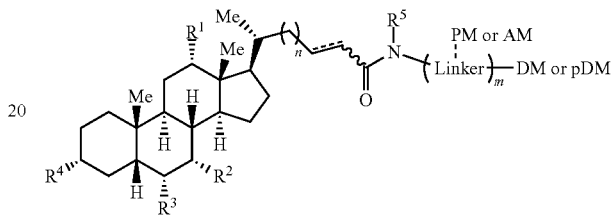

Formula IA

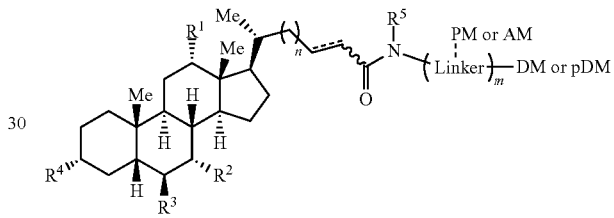

Formula IB

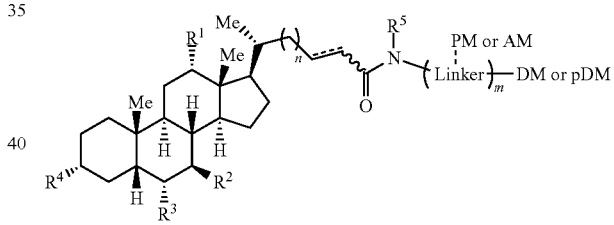

Formula IC

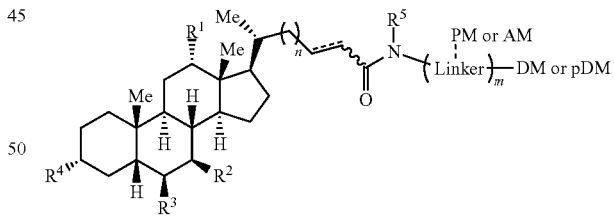

Formula ID

With reference to Formulas I and IA-ID, each of $R^1$, $R^2$, $R^3$, and $R^4$ independently can be selected from hydrogen or —OR, wherein each R independently is selected from hydrogen, a counterion that balances a negative charge on the oxygen atom (such as an alkali metal ion like $K^+$, $Na^+$, $Li^+$, or the like; an ammonium ion, or other positively charged ionized organic compounds), aliphatic, heteroaliphatic, aromatic, or any combination of aliphatic, heteroaliphatic, or aromatic (e.g., aliphatic-aromatic or heteroaliphatic-aromatic); $R^5$ can be hydrogen, aliphatic, heteroaliphatic, aromatic, or any combination of aliphatic, heteroaliphatic, or aromatic (e.g., aliphatic-aromatic or heteroaliphatic-aromatic); the linker, if present (such as when m is 1), can be aliphatic, heteroaliphatic, aromatic, or any combination of aliphatic, heteroaliphatic, or aromatic; DM, if present (such as when a pDM group is not present), is a detectable moiety; pDM, if present (such as when a DM group is not present), is a detectable moiety precursor; PM, if present (such as when an AM group is not present), is a photoactivatable moiety; AM, if present (such as when a PM group is not present), is an anchor moiety; n is an integer ranging from 0 to 10, such as 0 to 5, or 0 to 3, such as 0, 1, 2, or 3; and m is an integer selected from 0 or 1. With reference to Formulas I and IA-ID, the dashed bond (---) indicates that the bond may or may not be present and thus a PM or an AM group may be bound to the linker and/or a double bond may be present between the α and β carbons relative to the illustrated carbonyl group (and if a double bond is not present, a single bond is present). Also, the wavy bond ( ∿ ) in Formulas I and IA-ID (and other formulas disclosed below) indicates that, if a double bond is present, then the double bond can have an E or Z configuration.

In some embodiments, each $R^1$, $R^2$, $R^3$, and $R^4$ independently is hydrogen, hydroxyl, or alkoxy; $R^5$ is hydrogen or aliphatic; the linker is aliphatic (e.g., alkyl) or heteroaliphatic (e.g., an amide-containing group, a beta-lactam-containing group, or the like); DM, if present, is a fluorophore, a dye, or a member of a specific binding pair; pDM, if present, is a clickable functional group; PM, if present, is a diazirine or a benzophenone; AM, if present, comprises a clickable functional group (for example, an alkyne or an azide), a carboxylic acid, an NHS-ester, an amine, an alkyl halide or any other functional group that can be coupled to a surface-modified substrate as described herein; n is selected from 0, 1, or 2; and m is 0 or 1.

In some embodiments, the probe can have a structure satisfying any one of Formulas IIA or IIB.

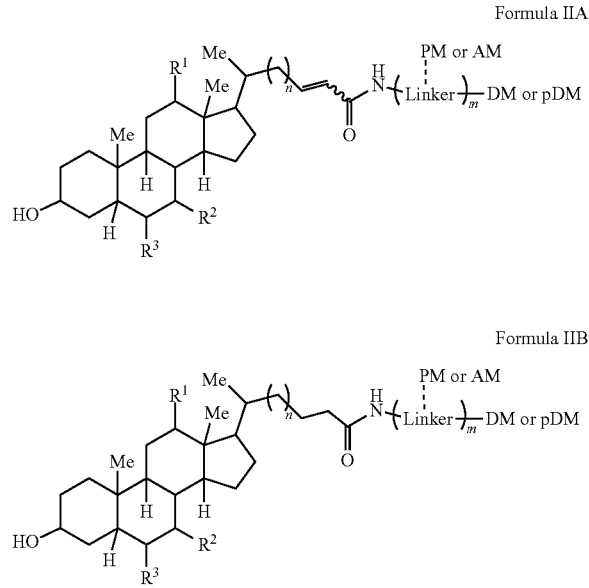

With reference to Formulas IIA and IIB, each of $R^1$, $R^2$, linker, DM, pDM, PM, AM, n, and m can be as recited above for Formulas I and IA.

In some embodiments, the probe can have a structure satisfying any one or more of Formulas IIIA-IIIF.

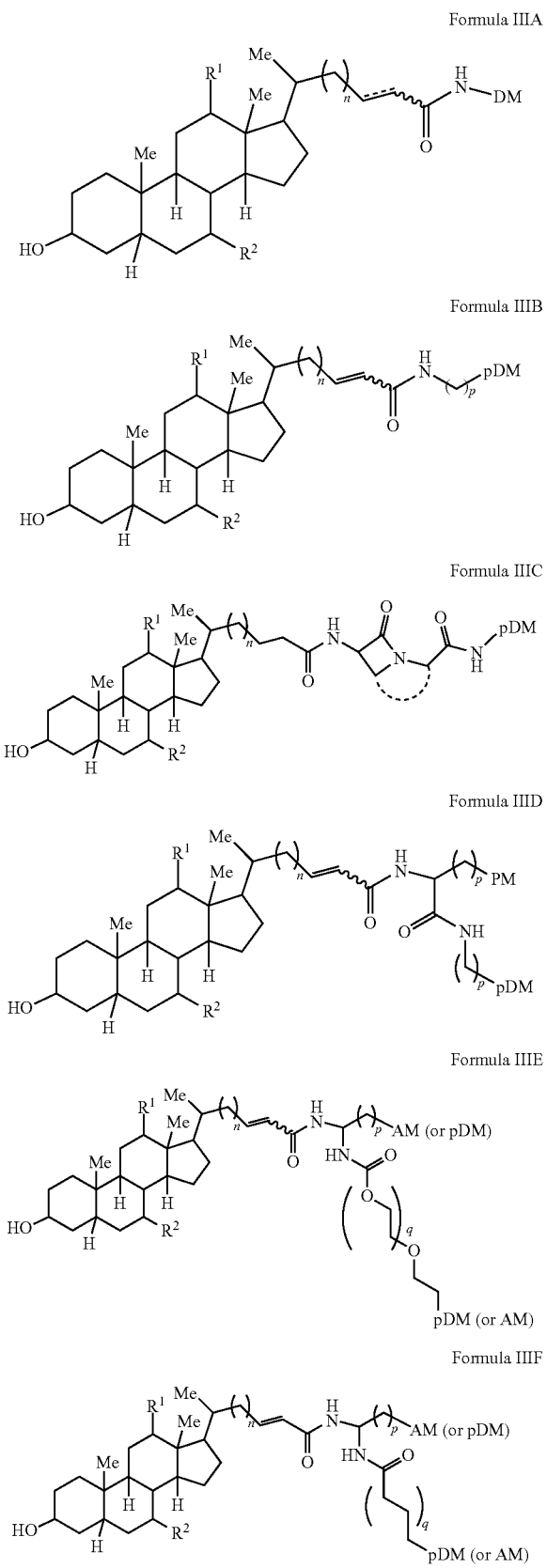

With reference to Formulas IIIA-IIIF, each of $R^1$, $R^2$, linker, DM, pDM, PM, AM, and n can be as recited above for Formulas I and IA. Further, p can be an integer selected from 1 to 10, such as 1 to 8, or 1 to 6, or 1 to 4; and q can be an integer ranging from 0 to 20, such as 1 to 20, or 1 to 15, or 1 to 10, or 1 to 5. In particular embodiments, p is 1, 2, 3, or 4 and q is 0, 1, 2, 3, 4, or 5. Formula IIIA provides a representative formula for probes that do not comprise a linker moiety between the amide nitrogen and a DM group. Formula IIIB comprises a representative aliphatic linker group (—$(CH_2)_s$—, wherein s is as an integer ranging from 1 to 10, such as 1 to 8, or 1 to 6, or 1 to 4). Formula IIIC comprises a representative heteroaliphatic linker group,

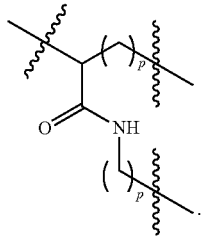

Formulas IIIE and IIIF also comprise representative heteroaliphatic linker groups that also serve as bi-functional linkers,

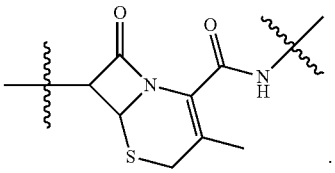 [SMILES: *NC(=O)C1=C(C)CSC2C(*)C(=O)N12]

Formula IIID comprises another representative heteroaliphatic linker group (which also serves as a bi-functional linker),

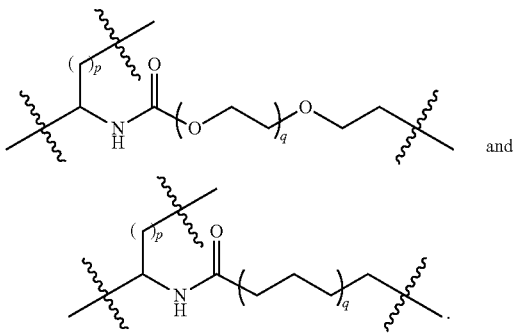

and

Exemplary probe embodiments are provided below.

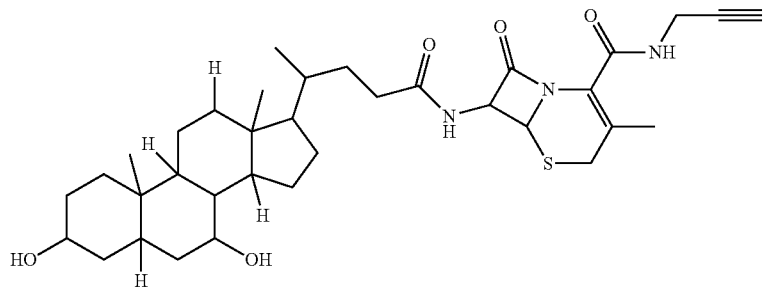

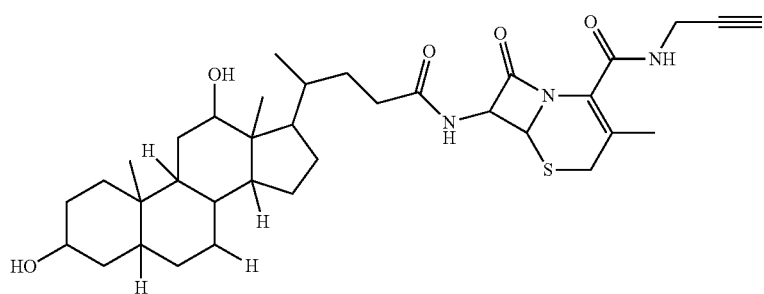

-continued
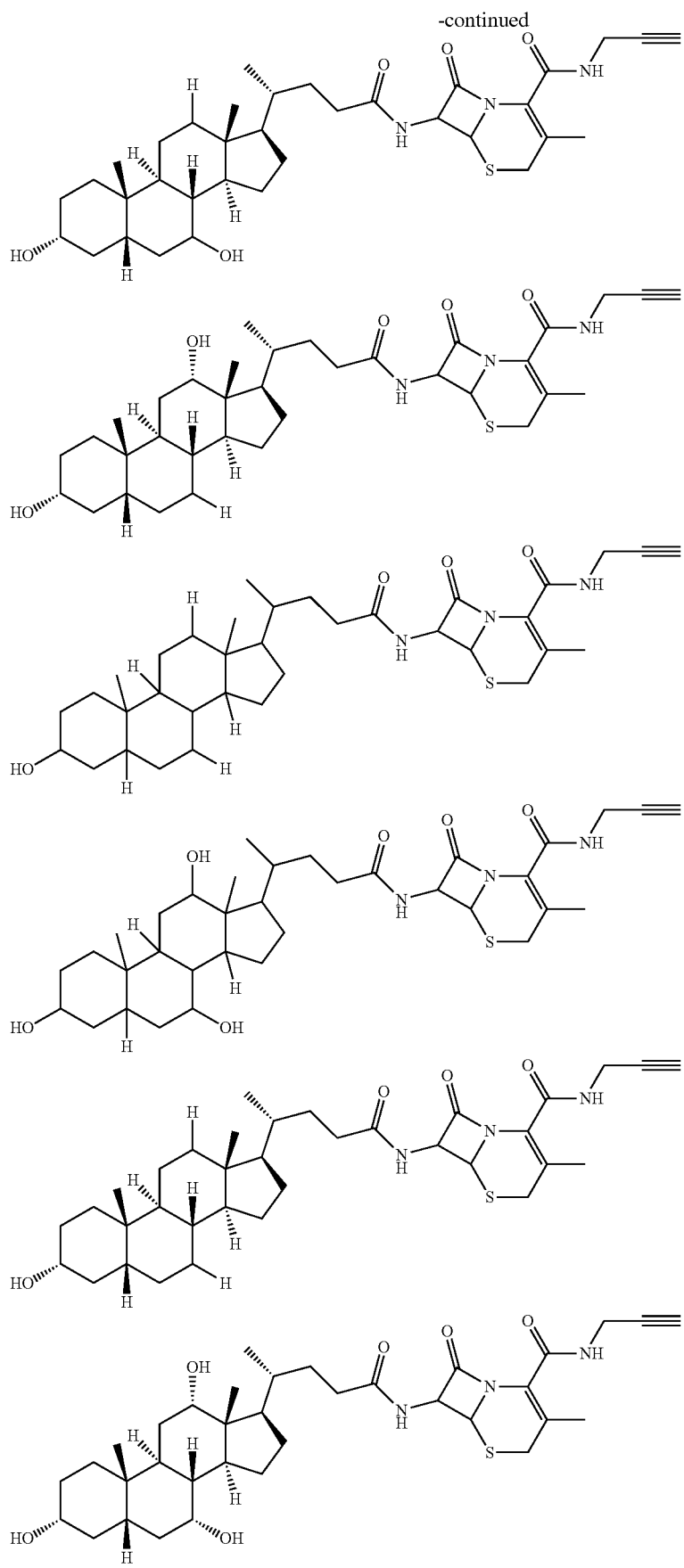

-continued
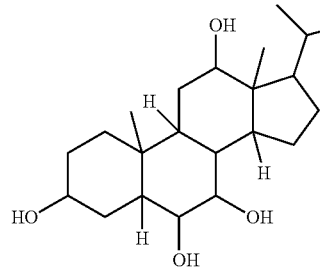 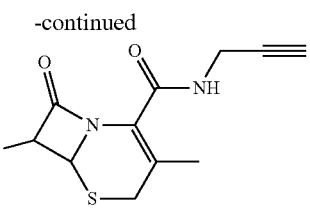
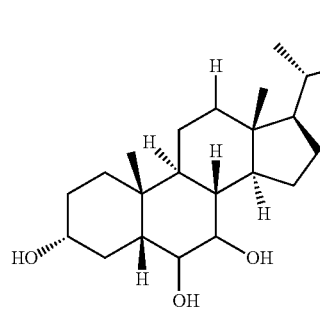 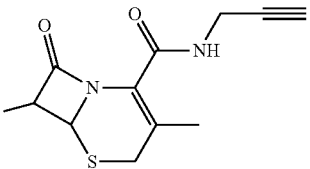
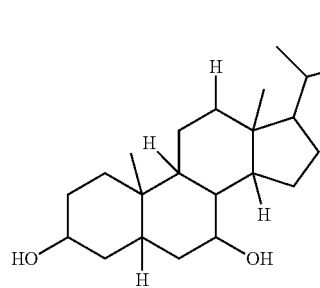 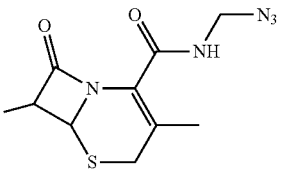
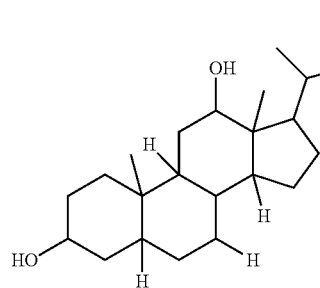 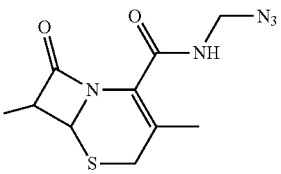
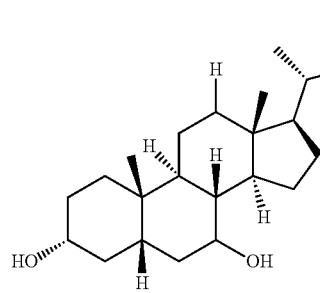 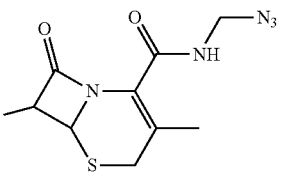

-continued
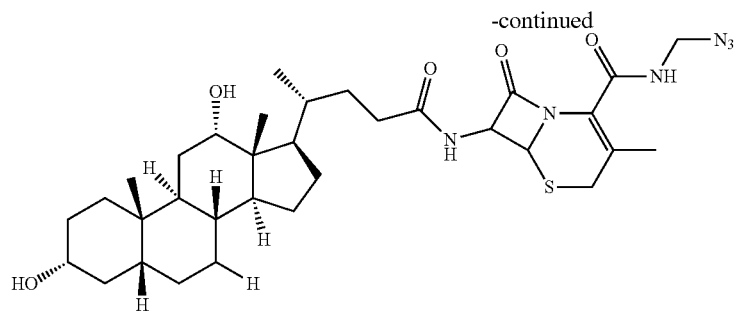
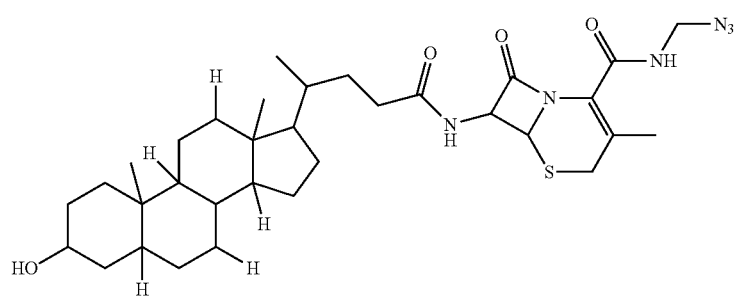
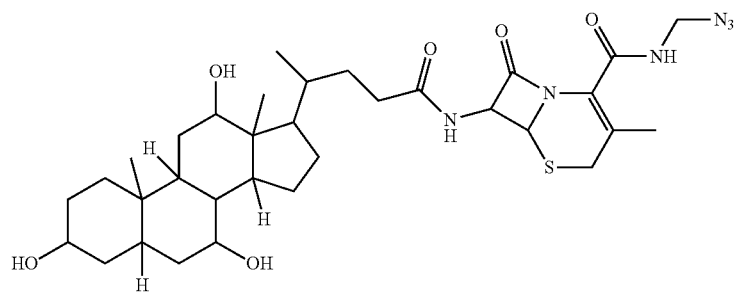
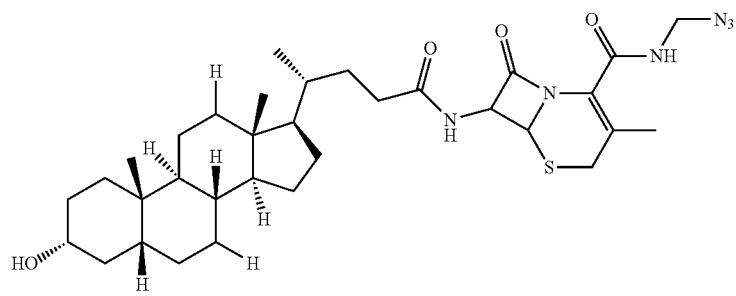
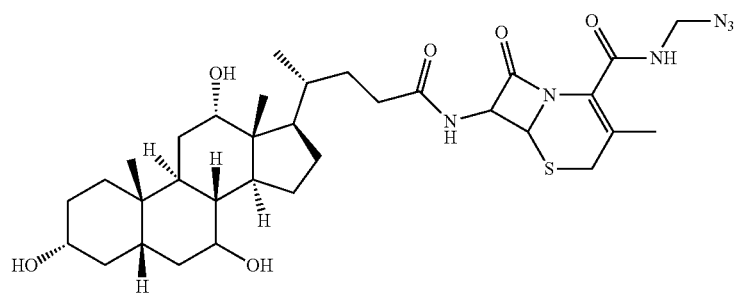

-continued
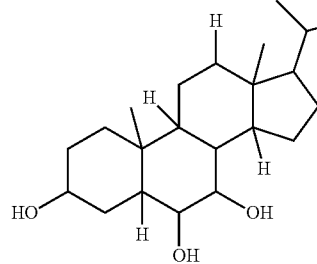
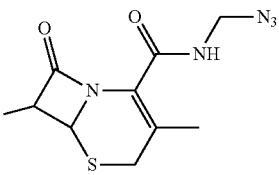
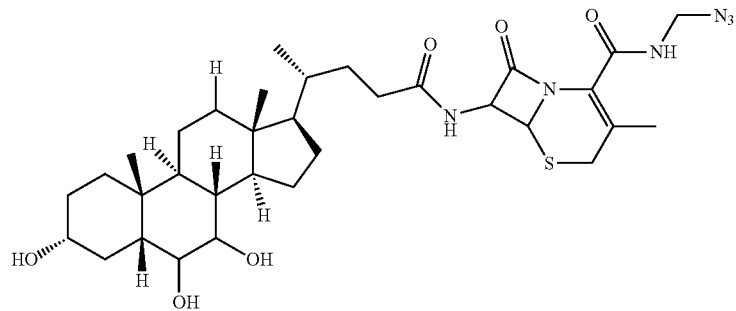
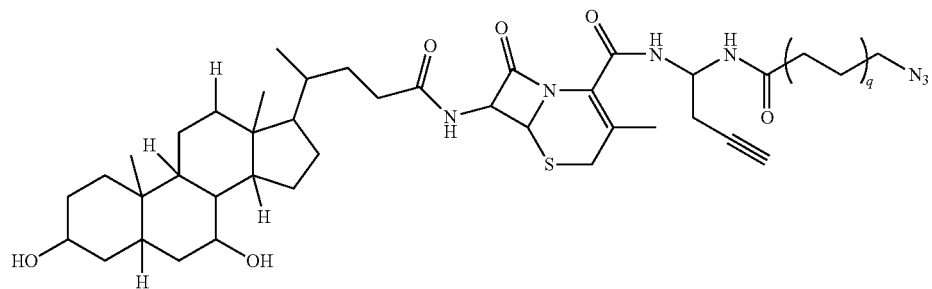
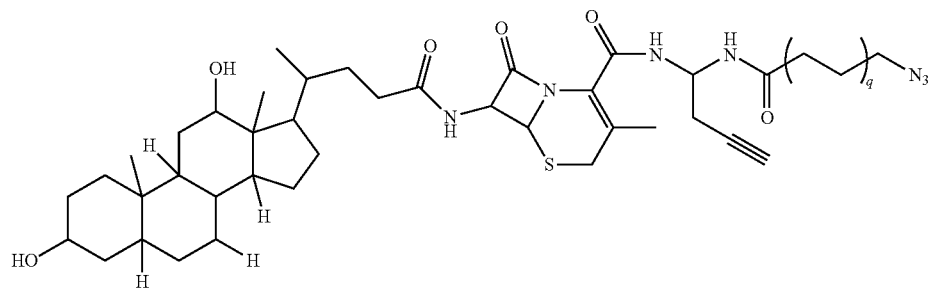
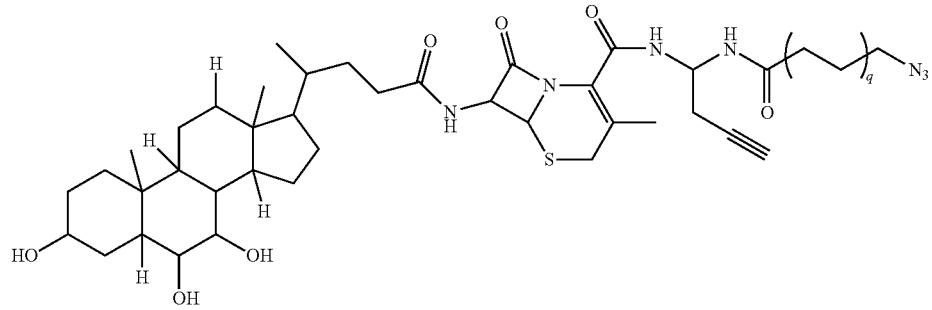

-continued
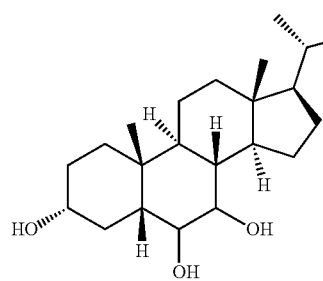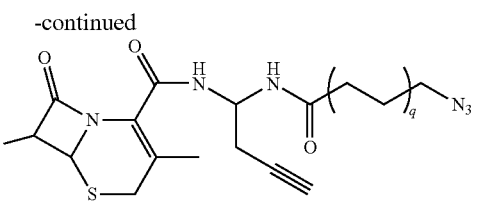
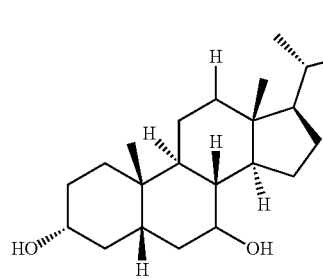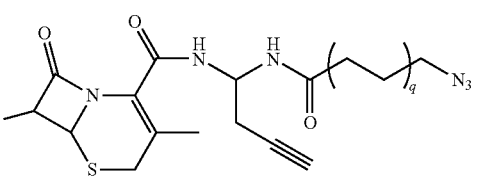
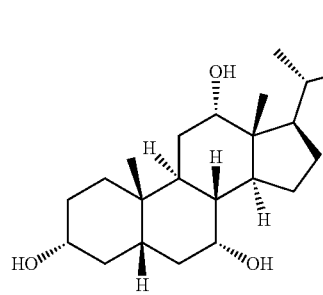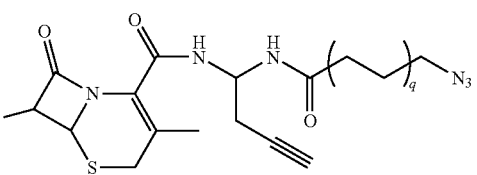
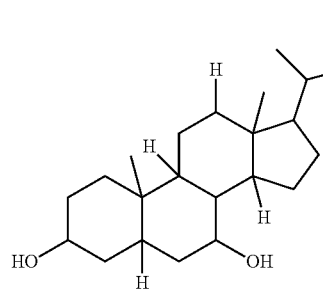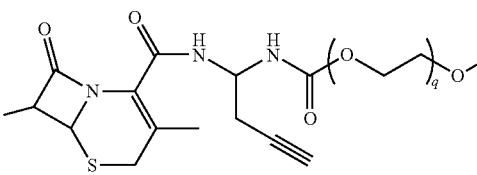
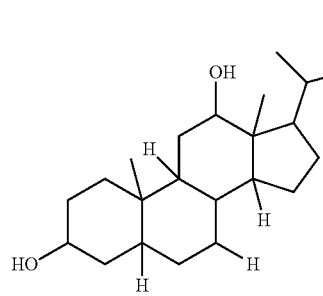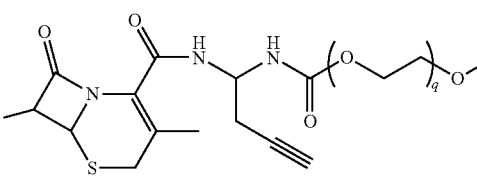

-continued
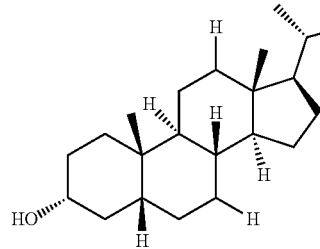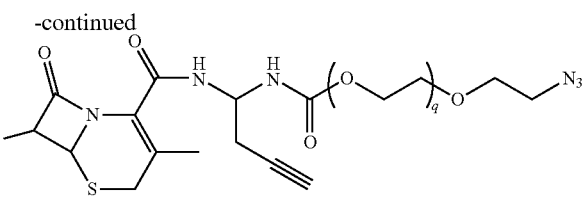
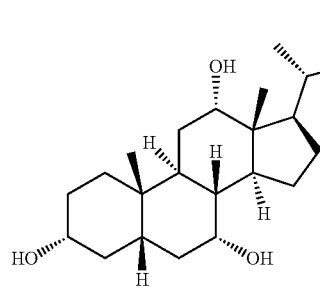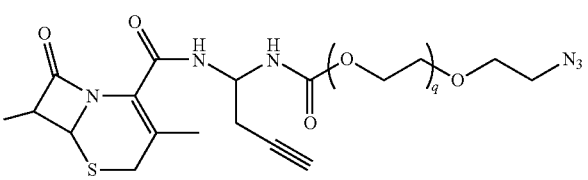
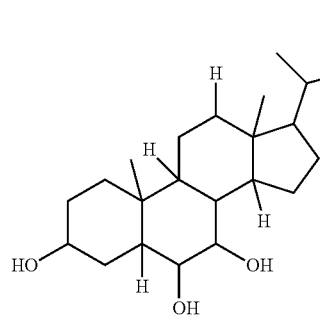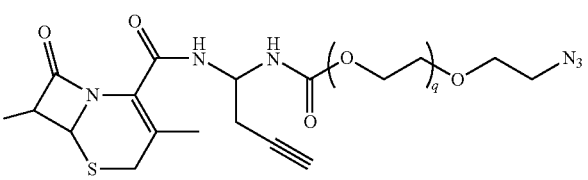
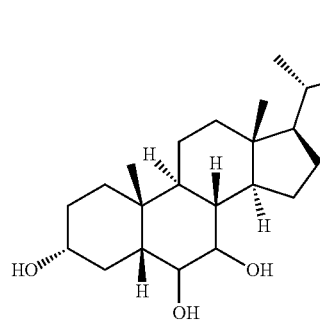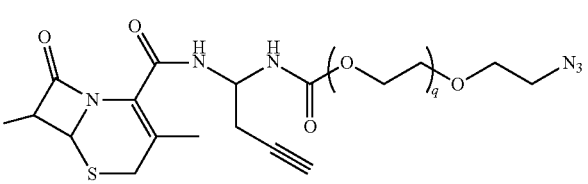
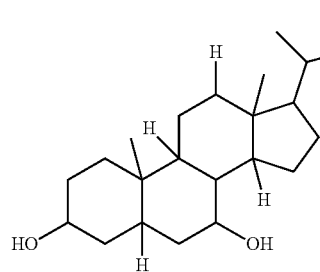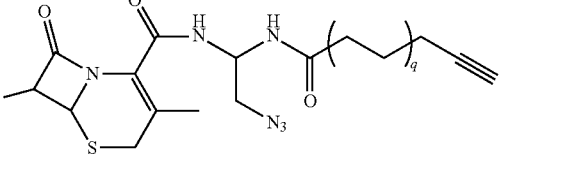

-continued
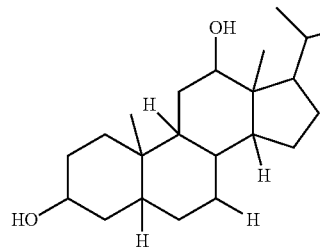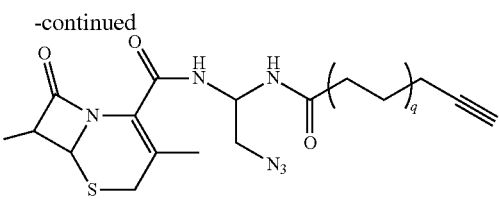
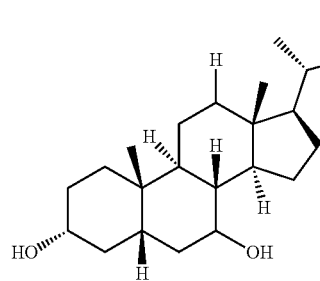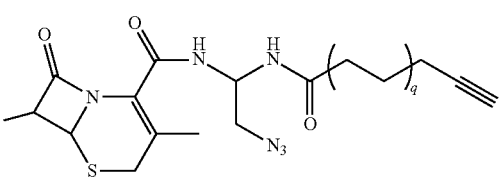
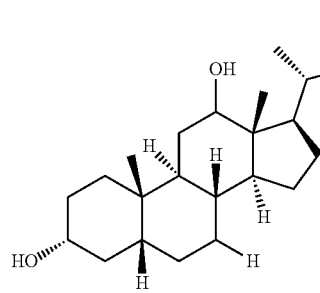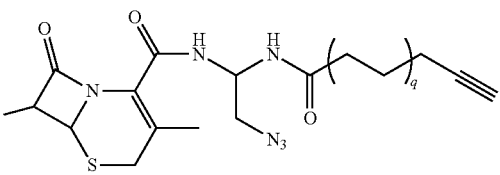
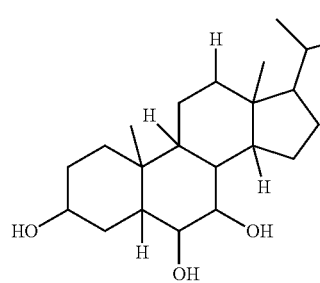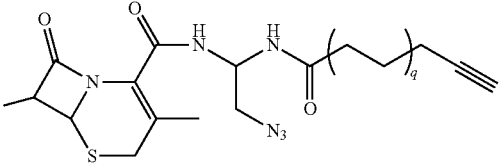
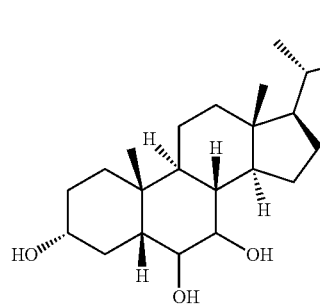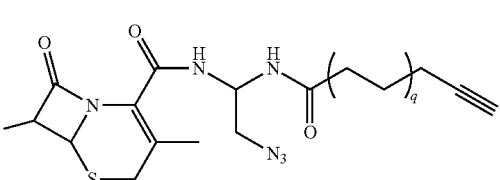

-continued
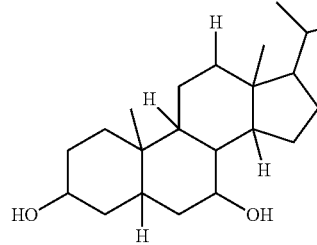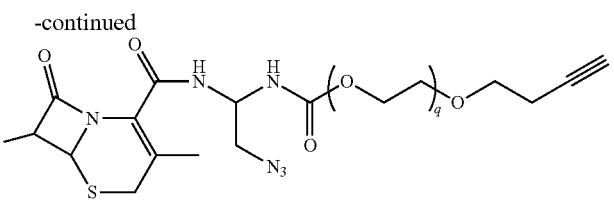
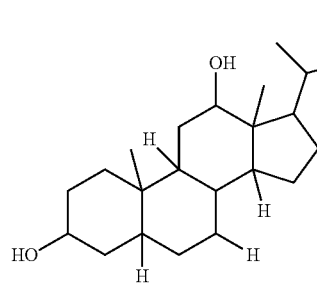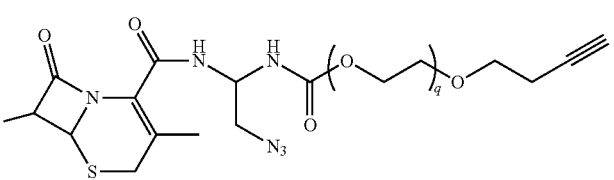
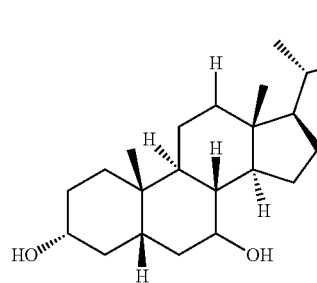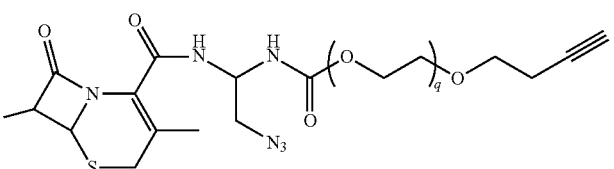
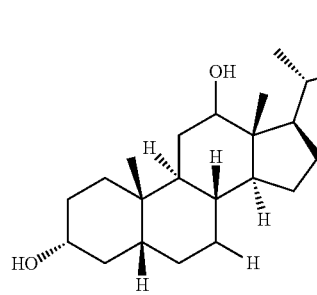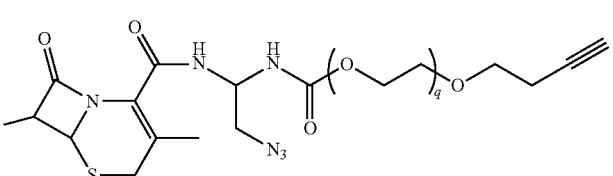
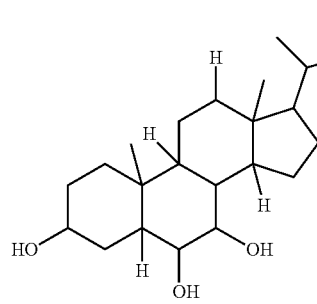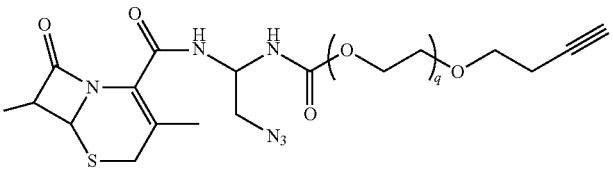

-continued
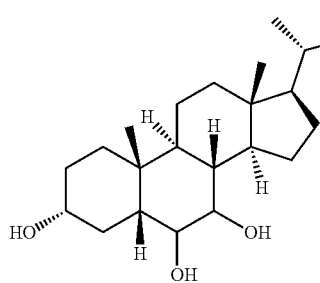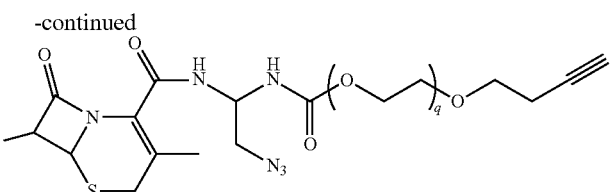
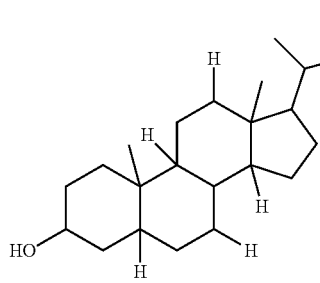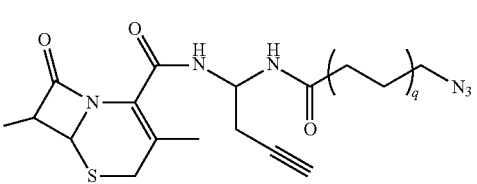
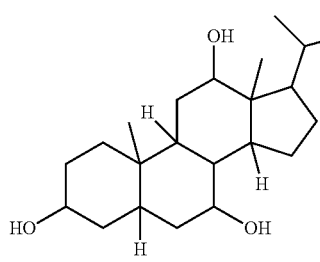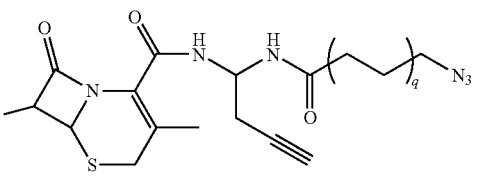
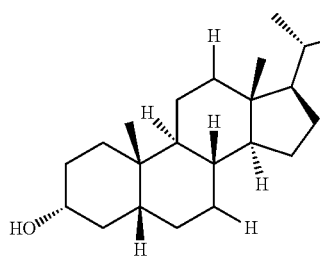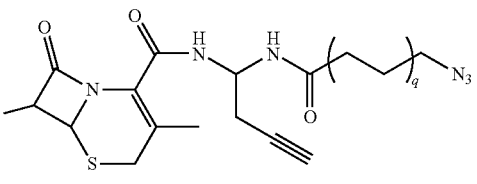
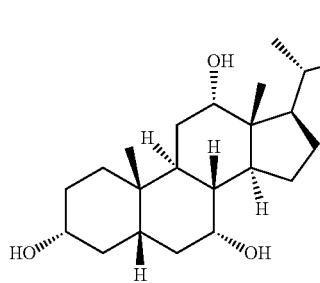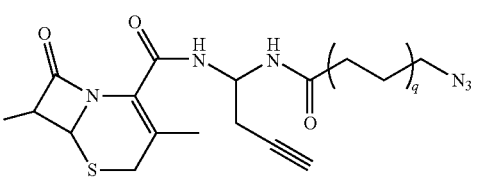

-continued
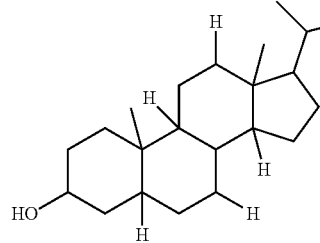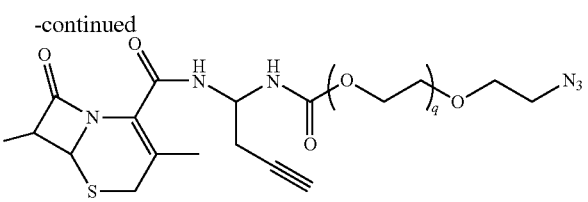
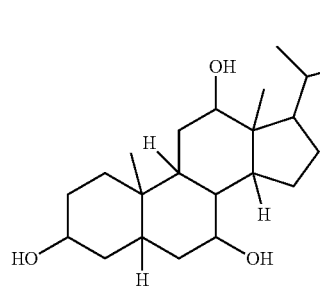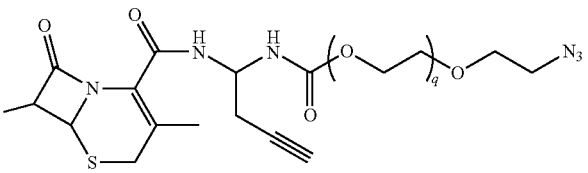
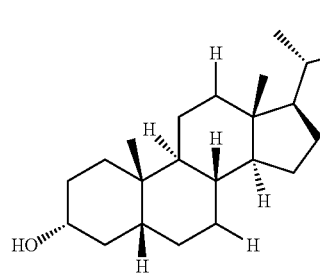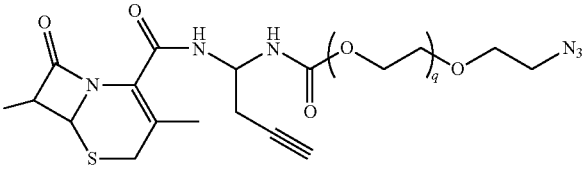
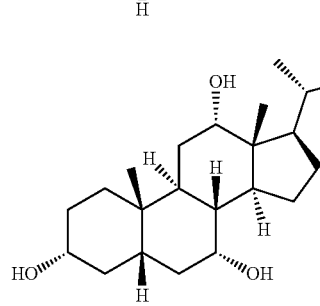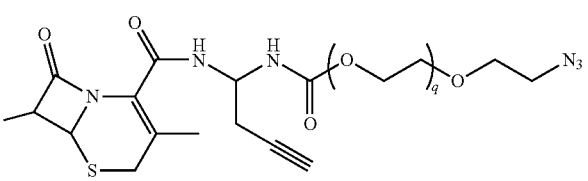
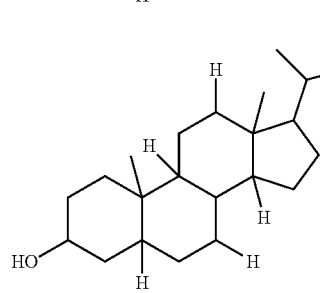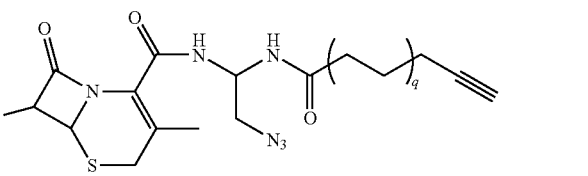
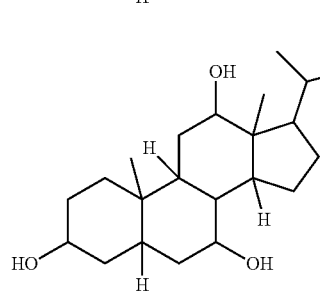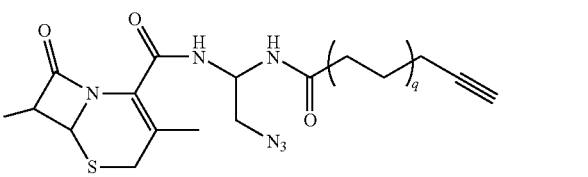

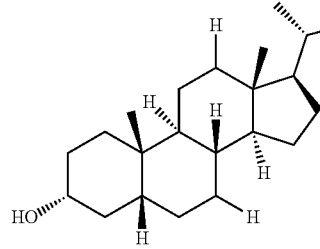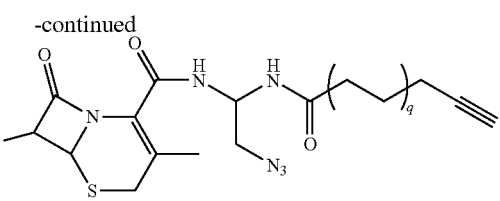
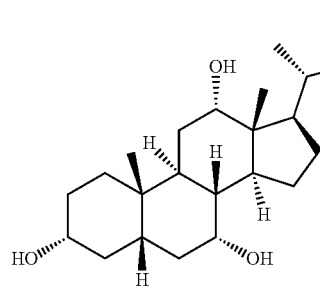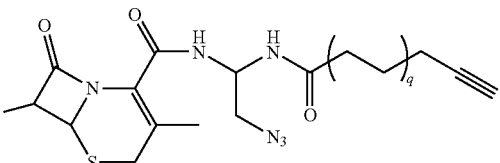
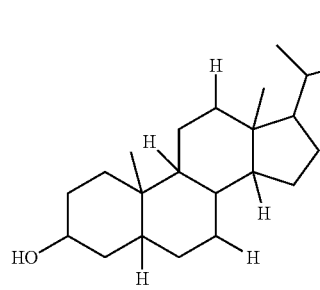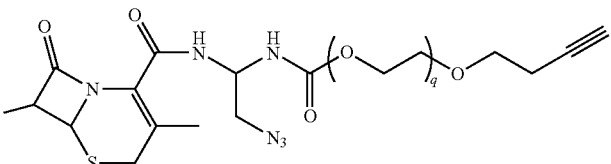
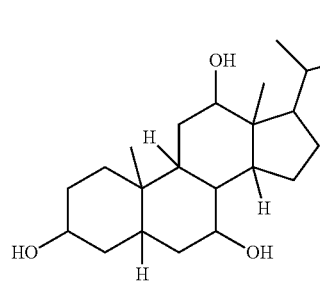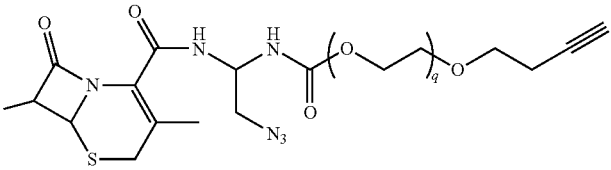
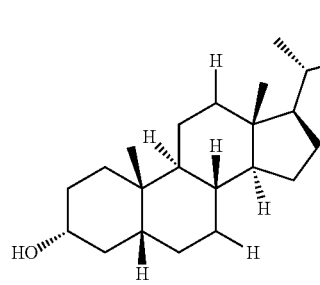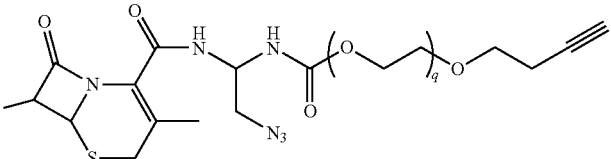
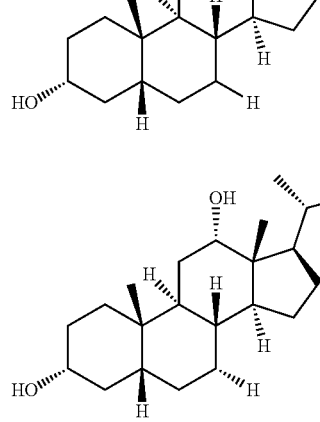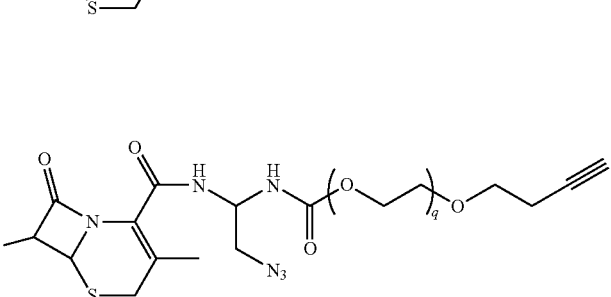

-continued
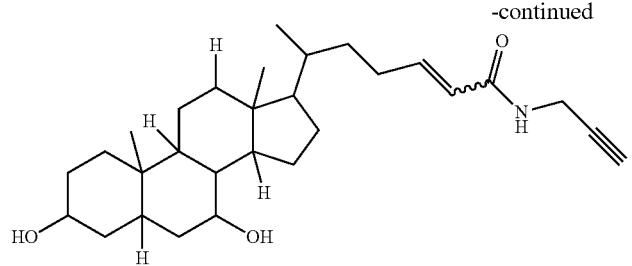
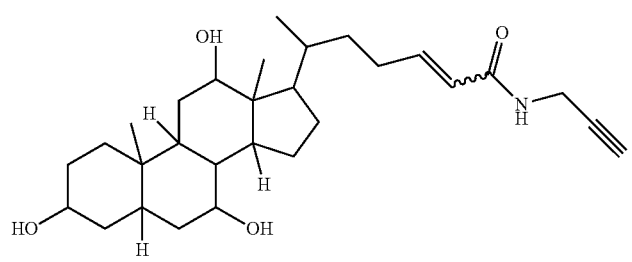
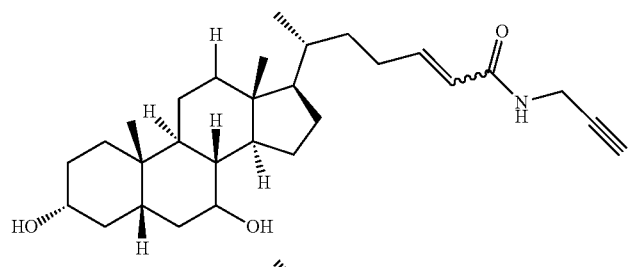
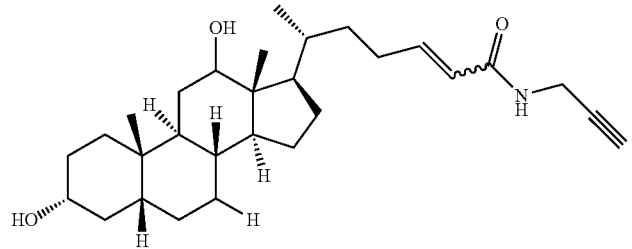
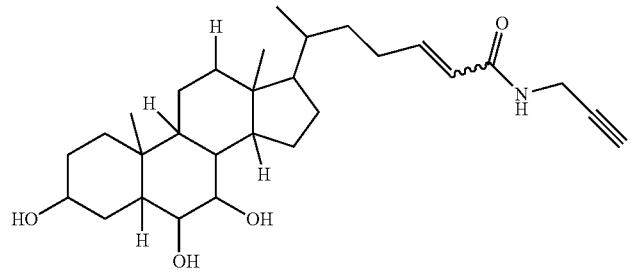
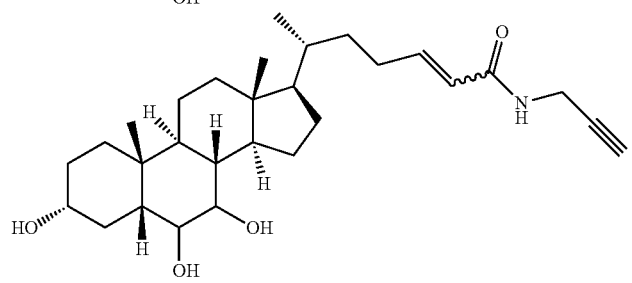

-continued
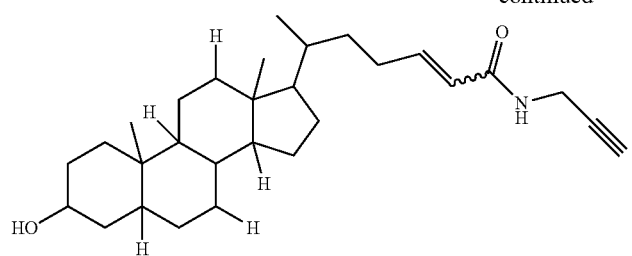
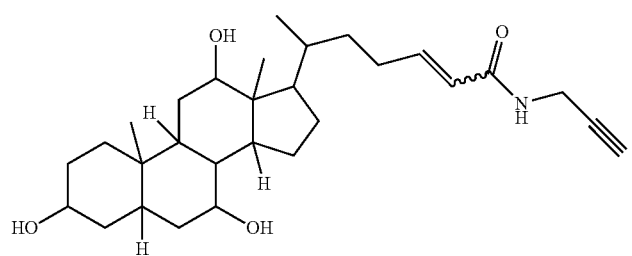
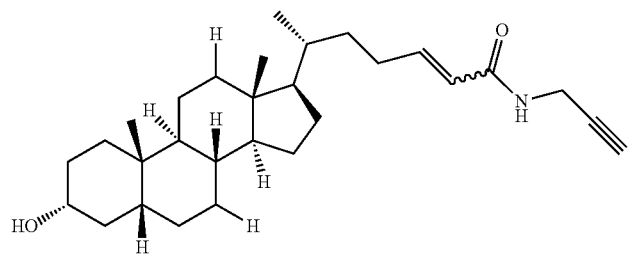
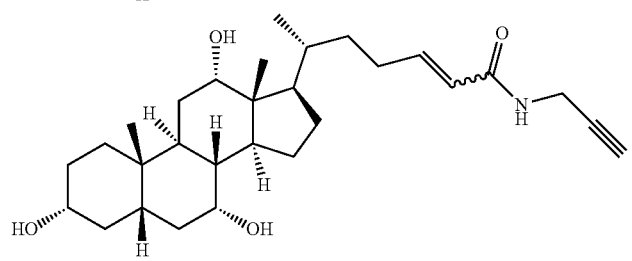
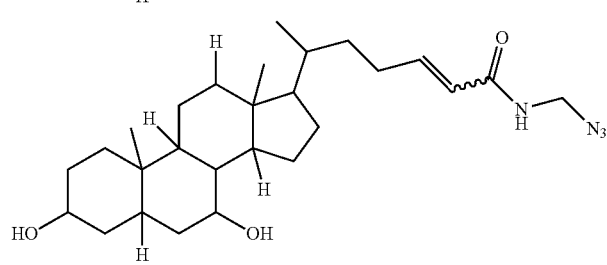
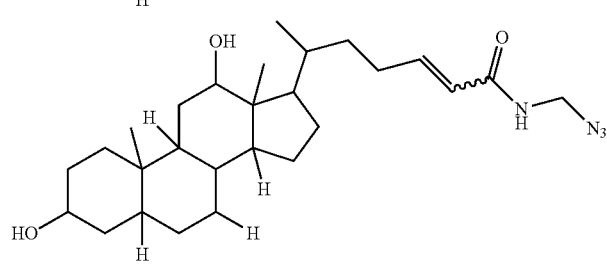

-continued
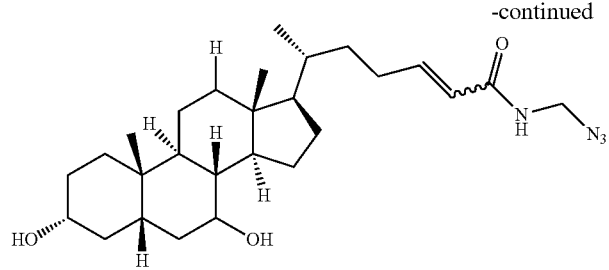
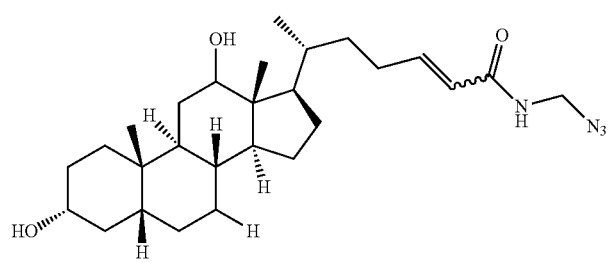
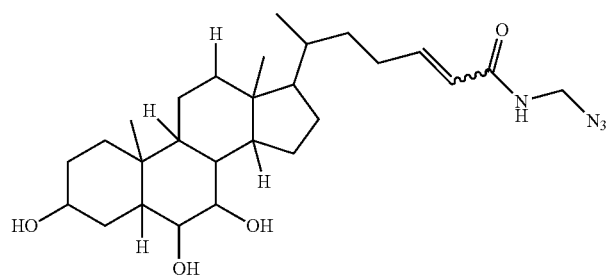
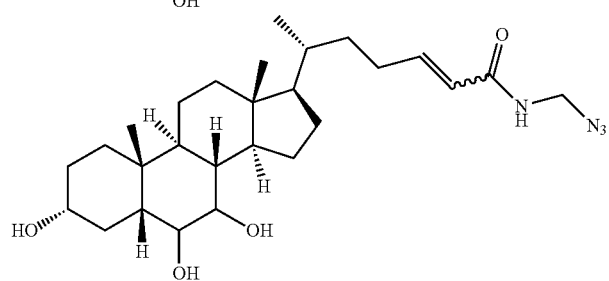
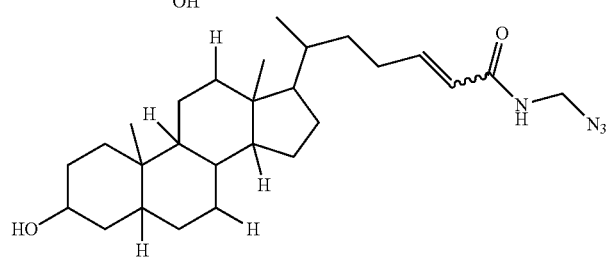
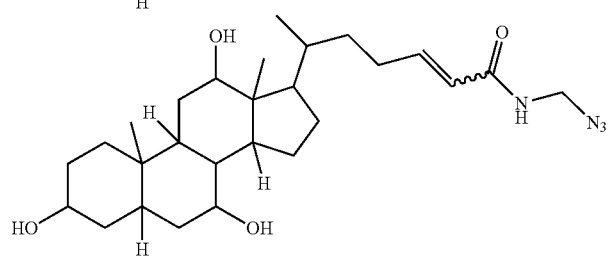

-continued
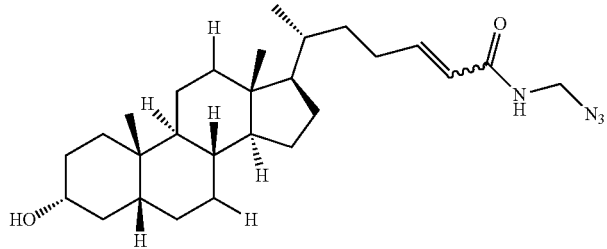
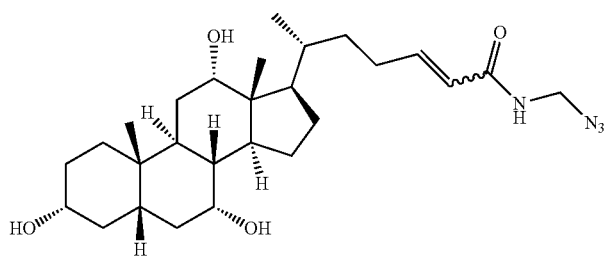
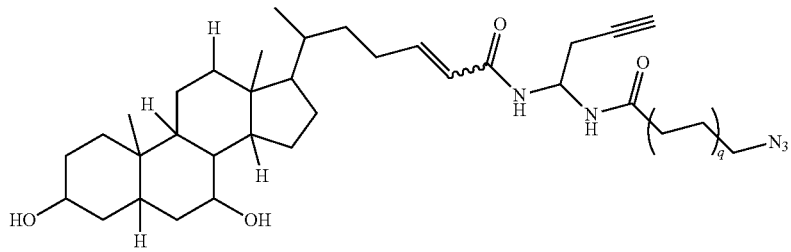
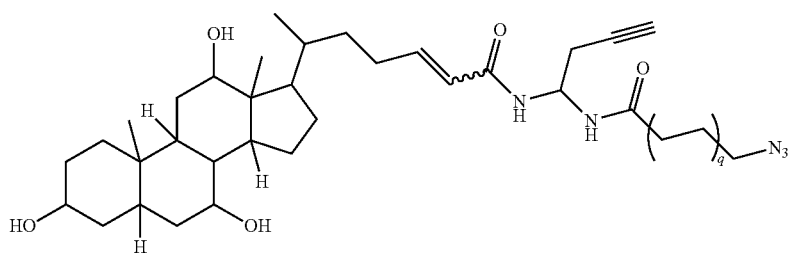
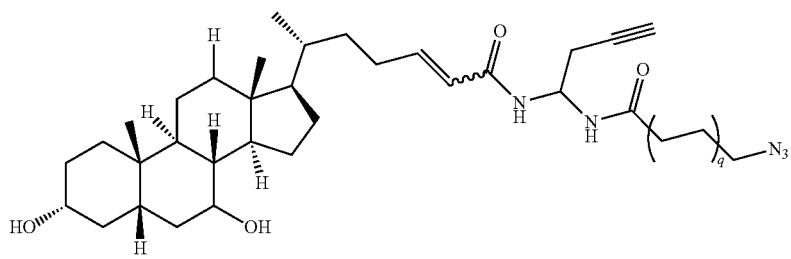
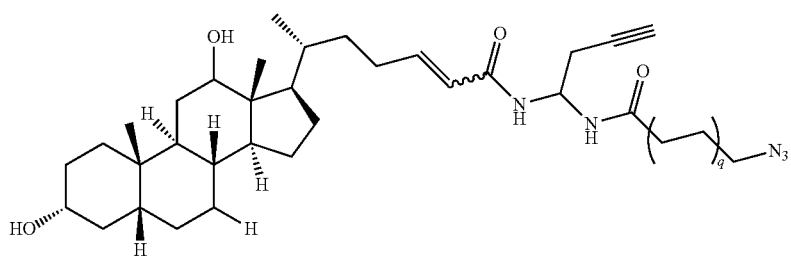

-continued
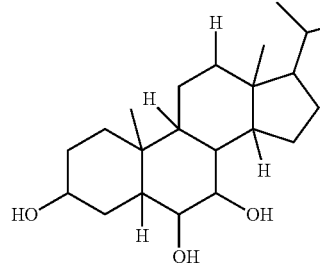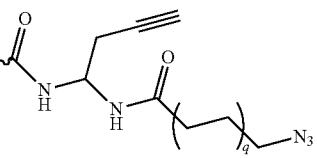
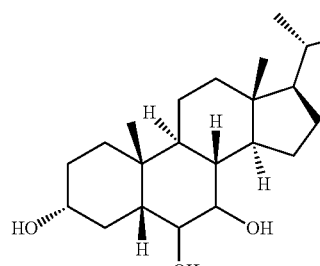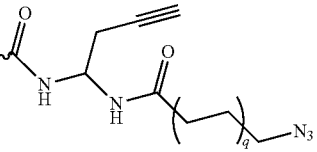
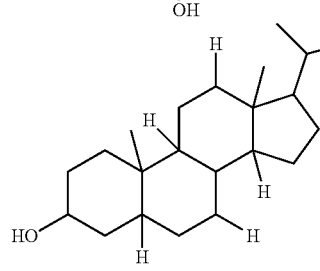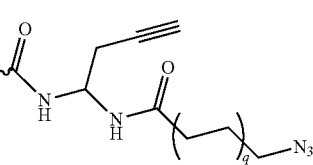
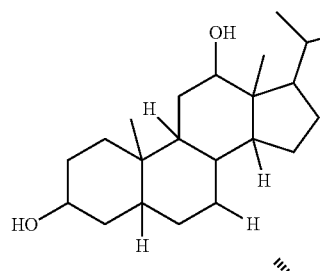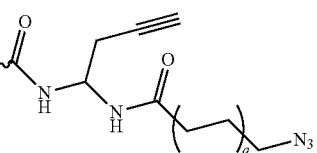
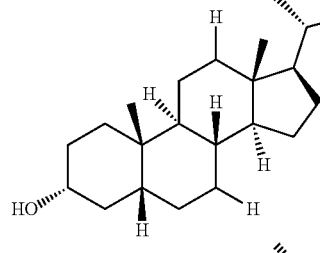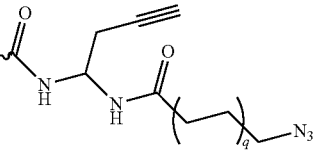
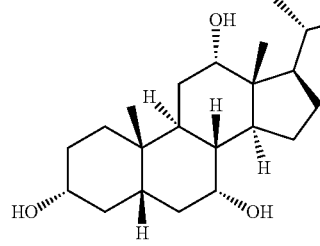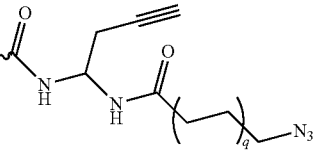

-continued
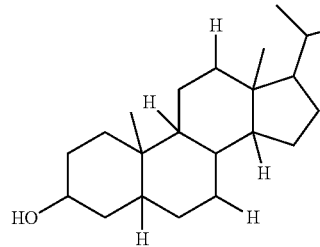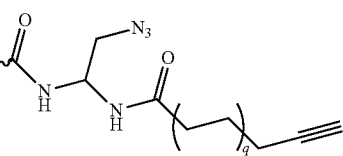
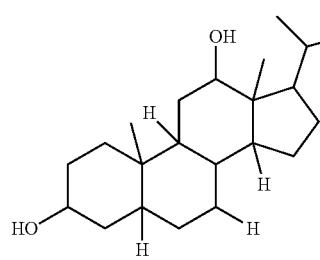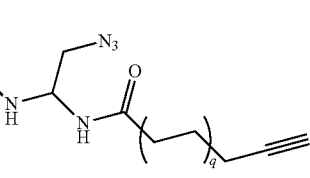
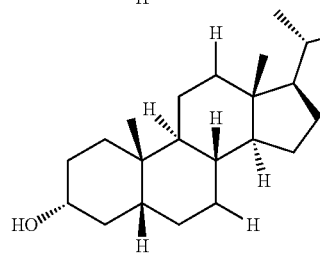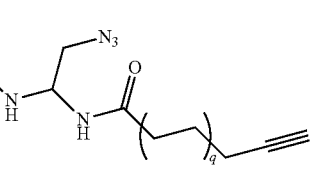
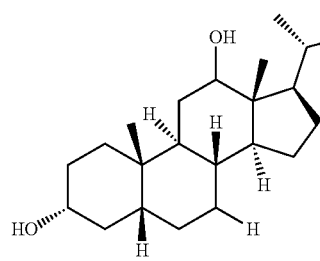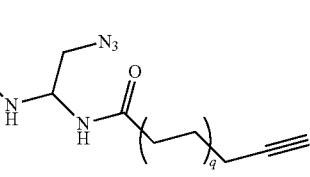
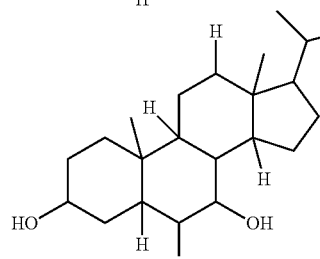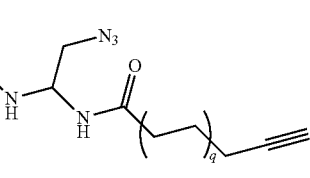
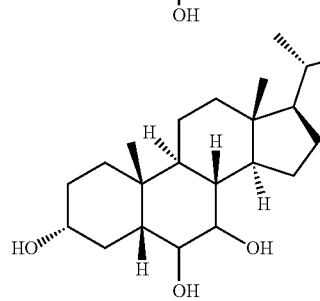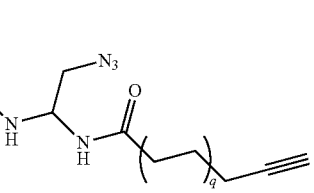

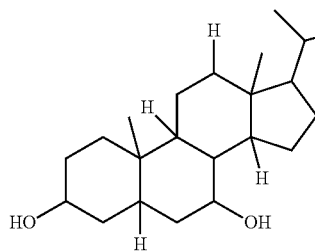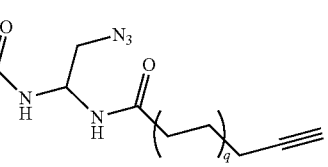
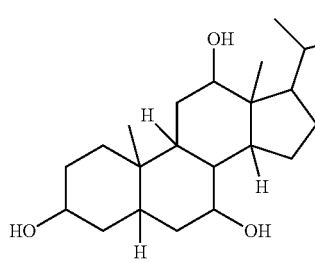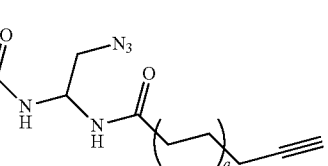
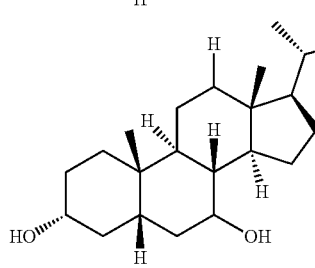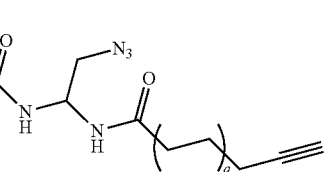
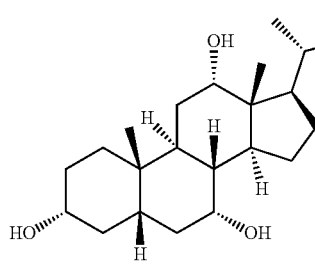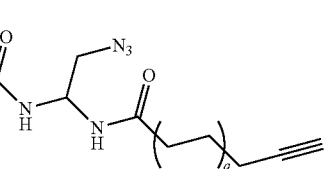
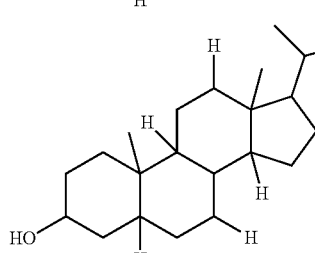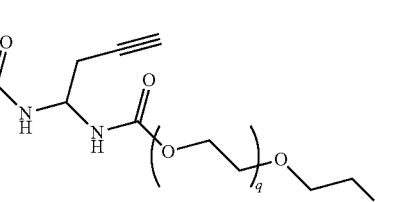
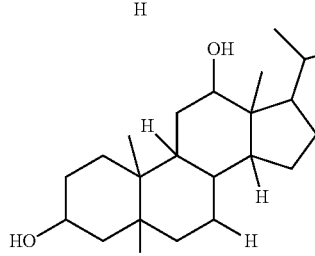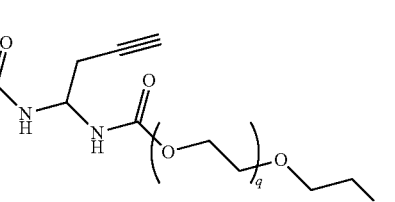

-continued
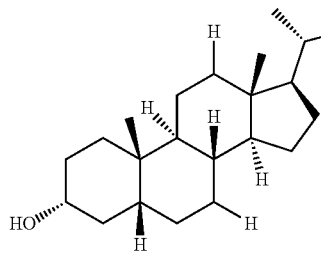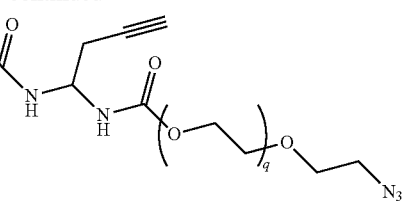
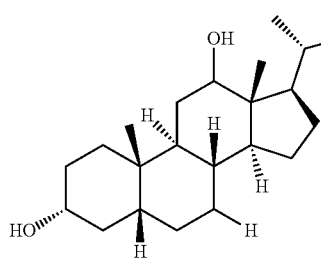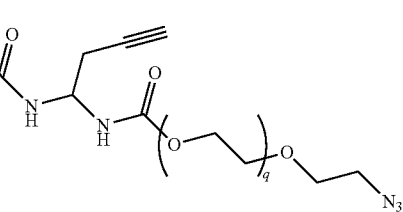
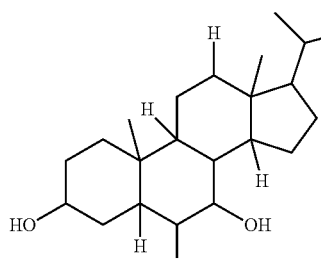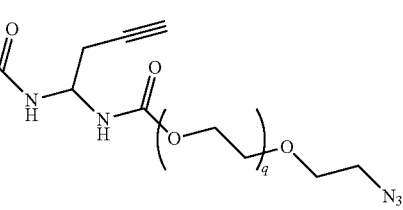
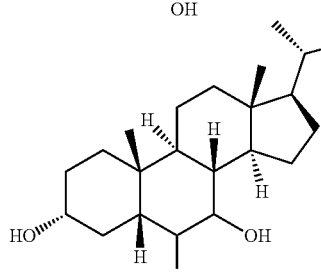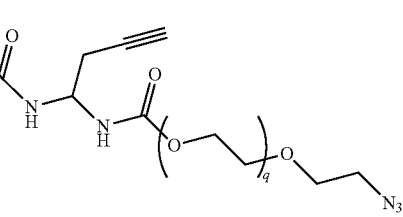
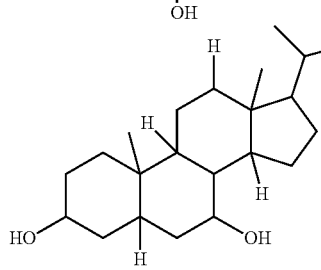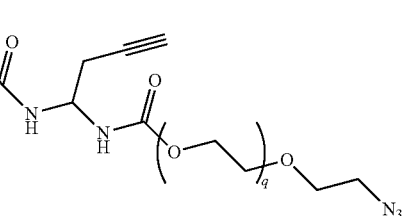
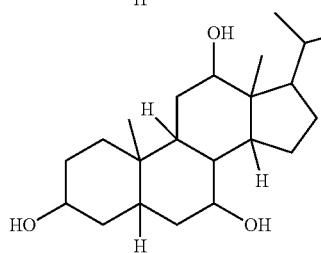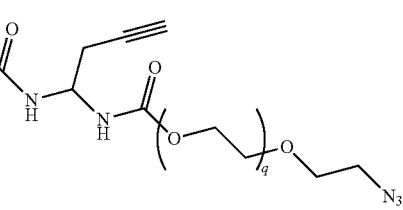

-continued
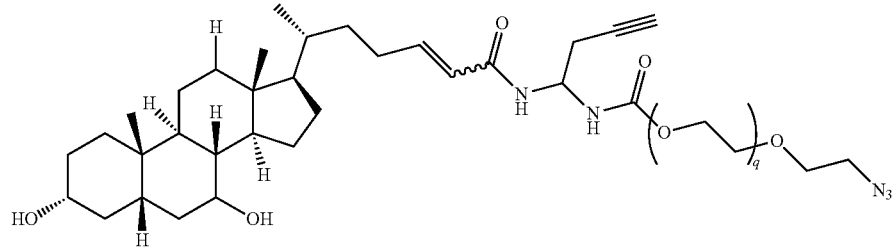
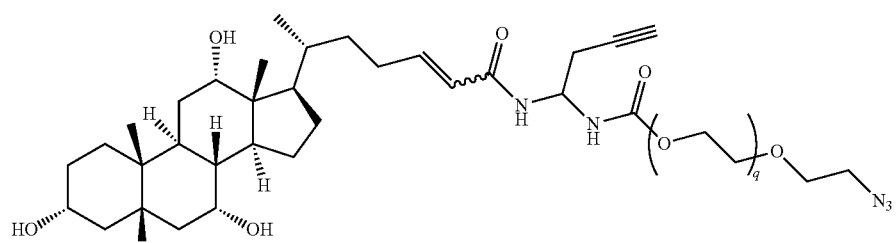
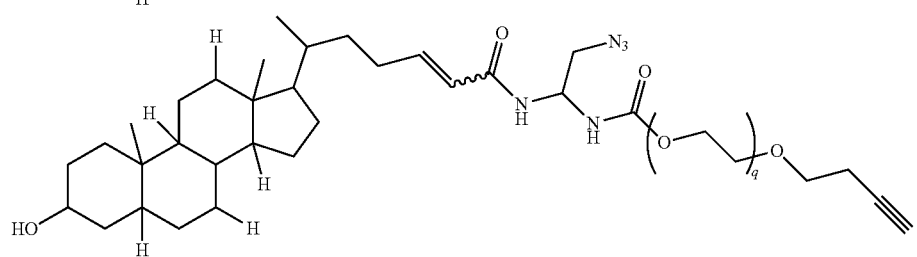
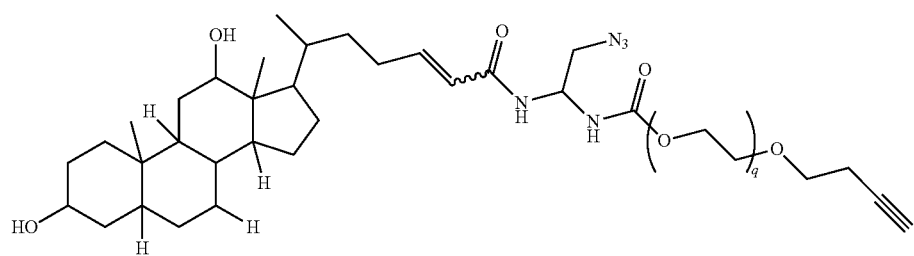
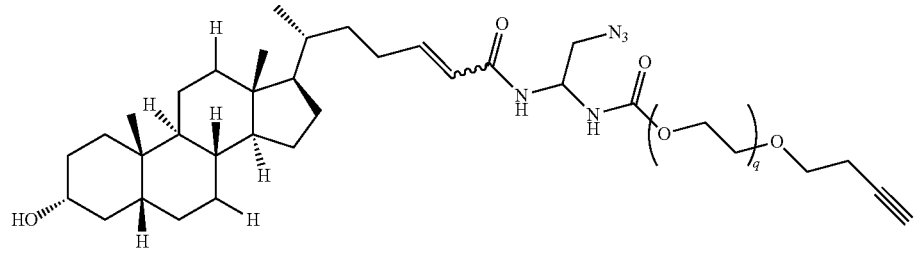
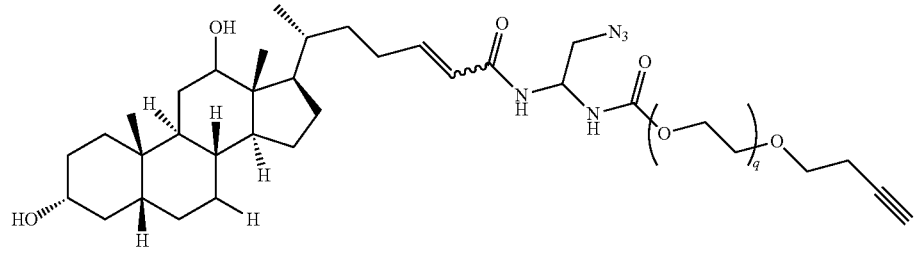

-continued
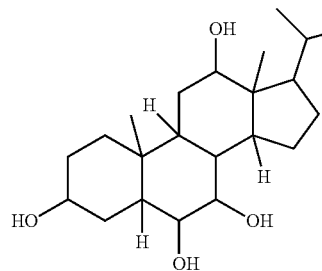
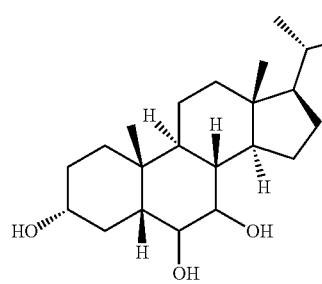
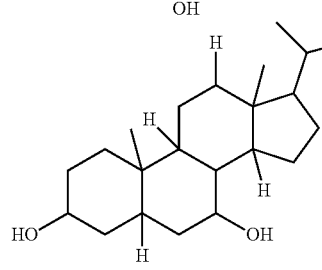
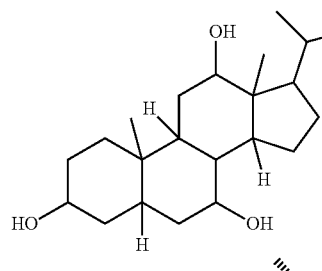
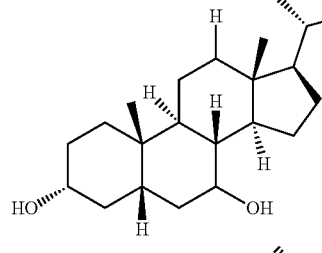
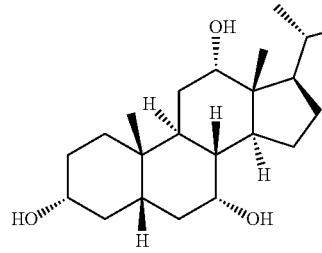

-continued
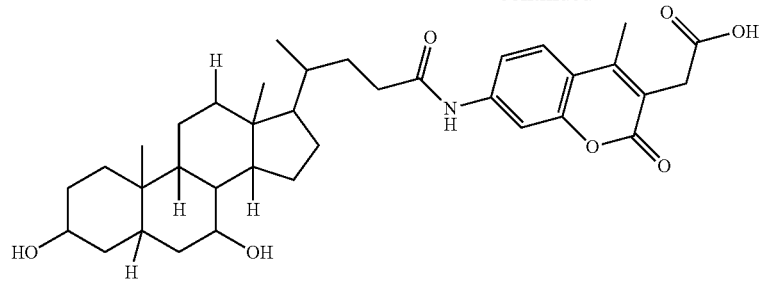
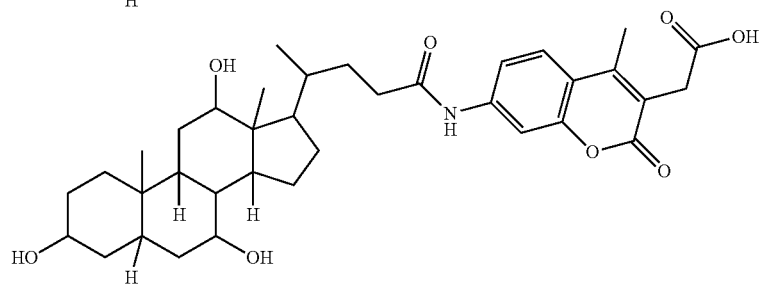
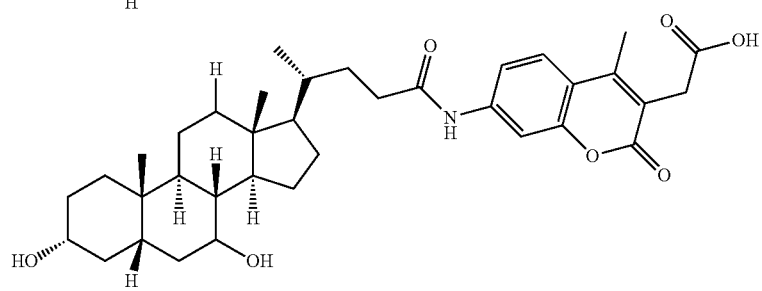
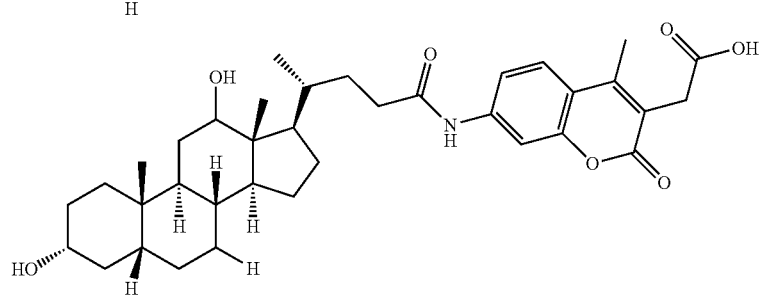
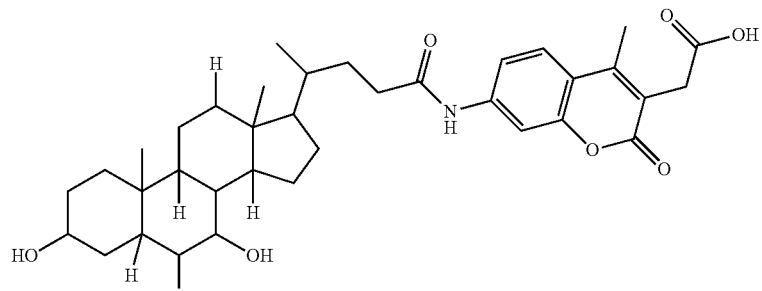
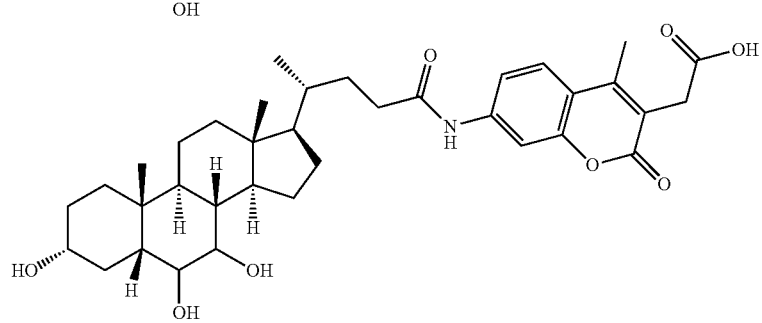

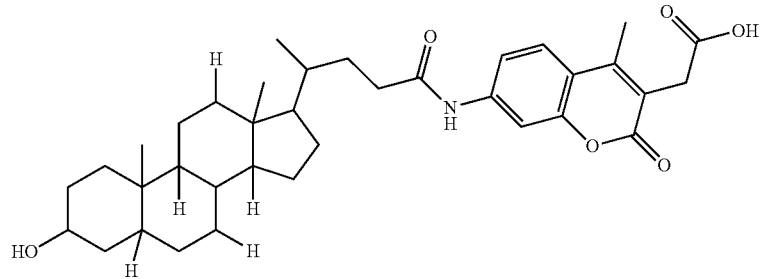
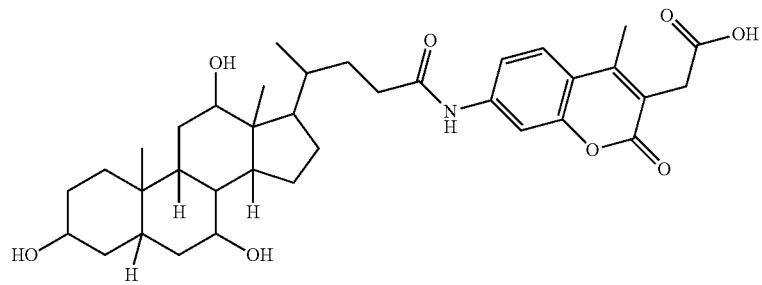
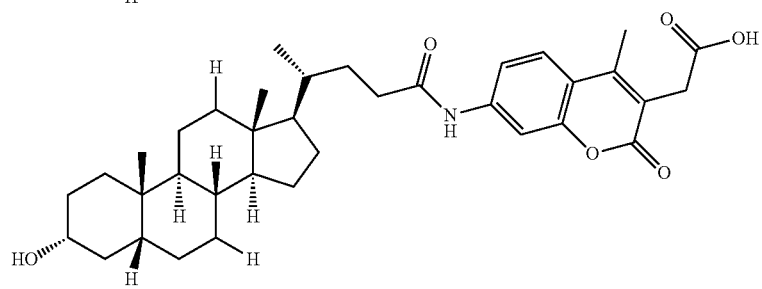
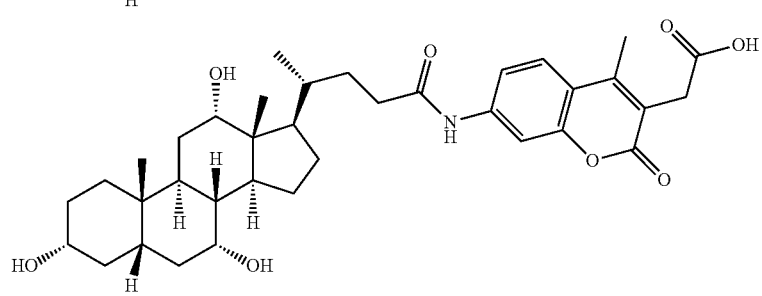
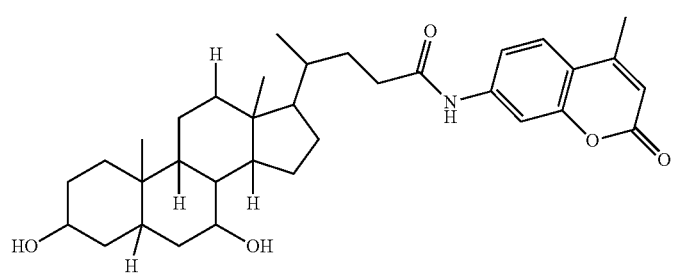
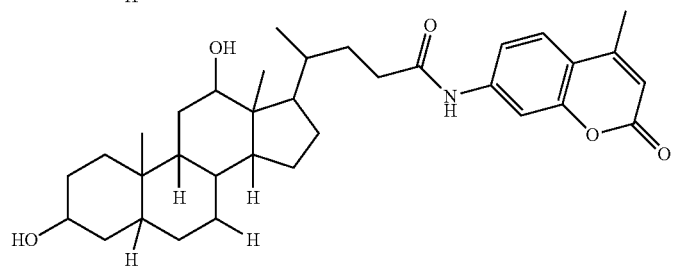

-continued
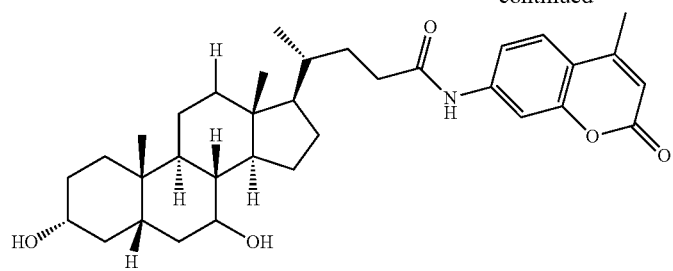
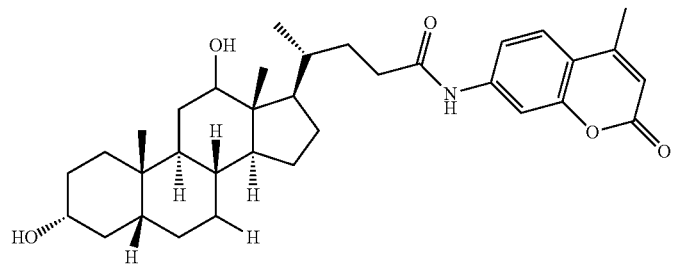
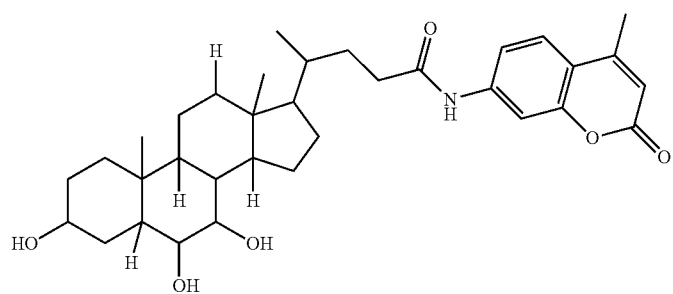
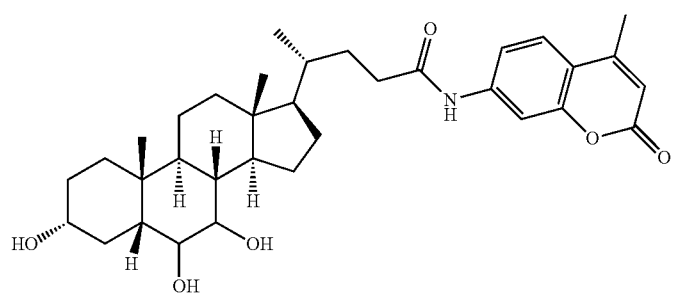
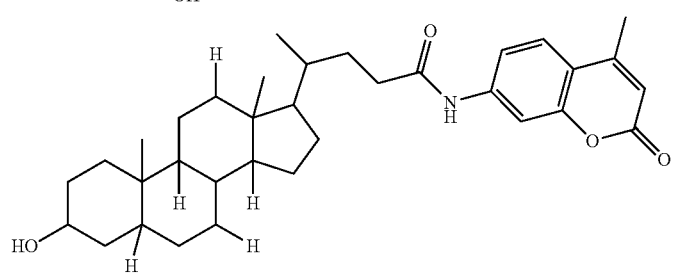
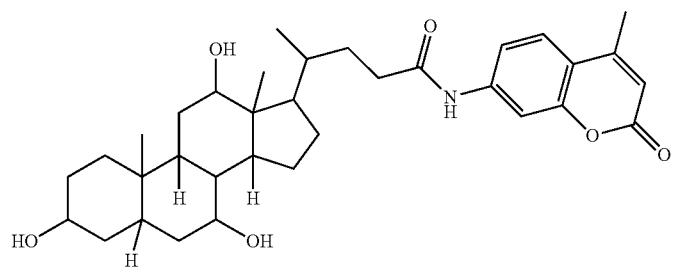

-continued
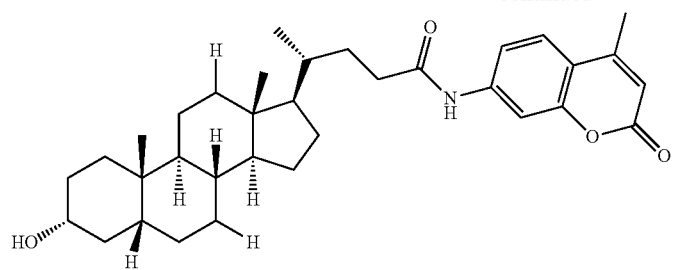
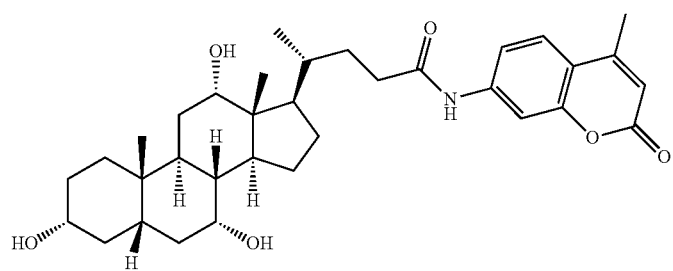
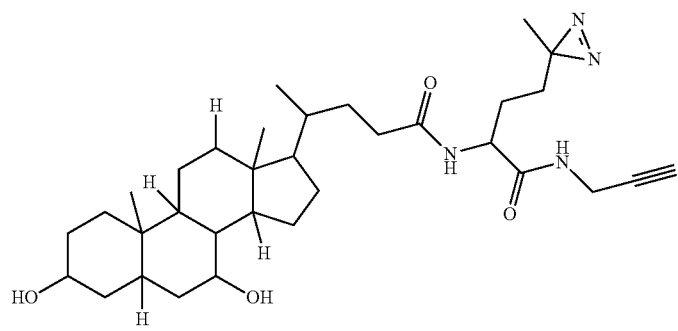
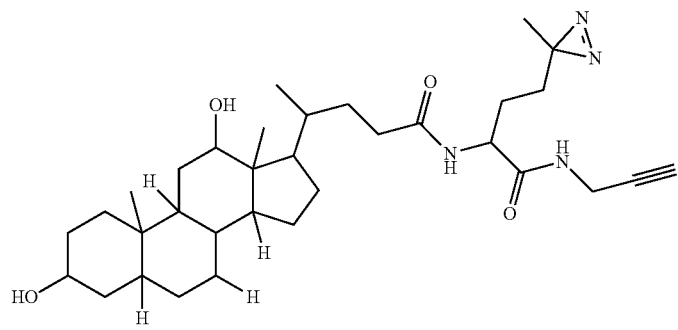
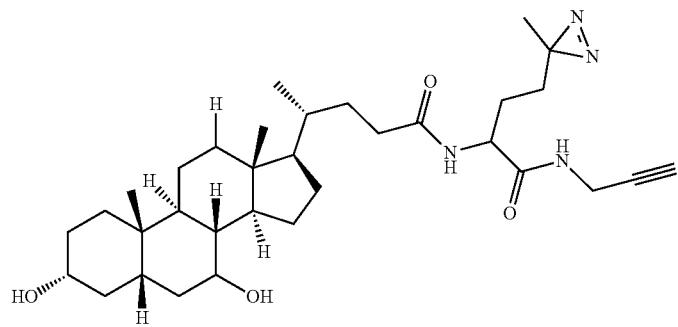

-continued
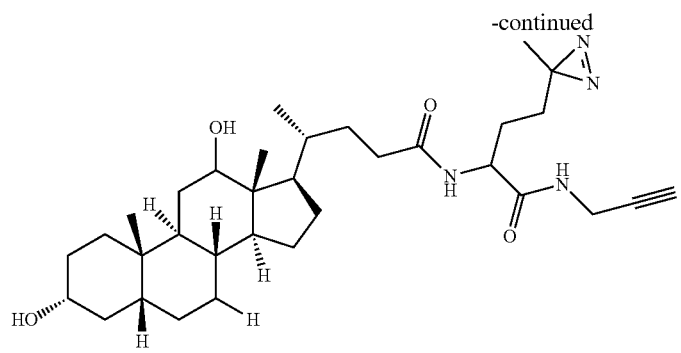
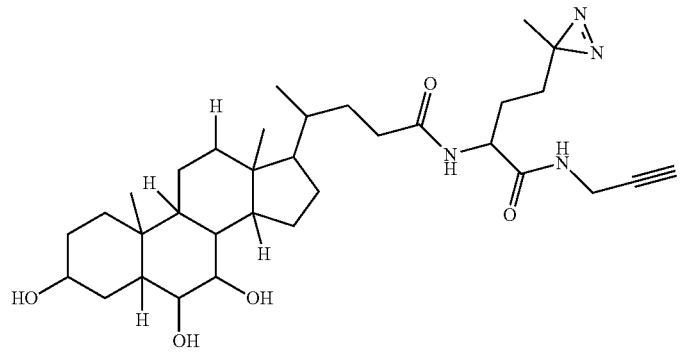
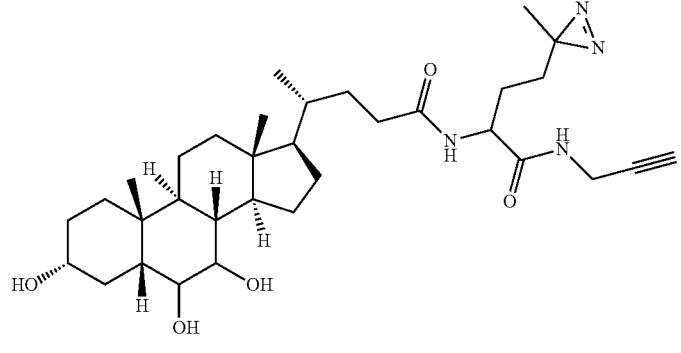
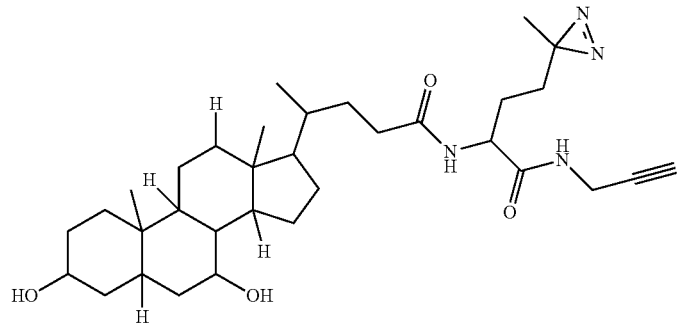
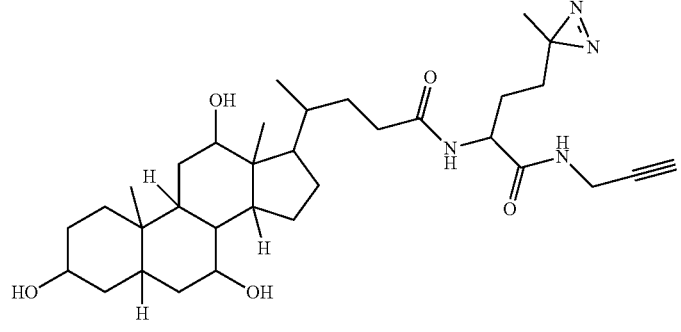

-continued
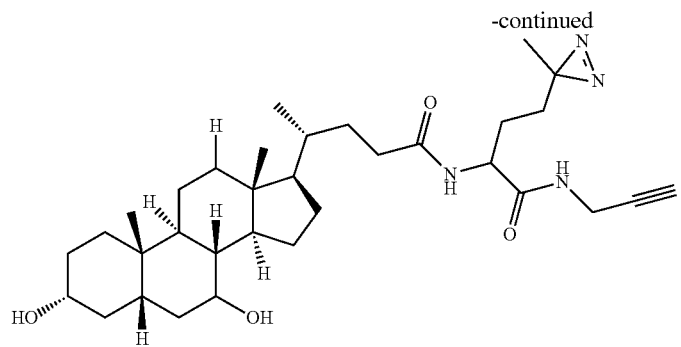
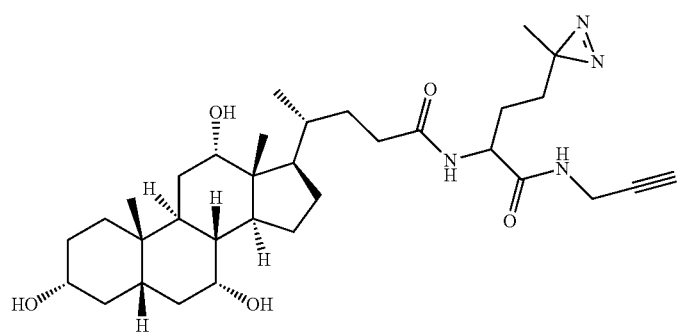
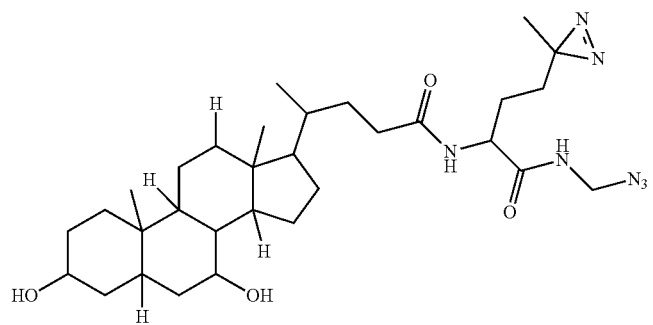
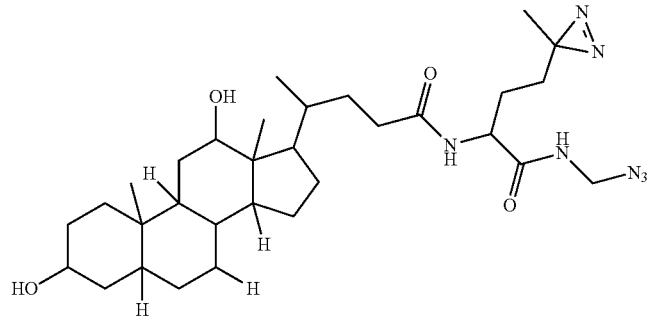
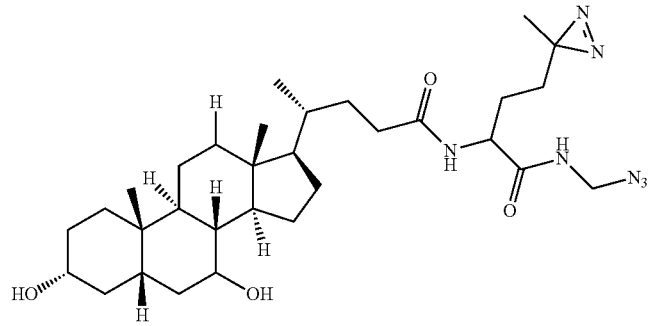

-continued
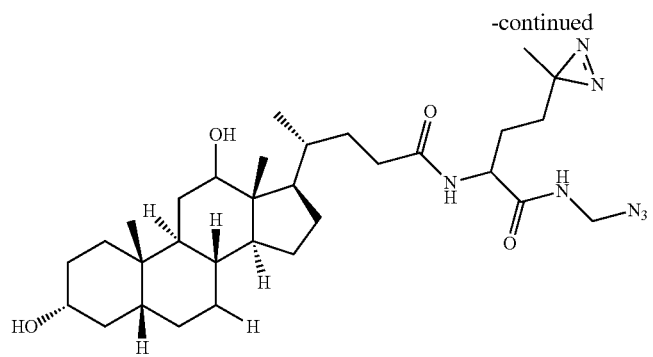
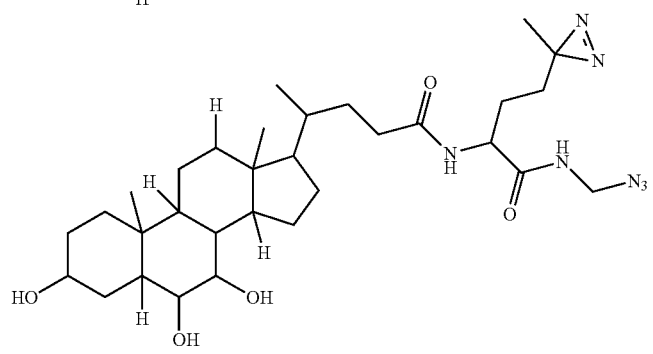
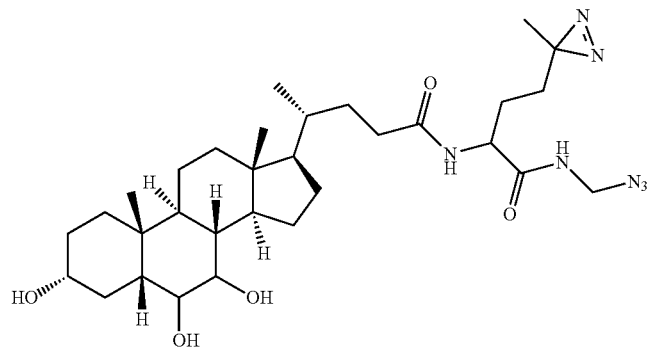
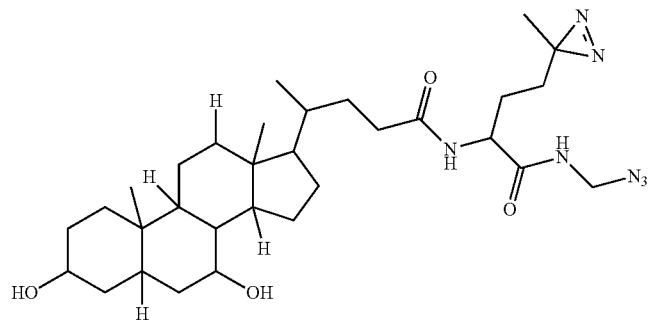
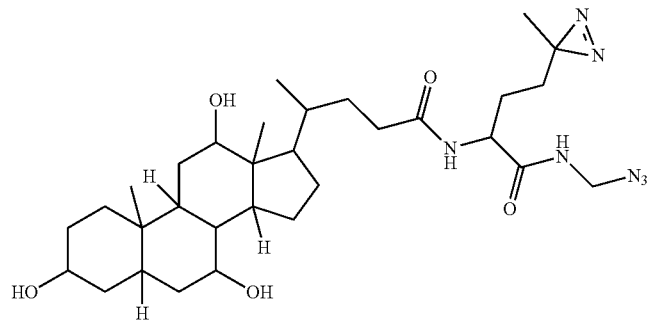

-continued

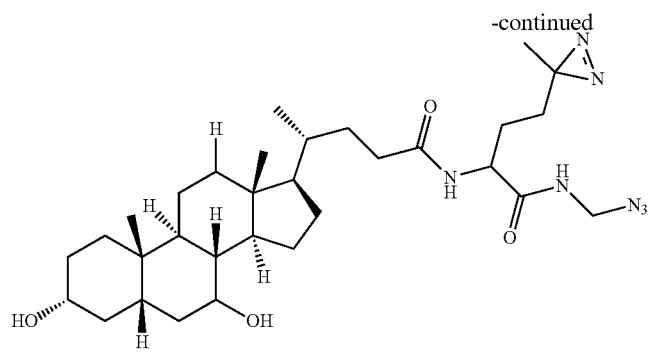

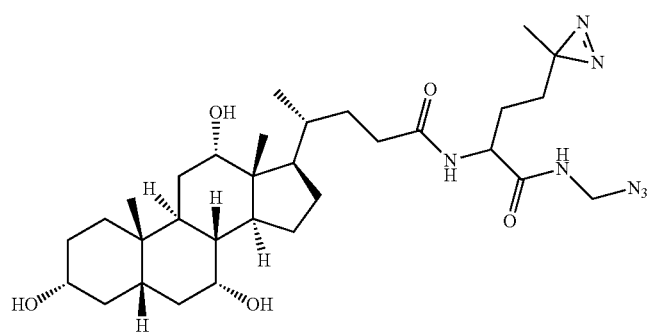

With reference to the above-illustrated species, the stereochemistry of any hydroxyl groups of the sterol moiety can be as defined in the structure. Where stereochemistry is not indicated for a particular hydroxyl group of the sterol moiety, each enantiomer is contemplated and thus any resulting diastereomeric products also are contemplated. For example, in embodiments comprising a murine-based sterol group (e.g., a muricholic sterol group), the α-muricholic, β-muricholic, γ-muricholic, and ω-muricholic sterol moieties are all contemplated. Additionally, any species illustrated above having a wavy bond (i.e., ⁓ ) connecting a double bond to a carbonyl group is intended to encompass the Z product, the E product, or, in some embodiments, a mixture of E and Z products.

The probes described herein can be used in composition embodiments, kit embodiments, and device embodiments described herein. In particular embodiments, the probe can be provided as a composition, which can comprise one or more probe embodiments and a pharmaceutically acceptable carrier, such as a pH-buffering agent. In some embodiments, the composition can further comprise a DM group that comprises a clickable functional group capable of reacting with a pDM group present on the probe. In some additional embodiments, the composition can further comprise click chemistry reagents, such as CuI, a base (e.g., triethylamine, diisopropylethylamine) and a solvent (e.g., DMSO); or a phosphine compound (e.g., tris(2-carboxyethyl) phosphine), a ligand (e.g., a copper-binding ligand known in the art), and a copper-containing compound (e.g., $CuSO_4$). Additional composition embodiments are disclosed below.

IV. Methods of Making Probe Embodiments

Methods of making the probe embodiments above are disclosed herein. In particular disclosed embodiments, a probe having a structure satisfying Formula I can be made according to embodiments of the method illustrated in Scheme 1. With reference to Scheme 1, a sterol-containing starting material, such as compound 100, can be converted to a probe having a structure satisfying Formula I (compound 104) using an amide bond forming step. In this step, the carboxylic acid moiety of compound 100 can be coupled with an amine-containing compound comprising various components of the probe (e.g., a DM group, a pDM group, a PM group, and/or an AM group), such as amine 102. Amide bond forming conditions recognizable to those of ordinary skill in the art with the benefit of the present disclosure can be used (for example, using a base and an amide forming coupling reagent, like HOBt, DCC, HATU, TBTU, PyBOP, or the like). Such methods can be used to make probes having structures that also satisfy Formula IIB.

In additional embodiments, sterol-containing compound 100 can be converted to other probe embodiments satisfying Formula IIA, as also illustrated in Scheme 1. In such embodiments, the sterol-containing compound 100 can be exposed to different functionalization steps, including (but not limited to) a methylation step, a protection step, a reduction step, and oxidation step, and any combination thereof, to thereby provide aldehyde 106. Reagents sufficient to perform such steps are readily recognizable to those of ordinary skill in the art with the benefit of the present disclosure; however, representative reagents are provided as examples in Scheme 2. In some embodiments, aldehyde 106 can be condensed with a diacid compound, such as malonic acid, using a base (e.g., piperidine, pyridine, or a combination thereof) to provide α,β-unsaturated acid compound 108. α,β-unsaturated acid compound 108 can then undergo an amide bond forming step similar to that described above for making compound 104 to thereby provide probe 110.

Scheme 1
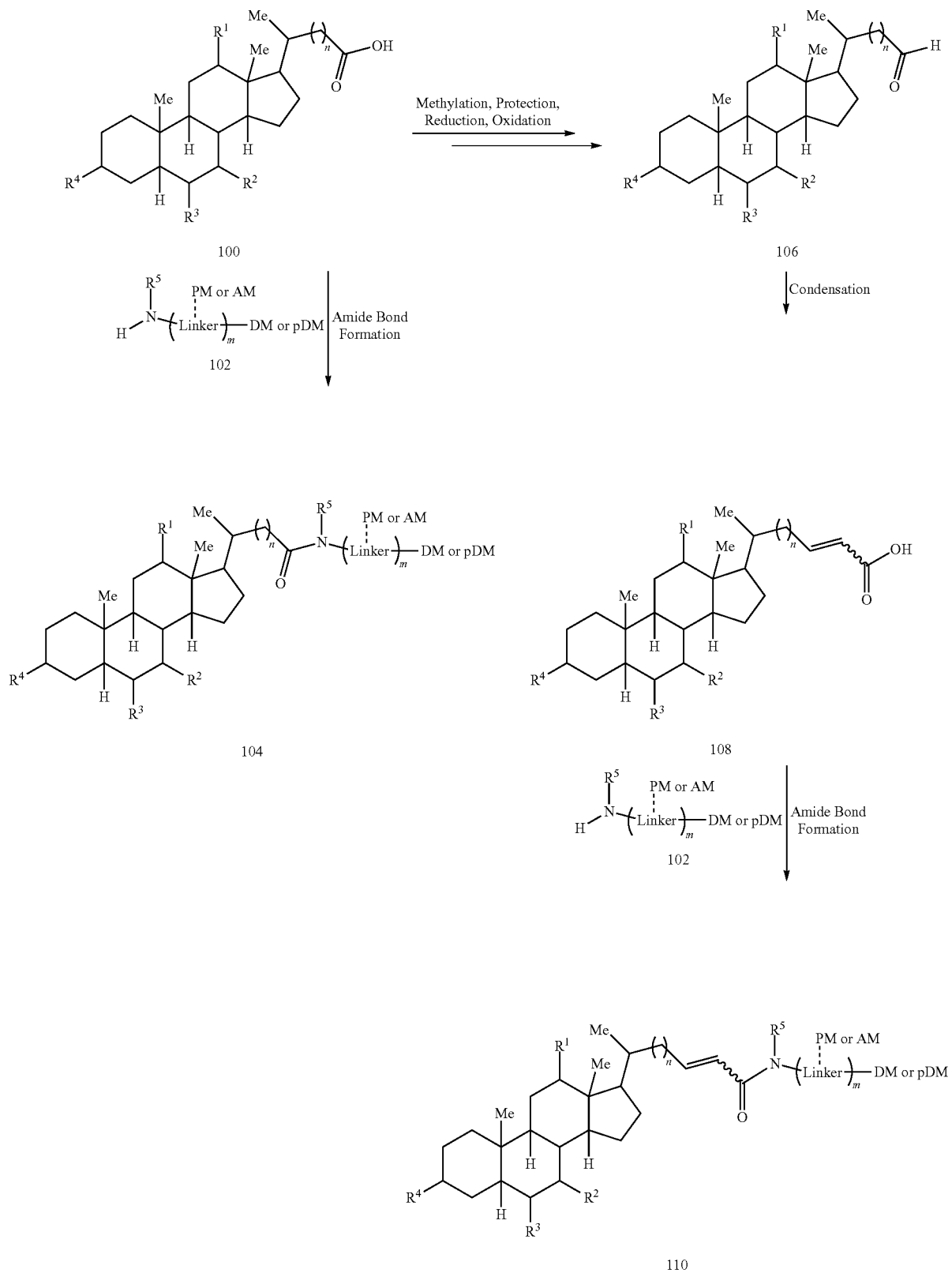

A representative method for making probe embodiments having structures satisfying any one or more of Formulas I, IA-ID, IIA, or IIIB is provided below in Scheme 2.
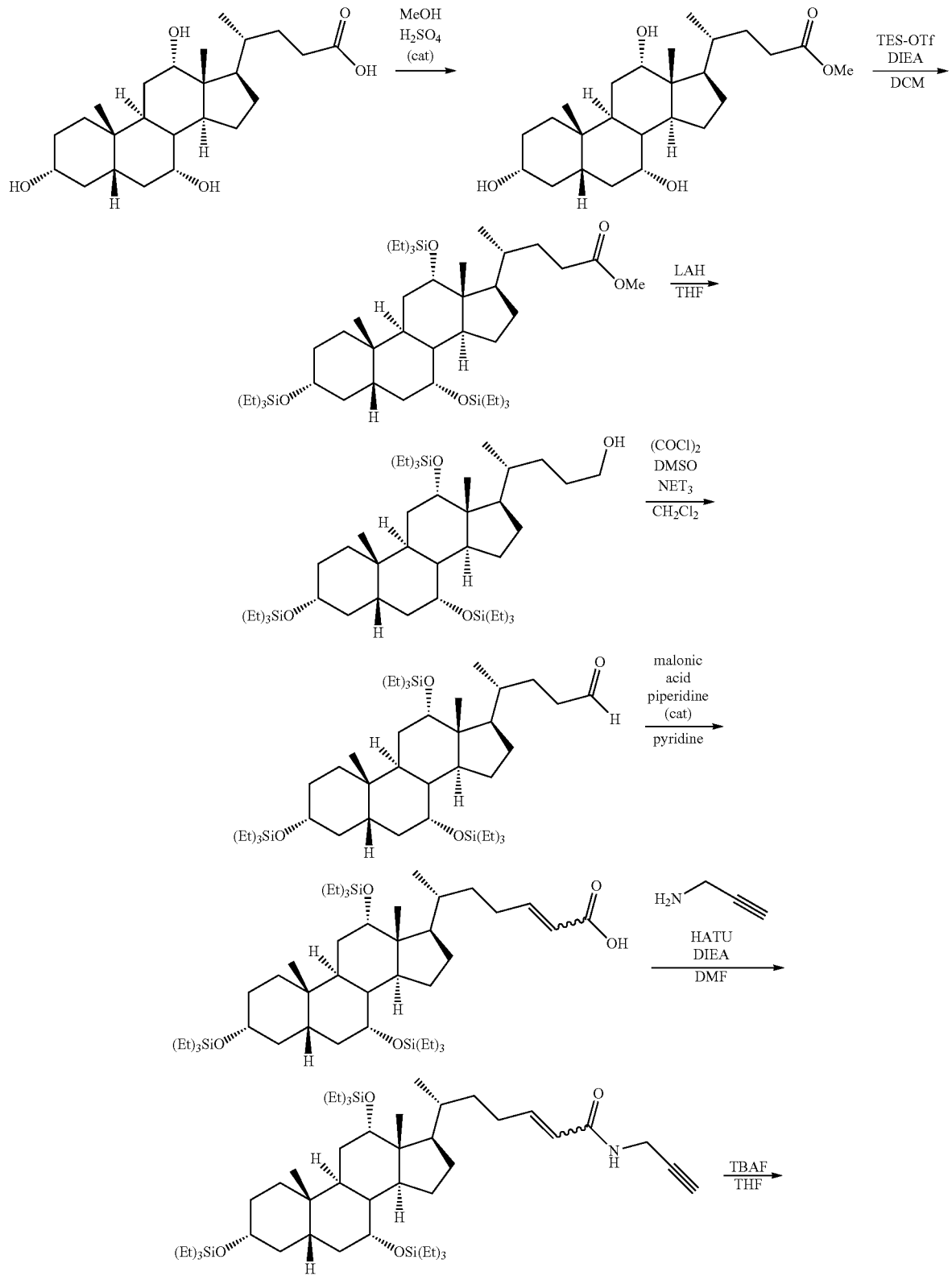
Scheme 2

-continued
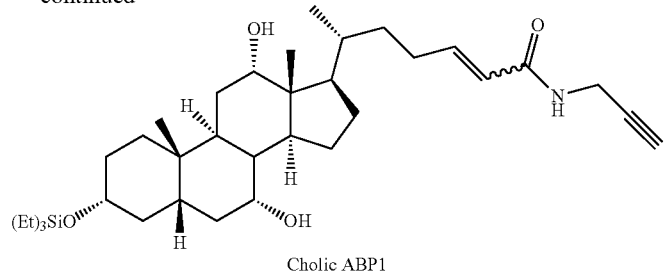
Cholic ABP1
A representative method for making probe embodiments having structures satisfying any one or more of Formulas I, IA-ID, IIA, and IIID-IIIF is provided below in Scheme 3.
Scheme 3
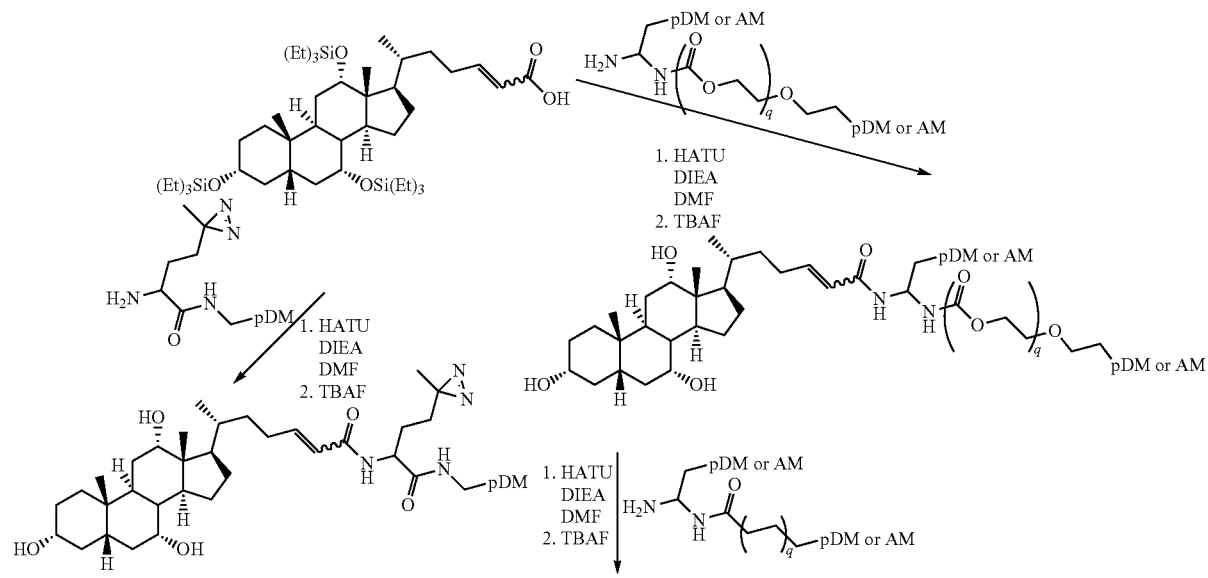
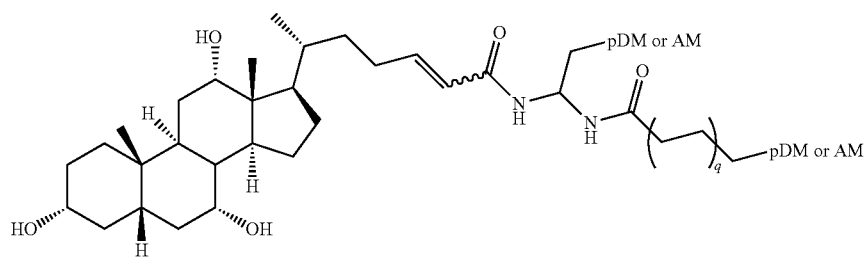

Additional probe embodiments, such as probes having structures satisfying any one or more of Formulas I, IA-ID, IIB, and IIIC, can be made using the representative method illustrated below in Scheme 4.

Scheme 4

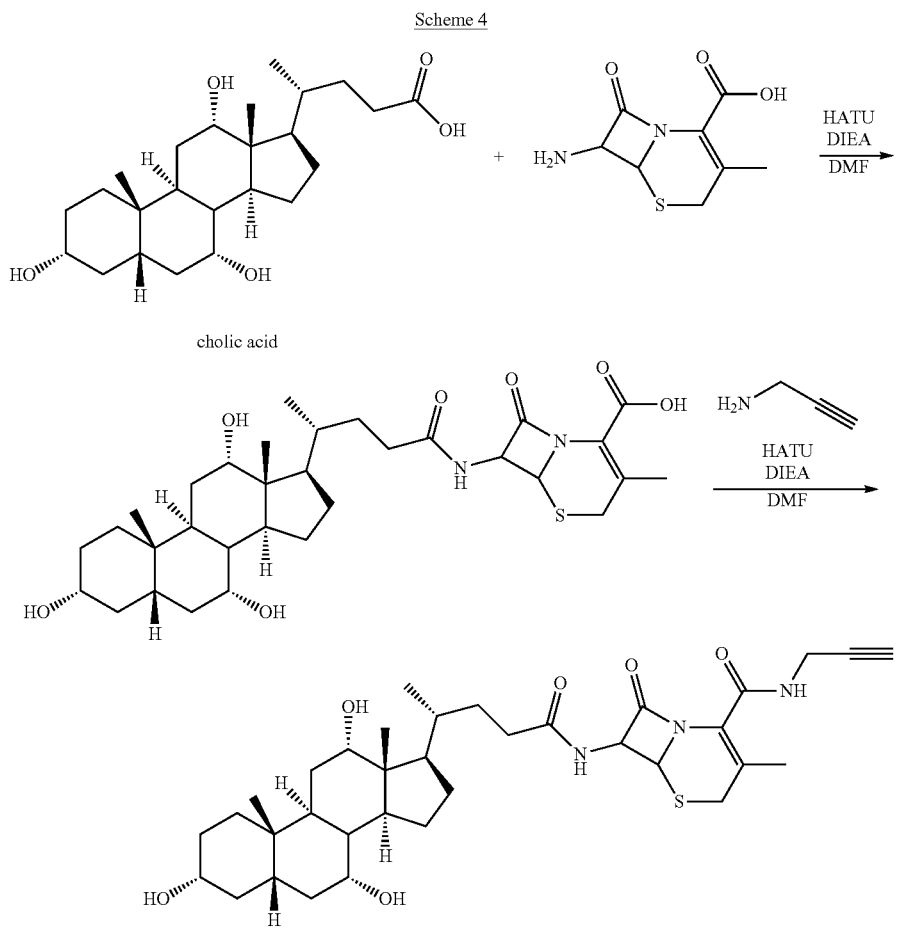

Additional probe embodiments, such as probes having structures satisfying any one or more of Formulas I, IA-ID, IIB, and IIIA can be made using the representative method illustrated below in Schemes 5 and 6.

Scheme 5

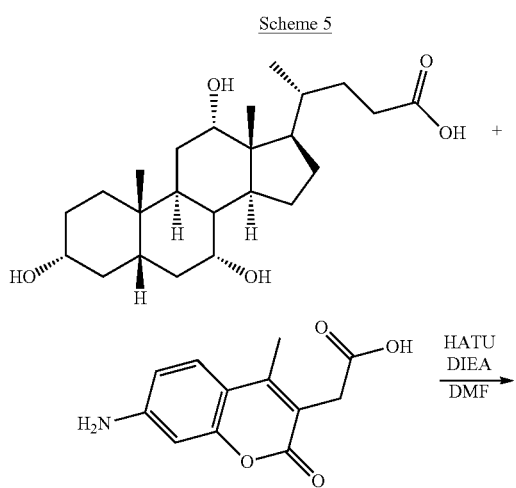

-continued

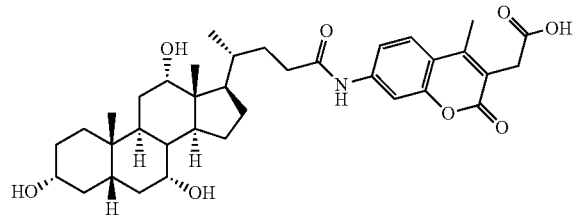

CA-AMCA

Scheme 6

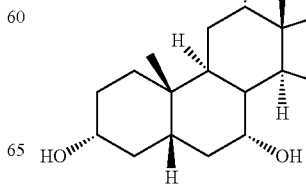

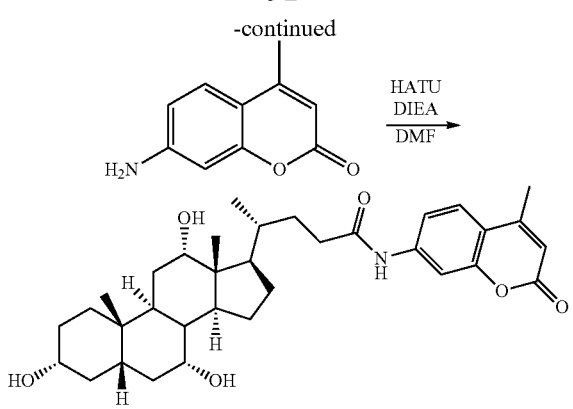

V. Device and Kit Embodiments

Probe embodiments described herein also can be configured for use in a device and/or a kit that can be used to analyze samples, such as biological samples. The device and kit can be used to assess and identify different species present in a biological sample and also to assess the functions/processes involving such species within the sample. In particular disclosed embodiments, the device can comprise one or more probe embodiments and a substrate, wherein the probe is (or a plurality of probes are) coupled to the substrate prior to exposure to a biological sample, or wherein the substrate and the probe are capable of being combined after exposure to a biological sample. The device and kit embodiments can be used to evaluate a plurality of biological samples and also can be used in a multiplexing context.

In particular embodiments, the substrate component of the device is any suitable substrate that be exposed to a biological sample. Representative substrates include, but are not limited to, glass-based substrates that can be functionalized with probe embodiments described herein such that the probe is coupled to functional groups present on the surface of the glass-based substrate. In some embodiments, glass plates, glass rods, and/or glass microspheres are used as the substrate component.

The probes used in the device and/or kit can be selected from any probe embodiments disclosed herein. In some embodiments, the probes comprise or are modified to comprise a bi-functional linker group comprising an anchor moiety that is capable of anchoring the probe to a substrate component of the device. In particular disclosed embodiments, the anchor moiety is a clickable functional group that can be reacted with a clickable functional group present on the substrate surface using a click chemistry reaction to thereby covalently anchor the probe to the substrate. In some embodiments, the probe can be pre-coupled to the substrate prior to sample exposure using such techniques. In some additional embodiments, the probe can be post-coupled to the substrate using such techniques after the probe has been exposed to a sample. The pre-coupled or post-coupled probe further comprises a pDM group that is converted to a detectable moiety during use of the device or, in some embodiments, the detectable moiety can be pre-installed on the probe.

In some embodiments, the device is pre-assembled such that the probe embodiments are pre-coupled to the substrate and any additional reagents used in analyzing the sample are pre-contained within the device. In some other embodiments, the device may be provided as part of a kit that comprises a pre-assembled device and any additional reagents used to analyze the sample are provided as separate components of the kit (for example, such as in reagent bottles). These components of the kit can then be combined by the user prior to use. In yet some additional embodiments, the kit can comprise a substrate that can be treated with probe embodiments, which are provided by separate reagent bottles within the kit, using suitable coupling conditions to thereby couple any desired probe embodiments to the substrate to ready the apparatus for use.

Methods of making the device embodiments of the present disclosure are also disclosed. In some embodiments, the device can be made by exposing the substrate to a probe embodiment comprising an anchor moiety, such as a clickable functional group or other functional group capable of chemically binding to functional groups of the substrate. In embodiments where the probe comprises a clickable functional group, the substrate typically also comprises a clickable functional group on its surface that can react with the clickable functional group of the probe. In some embodiments, the substrate is a glass substrate comprising a surface having hydroxyl groups that can be modified with alkoxysilane molecules to provide a silanized substrate surface. In some embodiments, the silanized substrate surface can further be reacted with a reagent comprising a clickable functional group. In particular disclosed embodiments, the anchor moiety of the probe forms a covalent bond with functional groups of the substrate surface (for example, hydroxyl groups, alkoxysilane groups, clickable functional groups, or the like). Exemplary alkoxysilane molecules include, but are not limited to, aminosilanes (for example, (3-aminopropyl)-triethoxysilane, (3-aminopropyl)-diethoxy-methylsilane, (3-aminopropyl)-dimethyl-ethoxysilane, (3-aminopropyl)-trimethoxysilane, and the like), glycidoxysilanes (for example, 3-glycidoxypropyl)-dimethyl-ethoxysilane and the like), and mercaptosilanes (for example, (3-mercaptopropyl)-trimethoxysilane, (3-mercaptopropyl)-methyl-dimethoxysilane, and the like). In some embodiments, these representative groups can be further chemically modified to convert one or more functional groups of the alkoxysilane to a functional group capable of coupling with the anchor moiety of the probe. Solely by way of example, an amine group of an aminosilane can be converted to an azide or can be coupled to an azide-containing reagent to provide a clickable group capable of undergoing a click chemistry reaction with an anchor moiety present on a probe (such as a clickable alkyne). In particular disclosed embodiments, the anchor moiety of the probe can be selected from a functional group capable of coupling with one or more functional groups present on the silanized substrate surface. For example, the probe can comprise one or more alkyne (or azide) moieties, which can react with any azides (or alkynes) present on the silanized substrate surface; or one or more carboxylic acid groups, which can react with any amines present on the silanized substrate surfaces; or one or more nucleophilic functional groups that can react with any epoxides present on the silanized substrate surface; or one or more alkene moieties that can react with any thiols present on the silanized substrate surface. Additional probe anchor moieties that can be coupled to hydroxyl groups present on the substrate surface and/or a silanized substrate surface will be recognized by those of ordinary skill in the art with the benefit of the present disclosure.

In a representative embodiment, a glass plate device is made by functionalizing a glass slide with an alkoxysilane reagent, such as triethoxysilaneamine. Then, a solution of a reagent comprising a clickable functional group, such as NHS-ester-PEG-azide, is added to the glass slide to functionalize the surface of the substrate with azide moieties. The functionalized glass slide is then either exposed to a probe embodiment prior to sample exposure or is exposed to a probe embodiment that has first been exposed to a sample. The probe comprises an anchor moiety, such as a clickable alkyne, that can react with the azide of the substrate (or, in some embodiments, comprises a clickable azide that can react with an alkyne of the substrate). The glass slide and the probe are exposed to reaction conditions that facilitate covalent coupling of the probe to the glass slide through a triazole formed between the alkyne group of the probe and the azide group of the substrate. In this embodiment, the reaction conditions include using DMSO as a solvent, triethylamine (or diisopropylethylamine) as a base, and CuI as a catalyst.

Figure 2:
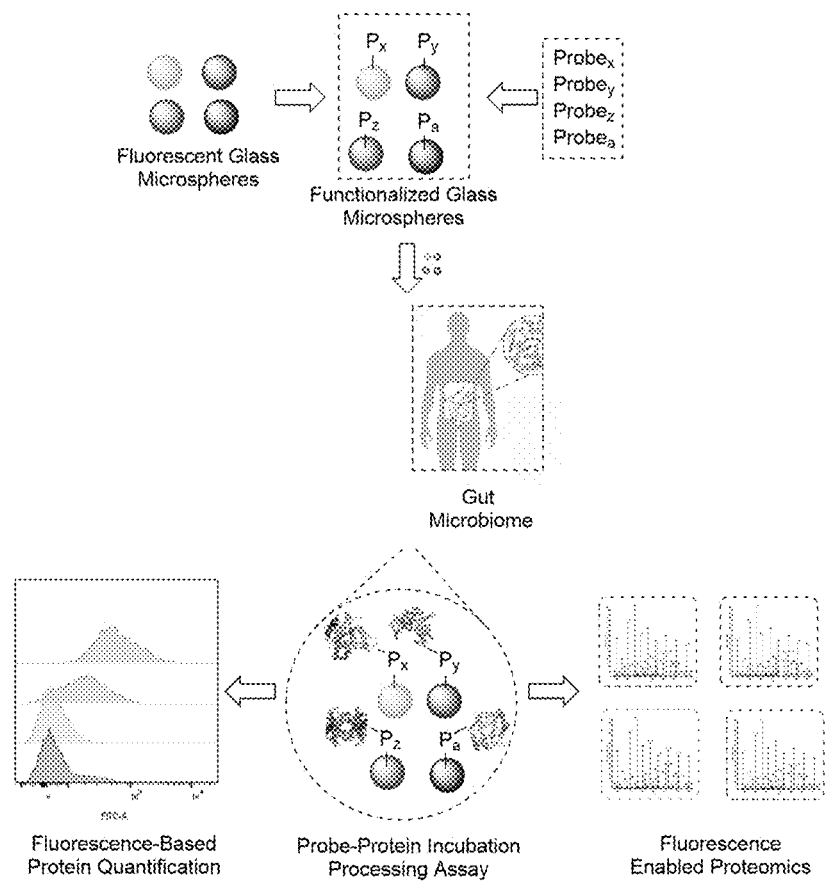
FIG. 2 shows an exemplary method using microspheres for multiplexed probing embodiments, wherein function-based probes ("P") are functionalized on fluorescent glass microspheres to enable flow cytometry, where each fluorophore is matched to a particular probe; the microspheres can be mixed and added to samples for multifunctional characterization of complex biological samples, such as samples that may comprise bile salt hydrolases, and after labeling, protein-probe-microspheres can be sorted further analysis (for example, determining the overall functional activity quantified based on their fluorescence emission and/or proteomics analysis of each sorted sample to yield identification of functionally active enzymes and their relative contribution to the overall functional activity).

In another example, probe embodiments can be coupled to fluorescent glass microspheres to provide a device for use in methods described herein. In such embodiments, a single probe embodiment can be coupled to a single microsphere. A plurality of microspheres can be made wherein each microsphere of the plurality is coupled to the same type of probe embodiment or wherein each microsphere of the plurality is coupled to different types of probe embodiments. Similar chemistry as described above can be used to couple the probe to the microsphere. Device embodiments comprising probes coupled to fluorescent glass microspheres enables the using various probes for several different enzyme targets in a single limited-size sample. Additionally, these device embodiments facilitate tandem direct quantification of target enzymes using Fluorescence-Activated Cell Sorting (FACS) and proteomics as depicted schematically in FIG. 2. In particular embodiments, the protein-probe-fluorescent microspheres are sorted and quantified by FACS. Then flow cytometry instruments can be used to provide quantitative fluorescence profiles, or full FACS systems can be used to sort by probe type and make subsequent proteomics measurements to enhance the measurement resolution.

In another representative example, a device comprising a well-plate having wells that are surface-modified with clickable functional groups (for example, azides or alkynes) are exposed to probe embodiments that each comprise at least one anchor moiety (for example, an alkyne or an azide) that can react with the clickable functional group of the surface-modified wells to covalently attach the probe to an individual well. In some embodiments, a single well can comprise a plurality of probes covalently bound thereto. In some embodiments, different wells of the well-plate can be functionalized with different probe embodiments.

VI. Methods of Use

Disclosed herein are embodiments of methods of using the disclosed probes and devices and/or kits comprising the probes. The probe and device/kit embodiments disclosed herein can be used to identify enzymes in the gut microbiome that exhibit BSH activity and to characterize the taxa to which such enzymes belong. Because probes disclosed herein are designed to specifically interact with BSH or enzymes exhibiting similar binding characteristics and/or reactivity to BSH in the presence of other analytes with which the probe does not interact, the device can be designed to include a probe embodiment disclosed herein (or a combination of such probes).

In some embodiments, the method comprises exposing a sample, such as a biological sample obtained from a subject (such as a mammal or other animal) to a probe embodiment described herein. In particular examples, the sample is one obtained from the stomach, small intestine, large intestine, rectum, or a fecal sample. Samples can be used directly, concentrated, or diluted. This step of the method can be carried out by using a device embodiment disclosed herein and exposing the device to the sample so that probes coupled to the substrate component of the device are in contact with the sample.

The sample typically is exposed to the probe embodiment(s) for a period of time that is sufficient to allow any analytes of interest (e.g., BSH enzymes or other enzymes capable of interacting with a probe embodiment disclosed herein) that may be present in the sample to identify and interact with the probe embodiments to form a conjugate, such as a probe-enzyme conjugate. In some embodiments, the analyte of interest is allowed to interact with the probe such that it forms a covalent bond with the probe. In some embodiments, additional steps may be performed to facilitate binding the analyte to the probe, such as an energy exposure step whereby the sample and the probes are exposed to an energy source (for example, a light source, such as a light source that provides light at wavelengths ranging from 10 nm to 400 nm, or from 10 nm to 370 nm, or from 10 nm to 365 nm) that activates a functional group on the probe, which then forms a covalent bond with the analyte. For example, certain probe embodiments disclosed herein can comprise a photoactivatable group (e.g., a diazirine or benzophenone functional group) that can be activated by light to form a covalent bond with the analyte. In additional embodiments, the probe and the analyte can be exposed to conditions sufficient to facilitate analyte-based activation of a functional group on the probe whereby the functional group is converted to a reactive species that forms a covalent bond with the analyte.

In some embodiments, the method also can further comprise exposing the probe to conditions sufficient to convert any pDM moieties present on the probe to DM moieties that can produce a detectable signal. In some such embodiments, the probe can be bound to an analyte of interest prior to converting the pDM moiety. Conditions suitable for converting the pDM group can include combining the probe with a reagent comprising a detectable moiety under click chemistry reaction conditions that promote forming a triazole moiety between the pDM moiety and a clickable functional group present on the detectable moiety of the reagent. This click chemistry based coupling covalently bonds the detectable moiety to provide a DM group on the probe. In some embodiments, the DM group can be a fluorophore or other visually-detectable moiety, such as a chromogen. In yet additional embodiments, the DM group can be a moiety that facilitates enrichment of the analyte bound to the probe. A representative example of such a DM group is biotin.

Once the DM group is generated, probes bound to analytes can be detected, identified, and quantified using a suitable detection method, such as fluorescent detection in SDS-Page methods, affinity chromatography, tryptic digestion, mass spectrometry, flow cytometry, and any combinations thereof. In some embodiments, a plurality of different probe embodiments can be used and the user is able to then identify the particular analytes present in the sample based on signals generated during use. Solely by way of example, a sample can be exposed to a device comprising any combination of the probe embodiments disclosed herein and if any species capable of binding to or otherwise interacting with such probes are present in the sample, they will interact with the corresponding probe embodiment to form a conjugate that can then be visualized and/or enriched after modifying the conjugate to comprise a DM group. For example, fluorescent DM moieties provide a detectable signal that the user can use as confirmation that the sample contains an analyte species that has been bound to the probe. In some additional embodiments, the device can provide qualitative results that allow the user not only to determine the presence or absence of particular analytes within the sample, but also that allow the user to determine how much of a particular analyte is present.

In yet additional embodiments, the probe can comprise a detectable moiety that can be cleaved upon reaction of the probe with a BSH (or other enzyme capable of exhibiting BSH activity) to provide a detectable signal, such as a fluorescent signal. In such embodiments, the detectable moiety is coupled to the probe, but exists in a quenched state (and thus is not visible). Once the detectable moiety has been released from the probe, such as by displacement by the enzyme, it will fluoresce and provide a detectable signal. Such probe and method embodiments can be used to provide a fluorescent readout in real time, providing an assay method that exhibits high sensitivity.

Exemplary embodiments of methods described herein are provided by the Examples section of the present disclosure.

VII. Composition and Method of Treatment Embodiments

Methods of treating diseases or conditions associated with bile salt hydrolase activity are described herein. In some examples, the methods can ameliorate a sign or symptom of a disease or condition. In specific examples, the diseases or conditions are related to BSH activity (e.g., obesity, hypercholesterolemia, liver cancer, diabetes (type I or II), dysbiosis, gallstones, colon cancer, or irritable bowel disease, including ulcerative colitis or Crone's disease).

In some examples, the methods include labeling at least one microbial protein (e.g., a bile salt hydrolase or other enzyme that exhibits bile salt hydrolase activity). In some examples, the methods include determining the presence of the at least one microbial protein (e.g., a bile salt hydrolase or other enzyme that exhibits bile salt hydrolase activity) in a sample (e.g., an intestinal sample). In some examples, the methods include sorting or isolating the at least one microbial protein or microbes that include the at least one labeled microbial protein. In some examples, the methods include identifying microbes comprising the at least one labeled microbial protein that has been attached to a probe. In some examples, the methods include selecting a physical environment (e.g., a human or animal, such as human or animal gut, skin, lung, oral, ocular, mouth, vaginal, and uterine environment, for example an intestinal environment) for alteration of bile salt hydrolase activity. In some examples, the methods include altering bile salt hydrolase activity in the selected physical environment, for example, by enriching the selected physical environment with the identified microbes, reducing the amount of the identified microbes in the selected physical environment, or modifying the activity of the identified microbe or microbial protein in the selected physical environment.

Any of the methods described herein can include performing genomic or proteomic assays using the at least one labeled microbial protein or microbes comprising the at least one labeled microbial protein. Any genomic assays can be used, including whole genome and/or whole exome sequencing (WGS and WES, respectively); sequencing for single nucleotide variants, insertions, and/or deletions (indels), copy number variations; RNA sequencing (e.g., RNA-seq or whole transcriptome shotgun sequencing), such as 16S sequencing; assaying interactions between nucleic acids and ligands and/or macromolecules (e.g., molecules typically with a mass of at least 2 kDa, such as nucleic acids with at least 10 nucleotides, polynucleotides, polypeptides, proteins, enzymes, and complexes with plurality of macromolecules); and metagenomics (e.g., Sharma and Lal, Indian J. Microbiol., 57(1):23-38, 2017, incorporated herein by reference). Genomics assays can include sequencing and sequence assembly and annotation, such as using de novo techniques, for example, shotgun sequencing or PCR, or next generation techniques (e.g., "next gen" or high-throughput), for example, real-time single-molecule, ion torrent, pyro, synthesis, combinatorial probe anchor, ligation (e.g., oligonucleotide ligation and detection or SOLiD), nanopore or Sanger sequencing; chromatin or cross-linking immunoprecipitation (e.g., ChI and CLIP, respectively); and bioinformatics and computational biology. In specific examples, performing genomic assays includes performing 16S sequencing and/or single cell genome sequencing.

Any proteomics assays can be used, including techniques for separating, identifying, and analyzing proteins (e.g., analyzing intermolecular or intramolecular interactions, such as protein structure, protein-protein interactions, or protein-ligand interactions; Lee, *Trends Biotechnol.*, 19(6): 217-22, 2001, the relevant portion of which is incorporated herein by reference). The proteomics assays can include using any tools available for proteomic analysis, for example, mass spectrometry (e.g., using hard or soft ionization techniques, including matrix-assisted laser desorption/ionization or electrospray ionization, for example, with mass analyzers, such as time of flight, quadrupole filter, or ion trapping, as well as other techniques, such as liquid chromatography, capillary electrophoresis, tandem mass spectrometry, or fragmentation techniques, for example, collision-induced dissociation); electrophoresis (e.g., 1 D- or 2D-gel electrophoresis or western blotting), immunological assays (e.g., immunological microarray assays or enzyme-linked immunosorbent assays, ELISAs), protein microarray assays (e.g., functional protein or target protein array assays), chromatography (e.g., affinity, size-exclusion, ion-exchange, or reverse-phase), tools for analyzing protein structure or electrochemistry (e.g., x-ray crystallography or nuclear magnetic resonance), computational or bioinformatics tools (e.g., protein identification, structure, or interaction modeling tools), or any combination thereof. In specific examples, mass spectrometry (MS), such as liquid chromatography MS (LC-MS), and/or ELISA is used.

Any of the methods described herein can include labeling in any environment (e.g., natural or artificial environments). Environments can vary relative to an organism and community and include, for example, a human or animal gut, skin, lung, oral, ocular, mouth, vaginal, uterine, or intestinal environment. In some examples, the methods include labeling in the native habitat of microbes that include the at least one microbial protein (e.g., an intestinal environment). In some examples, the methods include labeling a microbial protein or microbe in which the microbe is uncultured.

Any of the probes, devices, or kits described herein can be used for labeling. In some examples, the methods include labeling a microbial protein or microbe using the probes described herein, such as probes that include the structure of Formula I, for example, probes that include the structure of any one of Formulas IA-ID, IIA, IIB, IIIA, IIIB, IIIC, IIID, IIIE, or IIIF. In some examples, the methods include labeling a microbial protein or microbe using the devices or kits described herein.

In some examples, the at least one specific metabolic function includes BSH activity, such as producing at least one bile acid (e.g., cholic, chenodeoxycholic, deoxycholic, ursodeoxycholic, or lithocholic acid). In specific examples, the at least one bile acid specifically binds at least one nuclear or surface receptor, such as FXR, vitamin D receptor, or TGR5. In specific examples, the diseases or conditions are related to BSH activity (e.g., obesity, dysbiosis, hypercholesterolemia, liver or colon cancer, diabetes, gallstones, or irritable bowel disease, including ulcerative colitis or Crone's disease).

The methods can include selecting a subject with a disease or condition related to BSH activity. In some examples, the disease or condition is obesity, hypercholesterolemia, liver cancer, diabetes, irritable bowel disease (such as ulcerative colitis or Crone's disease), gallstones, colon cancer, or dysbiosis. In some examples, the methods include enriching the gut microbiome of a subject with microbes identified by labeling a bile salt hydrolase, such as by administering the microbes identified by labeling the bile salt hydrolase or by administering the bile salt hydrolase (e.g., where the disease or condition is related to inactive or underactive BSH or insufficient deconjugation of bile salts, such as dysbiosis, IBD, obesity, diabetes, hypercholesterolemia). In some examples, the methods include administering inhibitors of BSH (e.g., antibiotic growth promoters, carnosic acid, $FeSO_4$, $CoCl_2$, $NaSeO_3$, $NaIO_4$, retinol, and linolenic acid, $KIO_3$, $NaHIO_3$, $NaIO_4$, $CuSO_4$, $CuCl_2$, $ZnSO_4$, $ZnCl_2$, menadione, riboflavin, gossypetin, caffeic acid phenethyl ester [CAPE], epicatechin monogallate, purpurogallin, oxytetracycline, demeclocycline hydrochloride, methacycline hydrochloride, doxycycline hydrochloride, roxarsone, or lincomycin) or of the microbes identified by labeling bile salt hydrolase (e.g., where the disease or condition is related to overactive BSH or an overabundance of deconjugated bile salts, such as colon cancer, gallstones, or liver cancer).

In some examples, the methods include selecting a subject with obesity (e.g., subjects with a BMI of 30 or greater). Thus, in some examples, the subject treated has a BMI of 30 or greater, such as at least 30, at least 35, or at least 40. In some examples, the obesity is related or at least in part related to the presence, absence, or abundance of microbes or enzymes (e.g., microbial enzymes), such as microbes or enzymes with at least one specific metabolic function (e.g., BSH activity). In some examples, the methods include administering the microbes identified by labeling bile salt hydrolase or by administering bile salt hydrolase to the subject with obesity.

In some examples, the methods include selecting a subject with hypercholesterolemia, such as a subject with high levels of cholesterol in the blood, for example, a subject with LDL cholesterol greater than 190 mg/dL, greater than 160 mg/dL with one cardiovascular risk factor, or greater than 130 mg/dL with two cardiovascular risk factors (exemplary cardiovascular risk factors can include age for males 45 years or older and females 55 years or older, a positive family history of premature atherosclerotic cardiovascular disease at younger than 55 years in males and younger than 65 years in females, hypertension, diabetes, smoking, and low HDL cholesterol levels, such as less than 40 mg/dl in males and less than 55 mg/dl in female; e.g., Ibrahim and Jialal, *Hypercholesterolemia*, StatPearls Publishing, 2018, ncbi.nlm.nih.gov, the relevant portion of which is incorporated herein by reference). Thus, in some examples, the subject treated has a LDL cholesterol of at least 190 mg/dL, at least 200 mg/dL, or at least 250 mg/dL. Thus, in some examples, the subject treated has a LDL cholesterol of at least 160 mg/dL with one major risk factor, at least 170 mg/dL with one major risk factor, or at least 180 mg/dL with one major risk factor. Thus, in some examples, the subject treated has a LDL cholesterol of at least 130 mg/dL with two major risk factors, at least 140 mg/dL with two major risk factors, or at least 150 mg/dL with two major risk factors. The hypercholesterolemia can be genetic or acquired. In some examples, the methods include administering the microbes identified by labeling bile salt hydrolase or by administering bile salt hydrolase to the subject with hypercholesterolemia.

In some examples, the methods include selecting a subject with liver cancer. The methods include selecting subjects with any type of liver cancer, such as liver cancer related to obesity (e.g., Ridlon et al., *Curr. Opin. Gastroenterol.*, 30(3):332-338, 2014, the relevant portion of which is incorporated herein by reference). Thus, in some examples, the subject treated has a liver cancer, such as a liver cancer related to obesity. In some examples, the methods include administering inhibitors of BSH or of the microbes identified by labeling bile salt hydrolase.

In some examples, the methods include selecting a subject with diabetes. The methods include selecting subjects with any type of diabetes, such as type 2 diabetes (e.g., type 2 diabetes related to BSH activity; Labbe et al., *PLoS One*, 9(12):e115175, 2014, the relevant portion of which is incorporated herein by reference). Thus, in some examples, the subject treated has liver type II diabetes, such as one related to BSH activity. In some examples, the methods include administering the microbes identified by labeling bile salt hydrolase or by administering bile salt hydrolase to the subject with type 2 diabetes.

In some examples, the methods include selecting a subject with irritable bowel disease (IBD), such as ulcerative colitis or Crone's disease (e.g., ulcerative colitis or Crone's disease related to BSH activity; Labbe et al., *PLoS One*, 9(12): e115175, 2014, the relevant portion of which is incorporated herein by reference). Thus, in some examples, the subject treated has IBD, such as one related to BSH activity. In some examples, the methods include administering the microbes identified by labeling bile salt hydrolase or by administering bile salt hydrolase to the subject with IBD.

In some examples, the methods include selecting a subject with dysbiosis, such as dysbiosis related to BSH or a bile acid imbalance (e.g., Kakiyama et al., *J. Hepatol.*, 58(5): 949-955, 2013, the relevant portion of which is incorporated herein by reference). Thus, in some examples, the subject treated has dysbiosis, such as one related to BSH activity. In some examples, the methods include administering the microbes identified by labeling bile salt hydrolase or by administering bile salt hydrolase to the subject with dysbiosis.

In some examples, the methods include selecting a subject with colon (or colorectal) cancer. The methods can include selecting a subject with any type of colon cancer, such as colon cancer related to BSH (e.g., Ridlon et al., J Lipid Res., 47(2):241-59, 2006, incorporated herein by reference in its entirety). Thus, in some examples, the subject treated has a colon cancer, such as a colon cancer related to BSH. In some examples, the methods include administering inhibitors of BSH or of the microbes identified by labeling bile salt hydrolase to the subject with colon cancer.

In some examples, the methods include selecting a subject with gallstones (e.g., cholesterol gallstones). The methods can include selecting a subject with any type of gallstone, such as gallstones related to BSH or cholesterol gallstones (e.g., Ridlon et al., J Lipid Res., 47(2):241-59, 2006, incorporated herein by reference in its entirety). Thus, in some examples, the subject treated has gallstones, such as one related to BSH or cholesterol gallstones. In some examples, the methods include administering inhibitors of BSH or of the microbes identified by labeling bile salt hydrolase to the subject with gallstones.

In some examples, the subject is administered an additional protocol and/or pharmaceutical agent. Examples of additional protocols or pharmaceutical agents that can be administered include, but are not limited to, a change in diet or exercise, bariatric surgery, phentermine, Adipex-P®, Fastin®, Ionamin®, Suprenza®, Atti-Plex P®, Lomaira®, Phentercot®, Phentride®, topiramate, Topamax®, Topiragen®, Topamax Sprinkle®, phendimetrazine, Bontril Slow Release®, Bontril PDM®, Phendiet®, Prelu-2®, Melfiat@, Obezine®, Phendiet-105®, orlistat, Alli®, Xenical®, bupropion, diethylpropion, Tenuate®, Tenuate Dospan®, Tepanil®, methamphetamine, Desoxyn®, lorcaserin, Belviq®, Belviq XR®, bupropion/naltrexone, Contrave®, chorionic gonadotropin (hcg), HCG®, Pregnyl®, liraglutide, Saxenda®, phentermine/topiramate, Qsymia®, amphetamine, Evekeo®, benzphetamine, Didrex®, Recede®, Regimex®, cimetidine, Tagamet®, Equaline Acid Reducer®, Tagamet HB®, methylphenidate, or desvenlafaxine (e.g., for a subject with obesity); a change in diet, ceasing smoking, reducing alcohol consumption, increasing exercise, atorvastatin, Lipitor®, simvastatin, Zocor®, FloLipid®, pravastatin, Pravachol®, lovastatin, Altocor®, Altoprev®, rosuvastatin, Crestor®, gemfibrozil, Lopid®, ezetimibe, Zetia®, niacin, Niaspan®, Niacin SR®, SloNiacin®, B3-500-Gr®, Niacor®, B-3-50®, Nicotinex®, ezetimibe/simvastatin, Vytorin®, pitavastatin, Livalo®, Zypitamag®, fenofibric acid, Trilipix®, Fibricor®, colesevelam, Welchol®, fluvastatin, Lescol®, Lescol XL®, alirocumab, Praluent®, amlodipine/atorvastatin, Caduet@, evolocumab, Repatha®, Repatha Pushtronex®, mycophenolate mofetil, lomitapide, Juxtapid®, mipomersen, or Kynamro® (e.g., for a subject with hypercholesterolemia); surgery (including resection or liver transplant), percutaneous ablation, chemotherapy (such as local administration of cytotoxic drugs), radiotherapy, doxorubicin, cisplatin, or lipiodol (e.g., for a subject with liver cancer); change in diet and exercise, bariatric surgery, metformin, sulphonylureas (e.g., glibenclamide, tolbutamide, glimepiride), nateglinide, repaglinide, thiazolidinediones (e.g., rosiglitazone, pioglitazone), peroxisome proliferator-activated receptor (PPAR)-gamma-agonists (such as C1262570) and antagonists, PPAR-gamma/alpha modulators (such as KRP 297), alphaglucosidase inhibitors (e.g., acarbose, voglibose), dipeptidyl peptidase (DPP)-IV inhibitors (such as LAF237, MK-431), alpha2-antagonists, agents for lowering blood sugar, cholesterol-absorption inhibitors, 3-hydroxy-3-methylglutarylcoenzyme A (HMGCoA) reductase inhibitors (such as a statin), insulin and insulin analogues, GLP-1 and GLP-1 analogues (e.g., exendin-4), or amylin (e.g., for a subject with diabetes); surgery, antibiotics (e.g., Cipro® or Flagyl®), anti-diarrheal medications (e.g., fiber supplements, such as psyllium powder [for example, Metamucil®] or methylcellulose [for example, Citrucel®], or medications, such as loperamide, for example, Imodium A-D®), nutritional supplements (e.g., iron, calcium, or vitamin D), or nutritional intervention (e.g., for a subject with IBD); or antibiotics (e.g., ciprofloxacin, Cipro®, rifaximin, Xifaxan®, co-trimoxazole, or Septrin®) or nutritional intervention (e.g., for a subject with dysbiosis).

In additional embodiments, the subject can be administered an additional pharmaceutical agent. The phrase "combinatorial therapy" or "combination therapy" embraces administration of one or more microbes (e.g., microbes with BSH activity) or microbial proteins or enzymes (e.g., BSH) but also the addition of one or more therapeutic agents as part of a specific treatment regimen intended to provide beneficial effect from the co-action of these therapeutic agents.

For any of the methods disclosed herein, the one or more microbes (e.g., microbes with BSH activity) or microbial proteins or enzymes (e.g., BSH) can be administered systemically or locally.

VIII. Overview of Several Embodiments

Disclosed herein are embodiments of a probe, wherein the probe has a structure satisfying Formula I, as described herein. In any or all embodiments, and with reference to Formula I, each of $R^1$, $R^2$, $R^3$, and $R^4$ independently is selected from hydrogen or —OR, wherein each R independently is selected from hydrogen; a counterion that balances a negative charge on the oxygen atom; aliphatic; heteroaliphatic; aromatic; or any combination of aliphatic, heteroaliphatic, or aromatic; $R^5$ is hydrogen, aliphatic, heteroaliphatic, aromatic, or any combination of aliphatic, heteroaliphatic, or aromatic; the linker is aliphatic, heteroaliphatic, aromatic, or any combination of aliphatic, heteroaliphatic, or aromatic; DM is a detectable moiety; pDM is a detectable moiety precursor; PM is a photoactivatable moiety; AM is an anchor moiety; n is an integer ranging from 0 to 10; and m is an integer selected from 0 or 1.

In any or all of the above embodiments, m is 1 and the linker is —(CH$_2$)$_p$—;

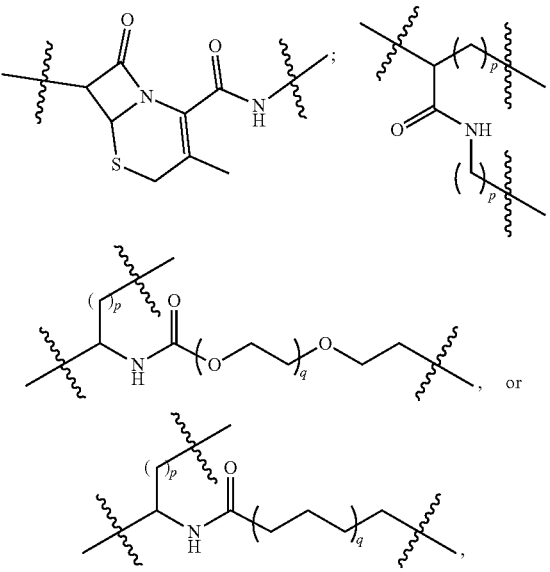

wherein each p independently is as an integer ranging from 1 to 10, and each q independently is an integer ranging from 0 to 10.

In any or all of the above embodiments, the DM group is present and is a fluorophore, a chromogen, or a member of a specific binding pair.

In any or all of the above embodiments, the pDM group is present and is an alkyne or an azide.

In any or all of the above embodiments, each of R¹, R², R³, and R⁴ independently is hydrogen, —OH, or —O-M⁺, wherein M⁺ is a counterion selected from Li⁺, K⁺, Na⁺, or NH₄⁺.

In any or all of the above embodiments, the PM group is present and is an aziridine or a benzophenone.

In any or all of the above embodiments, the AM group is present as is an alkyne, an azide, a carboxylic acid, an NHS-ester, an amine, or an alkyl halide.

In any or all of the above embodiments, m is 0 and the DM group is present and is

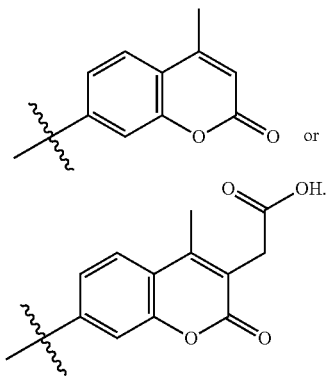

In any or all of the above embodiments, m is 1 and both the PM group and the pDM group are present.

In any or all of the above embodiments, m is 1 and both the AM group and the pDM group are present.

In any or all of the above embodiments, the probe has a structure satisfying Formula IIA or IIB as described herein.

In any or all of the above embodiments, the probe has a structure satisfying one or more of Formulas IIIA-IIIF as described herein and wherein each p independently of any one or more of Formulas IIIA-IIIF is an integer ranging from 1 to 10 and each q independently is an integer ranging from 0 to 20.

Also disclosed is a method, comprising: exposing a subject or a sample to a probe according to claim 1 for a time sufficient to allow the probe to bind to an enzyme capable of hydrolyzing a bile salt to thereby form a probe-enzyme conjugate; and analyzing the subject or the sample using a detection technique sufficient to identify a detectable signal produced by reaction between the probe and the enzyme.

In any or all of the above embodiments, a detectable moiety is released from the probe upon binding of the enzyme to the probe.

In any or all of the above embodiments, the probe comprises a pDM group and the method further comprises exposing the probe-enzyme conjugate to a detectable moiety group comprising a clickable functional group capable of reacting with the pDM group.

In any or all of the above embodiments, the probe comprises a PM group and the method further comprises exposing the sample or the subject to a light source to facilitate binding of the PM group to the enzyme to thereby form the probe-enzyme conjugate.

In any or all of the above embodiments, the method further comprises performing genomic or proteomic assays using the probe-enzyme conjugate or microbes comprising the probe-enzyme conjugate.

Also disclosed are embodiments of a method of treating a disease or condition related to bile salt hydrolase activity.

In any or all of the above embodiments, the method comprises: labeling at least one enzyme capable of hydrolyzing a bile salt with a probe according to any or all of the above probe embodiments to provide at least one labeled enzyme; determining the presence of the at least one labeled enzyme in a sample by detecting a detectable signal; sorting or isolating the at least one labeled enzyme or microbes comprising the at least one labeled enzyme; identifying the microbes comprising the at least one labeled enzyme; selecting a physical environment for altering the bile salt hydrolase activity of the at least one enzyme; and/or altering bile salt hydrolase activity in the selected physical environment to thereby treat the disease or condition by enriching the selected physical environment with identified microbes, or by reducing the amount of identified microbes in the selected physical environment, or by reducing the bile salt hydrolase activity in the selected physical environment, or any combination thereof.

Also disclosed is a kit, comprising a substrate; and a probe having a structure satisfying Formula I, wherein each of R¹, R², R³, and R⁴ independently is selected from hydrogen or —OR, wherein each R independently is selected from hydrogen; a counterion that balances a negative charge on the oxygen atom; aliphatic; heteroaliphatic; aromatic; or any combination of aliphatic, heteroaliphatic, or aromatic; R⁵ is hydrogen, aliphatic, heteroaliphatic, aromatic, or any combination of aliphatic, heteroaliphatic, or aromatic; the linker is aliphatic, heteroaliphatic, aromatic, or any combination of aliphatic, heteroaliphatic, or aromatic; DM is a detectable moiety; pDM is a detectable moiety precursor; AM is an anchor moiety; n is an integer ranging from 0 to 10; and m is an integer selected from 0 or 1; and wherein the probe is covalently bound to a surface of the substrate via the AM group.

IX. Examples

Cell Lines and Media

*Lactobacillus plantarum* (Orla-Jensen) was purchased from ATCC (ATCC BAA-793) and cultured according to the vendor's recommendations using MRS media (Fisher Scientific, Difco Lactobacilli MRS Broth, BD288130). ElectroMAX DH5α-E Competent Cells were purchased from ThermoFisher (Ser. No. 11/319,019) and were cultured in LB media (FisherScientific, AC612725000) according to the vendor's recommendations.

Representative Assay Conditions for Purified Protein

Reaction volumes of 100 μL were used in Microfluor1 black flat bottom microtiter 96 well plates (Thermo Scientific). 50 μl BSH (80, 40, 20, 10, 5, 2.5, 1.3, 0 μg/ml) in 0.1 M sodium phosphate buffer (pH=6) were added to the appropriate wells. A 50 μL solution of probe (300 μM) in buffer with 5% DMSO was then added to initiate the reaction. Reactions were immediately placed in a plate reader (SPECTRAmax Gemini XS) pre-warmed to 37° C., and reaction progress was monitored at 450 nm (excitation 350 nm) for 20 minutes. Reactions had final concentrations of 150 μM probe and 2.5% DMSO.

Representative Assay Conditions for Cell Lysates

Reaction volumes of 100 μL were used in Microfluor1 black flat bottom microtiter 96 well plates (Thermo Scientific). 50 μL of *L. plantarum* lysate (3000, 1500, 750, 375, 188, 94, 47 μg/ml) in buffer (0.1 M sodium phosphate, pH=6) was added to each well. A 50 μL solution of probe (300 μM) in buffer with 5% DMSO was then added to initiate the reaction. Reactions were immediately placed in a plate reader (SPECTRAmax Gemini XS) pre-warmed to 37° C., and reaction progress was monitored at 450 nm (excitation 350 nm) for 20 minutes. Reactions had final concentrations of 150 μM probe, 0.1 M sodium phosphate (pH 6), and 2.5% DMSO.

Representative Assay Conditions for Whole Cells

A starter culture was created by inoculation of 5 ml MRS broth from a *L. plantarum* colony grown on MRS agar. The starter culture was incubated overnight at 37° C. overnight. The 5 ml starter culture was then added to 95 ml fresh MRS broth and grown until the optical density at 600 nm reached 0.7. At that point, the cells were pelleted via centrifugation. The cell pellet was resuspended in 15 ml PBS, and centrifuged. The cells were additionally washed with PBS and pelleted once more. The resulting pellet was suspended in 380 μl PBS. The cell suspension was then serially diluted two-fold.

50 μl of the cell suspension was added to Microfluor1 black flat bottom microtiter 96 well plates (Thermo Scientific). A 50 μL solution of probe (300 μM) in buffer with 5% DMSO was then added to initiate the reaction. Reactions were immediately placed in a plate reader (SPECTRAmax Gemini XS) pre-warmed to 37° C., and reaction progress was monitored at 450 nm (excitation 350 nm) for 60 minutes. Reactions had final concentrations of 150 μM probe and 2.5% DMSO.

Purified BSH Assay

Reaction volumes of 100 μL were used in Microfluor1 black flat bottom microtiter 96 well plates (Thermo Scientific). 50 μl BSH (80, 40, 20, 10, 5, 2.5, 1.3, 0 μg/ml) in 0.1 M sodium phosphate buffer (pH=6) were added to the appropriate wells. A 50 μL solution of probe (300 μM) in buffer with 5% DMSO was then added to initiate the reaction. Reactions were immediately placed in a plate reader (SPECTRAmax Gemini XS) pre-warmed to 37° C., and reaction progress was monitored at 450 nm (excitation 350 nm) for 20 minutes. Reactions had final concentrations of 150 μM probe and 2.5% DMSO.

GCA and Iodoacetamide Competition Assay

Experiments were run analogously to the purified BSH assay, except that competitors were added before CA-AMCA probe. Final concentrations were: BSH (10 μg/ml), DMSO (2.5% v/v), CA-AMCA (150 μM), and GCA (10 mM) or IAA (12 mM), respectively.

$K_m$ Determination

Reaction volumes of 100 μL were used in Microfluor1 black flat bottom microtiter 96 well plates (Thermo Scientific). 50 μL of enzyme (40 μg/ml) in buffer (0.1 M sodium phosphate, pH=6) was added to each well. 50 μL of appropriate CA-AMCA substrate dilution (2500, 1250, 625, 312.5, 156.2, 78.1, 39.1, 0 μM) dissolved in buffer with 5% DMSO was added to start the reaction. Reactions were immediately placed in a plate reader (SPECTRAmax Gemini XS) pre-warmed to 37° C., and reaction progress was monitored at 450 nm (excitation 350 nm) for 20 minutes. Reactions had final concentrations of 20 μg/ml enzyme, 0.1 M sodium phosphate (pH 6), and 2.5% DMSO.

The initial rate data was used for determination of $K_m$ values. For $K_m$ determination, the kinetic values were obtained directly from nonlinear regression of substrate-velocity curves in the presence of varying concentrations of BA-AMCA. The equation $Y=(V_{max}*X)/(K_m+X*(1+X/K_i))$, X=substrate concentration (μM) and Y=enzyme velocity (RFU/s); was used in the nonlinear regression. Each BA-AMCA $K_m$ value was determined using at least three independent experiments.

$K_i$ Determination

Reaction volumes of 100 μL were used in Microfluor1 black flat bottom microtiter 96 well plates (Thermo Scientific). 50 μL of enzyme (10 μg/ml) in buffer (0.1 M sodium phosphate, pH=6) was added to each well. A 50 μL solution of probe (50 μM) and CAPE (10000, 3333, 1111, 370, 123, 41, 14 μM) in buffer with 5% DMSO was then added to initiate the reaction. Reactions were immediately placed in a plate reader (SPECTRAmax Gemini XS) pre-warmed to 37° C., and reaction progress was monitored at 450 nm (excitation 350 nm) for 20 minutes. Reactions had final concentrations of 5 μg/ml enzyme, 0.1 M sodium phosphate (pH 6), and 2.5% DMSO.

HPLC Assay

10 μL of 6 mM CA-AMCA in DMSO was mixed with 190 μL of 0.1 M sodium phosphate buffer (pH 6). 200 μL of enzyme in buffer was added to start the reaction. At varying time points (0, 1, 2, 3, 4, 5, 7.5, 10, 15, 20 minutes) 30 μL aliquots were removed and immediately mixed with 2 μL of 500 mM iodoacetamide to inactivate the hydrolase. After all samples were collected, 10 μL of each was loaded onto a C18 reverse-phase HPLC column (Phenomenex) on an Agilent 100 series analytical HPLC for characterization. A 5→100% MeOH in $H_2O$ linear gradient over 15 minutes was used and elution stream was monitored at 450 nm (excitation 350 nm).

Purified BSH Added to *E. coli* Lysate

Reaction volumes of 100 μL were used in Microfluor1 black flat bottom microtiter 96 well plates (Thermo Scientific). 50 μl of *E. coli* lysate (2 mg/ml) with varying concentrations of BSH (80, 40, 20, 10, 5, 2.5, 1.3, 0 μg/ml) in 0.1 M sodium phosphate buffer (pH=6) were added to the appropriate wells. A 50 μL solution of probe (300 μM) in buffer with 5% DMSO was then added to initiate the reaction. Reactions were immediately placed in a plate reader (SPECTRAmax Gemini XS) pre-warmed to 37° C., and reaction progress was monitored at 450 nm (excitation 350 nm) for 20 minutes. Reactions had final concentrations of 150 μM probe and 2.5% DMSO.

*Lactobacillus plantarum* Lysate Assay

Reaction volumes of 100 μL were used in Microfluor1 black flat bottom microtiter 96 well plates (Thermo Scientific). 50 μL of *L. plantarum* lysate (3000, 1500, 750, 375, 188, 94, 47 μg/ml) in buffer (0.1 M sodium phosphate, pH=6) was added to each well. A 50 μL solution of probe (300 μM) in buffer with 5% DMSO was then added to initiate the reaction. Reactions were immediately placed in a plate reader (SPECTRAmax Gemini XS) pre-warmed to 37° C., and reaction progress was monitored at 450 nm (excitation 350 nm) for 20 minutes. Reactions had final concentrations of 150 µM probe, 0.1 M sodium phosphate (pH 6), and 2.5% DMSO.

Whole-Cell *Lactobacillus plantarum* Assay

A starter culture was created by inoculation of 5 ml MRS broth from a *L. plantarum* colony grown on MRS agar. The starter culture was incubated overnight at 37° C. overnight. The 5 ml starter culture was then added to 95 ml fresh MRS broth and grown until the optical density at 600 nm reached 0.7. At that point, the cells were pelleted via centrifugation. The cell pellet was resuspended in 15 ml PBS, and centrifuged. The cells were additionally washed with PBS and pelleted once more. The resulting pellet was suspended in 380 µl PBS. The cell suspension was then serially diluted two-fold.

50 µl of the cell suspension was added to Microfluor1 black flat bottom microtiter 96 well plates (Thermo Scientific). A 50 µL solution of probe (300 µM) in buffer with 5% DMSO was then added to initiate the reaction. Reactions were immediately placed in a plate reader (SPECTRAmax Gemini XS) pre-warmed to 37° C., and reaction progress was monitored at 450 nm (excitation 350 nm) for 60 minutes. Reactions had final concentrations of 150 µM probe and 2.5% DMSO.

Preparation of Gut Microbiome Cell Lysate

Human fecal sample was obtained from Lee BioSolutions (Cat no 991-18). Sample (1 g) was vortexed for 30 seconds and allowed to rest on ice for 10 minutes to settle beads and large debris. The supernatant was transferred to a clean 50 mL conica tubel. The supernatant was centrifuged at 700 g for 15 minutes at 4° C. The supernatant was transferred to a clean 15 mL conical. The supernatant was then centrifuged at 7000 g for 15 minutes at 4° C. to pellet the bacterial cells. The supernatant was then discarded. The cell pellet was resuspend in 1 mL cold PBS, and transferred to a 1.7 mL eppendorf tube. The sample was vortexed briefly to homogenize the solution. The cells were then pelleted at 8000 g. The pellet was then washed in 1 mL cold PBS. The pellet was then resuspended in 2 mL of PBS. Samples were transferred to 1.5 mL SafeLock tubes. 50-100 µL of small (0.3 mm) glass beads were added. Samples were bead beat in a bullet blender at max speed for 5 minutes. Bead beating was repeated two more times for a total of 3 rounds. Protein content was then determined by BCA assay (Thermo Scientific).

Analysis of BSH Activity in a Gut Microbiome Sample

Reaction volumes of 100 µL were used in Microfluor1 black flat bottom microtiter 96 well plates (Thermo Scientific). 50 µl of gut microbiome lysate (1 mg/ml) with BSH (40 µg/ml) or buffer were added to the appropriate wells. A 50 µL solution of probe (300 µM) in buffer with 5% DMSO was then added to initiate the reaction. Reactions were immediately placed in a plate reader (SPECTRAmax Gemini XS) pre-warmed to 37° C., and reaction progress was monitored at 450 nm (excitation 350 nm) for 20 minutes. Reactions had final concentrations of 20 µg/ml BSH, 500 µg/ml lysate protein, 150 µM probe and 2.5% DMSO.

Example 1

Chemical probes were designed using an aminocoumarin fluorophore that can be quenched though amide coupling of the amine to the carboxylic acid of a bile acid, where, upon exposure of the synthetic substrate to a BSH, the amide bond is cleaved, and a free bile acid as well as an unquenched free aminocoumarin fluorophore are produced. Therefore, product formation can be continuously and quantitatively monitored using a fluorimeter.

Figure 3:
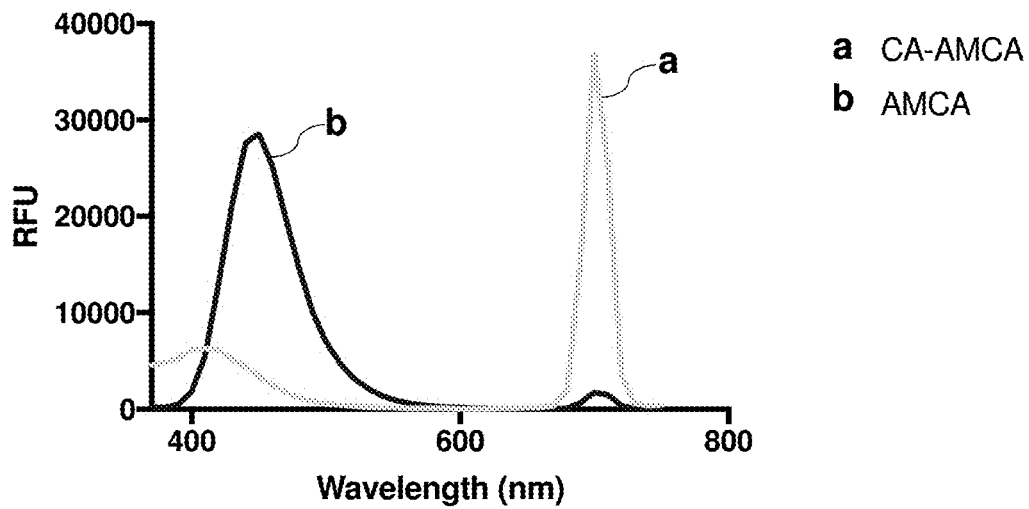
FIG. 3 shows combined emission spectra obtained from characterizing solutions of 150 µM of a representative probe embodiment comprising a 7-amino-4-methyl-3-coumarinylacetic acid (AMCA) moiety in PBS, wherein the analysis revealed that the probe is much less fluorescent when compared to free 7-amino-4-methyl-3-coumarinylacetic acid.

In this example, two probes based on cholic acid (CA-AMCA) and chenodeoxycholic acid (chenodeoxycholic-AMCA) were synthesized through an amide coupling of the appropriate bile acid and 7-amino-4-methyl-3-coumarinylacetic acid. Spectrographic characterization of the probe products revealed that, similar to the analogous protease substrates, the conjugated probes were much less fluorescent than the unconjugated aminocoumarin (FIG. 3).

Figure 4A:
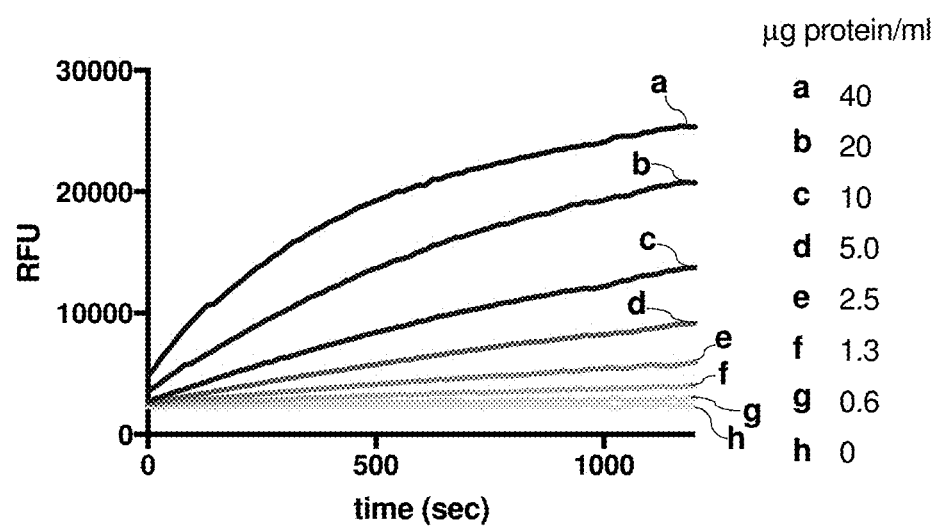
FIGS. 4A and 4B show that a representative probe embodiment, "CA-AMCA," continuously reports on activity of purified recombinant BSH in buffer.
Figure 4B:
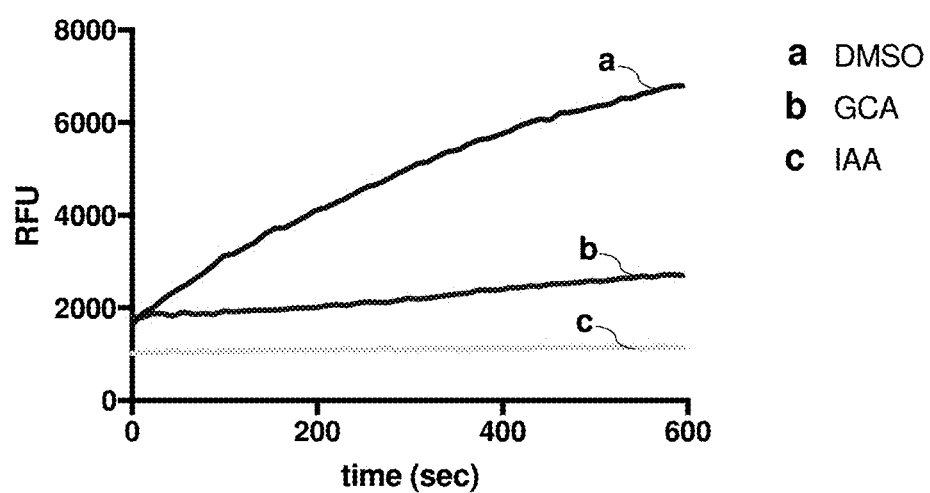
Figure 5:
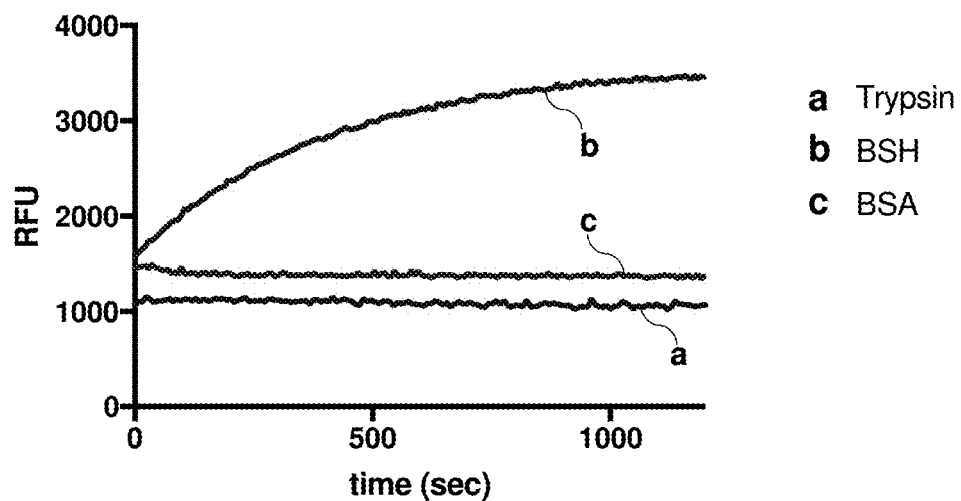
FIG. 5 is a graph showing results from treating purified protein with the CA-AMCA probe and evaluating the reaction kinetics by monitoring of fluorescence at 450 nm when excited at 350 nm; it was established that the CA-AMCA probe reacts with BSH, but not BSA or an unrelated hydrolase (trypsin).
Figure 6A:
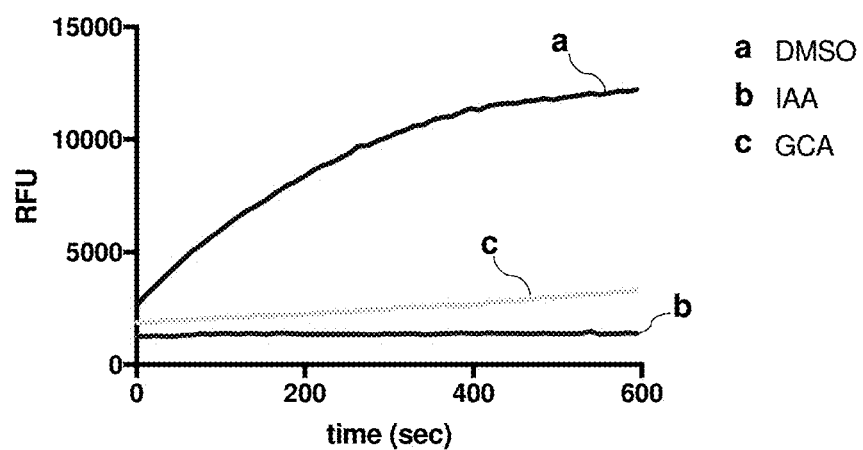
FIGS. 6A-6C are graphs produced from analyzing individual replicates wherein purified BSH is treated with iodoacetamide (IAA) or glycocholic acid (GCA) prior to CA-AMCA addition wherein each replicate shows that the CA-AMCA probe binds to canonical BSH substrate-binding site, and is turned over in a cysteine-dependent manner.
Figure 6B:
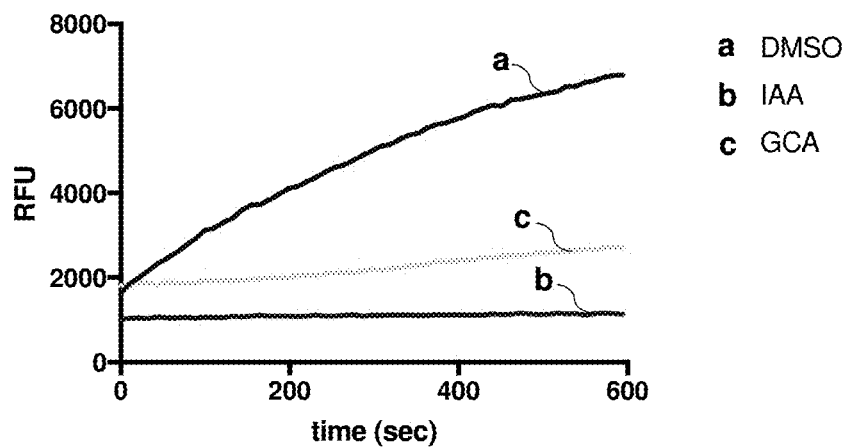
Figure 6C:
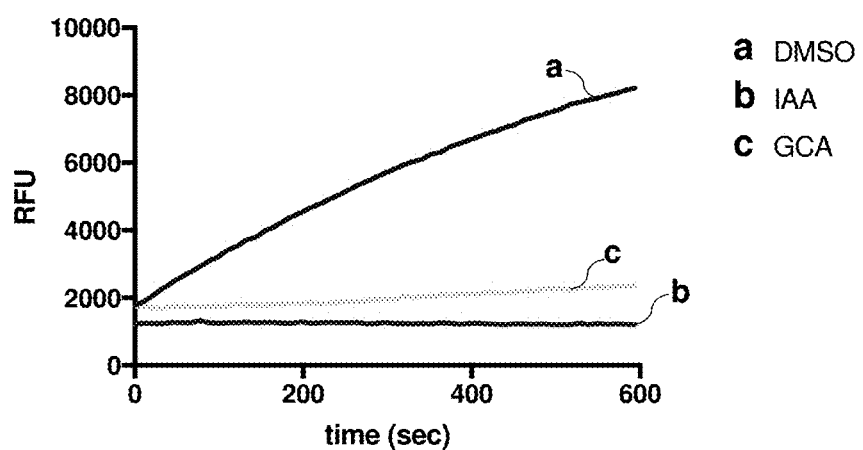

When the CA-AMCA probe was added to buffer containing purified BSH, a fluorescence curve consistent with enzymatic turnover of the synthetic substrate was observed (FIG. 4A). No increase in fluorescence was observed when the probe was added to buffer alone or to buffer containing an unrelated hydrolase (FIG. 5), implying that the probe is stable in aqueous solutions and has selectivity for BSH. Fluorescent signals for substrate turnover could be detected with as low as mid-nanomolar enzyme concentrations, which is considerably less enzyme when compared to micromolar concentrations required for conventional ninhydrin assays with purified BSH. The probes unexpectedly displayed substrate inhibition, which is not observed with native BSH substrates, but is commonly observed with many other enzyme-substrate reactions. Furthermore, robust signals could be reliably observed in the low micromolar substrate concentration range before any indication of substrate inhibition. Product formation was additionally confirmed through coupling of the BSH reaction to a secondary HPLC-based assay. Attenuated activity was observed when a large amount of the native substrate, glycocholic acid, was added to the reaction (FIG. 4B and FIGS. 6A-6C), which indicates that the probes bind the canonical BSH substrate-binding site. Addition of iodoacetamide, which covalently caps nucleophilic cysteines, completely ablated substrate turnover, which suggests that the probes are being hydrolyzed in a cysteine-dependent mechanism that is consistent with native substrate hydrolysis (FIG. 4B and FIGS. 6A-6C). After confirming that CA-AMCA was behaving similarly to a native substrate, the efficiency of CA-AMCA turnover by BSH was quantitatively analyzed, and further biochemical characterization revealed a low two-digit micromolar Michaelis-Menten constant ($K_m$=26 µM; FIG. 7 and FIGS. 8A-8C), which is unexpectedly lower than reported values for native BSH substrates.

Figure 7:
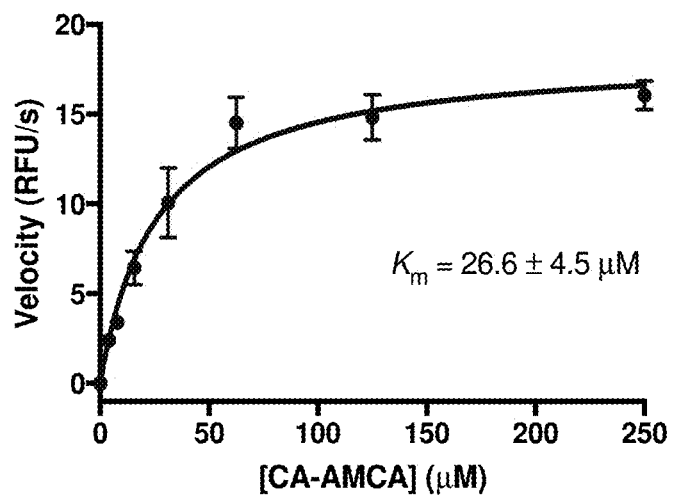
FIG. 7 is a Michaelis-Menten curve for the CA-AMCA probe generated by treating a buffered solution of purified BSH with varying concentrations of CA-AMCA and plotting the turnover rates against substrate concentration.
Figure 8A:
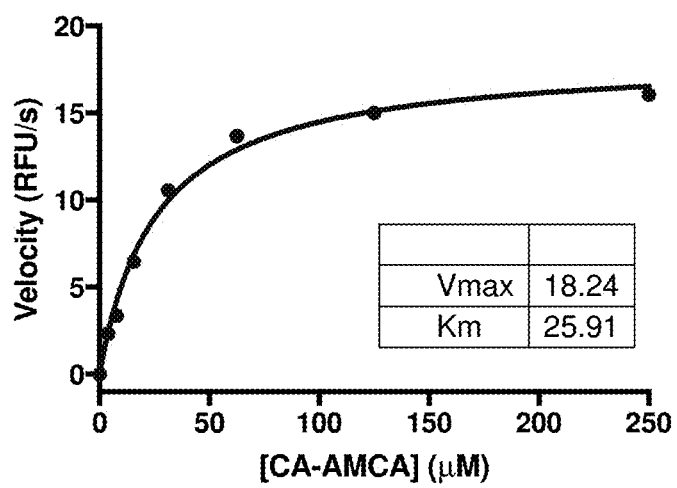
FIGS. 8A-8C are graphs showing results from analyzing individual replicates wherein BSH was treated with 150 µM CA-AMCA, and substrate turnover was assessed through monitoring fluorescence at 450 nm when excited at 350 nm; initial velocities were recorded at several probe concentrations and plotted as a $K_m$ curve; the triplicate results show that individual Km curves for the probe show affinities similar to reported values for native substrates.
Figure 8B:
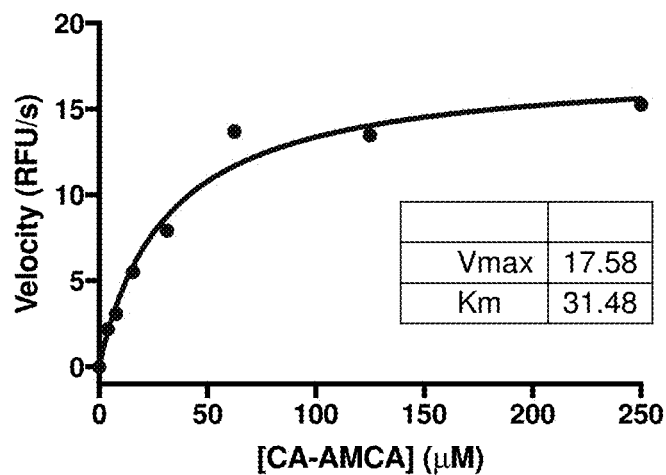
Figure 8C:
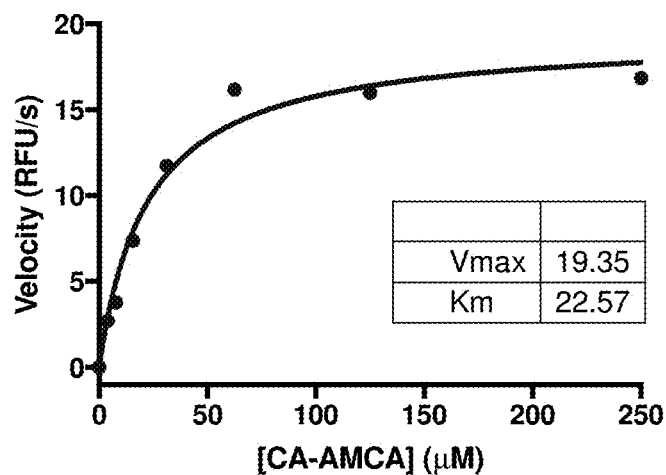

Next, the assay was used to determining the affinity of small-molecule modulators of BSH. Selective pharmacological modulators of BSH have applications in both medicine and animal husbandry. Furthermore, previous activity-based assays for BSH are incompatible with either monocultures of living cells or multi taxa-containing gut microbiome samples. Therefore, the disclosed probe embodiments are especially well-suited for characterization of small-molecule BSH modulators in protein, whole cell, and microbial community samples. The BA-AMCA probes provided $IC_{50}$ values for the BSH inhibitor CAPE (FIG. 7).

Figure 9A:
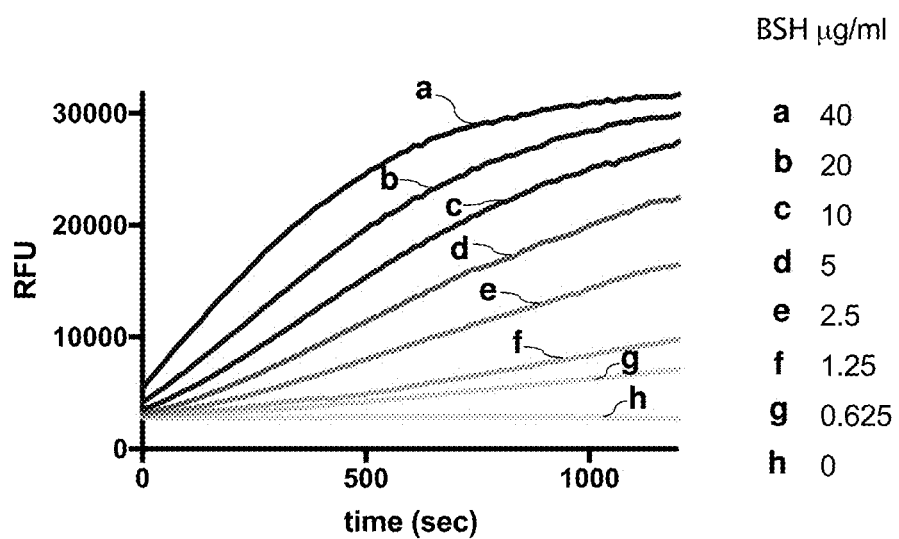
FIGS. 9A-9C are replicate graphs obtained from different replications of adding purified BSH to *E. coli* lysate and further showing that the CA-AMCA probe is capable of reporting on BSH activity in cell lysates.
Figure 9B:
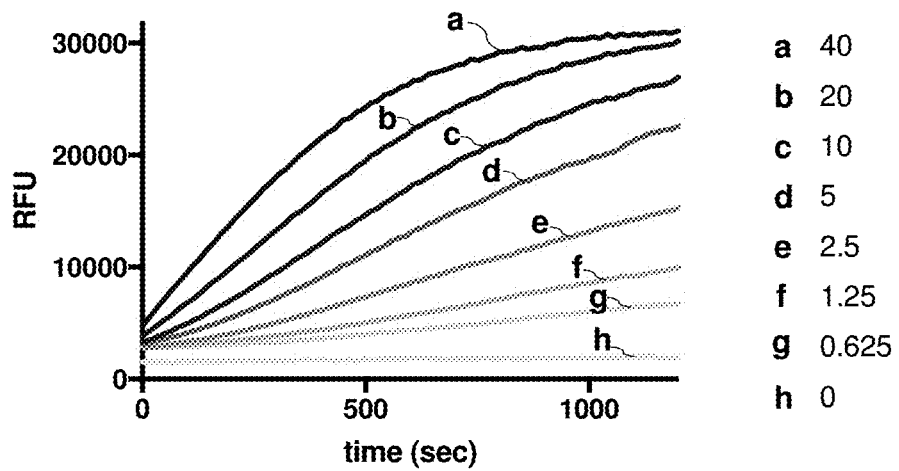
Figure 9C:
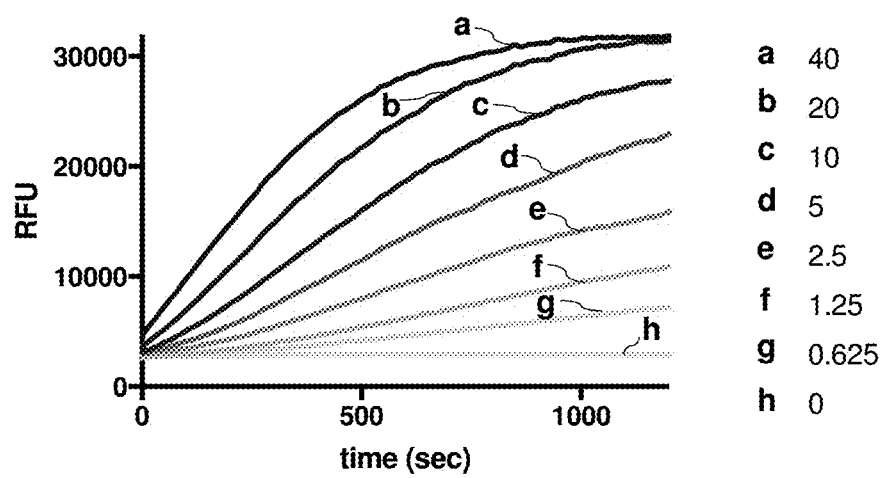
Figure 10A:
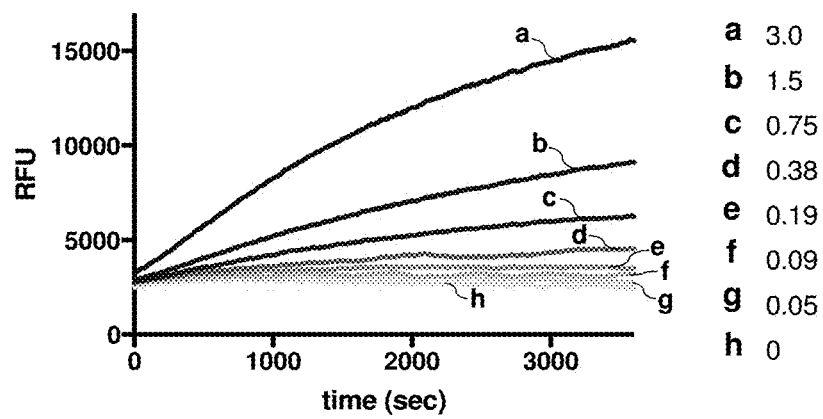
FIGS. 10A and 10B are graphs showing that the CA-AMCA probe is capable of detecting endogenously expressed BSH both in cell lysates and in vivo for *L. plantarum*, which is a BSH-expressing habitant of human gut; the graph of FIG. 10A was obtained by adding CA-AMCA (150 µM) to buffered solutions containing varying amounts of *L. plantarum* lysate.
Figure 10B:
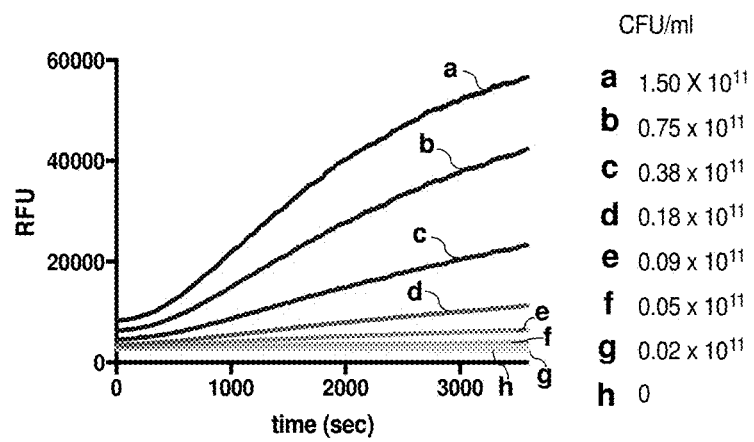
Figure 11A:
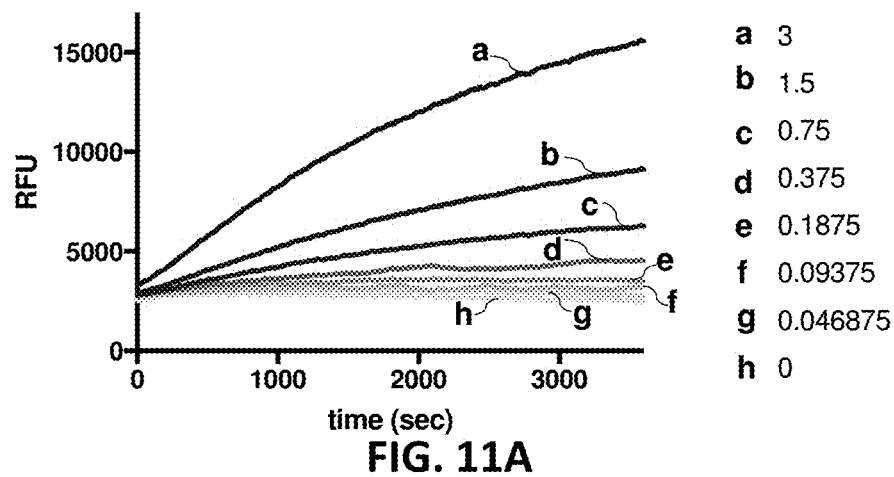
FIGS. 11A-11C are graphs of replicates of results obtained from treating varying concentrations of *L. plantarum* lysate with 150 µM CA-AMCA and that establish that the CA-AMCA probe reports on activity of endogenously expressed BSH in *L. plantarum* lysate; reaction kinetics were monitored through fluorescence quantification.
Figure 11B:
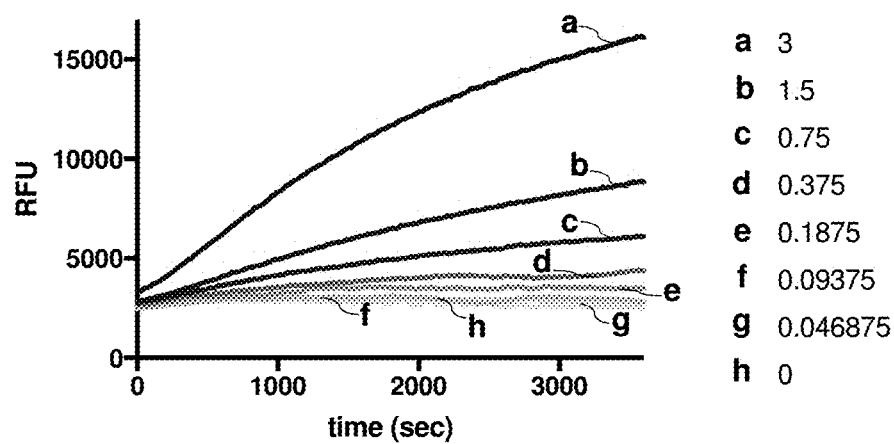
Figure 11C:
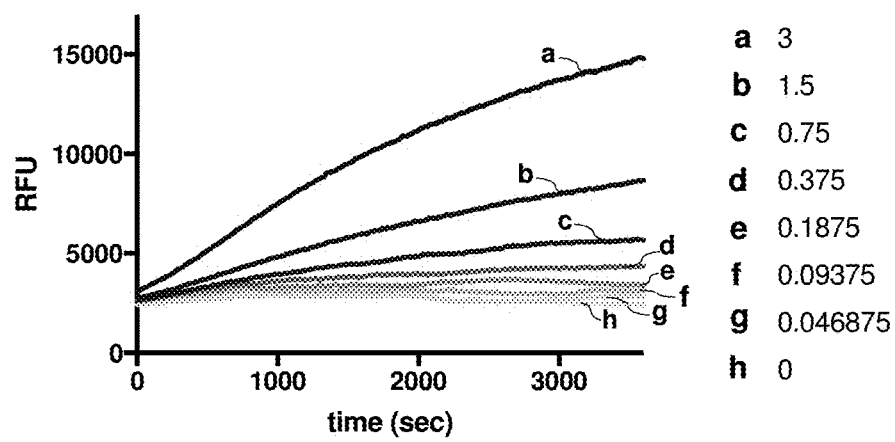

After establishing that the CA-AMCA reporter functions reliably with purified protein, the possibility of analyzing complex biological mixtures was explored through addition of known amounts of BSH to a lysate of *E. coli* cells, which do not express BSH (FIGS. 9A-9C). Rates of substrate turnover correlated with BSH concentration and were comparable to the results obtained with purified protein, suggesting that this assay accurately reports on BSH activity in complex biological samples.

There currently is no quantitative method to continuously and non-destructively monitor bile salt hydrolase activity in vivo, and so the CA-AMCA reporter was evaluated to this end. *Lactobacillus plantarum* is a well-characterized gut symbiont that expresses four forms of BSH. This species is of particular interest because it is a commonly ingested probiotic, which has shown to positively impact hypercholesterolemia. Therefore, *L. plantarum* was employed as a model organism for in vivo characterization of the CA-AMCA probe.

Figure 12A:
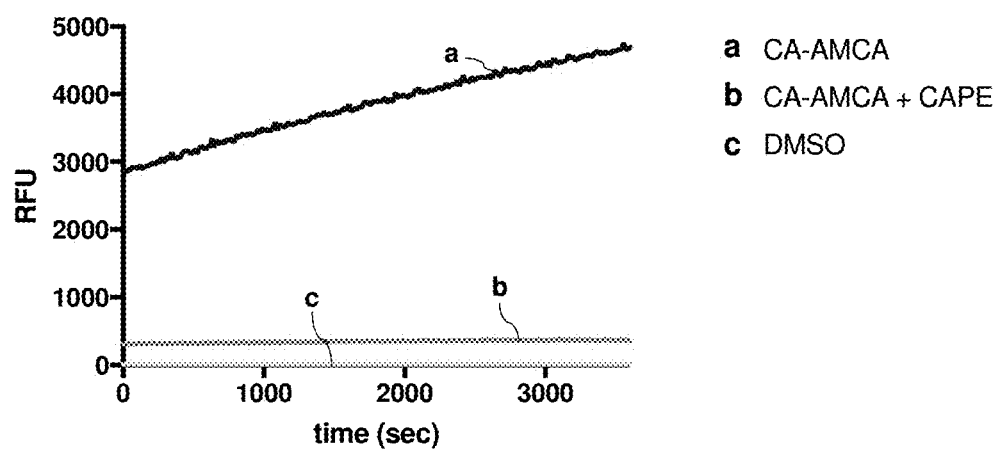
FIGS. 12A-12C are graphs of replicates of results obtained to establish that pharmacological inhibition confirms that observed activity of the CA-AMCA probe is due to BSH; as can be seen by the graphs, no substrate turnover is observed in *L. plantarum* lysate when the BSH inhibitor, CAPE (2 mM), is added to the reaction.
Figure 12B:
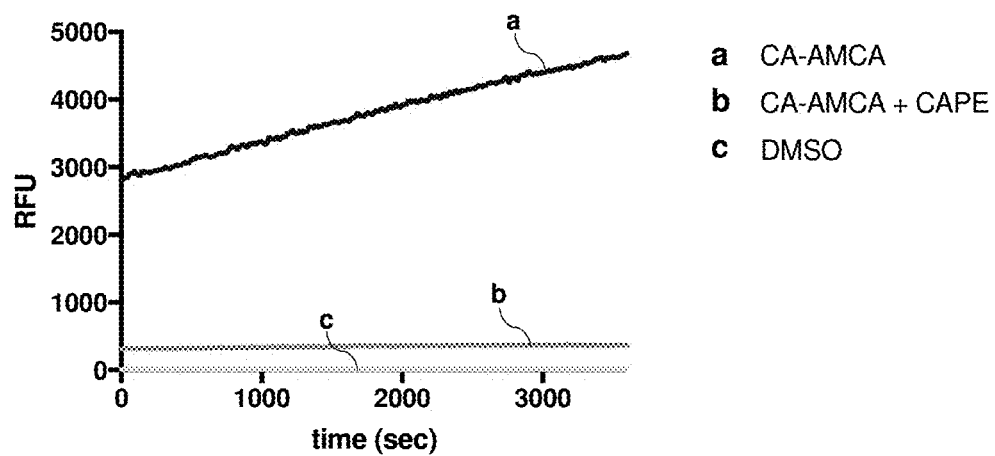
Figure 12C:
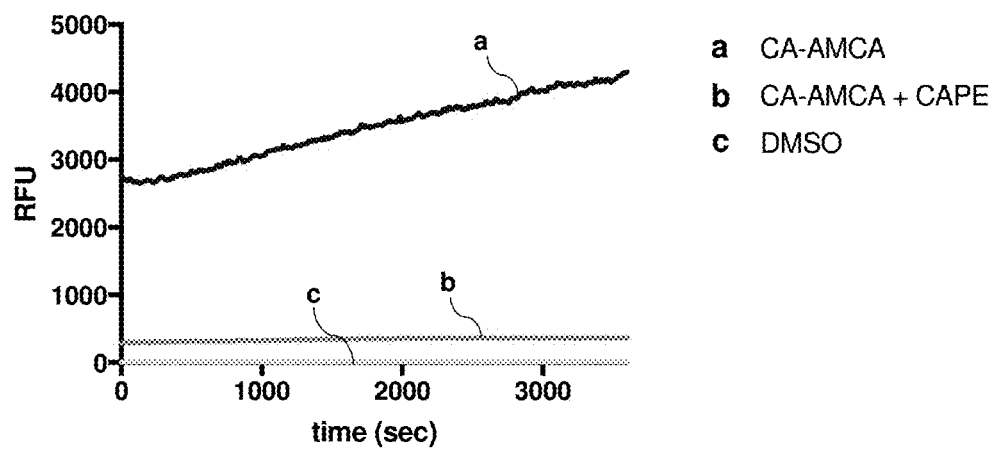
Figure 13A:
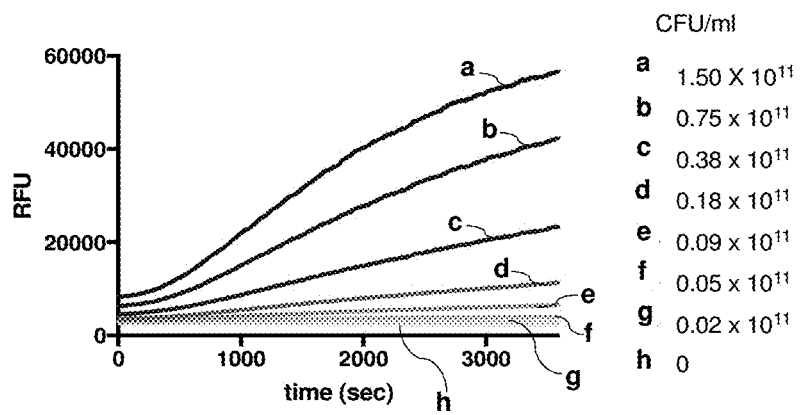
FIGS. 13A-13C are graphs of replicates of results obtained from adding CA-AMCA (150 µM) to whole cell suspensions of *L. plantarum* of varying density, and which confirm that the CA-AMCA probe is capable of evaluating BSH activity in vivo; reaction kinetics were followed through quantification of fluorescence (Ex: 350, Em: 450).
Figure 13B:
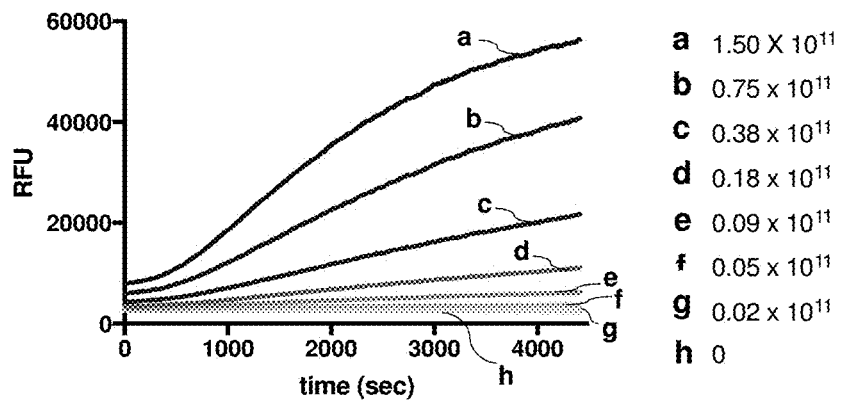
Figure 13C:
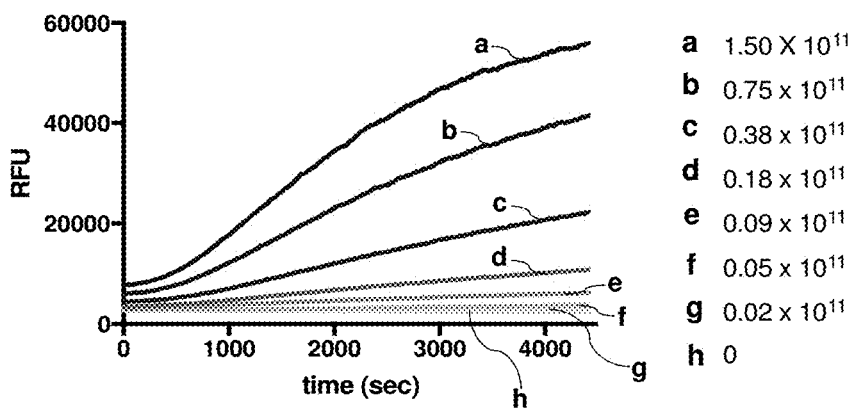
Figure 14A:
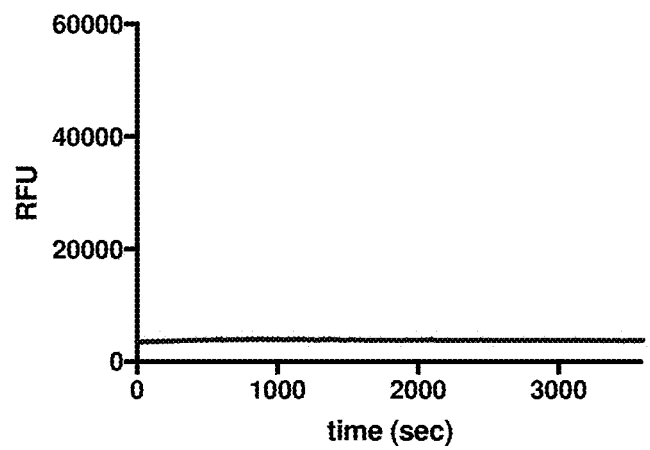
FIGS. 14A-14C are graphs of replicates of results obtained from adding CA-AMCA (150 µM) to whole cell suspensions of *E. coli*, which do not express BSH; the graphs confirm that adding the CA-AMCA does not cause an increase in fluorescence, confirming that it is not turned over in cell lines that do not have BSH; the Y-axis range was set the same as the *L. plantarum* plots for ease of comparison.
Figure 14B:
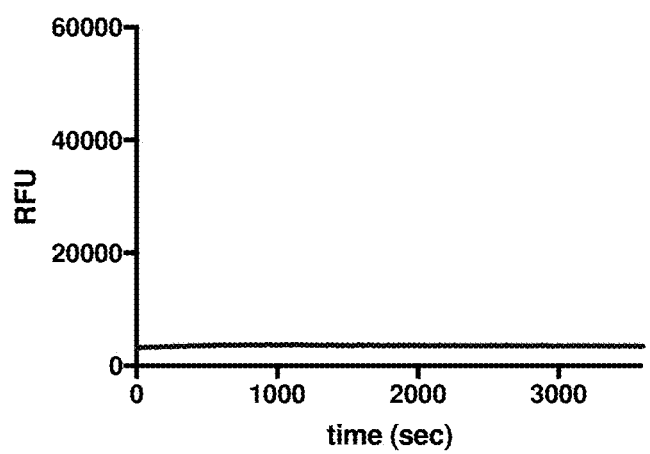
Figure 14C:
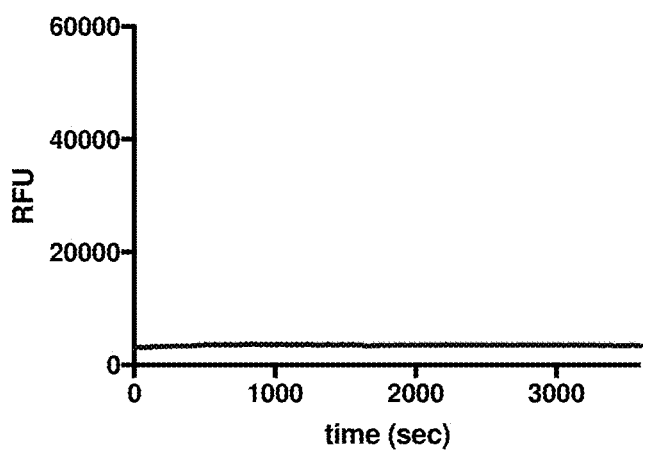
Figure 15:
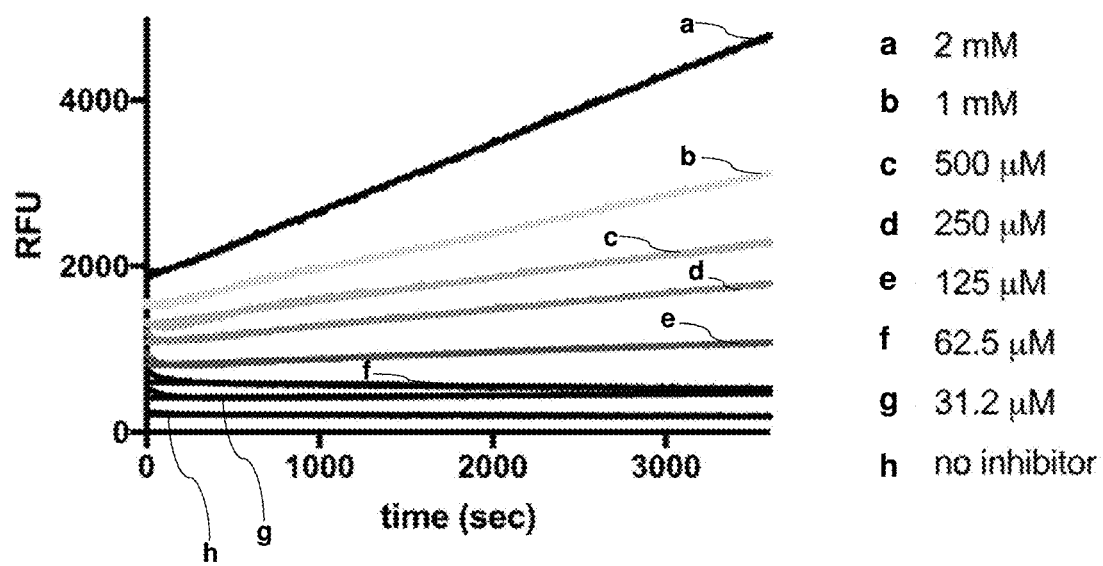
FIG. 15 shows characterization of substrate turnover of another probe embodiment comprising a coumarin detectable moiety in a microbe that is known to endogenously express BSH.
Figure 16:
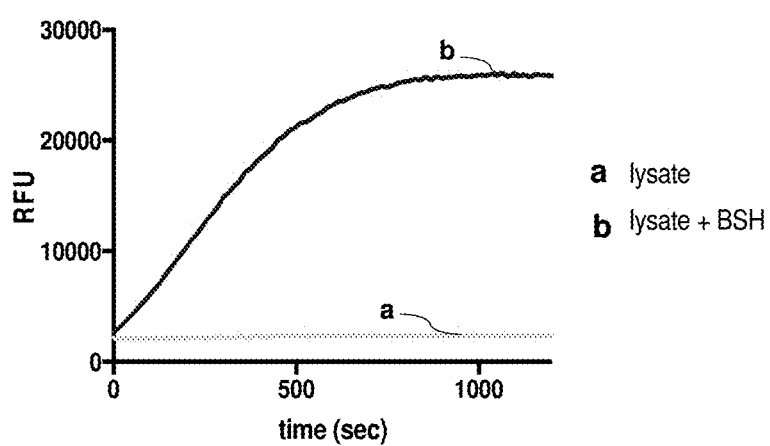
FIG. 16 is a graph showing that CA-AMCA robustly reports on BSH activity in the context of gut microbiome lysates; the graph was generated after CA-AMCA (150 µM) was added to a prepared sample of buffered human gut microbiome lysate (500 g/ml protein) with purified BSH (20 µg/ml) added; substrate turnover was monitored using a fluorimeter.
Figure 17A:
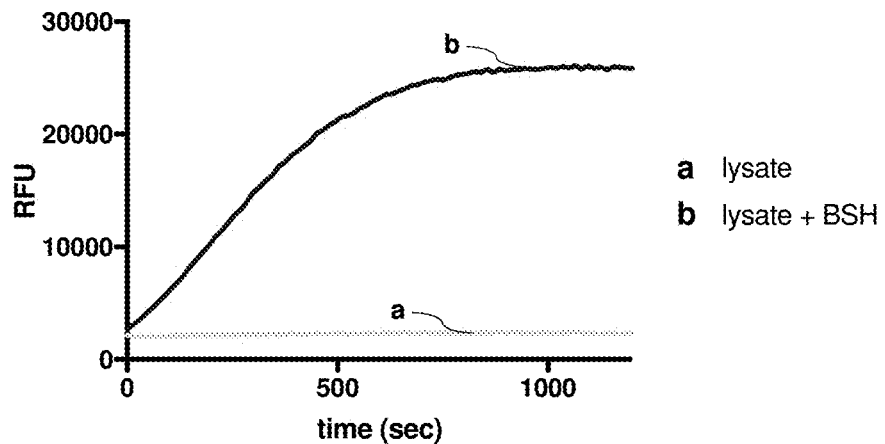
FIGS. 17A-17C are graphs of replicates of results wherein purified BSH was added to gut microbiome lysate and further showing that the CA-AMCA probe reports on BSH activity in gut microbiome lysates.
Figure 17B:
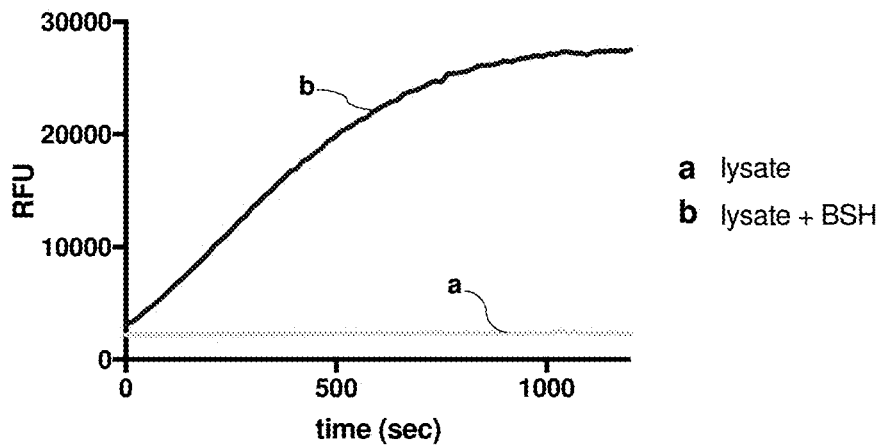
Figure 17C:
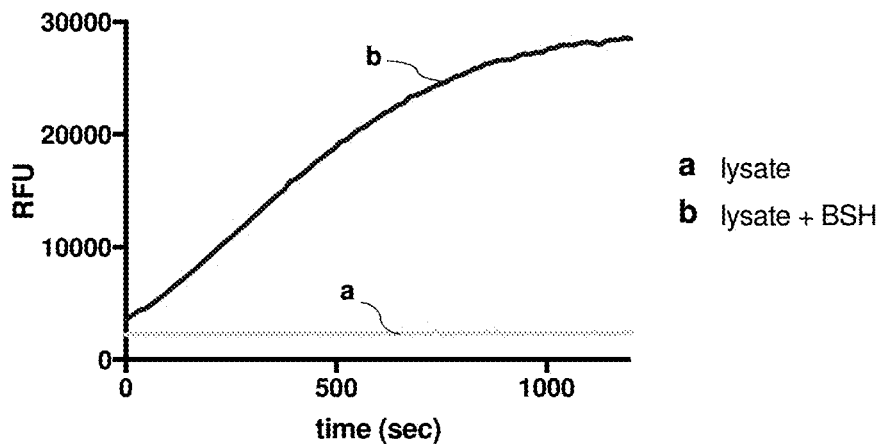

First, *L. plantarum* cell lysate was treated with CA-AMCA, and substrate turnover was observed as expected (FIG. 10A, FIGS. 11A-11C). Activity was not observed when lysate was treated with CAPE, suggesting that the observed activity is due to BSH (FIGS. 12A-12C). No substrate turnover was observed when the probe was added to a cell lysate of a microbe (*E. coli*) that does not express BSH (FIGS. 9A-9C). Second, CA-AMCA was evaluated in whole-cell monocultures of *L. plantarum*. Cells were grown until exponential phase and suspended in buffer for analysis. Addition of BA-AMCA to a suspension of live *L. plantarum* cells yielded fluorescence plots that are consistent with substrate turnover (FIG. 10B, FIGS. 13A-13C). No activity was observed when the probe was added to a suspension of living microbes that do not express BSH (FIGS. 14A-14C). This is currently believed to be the first non-destructive whole-cell analysis of BSH activity. Finally, showing that small-molecule BSH modulators can be characterized using the BA-AMC reporters, the probe velocities were consistent with the amount of CAPE added to the whole-cell suspension (FIG. 15).

This assay is especially beneficial for the characterization of BSH activity in gut microbiome extracts from human fecal samples because there are currently no simple methods for this. Such a method could be valuable for clinicians to quantify net BSH activity in patient samples. So, it was next determined if the CA-AMCA reporters could function in complex gut microbiome samples. For the representative gut microbiome model, human samples that were purchased from a commercial vendor were used. The cell fraction was isolated via centrifugation and subsequently subjected to lysis. Purified BSH was added to processed human gut microbiome samples, and a proportionate increase in substrate turnover was observed (FIG. 16, FIGS. 17A-17C). No basal activity was observed in the control microbiome sample, but it currently is believed that activity could be quantified in native samples that were more recently obtained. Nonetheless, this is the first demonstration of continuous quantitative analysis of BSH activity in a gut microbiome sample.

This assay is the first example of real-time continuous monitoring of BSH activity. It is also demonstrated, for the first time, that BSH activity can be monitored using this approach in whole cells and in the presence of gut microbiome homogenate. The compositions and methods herein can be used clinically to quantify BSH activity in patient samples and form a superior strategy for discovering small molecule modulators of BSH because they are applicable to both whole-cell and gut microbiome samples.

Example 2

Several bile acid based chemical probes were generated to assay for active enzymes that bind bile acids. Activity-based protein profiling probes were used, which include applying chemical probes to selectively and covalently label active enzymes with a specific activity. Subsequent to protein labeling, the sample can be enriched and subject to various analyses, including imaging and mass spectrometry.

Probes were designed to specifically react with enzymes that hydrolyze bile salts to free bile acids. In the animal and human gut, this activity is attributed primarily to bile salt hydrolases, which are enzymes common to many probiotic formulations, and upregulation of their activity has been correlated with healthy cholesterol profiles. Bile salt hydrolases include cysteine hydrolases that react via a catalytic triad, which includes an N-terminal cysteine. BSH is trapped through incorporation of functional group into the bile acid core that reacts with the catalytic cysteine, but is not susceptible to subsequent hydrolysis. An acrylamide moiety was employed, which can be used to label nucleophilic cysteines, and the electrophilic center was placed at the carbon reacting with the nucleophilic cysteine. The acrylamide is internal, and therefore, decreases non-specific thiol adduct formation through steric effects. Additionally, an alkyne tag was incorporated into a part of the molecule that should not interfere with ligand binding, as shown by x-ray co-crystal structures.

Binding of BA-ABP to purified recombinant *Lactobacillus plantarum* BSH was assessed through incubation with probe in buffer (FIG. 18A). Labeling of BSH was dose-dependent and could be attenuated upon addition of free bile salts, indicating that the BA-ABP probes compete for the same site as the authentic substrate (FIG. 18B). Binding was ablated upon pre-treatment with iodoacetimide, indicating that BA-ABP labeling likely occurs through a reactive cysteine, which is consistent with the proposed mechanism. Additionally, labeling was time-dependent.

The BSH probes were then assayed for retention of function in the presence of a complex cell lysate. Purified BSH was added to an organism that is not known to endogenously express BSH to precisely control this variable. BA-ABP did produce a fluorescent band that is consistent with BSH labeling, along with several other unknown targets (FIG. 19A). After confirming that the BSH-ABP is capable of labeling BSH in complex biological mixtures, application of the probe was assayed for detection of endogenous BSH. *L. plantarum* was used because its expression of BSH is well-documented, and this organism is found in many popular over-the-counter probiotic formulations for support of healthy cholesterol levels. Subsequent to incubation of the probe with lysate, fluorescence imaging revealed a band consistent with BSH, along with several others (FIG. 20A). Labeling in vivo was also confirmed, and a considerably less complex profile was observed (FIG. 20B).

Figure 21:
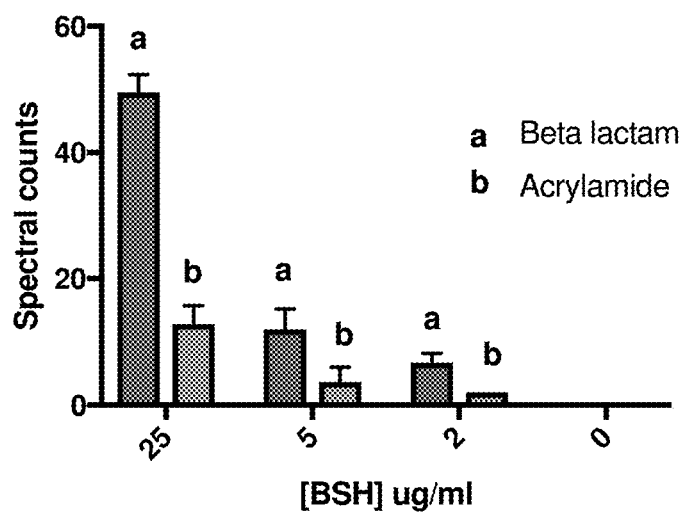
FIG. 21 shows that representative probe embodiments disclosed herein quantitatively track BSH activity in bacterial lysates via mass spectrometry.

BSH presence in a bacterial lysate was then quantified using proteomics. The amount of BSH in the sample correlated strongly with the peptides observed with activity-based protein profiling (FIG. 21).

Figure 22:
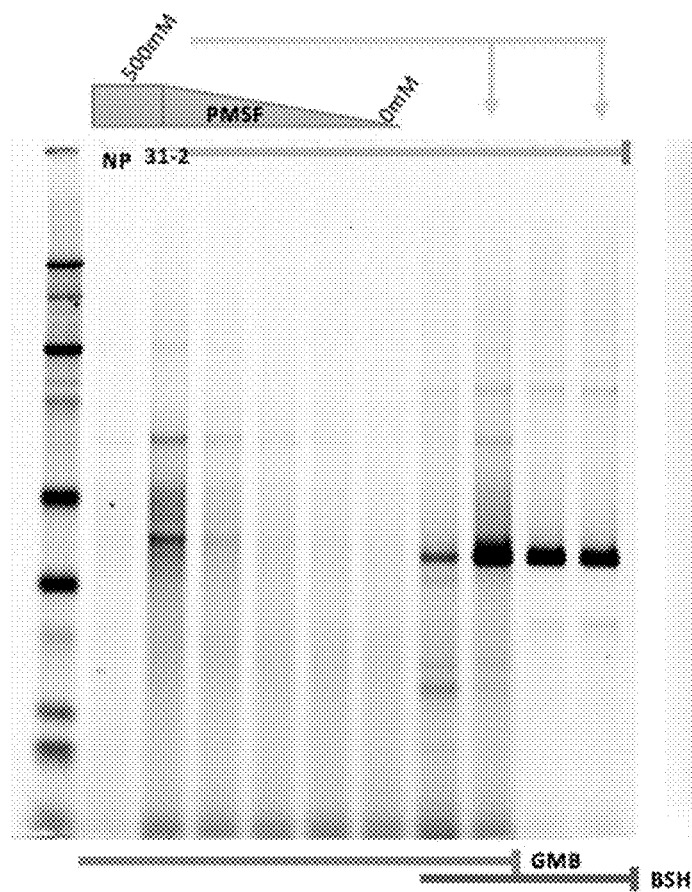
FIG. 22 shows labeling of BSH in the presence of human gut microbiome lysate.

The probes were assayed for activity in human gut microbiome extracts. Gut microbiome lysate was treated with a BSH ABP, and labeling was observed (FIG. 22).

Example 3

Unless otherwise noted, all reagents were obtained from commercial sources and used without further purification. All reagents and solvents were obtained from commercial suppliers and were used as is without further purification. Chemical shifts are reported in ppm ($\delta$) referenced to the NMR solvent residual peak, and coupling constants (J) are in hertz. All reactions were monitored using TLC and LTQ-MS. For characterization of new compounds, $^1$H, $^{13}$C NMR and LTQ-MS data have been included. Mass Spectrometry (HRMS) was carried out at PNNL.

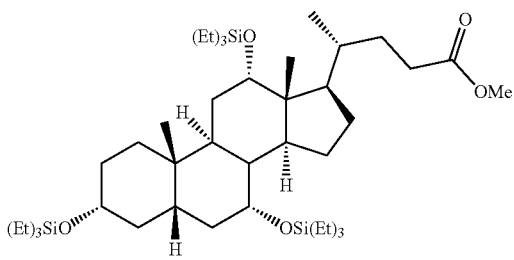

Cholic acid methyl ester was synthesized according to a literature protocol. Cholic acid methyl ester (1.5 g, 4.75 mmol) was added to an oven-dried round-bottom flask charged with a stir bar and sealed with a rubber septum. The flask was evacuated and then filled with nitrogen, and this cycle was repeated for an additional two times. Dichloromethane (15 mL) was added, and the reaction was cooled in an ice bath. TES-OTf was added slowly to the stirring solution. DIEA was then slowly added. The ice bath was removed and the reaction was allowed to warm to room temperature for one hour. The reaction was then diluted in ethyl acetate and washed with NH4Cl and then brine. After removing solvent via rotary vaporization, the crude reaction mixture was purified through silica gel chromatograpy using a Biotage Isolera. Product was isolated as a clear colorless oil (2.7 g, 75% yield).

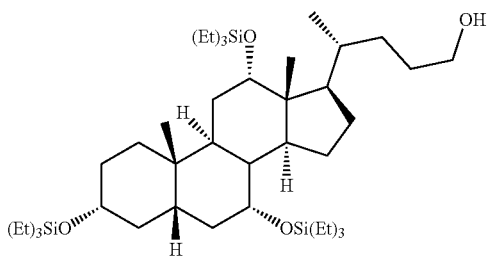

To an oven-dried round bottom flask charged with a stir bar, was added (1.5 g, 2.0 mmol) of the ester product illustrated above. The flask was sealed with a rubber septum and subsequently evacuated using a vacuum pump followed by a nitrogen fill, and this cycle was repeated twice more. THF (10 ml) was then added. The reaction was then cooled with an ice bath. A suspension of lithium aluminum hydride (228 mg, 6 mmol) was then slowly added. After stirring for thirty minutes, the reaction was kept at 0° C., and 240 ul water was added and the solution was allowed to stir. 240 ul 1M NaOH was then added, and the reaction was allowed to stir. 720 uL of water was then added, and the solution was allowed to stir while warming to room temperature over the course of thirty minutes. Two scoopfuls of MgSO4 were added and the mixture was allowed to stir for 15 minutes. The reaction mixture was then filtered through a bed of Celite. The Celite bed was washed with ethyl acetate. The filtrate was then dried over sodium sulfate. After removal of solvent via rotary vaporization, the crude reaction mixture was subjected to silica gel chromatography using a Biotage Isolera. Product was isolated as a clear colorless oil (1.3 g).

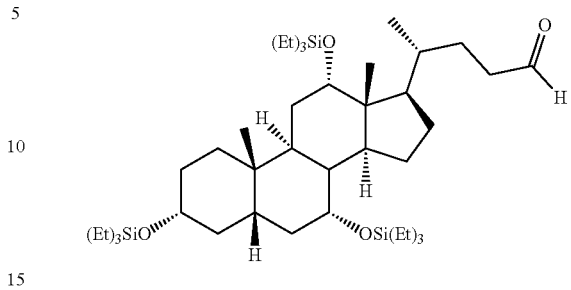

An oven-dried round bottom flask was charged with a stir bar and sealed with a rubber septum. The flask was placed under inert atmosphere through subjection of three cycles of evacuation-nitrogen filling. Dichloromethane (5 mL) was then added, followed by oxalyl chloride (214 ul, 2.5 mmol). The reaction was then cooled to −78° C. using a dry ice/acetone bath. DMSO (354 ul, 5 mmol) was then added dropwise. The reaction was allowed to stir for 15 minutes. The alcohol from above (377 mg, 0.5 mmol) was then added dropwise in a 2 mL solution of dichloromethane. The reaction was allowed to stir for 30 minutes. Triethylamine (1.1 ml, 7.5 mmol) was then added dropwise. The reaction was then allowed to stir for an additional 30 min at −78° C., after which time it was allowed to warm to room temperature and stir for an additional hour. The reaction was suspended in ethyl acetate and washed with water, followed by ammonium chloride, and then brine. The organic layer was then dried over sodium sulfate. After solvent was removed through rotary vaporization the crude mixture was subjected to silica gel chromatography. The product would not be separated from a close running TLC spot, and was carried on to the next reaction without further purification.

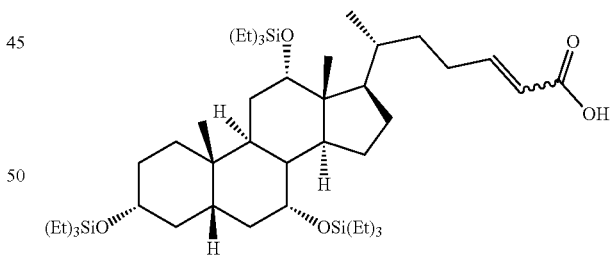

The crude aldehyde intermediate illustrated above (180 mg) was added to an oven-dried round bottom flask charged with a stir bar. Malonic acid (26 mg, 0.25 mmol) was then added, followed by pyridine (1 ml), and then piperidine (1 drop). The reaction was then heated to 95° C. for 1 hour. Pyridine was removed via rotary vaporization. The crude residue was diluted in ethyl acetate and then washed with 1 N HCl. The organic layer was then dried over Na2SO4. After removing solvent via rotary vaporization, the crude reaction was subjected to silica gel chromatography using a Biotage Isolera. Product was isolated as clear colorless gelatinous oil (193 mg mg).

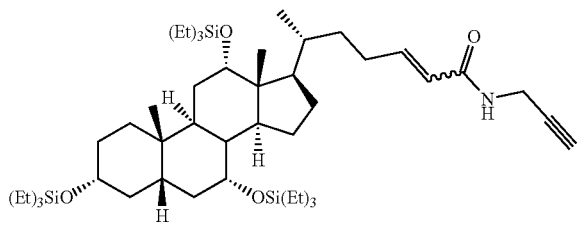

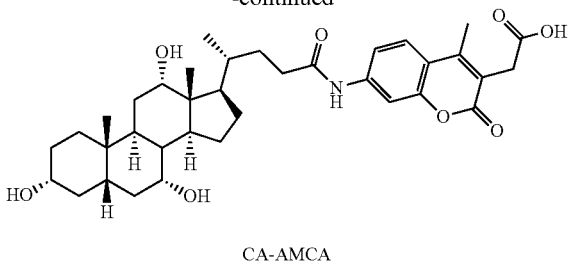

CA-AMCA

Figure 23:
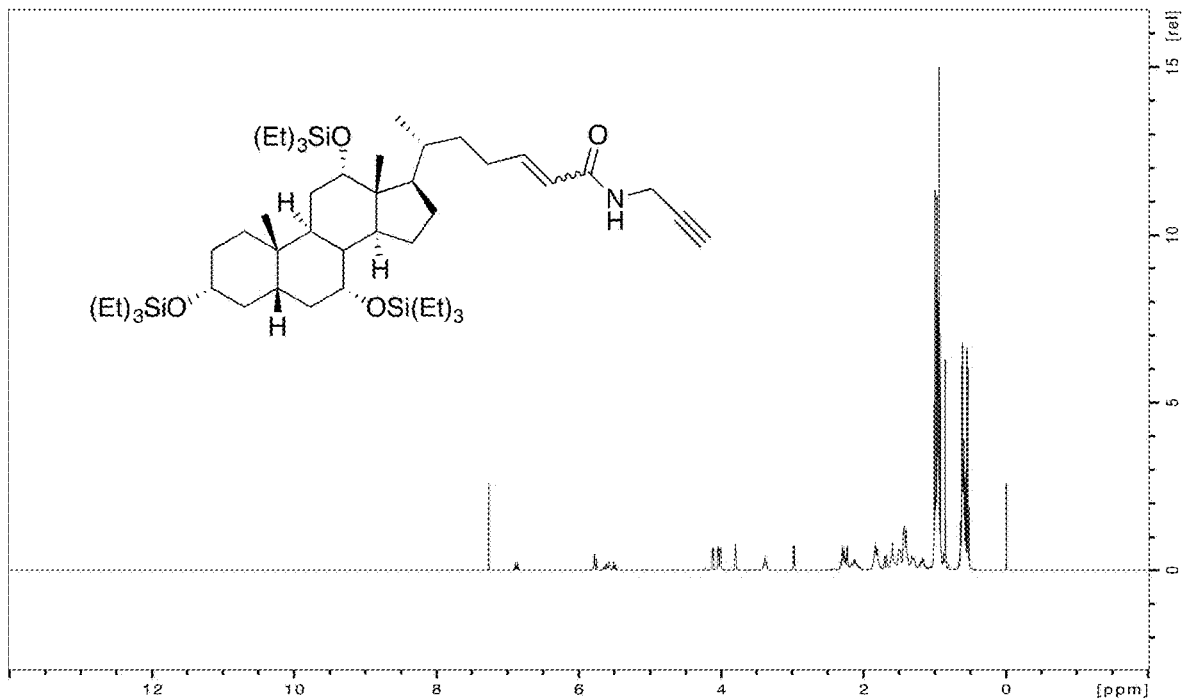
FIG. 23 is a $^1$H-NMR spectrum of a representative probe embodiment comprising protected hydroxyl groups on the sterol component of the probe.

The α,β-unsaturated acid from above was placed into an oven-dried round bottom flask charged with a stir bar. HATU was added followed by DMF, DIEA, and propargylamine. The reaction was allowed to stir at room temperature overnight. The reaction mixture was then diluted in to ethyl acetate, and washed with brine followed by ammonium chloride. The organic layer was then dried over sodium sulfate. After removal of the solvent via rotary vaporization, the crude mixture was purified via silica gel column chromatography. Product was isolated as a clear colorless resin. FIG. 23 shows a $^1$H NMR spectrum of the product.

Synthesis of CA-AMCA. Cholic acid (120 mg, 0.295 mmol) and HATU (112.2 mg, 0.295 mmol), were added to an oven-dried round-bottomed flask charged with a stir bar, followed by DMF (2 ml) and diisopropylethylamine (310 µl). The reaction was allowed to stir for 15 minutes at room temperature, and then AMCA (137.7 mg, 0.59 mmol) was added. The reaction was heated to 50° C. for 4 hrs. The reaction mixture was allowed to cool to room temperature, and then directly loaded onto a reverse phase HPLC column for purification (linear gradient of 10-95% CH$_3$CN in H$_2$O). The product was isolated as a pale orange solid (44.5 mg, 24.3% yield).

Spectral data. $^1$H NMR (500 MHz, DMSO-d6): δ 10.30 (1H, s), 7.79-7.67 (2H, m), 7.51-7.43 (1H, m), 4.32-4.21 (1H, m), 4.11-4.04 (1H, m), 4.00-3.94 (1H, m), 3.81-3.73 (1H, m), 3.64-3.48 (3H, m), 3.21-3.10 (1H, m), 2.53-2.51 (1H, m), 2.42-2.08 (7H, m), 2.03-1.93 (1H, m), 1.87-1.70 (3H, m), 1.68-1.58 (2H, m), 1.47-1.10 (10H, m), 1.00-0.90 (4H, m), 0.80 (3H, s), 0.58 (3H, s); $^{13}$C NMR (125 MHz, DMSO-d6) δ 176.18, 175.05, 173.32, 173.00, 171.92, 168.94, 161.35, 152.79, 149.02, 142.58, 126.47, 115.63, 115.53, 105.65, 71.47, 70.90, 66.70, 46.55, 41.99, 41.85, 40.92, 40.60, 35.78, 35.60, 35.37, 34.05, 33.44, 31.69, 30.87, 29.05, 27.73, 26.69, 23.27, 17.63, 15.36, 12.83. HRMS-ESI (m/z): [M+Na]$^+$ calculated for C$_{36}$H$_{49}$NO$_8$, 646.335; found 646.333.

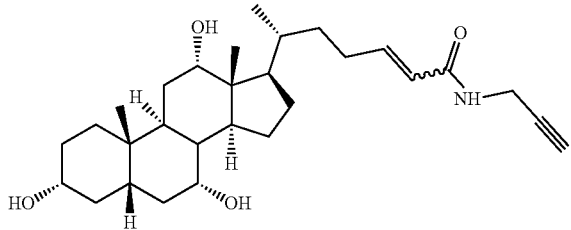 [SMILES: C#CCNC(=O)C=CCC[C@@H](C)[C@H]1CC[C@H]2C3[C@H](O)C[C@@H]4C[C@H](O)CC[C@]4(C)[C@H]3C[C@H](O)[C@]12C]

Figure 24:
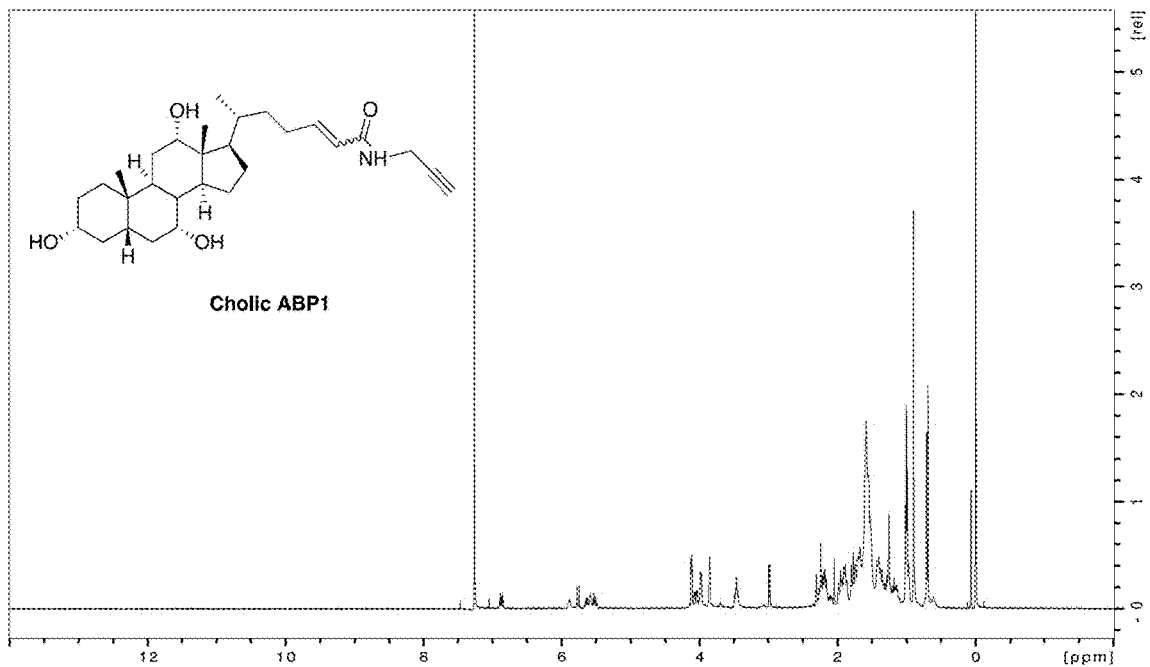
FIG. 24 is a $^1$H-NMR spectrum of a representative probe embodiment comprising free hydroxyl groups on the sterol component of the probe.

The TES protected compound from above (25 mg, 0.03 mmol) was added to an oven-dried round bottom flask charged with a stir bar. THF (1 ml) was added, followed by 1 M TBAF-THF solution (0.3 ml). The reaction was then stirred at room temperature overnight. The reaction was then evaporated onto silica gel and loaded onto a Biotage silica gel column for chromatography. Product was isolated (10 mg). FIG. 24 shows a $^1$H NMR spectrum of the product.

Figure 25:
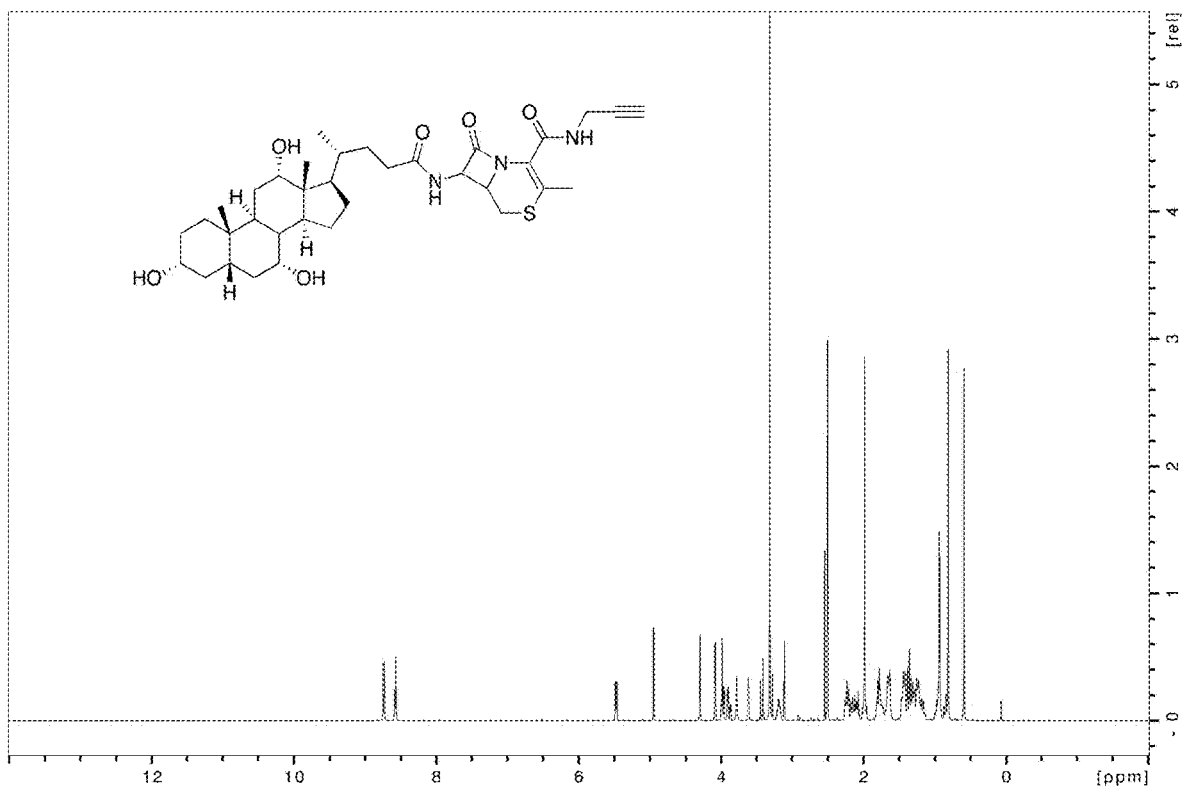
FIG. 25 is a $^1$H-NMR spectrum of another representative probe embodiment.

Using a similar method, the probe illustrated in FIG. 25 can be made; FIG. 25 also provides the $^1$H NMR spectrum of this product.

In view of the many possible embodiments to which the principles of the present disclosure may be applied, it should be recognized that the illustrated embodiments are only examples and should not be taken as limiting the scope of the disclosure. Rather, the scope is defined by the following claims. We therefore claim as our invention all that comes within the scope and spirit of these claims.

We claim:

1. A probe having a structure satisfying Formula I

Example 4

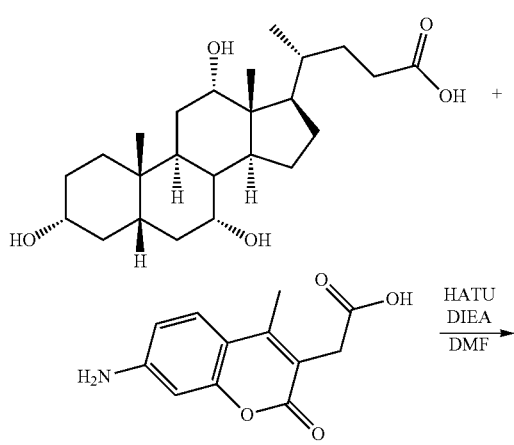

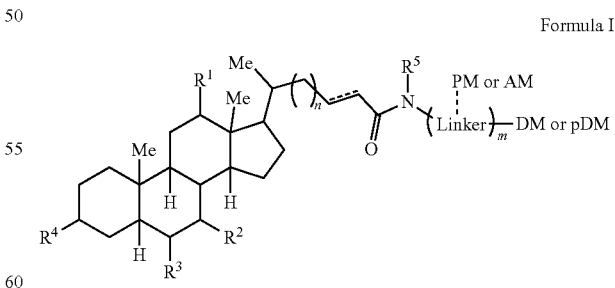

Formula I wherein each of R$^1$, R$^2$, R$^3$, and R$^4$ independently is hydrogen or —OR, wherein each R independently is hydrogen, a counterion that balances a negative charge on the oxygen atom of the —OR group, or heteroaliphatic; R$^5$ is hydrogen or aliphatic; the linker is aliphatic or heteroaliphatic; DM is (i)

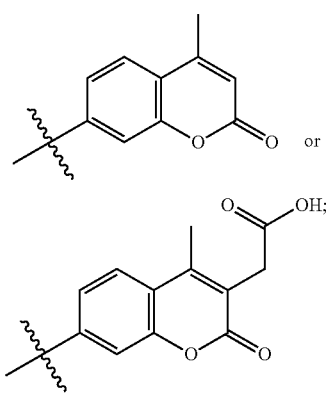

or

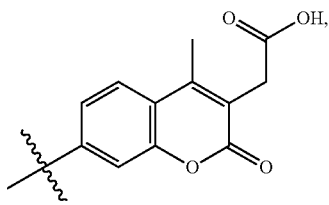

or biotin.

or (ii) biotin; pDM is an alkyne or an azide; PM comprises a benzophenone group or a diazirine group; AM is an alkyne, an azide, an activated ester, a carboxylic acid, a halide, or an alkyl halide; n is an integer ranging from 0 to 10; and m is 0 or 1.

4. The probe of claim 1, wherein each of $R^1$, $R^2$, $R^3$, and $R^4$ independently is hydrogen, —OH, or —O-M$^+$, wherein M$^+$ is Li$^+$, K$^+$, Na$^+$, or NH$_4^+$.

5. The probe of claim 1, wherein the activated ester is an NHS-ester.

2. The probe of claim 1, wherein m is 1 and the linker is —(CH$_2$)$_p$—;

6. The probe of claim 1, wherein m is 0 and the DM group is present and is

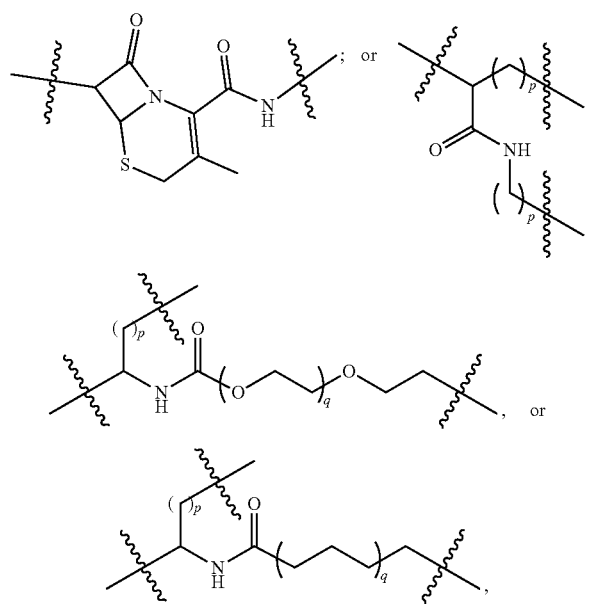

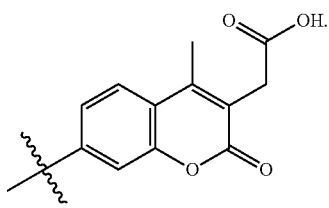 [SMILES: *c1ccc2c(C)c(CC(=O)O)c(=O)oc2c1]

7. The probe of claim 1, wherein m is 1 and both the PM group and the pDM group are present.

8. The probe of claim 1, wherein m is 1 and both the AM group and the pDM group are present.

9. The probe of claim 1, wherein the probe has a structure satisfying Formula IIA or IIB

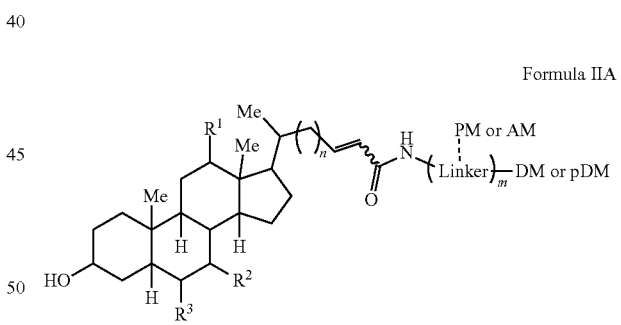

Formula IIA wherein each p independently is as an integer ranging from 1 to 10, and each q independently is an integer ranging from 0 to 10.

3. The probe of claim 1, wherein the DM group is present and is

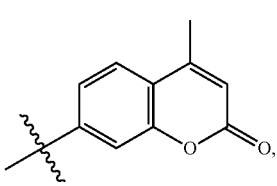 [SMILES: *c1ccc2c(C)cc(=O)oc2c1]

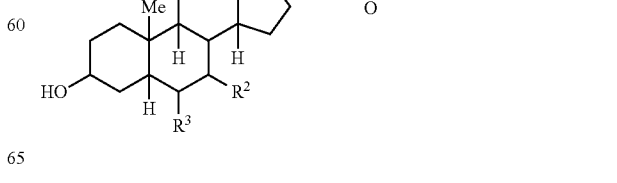

Formula IIB

10. The probe of claim 1, wherein the probe has a structure satisfying one or more of Formulas IIIA-IIIF
Formula IIIA
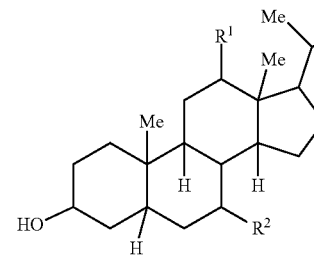
Formula IIIB
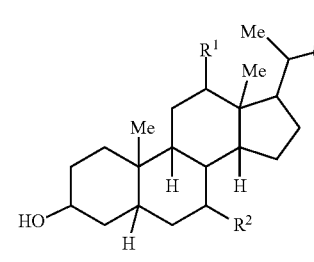
Formula IIIC
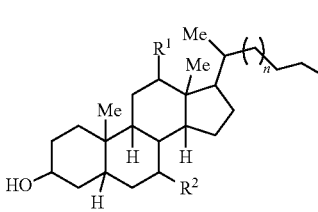
Formula IIID
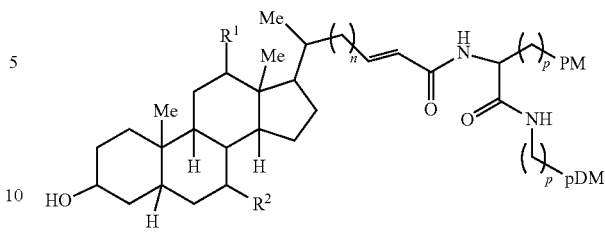
Formula IIIE
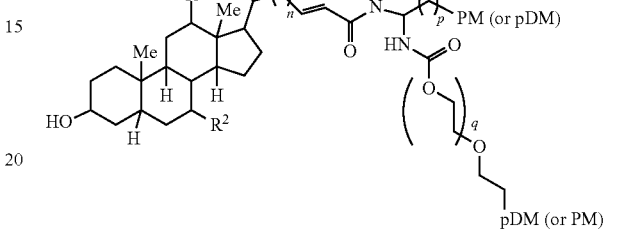
Formula IIIF
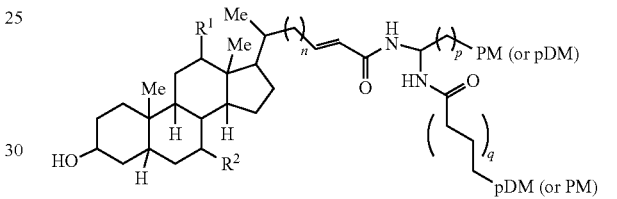
wherein each p independently is an integer ranging from 1 to 10 and each q independently is an integer ranging from 0 to 20.
11. A probe having one of the following sctructures
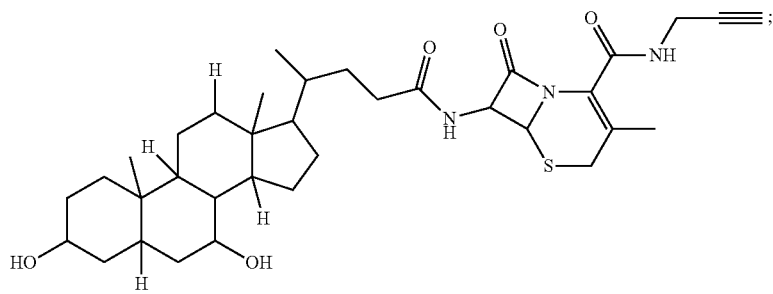
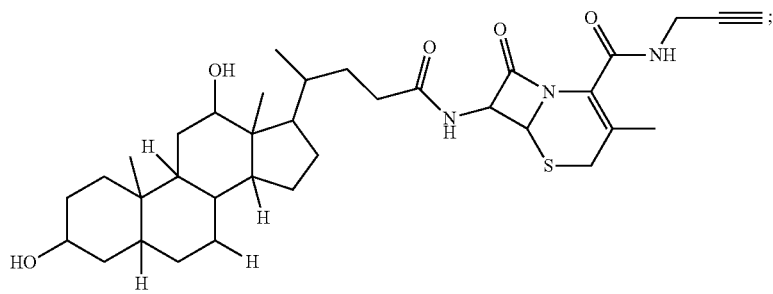

-continued
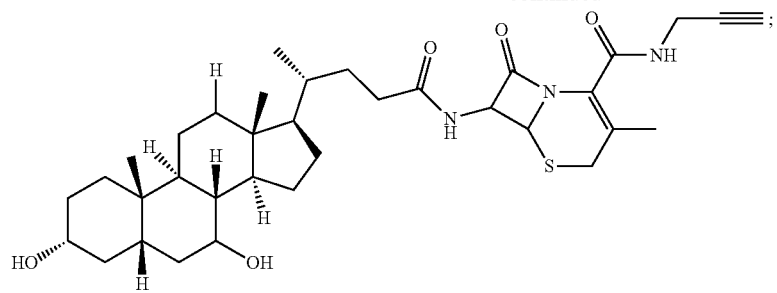
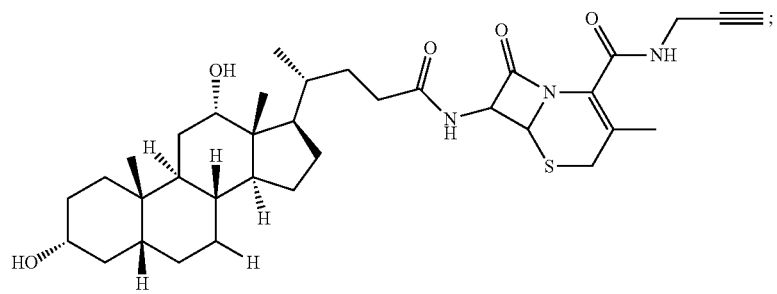
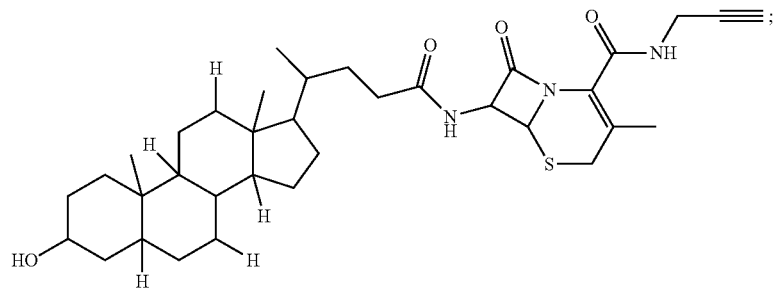
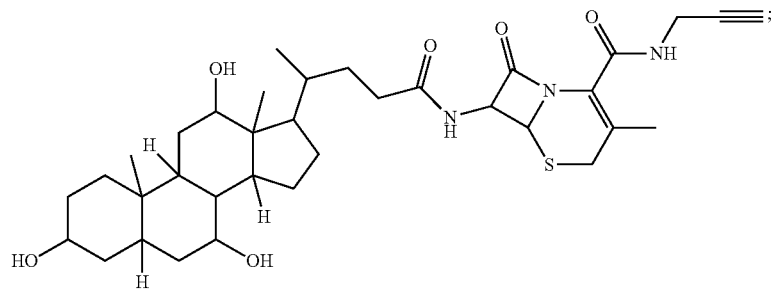
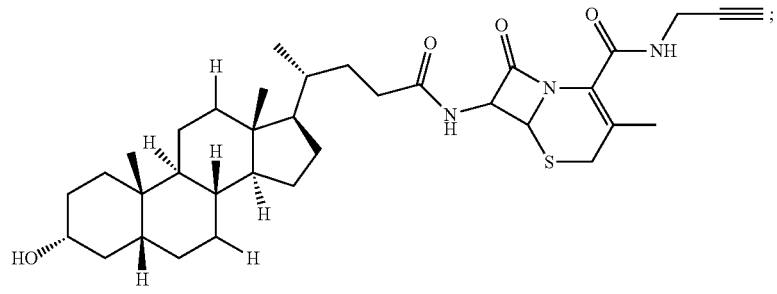

-continued
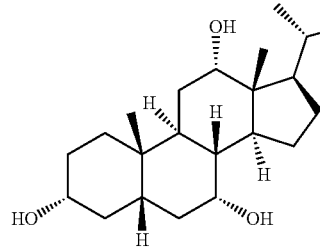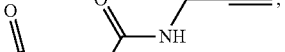
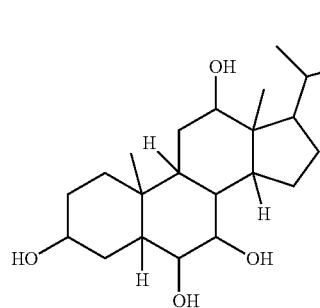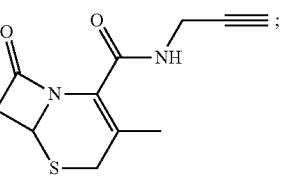
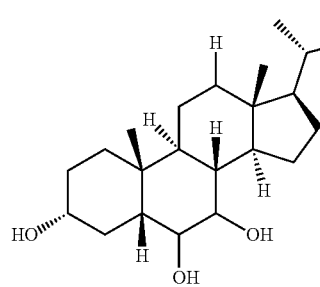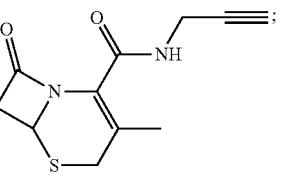
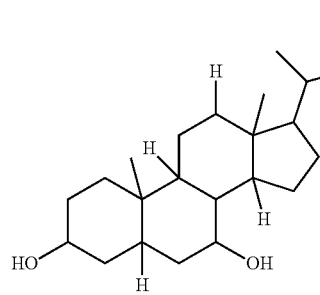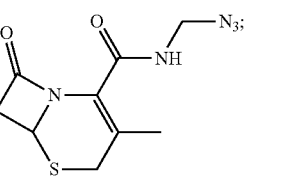
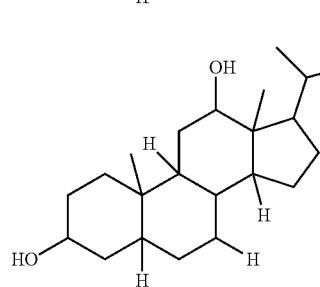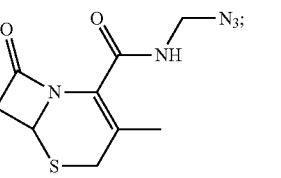

-continued
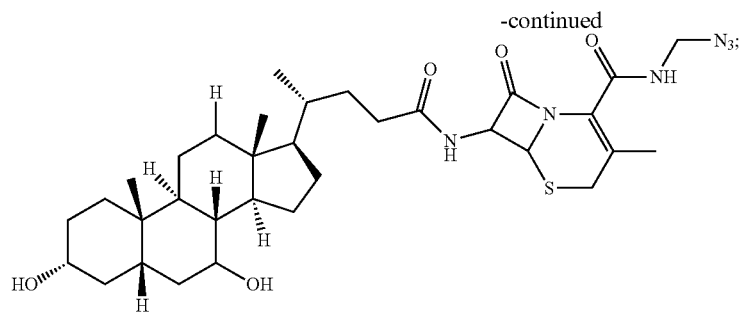
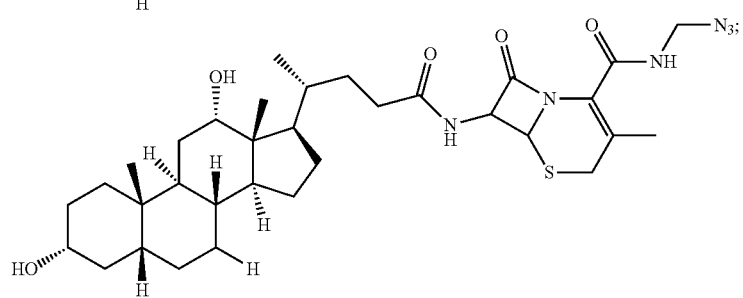
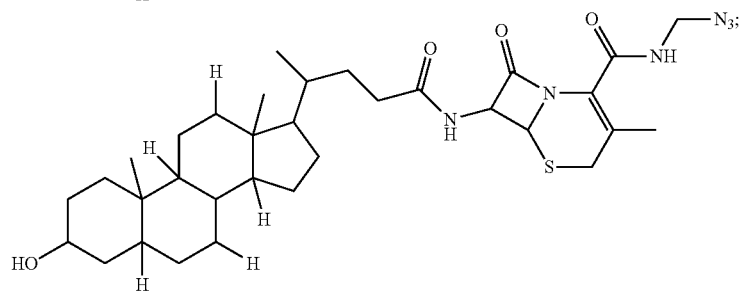
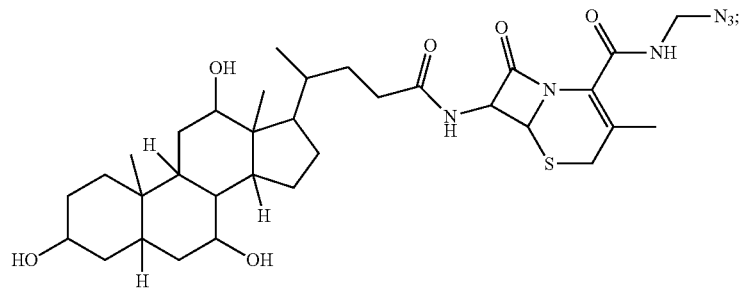
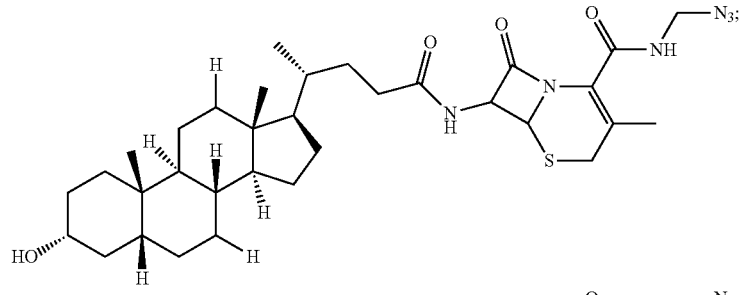
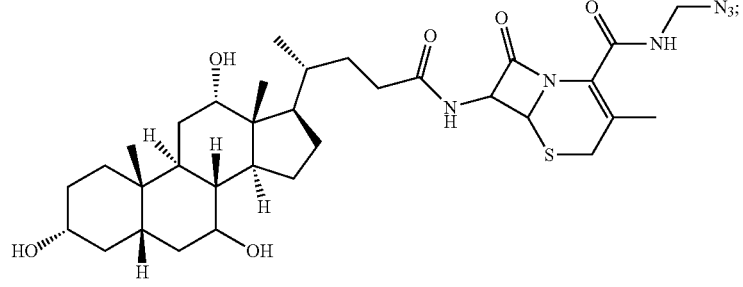

-continued
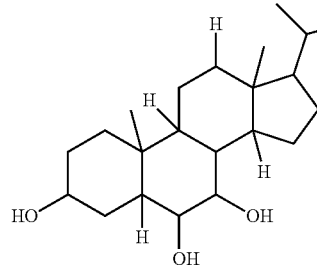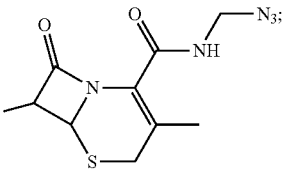
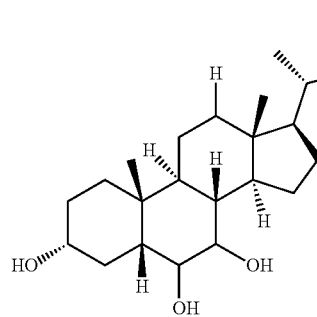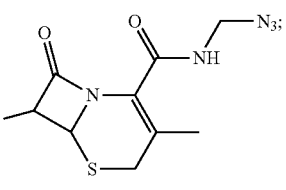
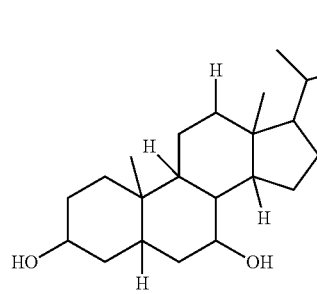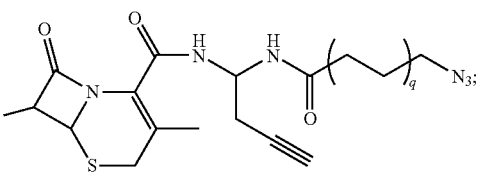
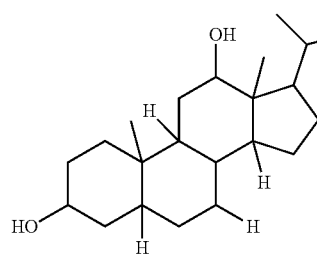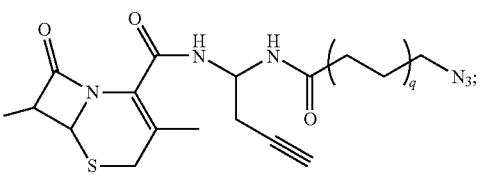
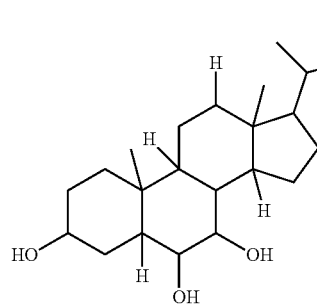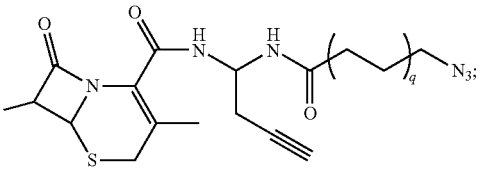

-continued
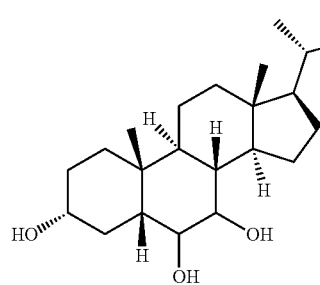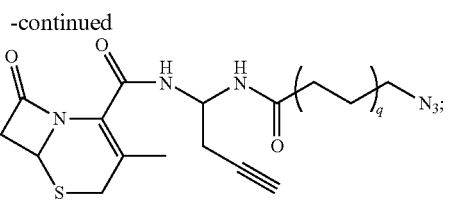
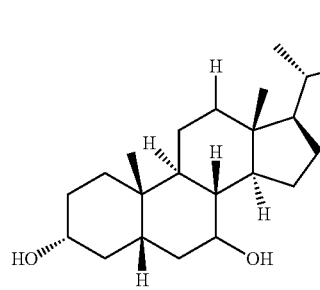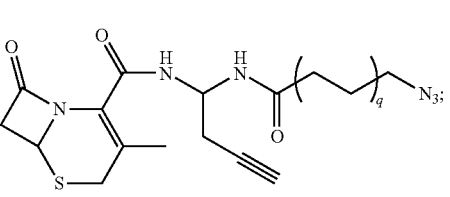
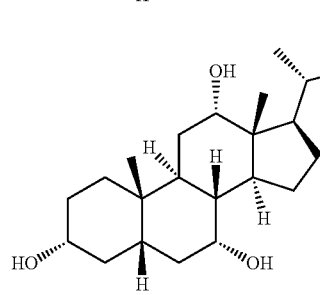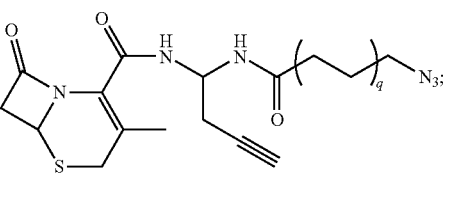
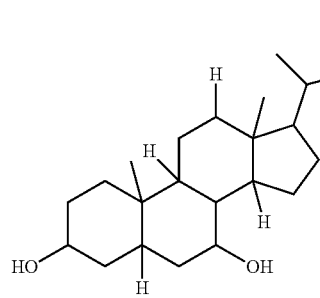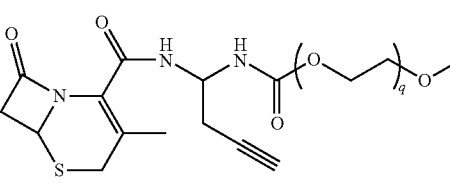
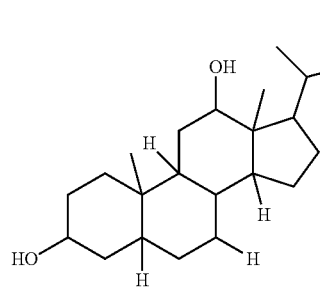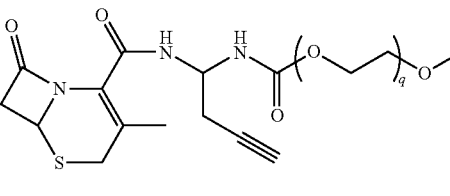

-continued
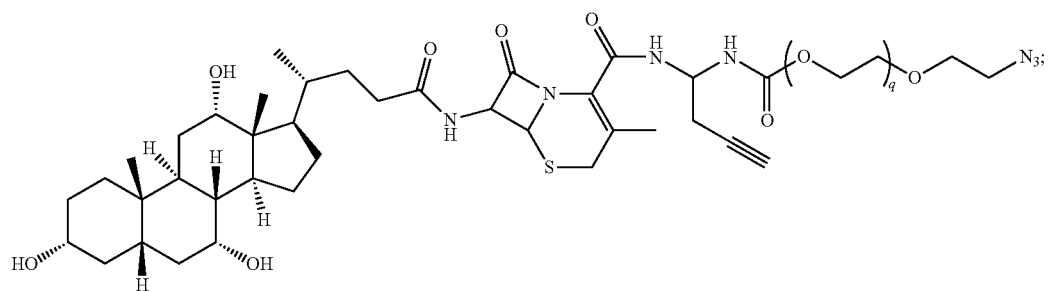
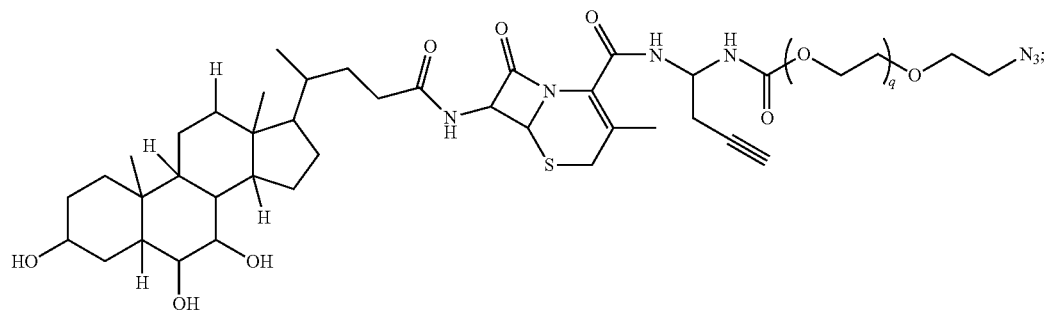
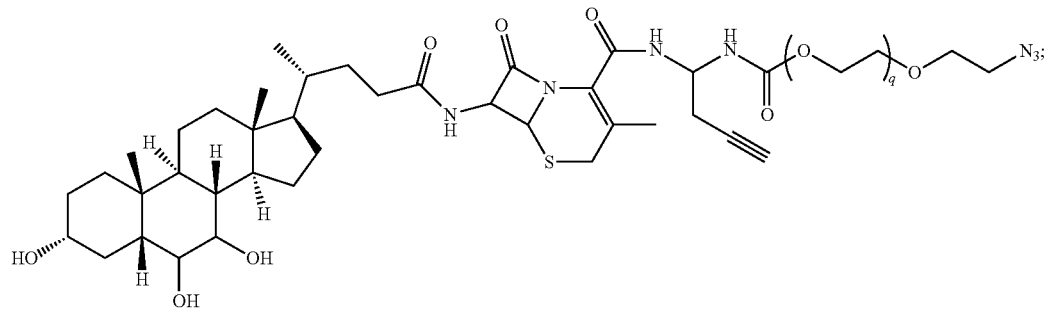
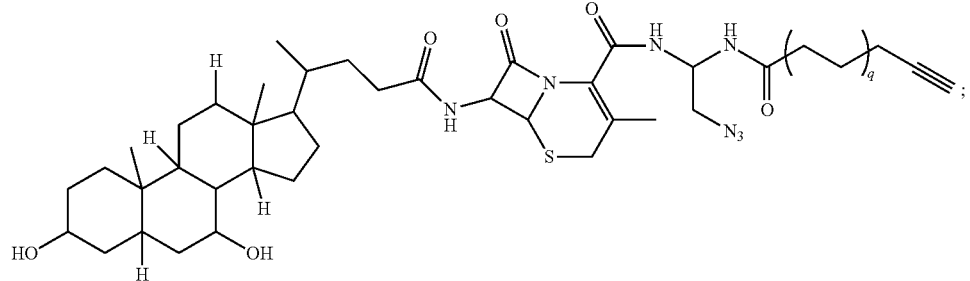

-continued
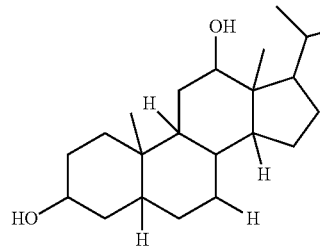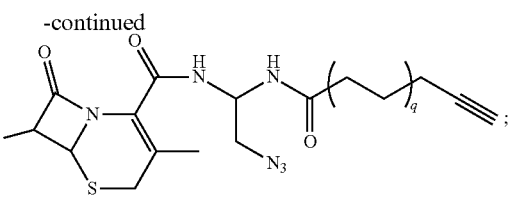
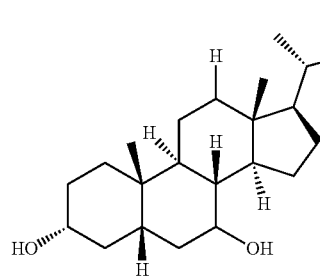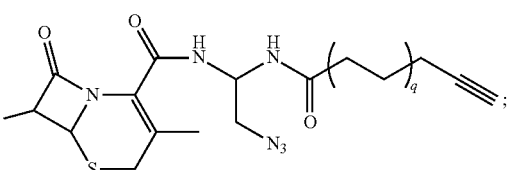
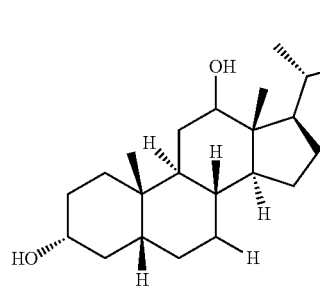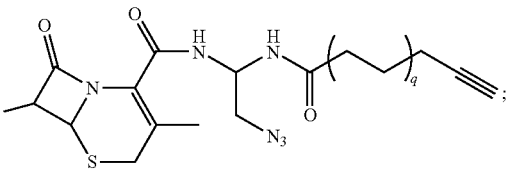
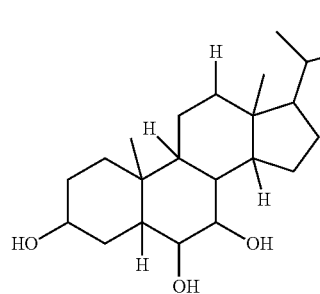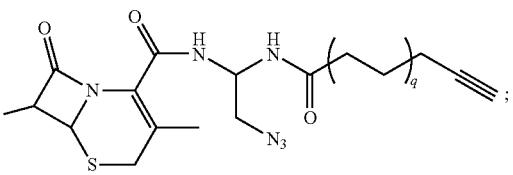
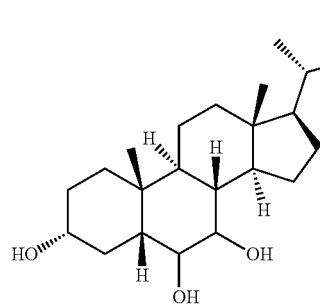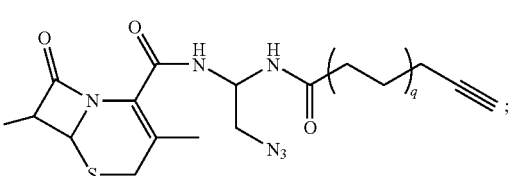

-continued
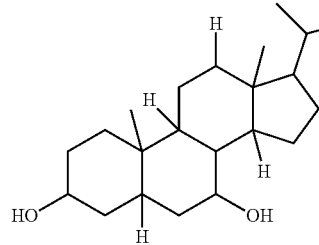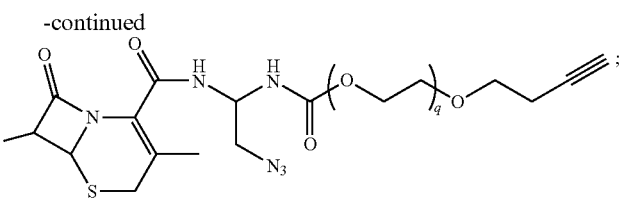
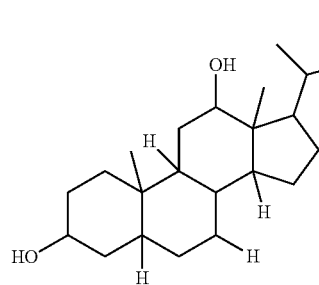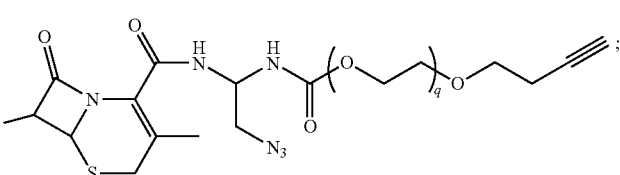
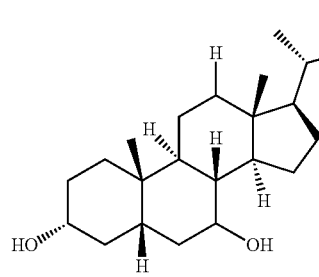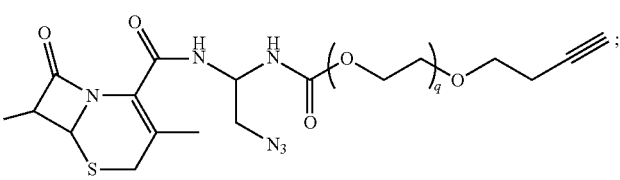
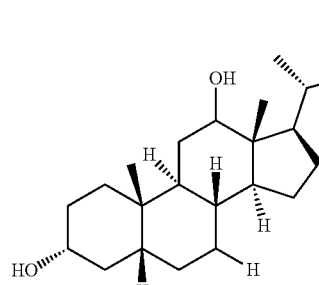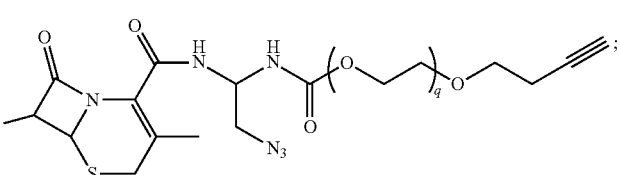
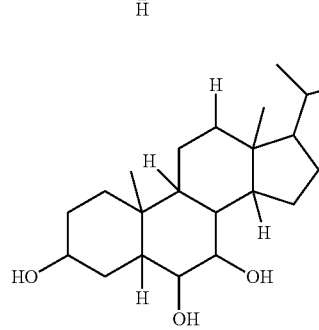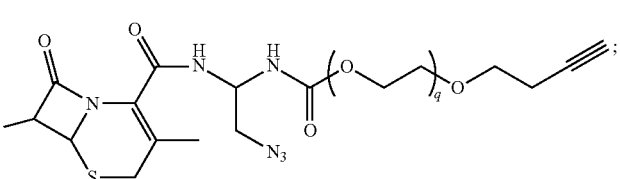

-continued
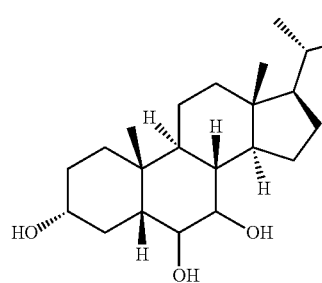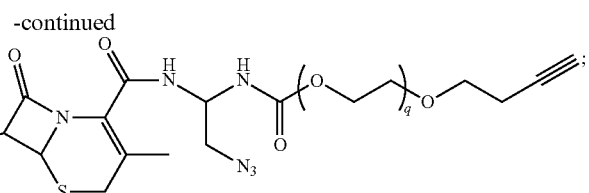
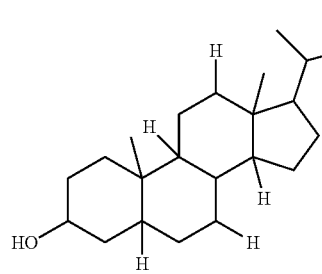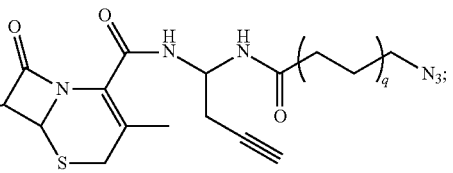
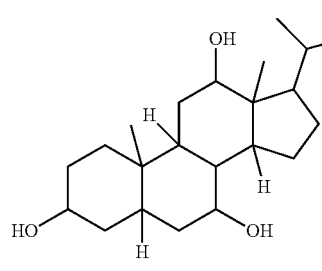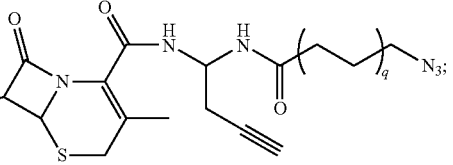
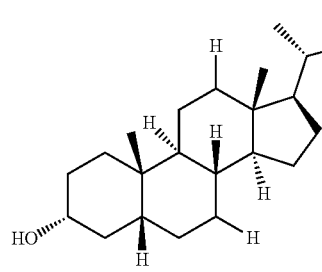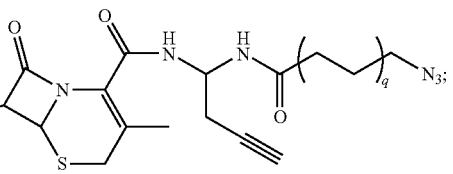
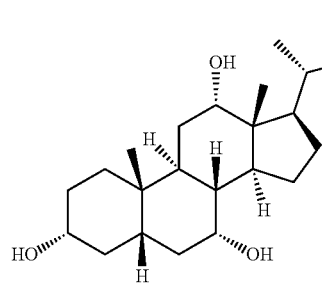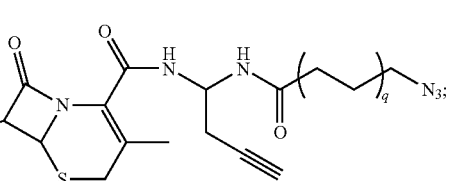

-continued
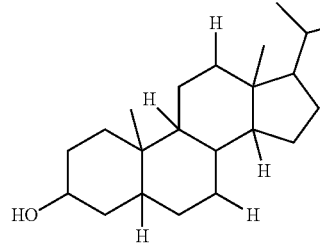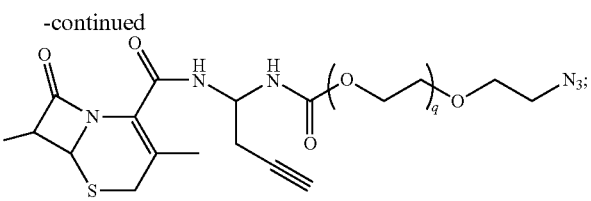
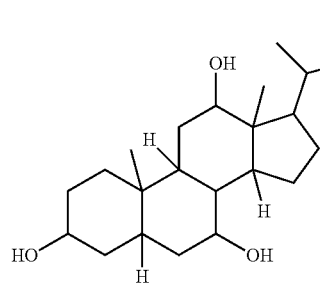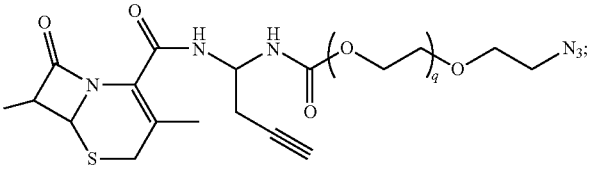
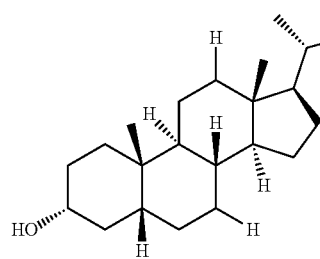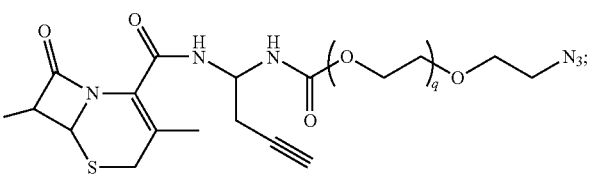
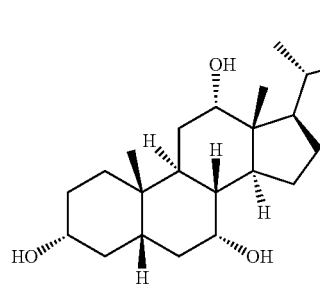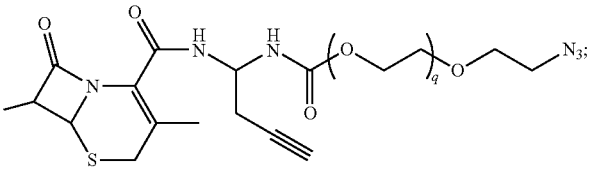
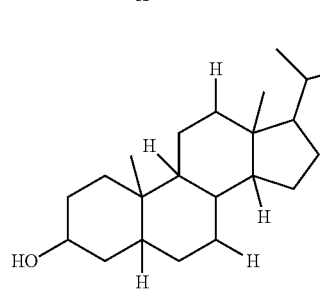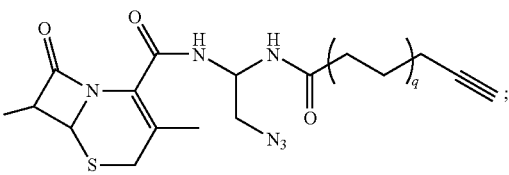
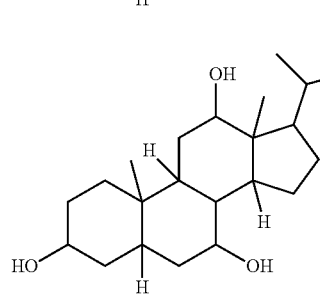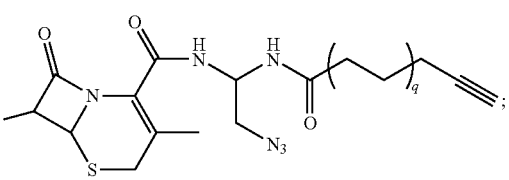

-continued
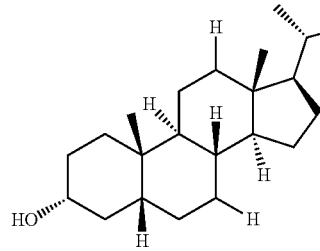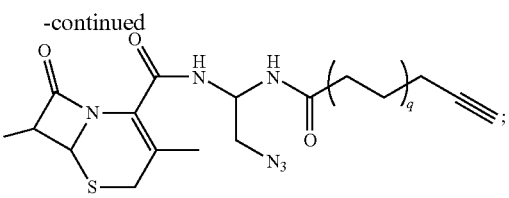
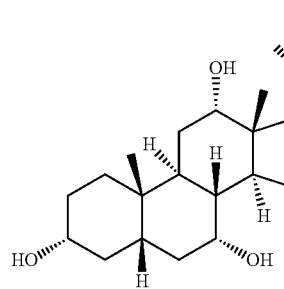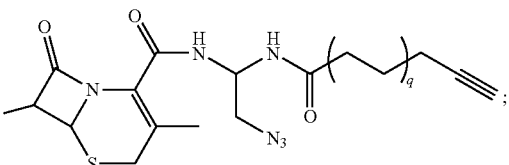
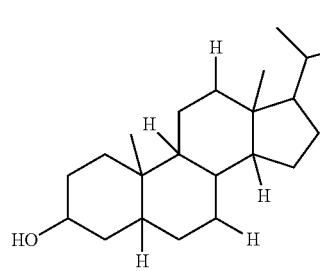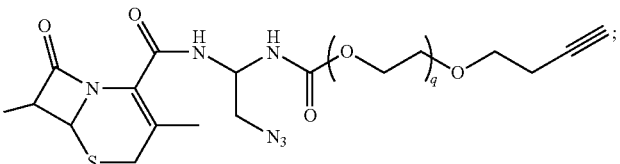
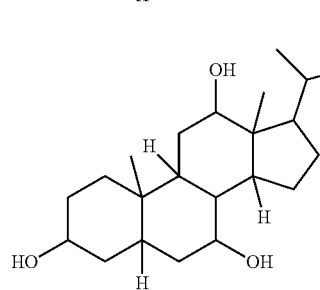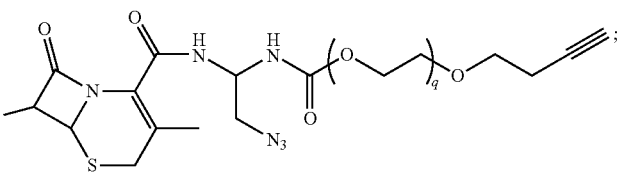
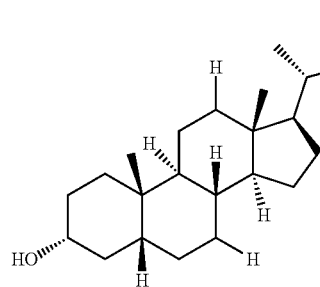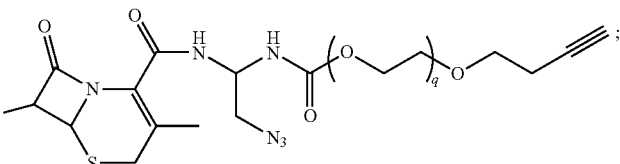
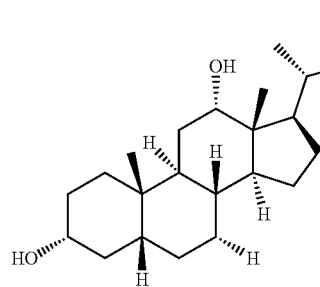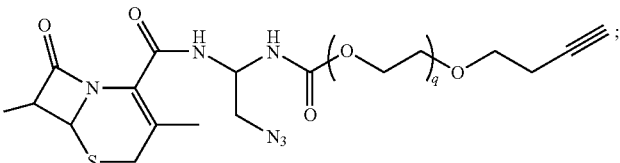

-continued
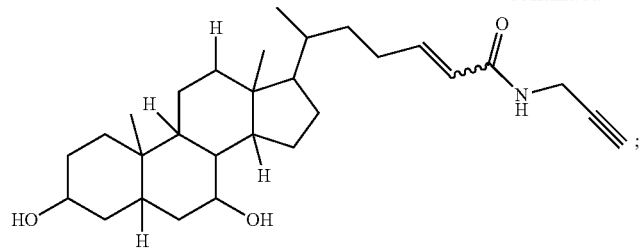
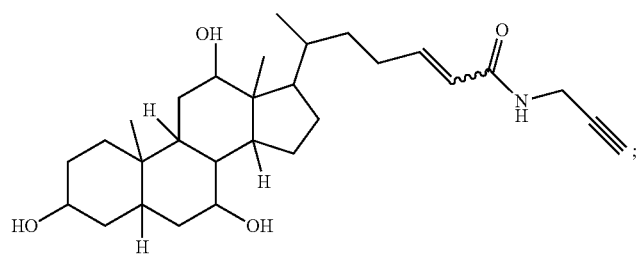
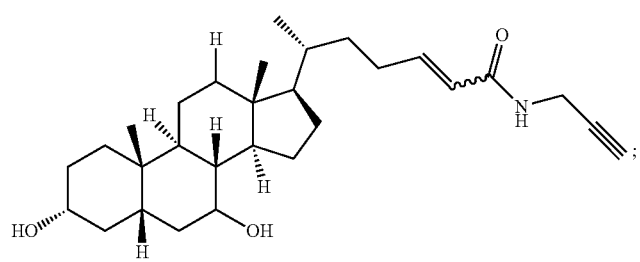
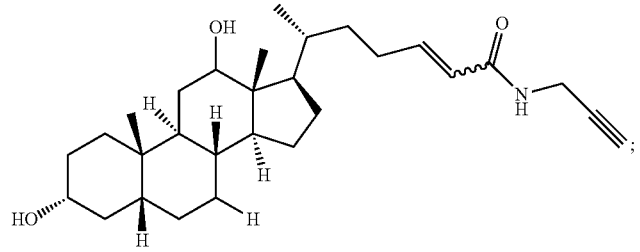
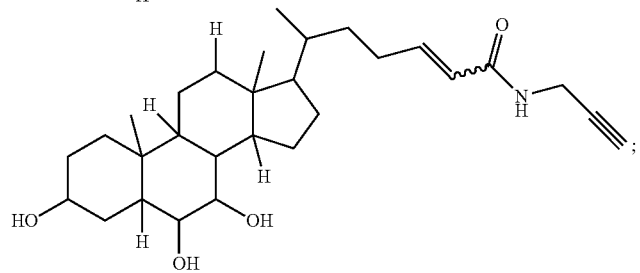
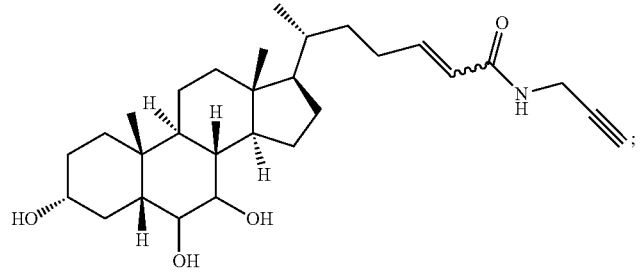

-continued
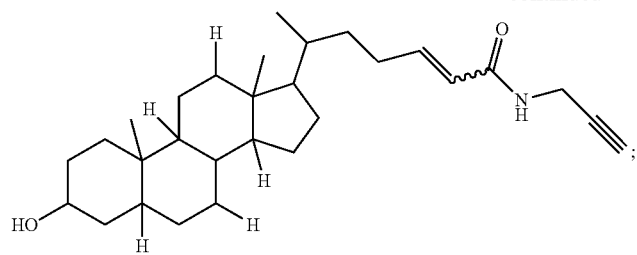
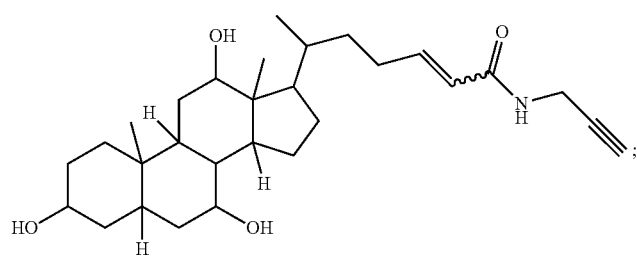
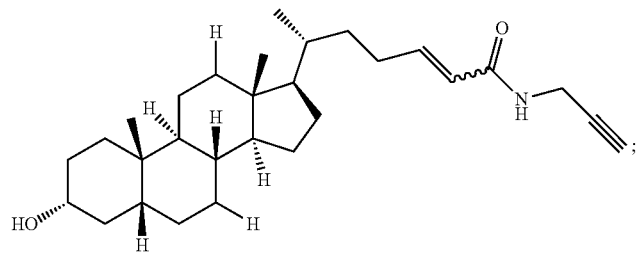
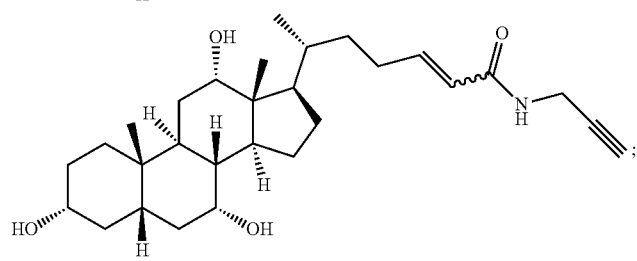
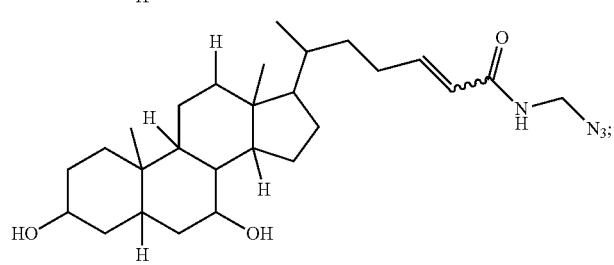
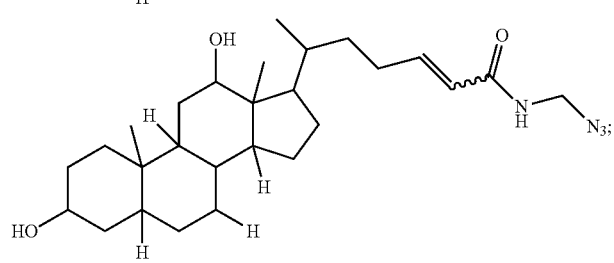

-continued
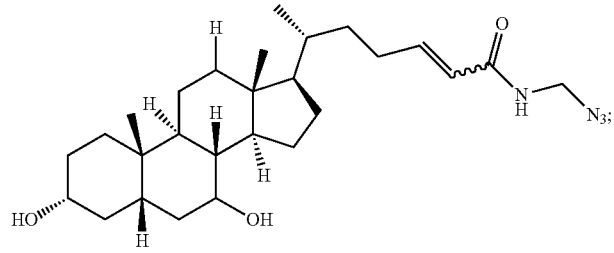
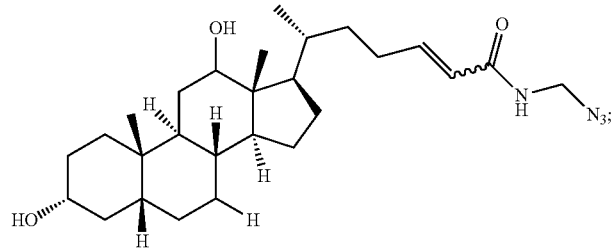
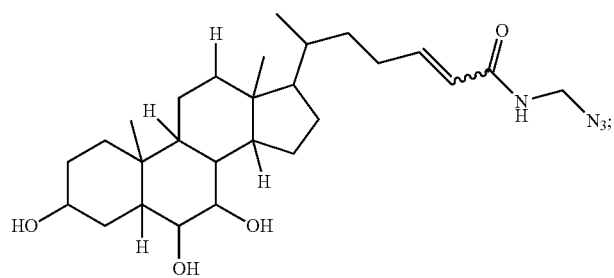
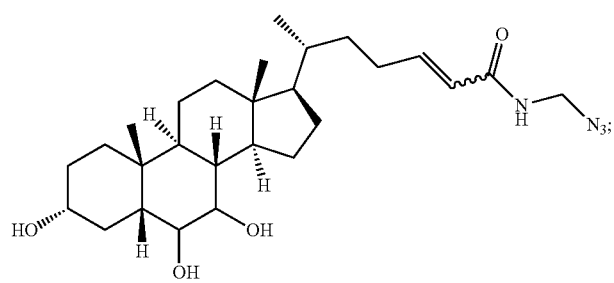
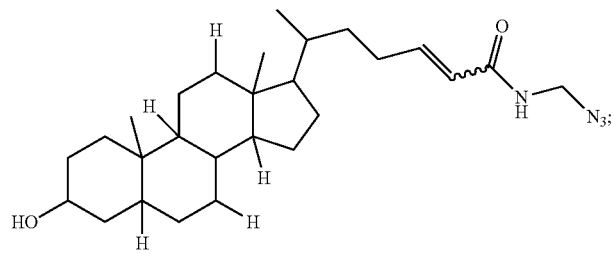
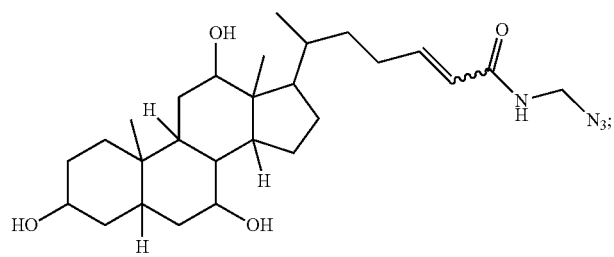

-continued
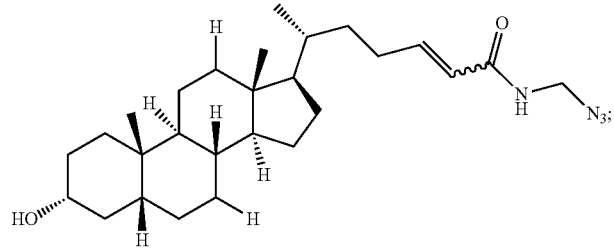
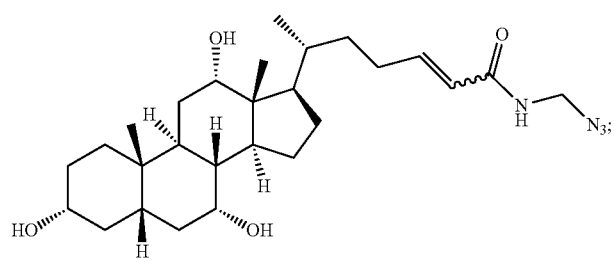
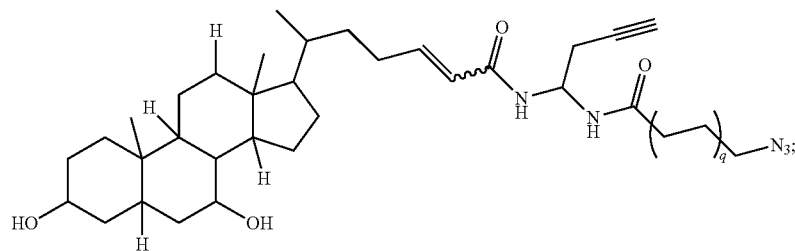
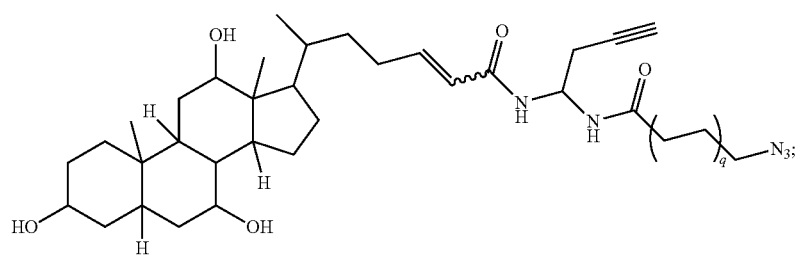
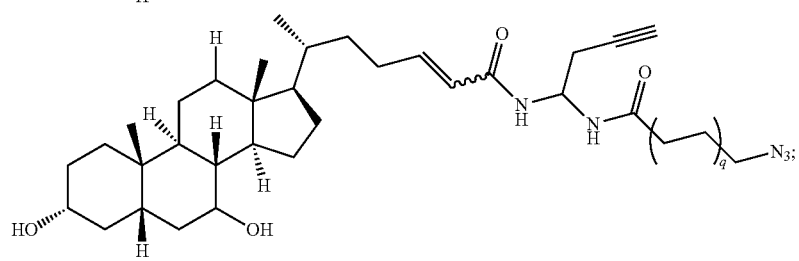
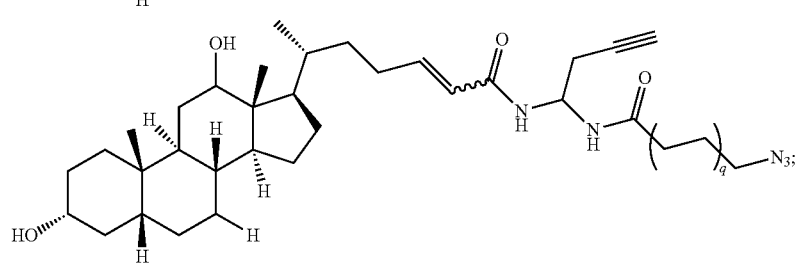

-continued
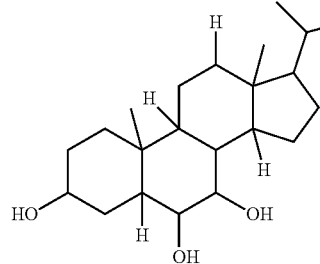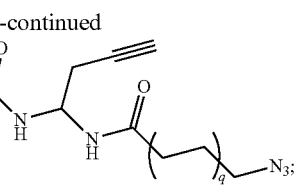
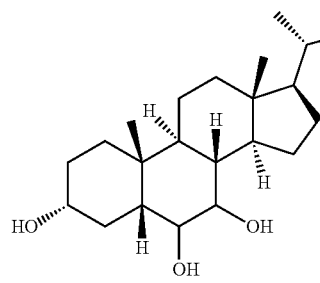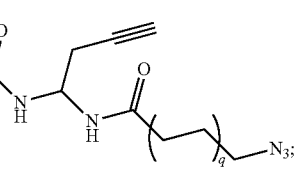
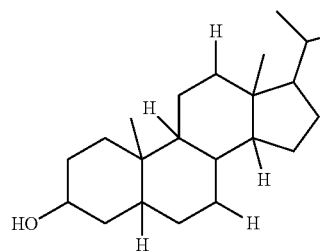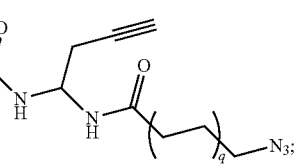
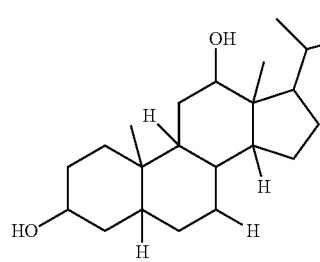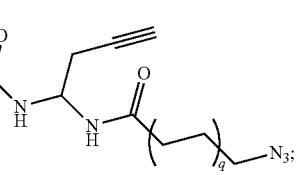
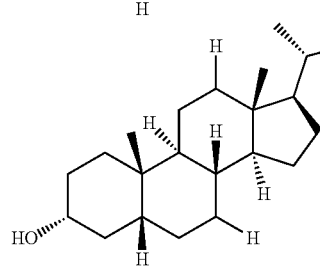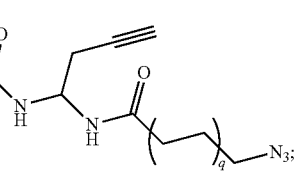
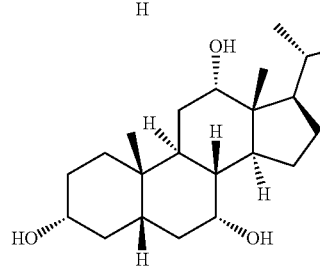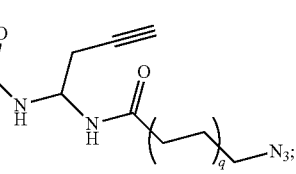

-continued
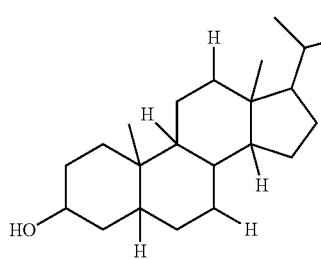 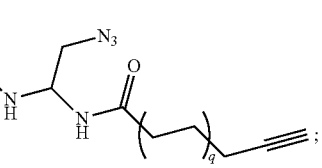
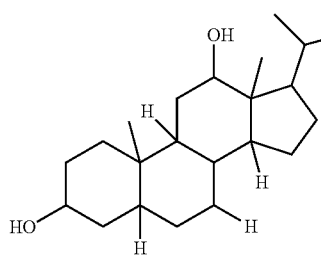 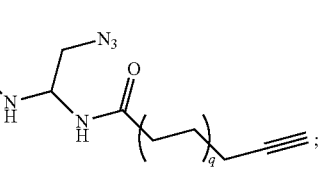
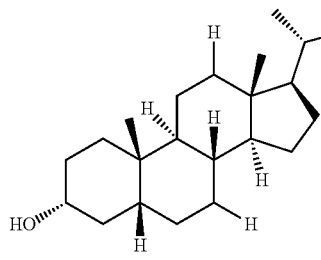 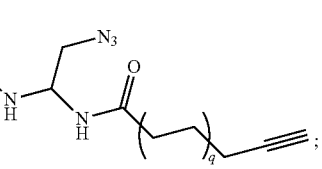
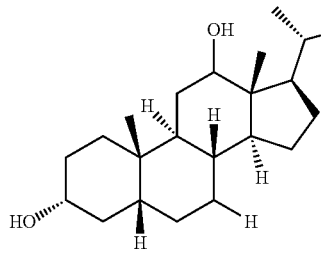 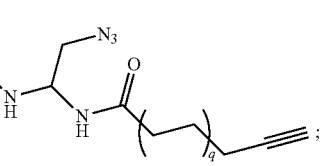
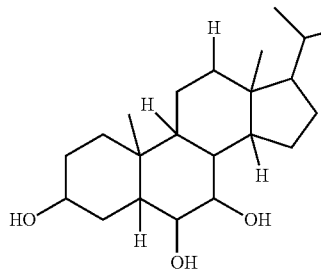 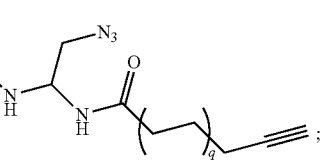
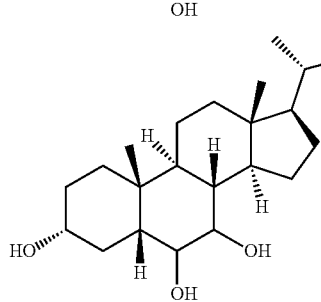 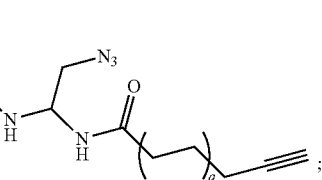

-continued
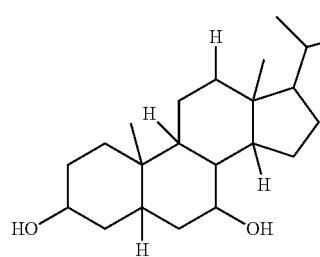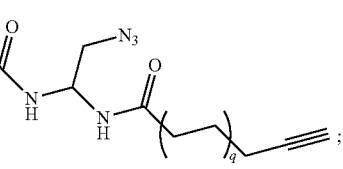
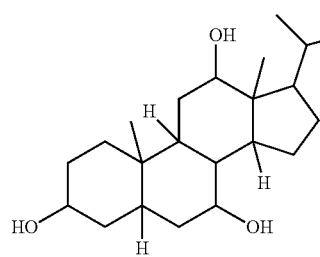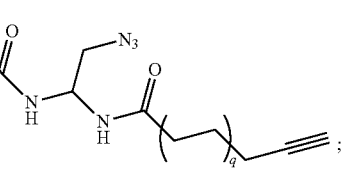
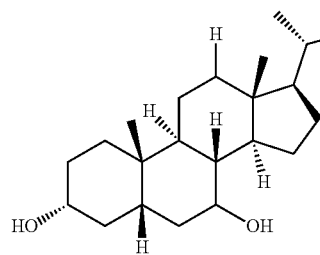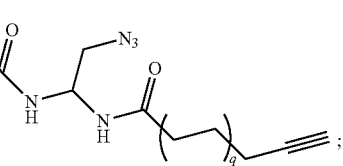
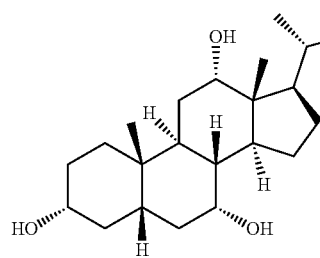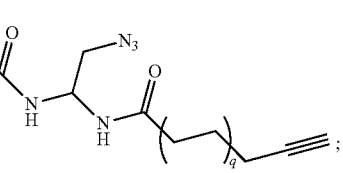
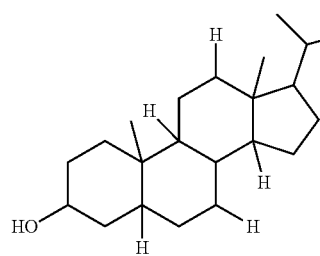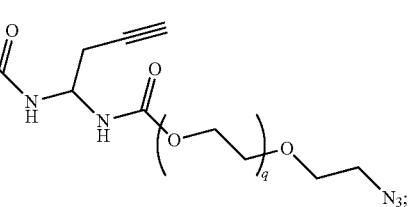
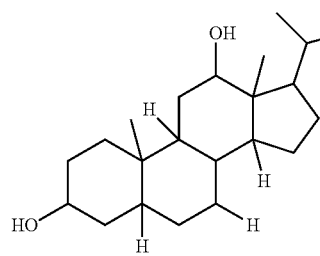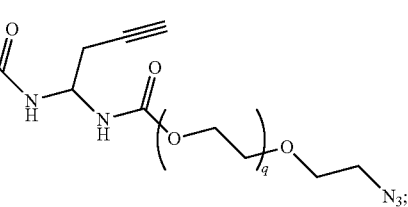

-continued
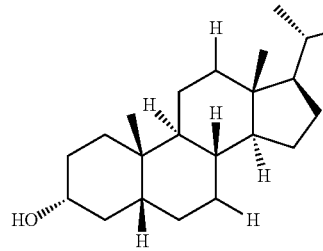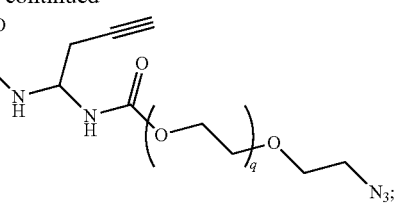
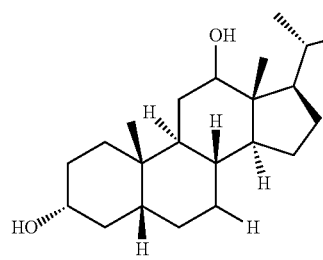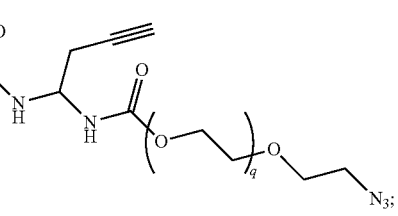
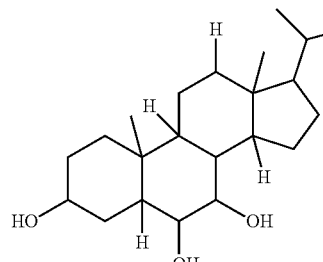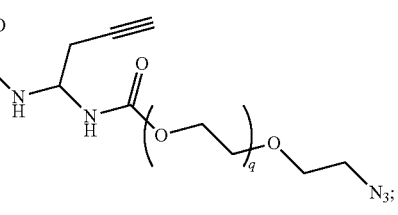
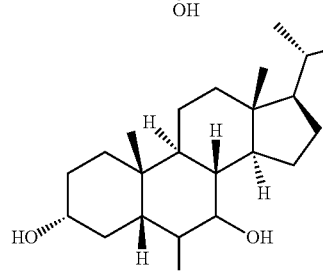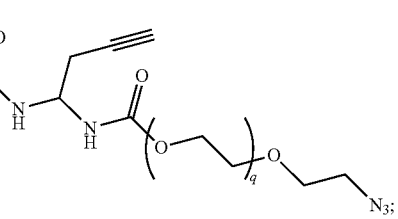
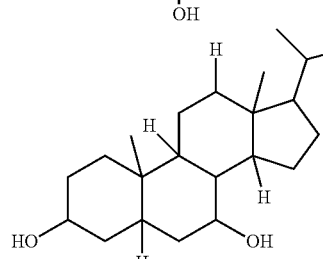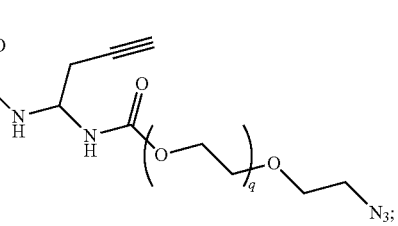
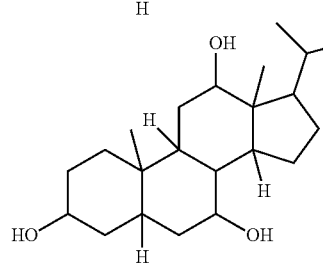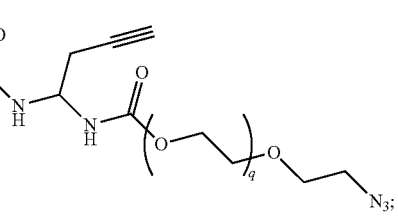

-continued
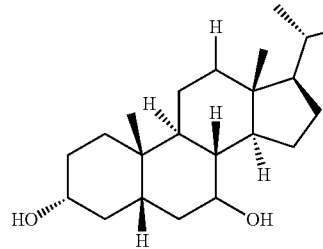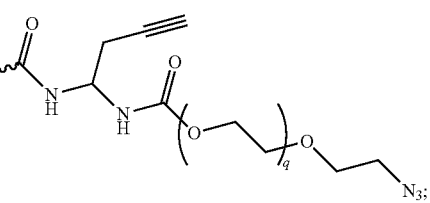
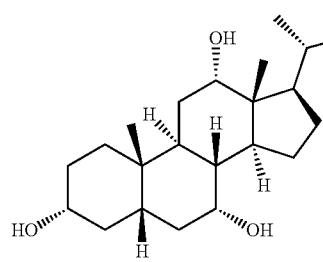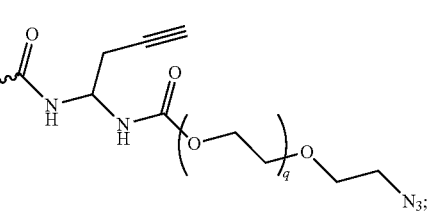
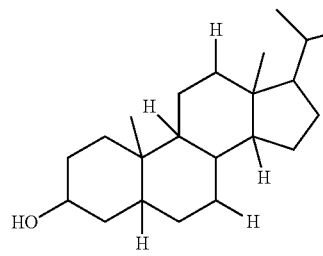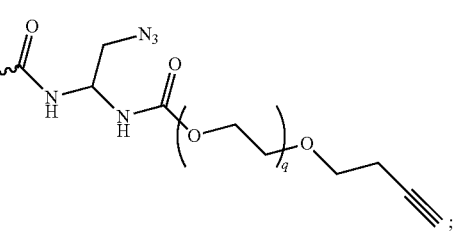
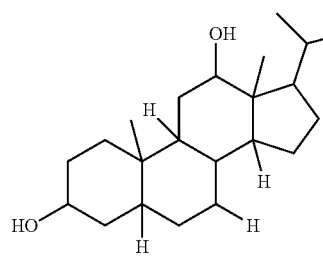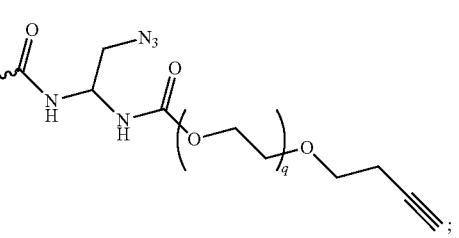
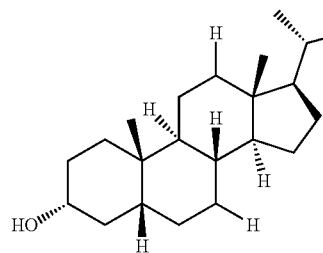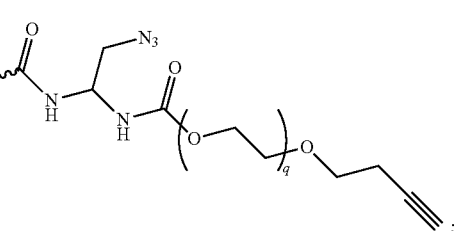
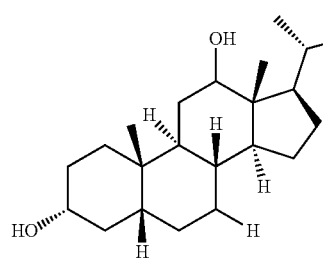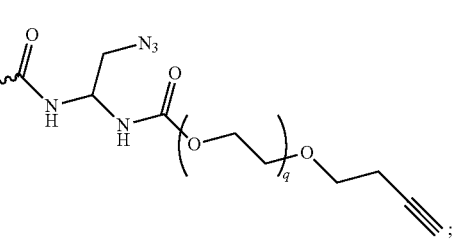

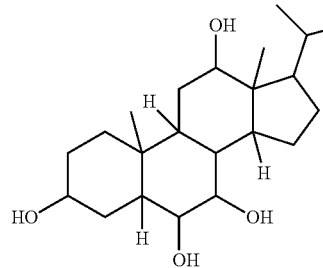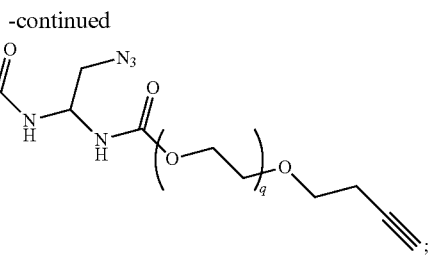
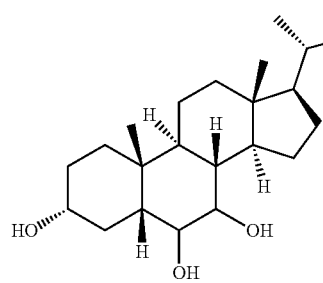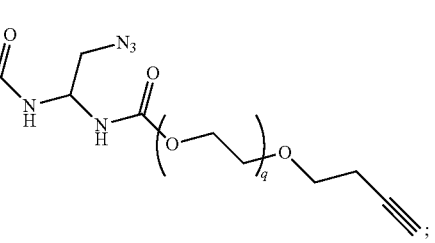
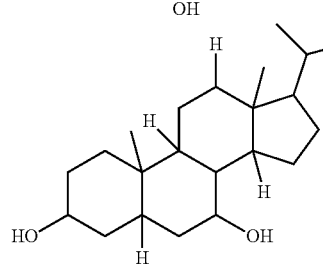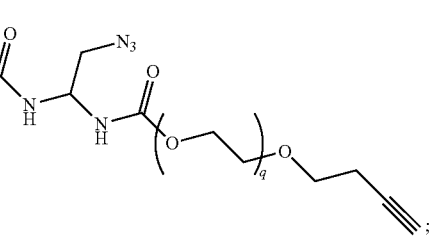
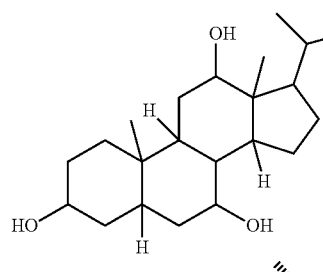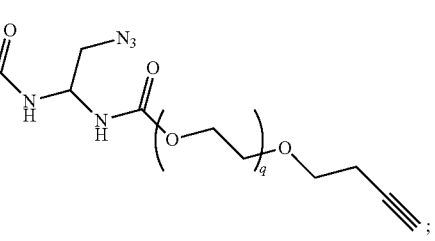
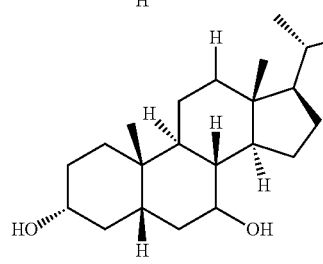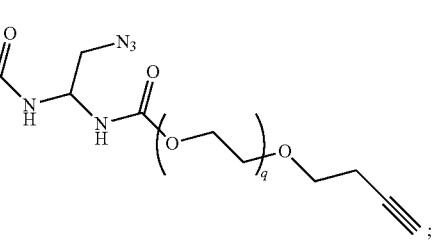
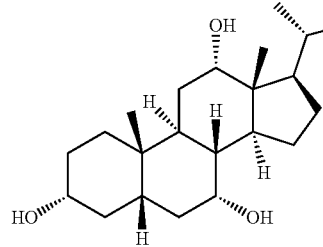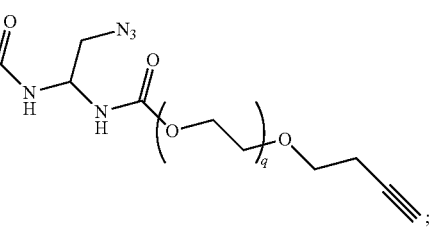

-continued
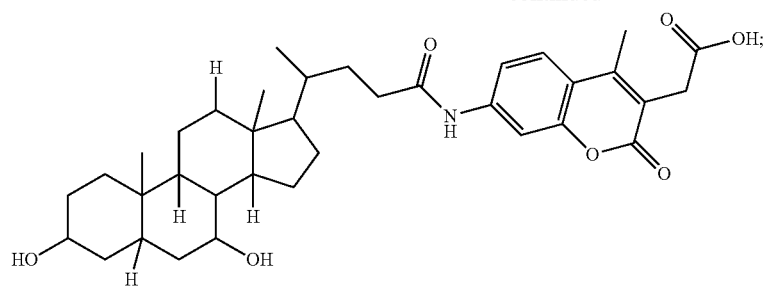
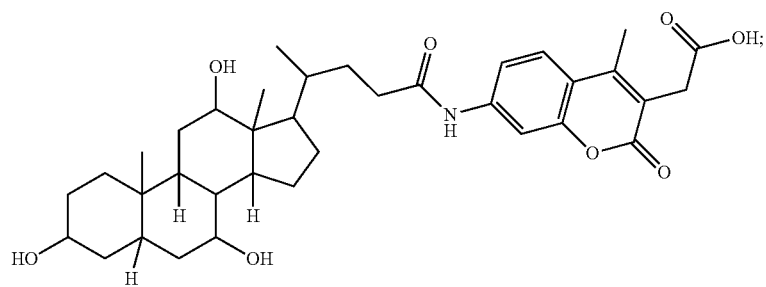
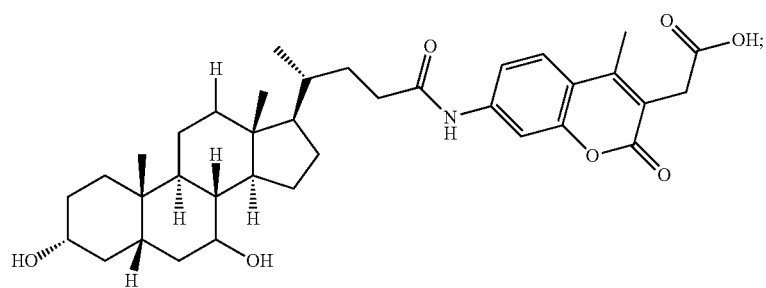
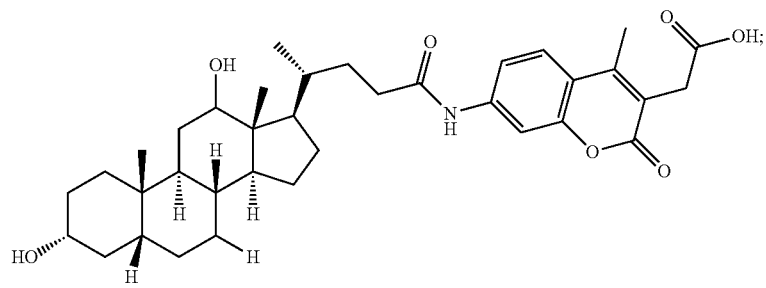
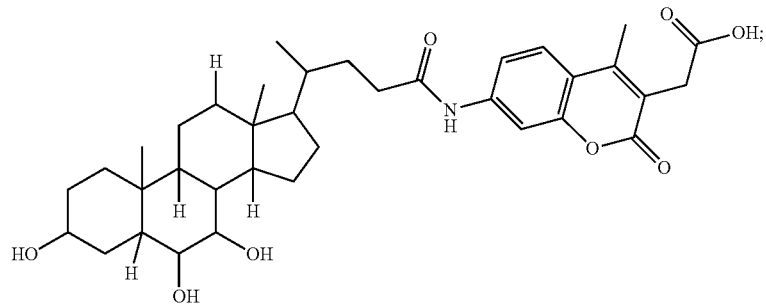

-continued
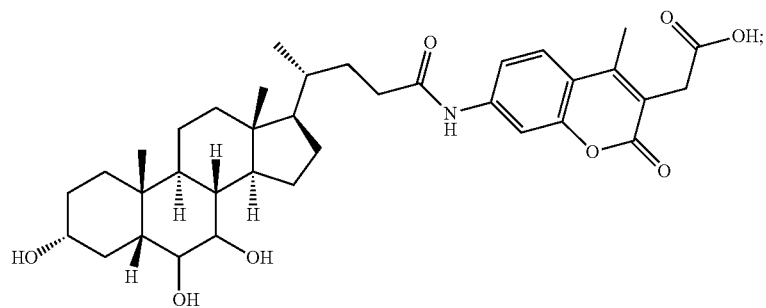
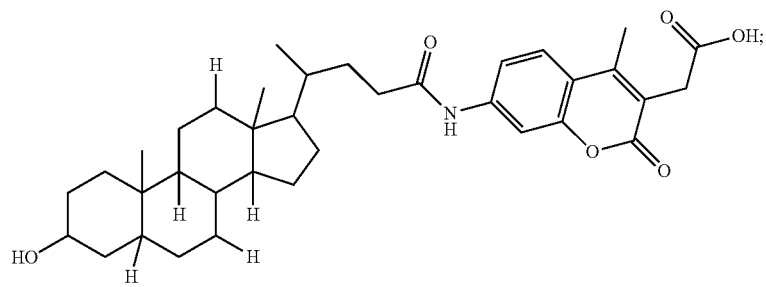
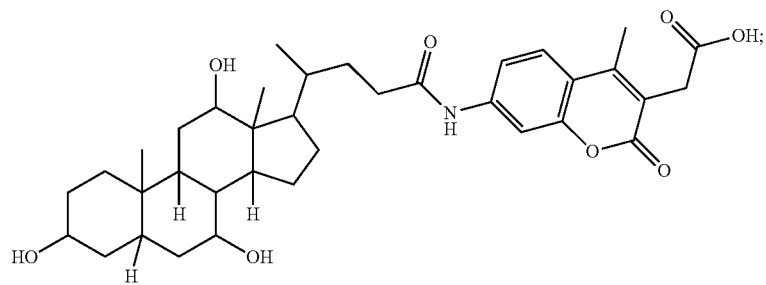
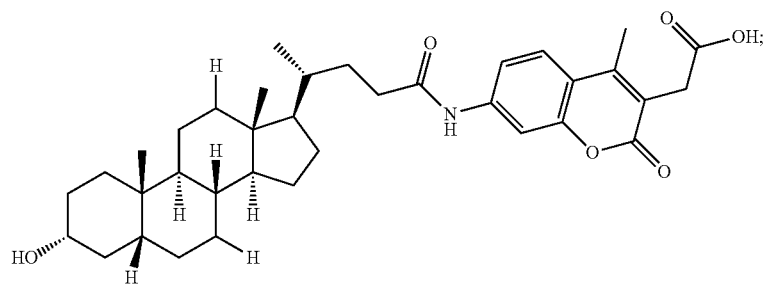
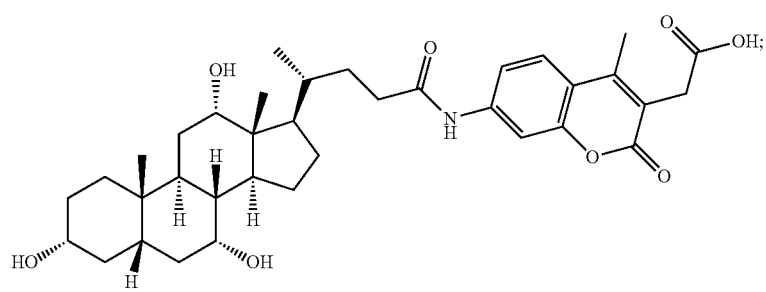
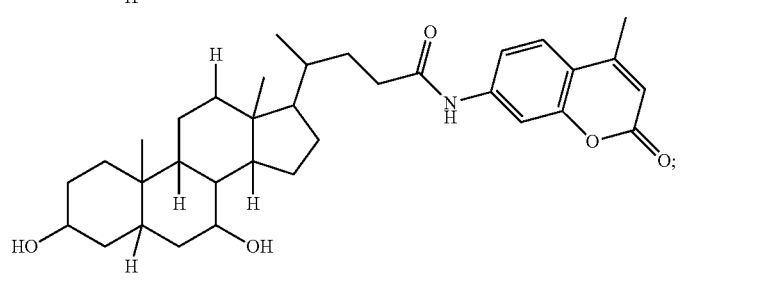

-continued
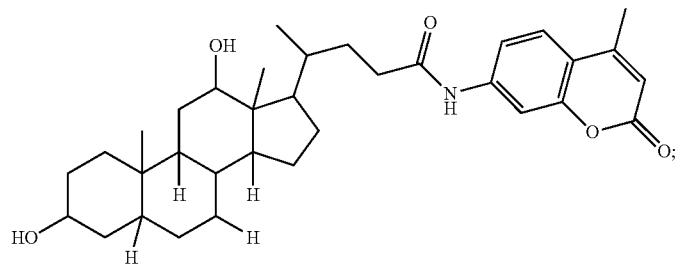
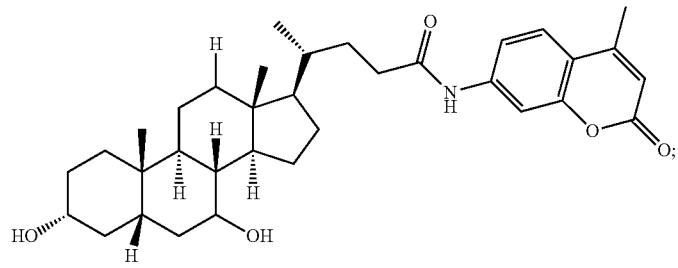
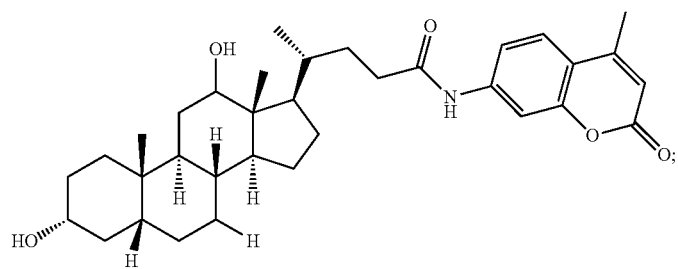
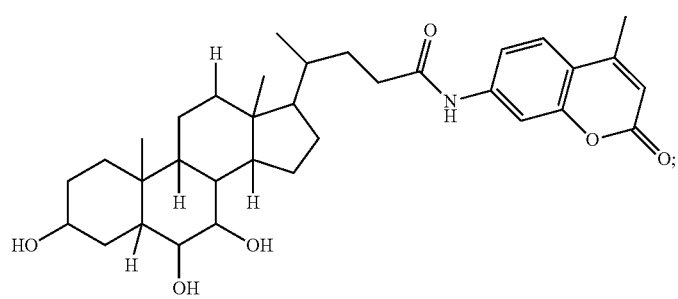
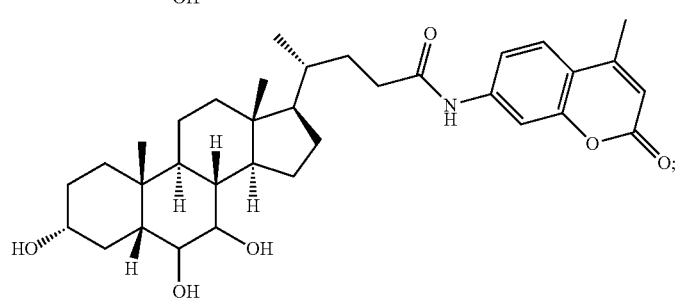
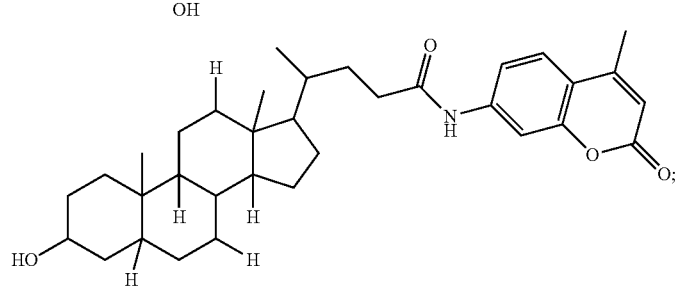

-continued
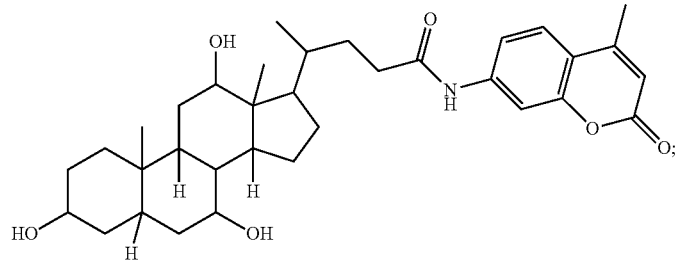
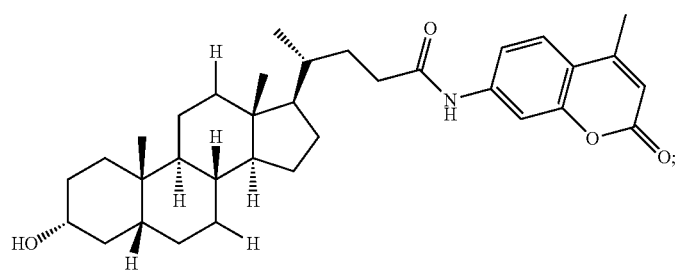
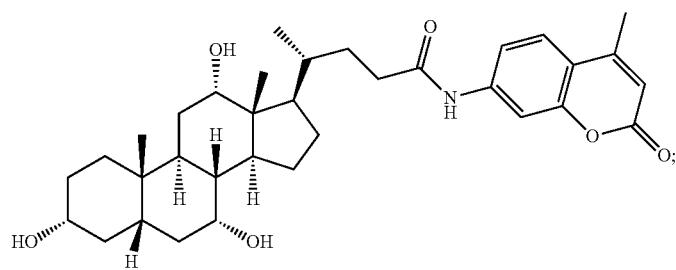
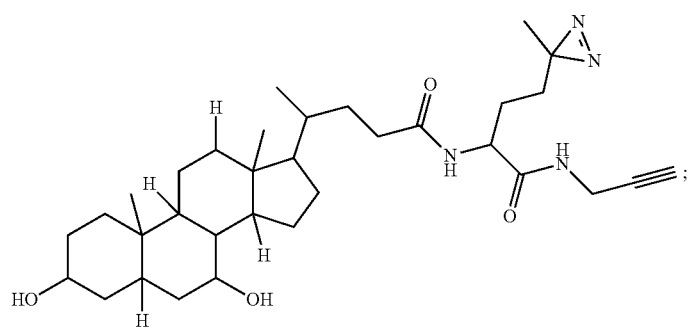
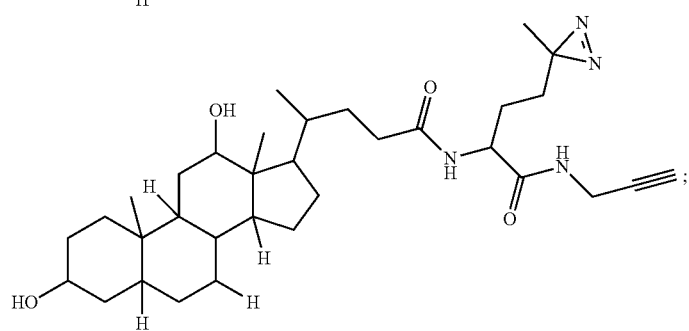

-continued
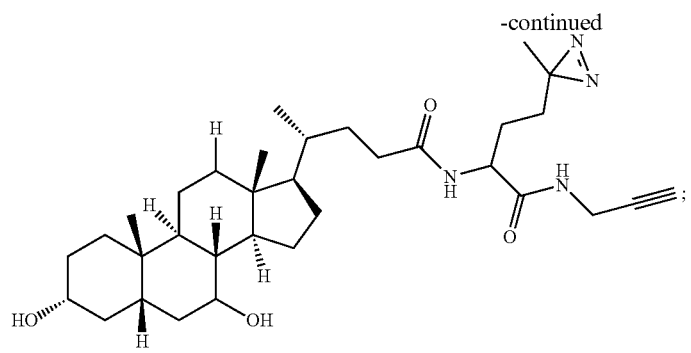
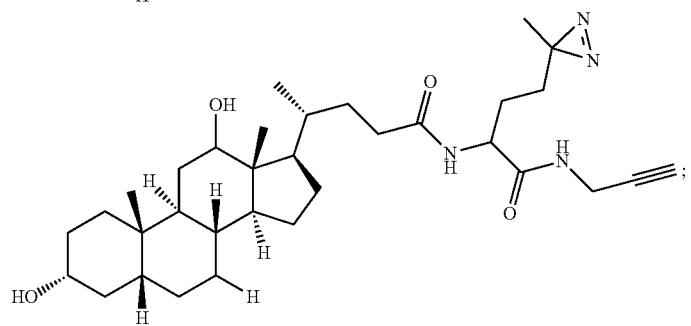
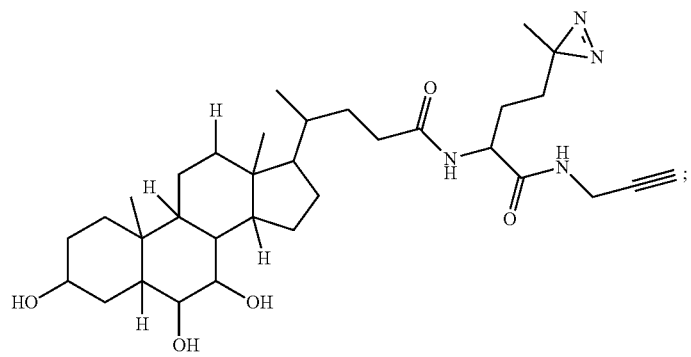
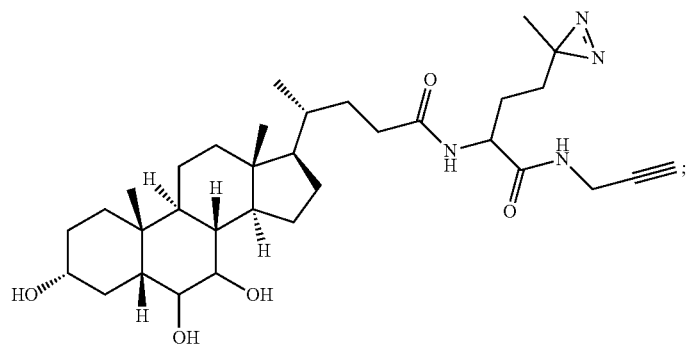
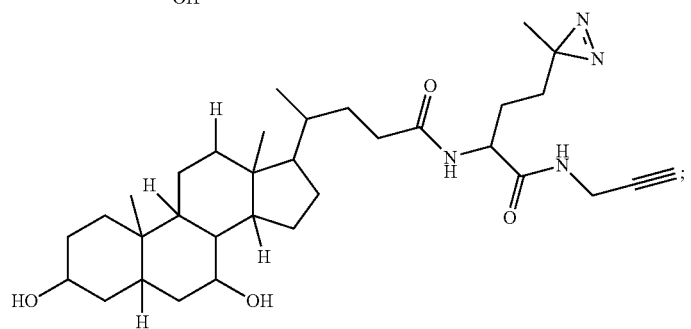

-continued
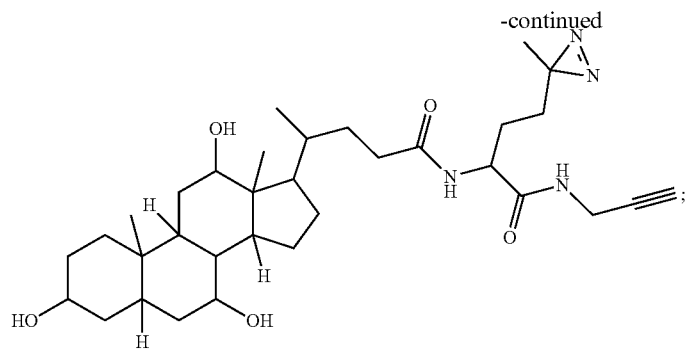
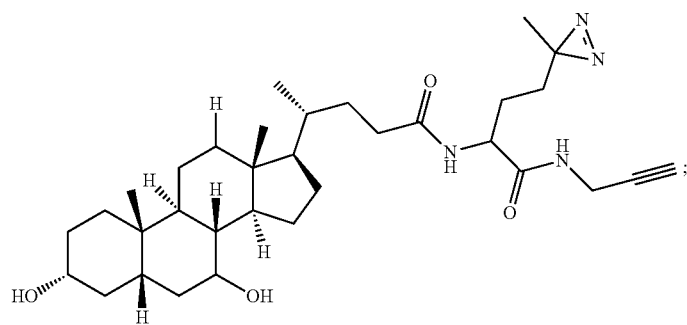
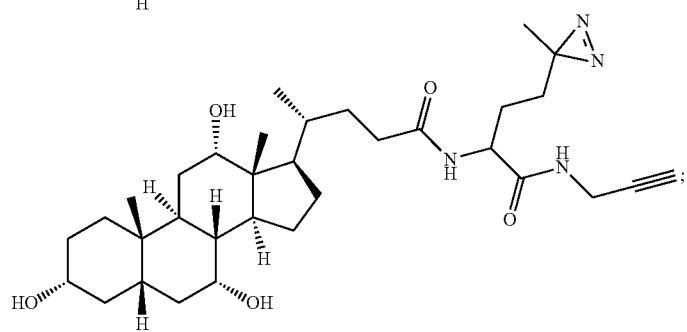
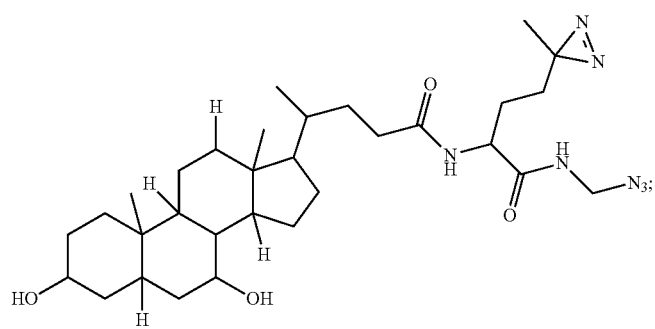
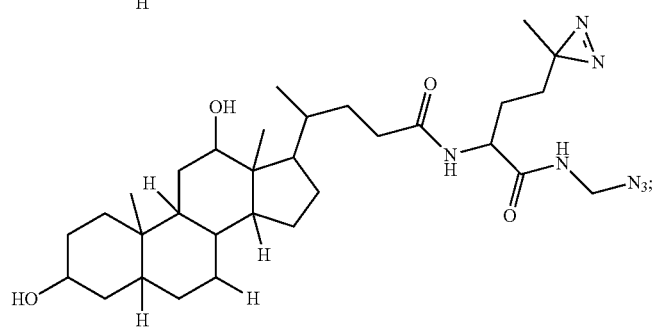

-continued
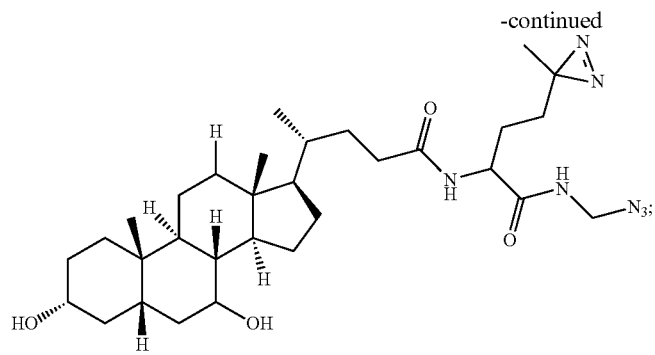
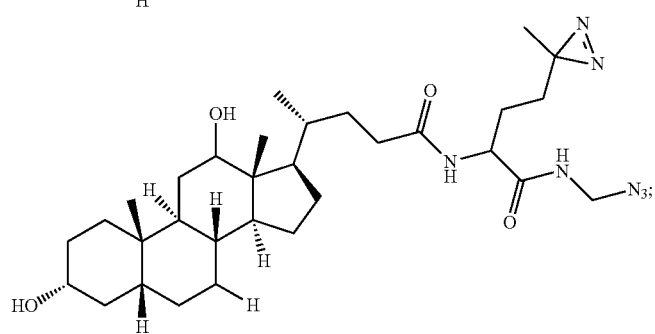
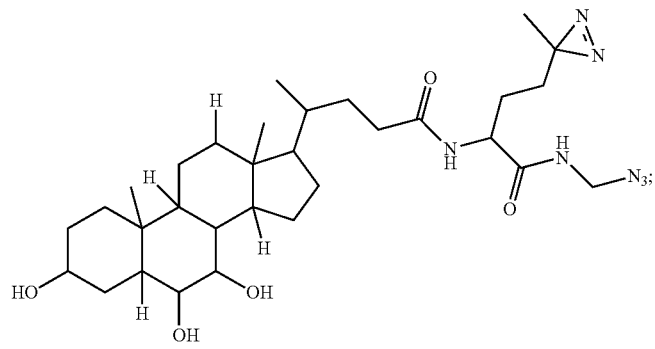
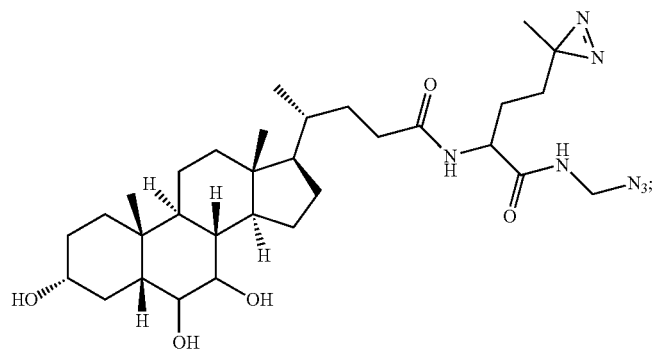
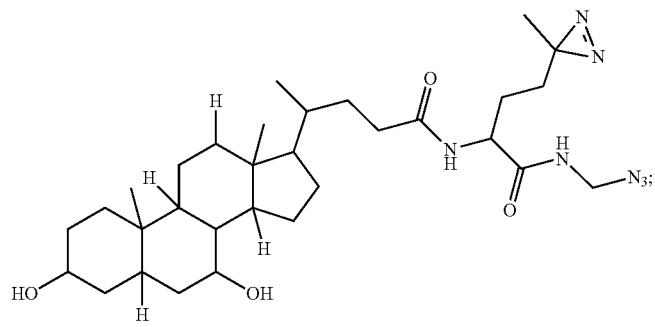

-continued

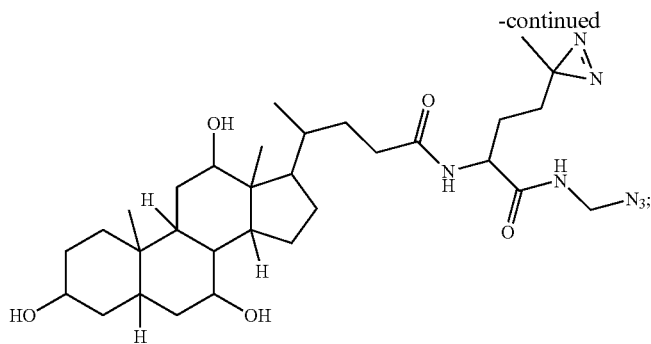

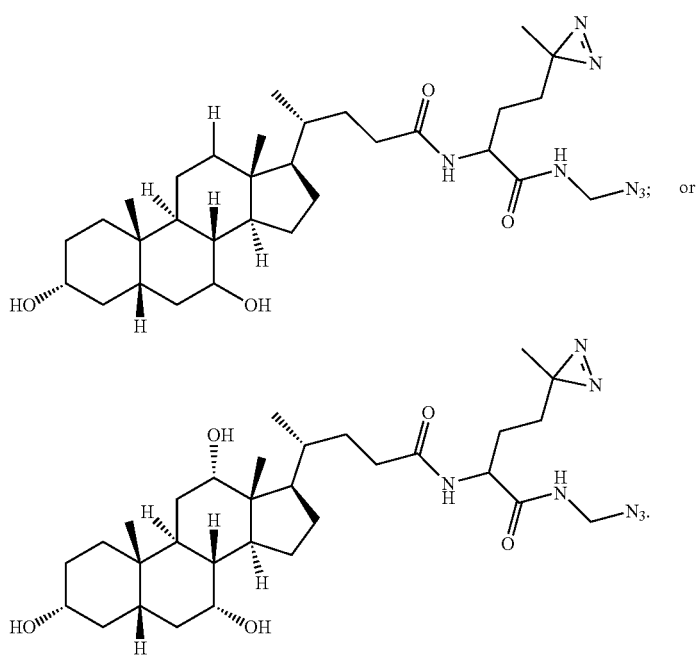

wherein q is an integer ranging from 0 to 10.

12. A method, comprising:
exposing a subject or a sample to a probe according to claim 1 for a time sufficient to allow the probe to bind to an enzyme capable of hydrolyzing a bile salt to thereby form a probe-enzyme conjugate; and
analyzing the subject or the sample using a detection technique sufficient to identify a detectable signal produced by reaction between the probe and the enzyme.

13. The method of claim 12, wherein a detectable moiety is released from the probe upon binding of the enzyme to the probe.

14. The method of claim 12, wherein the probe comprises a pDM group and the method further comprises exposing the probe-enzyme conjugate to a detectable moiety group comprising an azide or an alkyne.

15. The method of claim 12, wherein the probe comprises a PM group and the method further comprises exposing the sample or the subject to a light source to facilitate binding of the PM group to the enzyme to thereby form the probe-enzyme conjugate.

16. The method of claim 12, further comprising performing genomic or proteomic assays using the probe-enzyme conjugate or microbes comprising the probe-enzyme conjugate.

17. A method, comprising:
labeling at least one enzyme capable of hydrolyzing a bile salt with a probe according to claim 1 to provide at least one labeled enzyme;
determining the presence of the at least one labeled enzyme in a sample by detecting a detectable signal;
sorting or isolating the at least one labeled enzyme or microbes comprising the at least one labeled enzyme;
identifying the microbes comprising the at least one labeled enzyme;
selecting a physical environment for altering the bile salt hydrolase activity of the at least one enzyme; and
altering bile salt hydrolase activity in the selected physical environment to thereby treat the disease or condition by enriching the selected physical environment with identified microbes, or reducing the amount of identified microbes in the selected physical environment, or reducing the bile salt hydrolase activity in the selected physical environment, or a combination thereof.

18. A kit, comprising:
a substrate; and
a probe having a structure satisfying Formula I Formula I

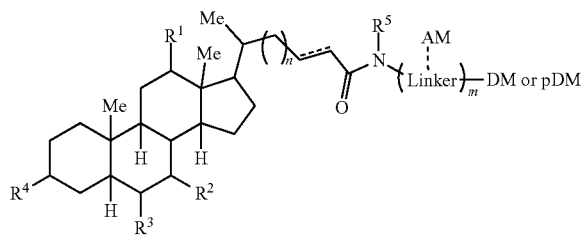

wherein each of R¹, R², R³, and R⁴ independently is hydrogen or —OR, wherein each R independently is hydrogen, a counterion that balances a negative charge on the oxygen atom of the —OR group, or heteroaliphatic; R⁵ is hydrogen or aliphatic; the linker is aliphatic or heteroaliphatic; DM is a fluorophore, a chromogen, or biotin; pDM is an alkyne or an azide; AM is an alkyne, an azide, an activated ester, a carboxylic acid, a halide, or an alkyl halide; n is an integer ranging from 0 to 10; and m is 1; and wherein the probe is covalently bound to a surface of the substrate via the AM group.

19. A probe having a structure satisfying Formula I

Formula I

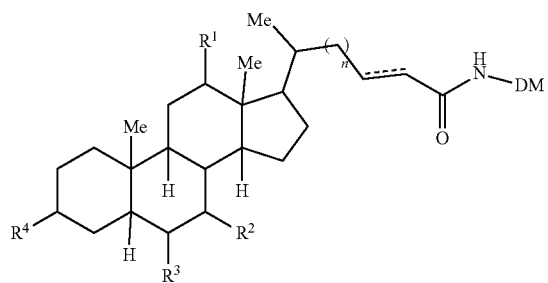

wherein each of R¹, R², R³, and R⁴ independently is hydrogen or —OR, wherein each R independently is hydrogen, a counterion that balances a negative charge on the oxygen atom of the —OR group, or heteroaliphatic; DM is

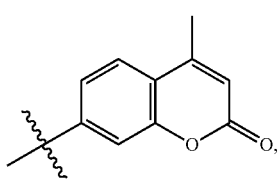

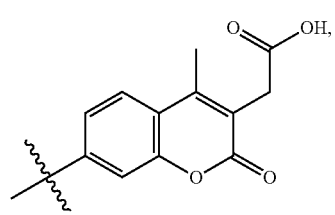 [SMILES: *c1ccc2c(C)c(CC(=O)O)c(=O)oc2c1]

or biotin; and n is an integer ranging from 0 to 10.

20. A probe having one of the following structures:

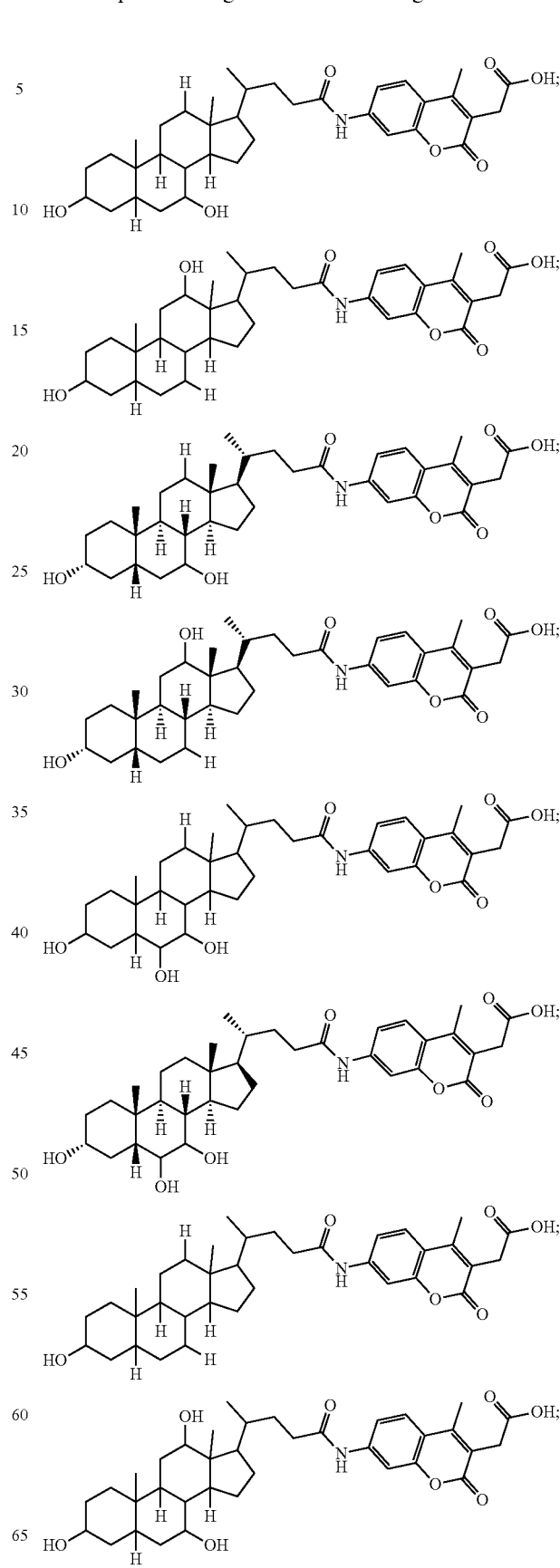

177
-continued
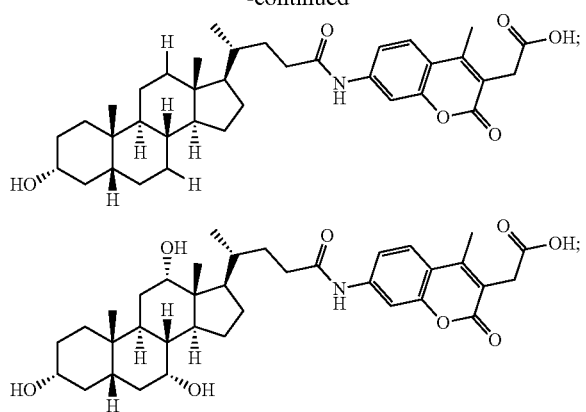
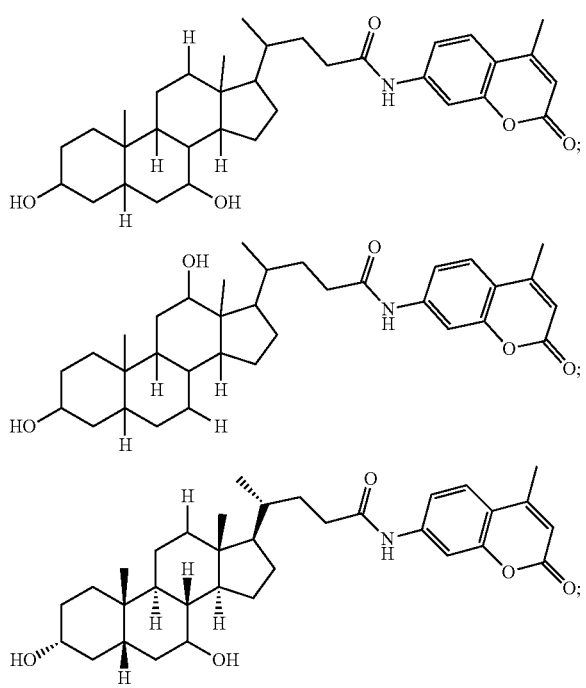
178
-continued
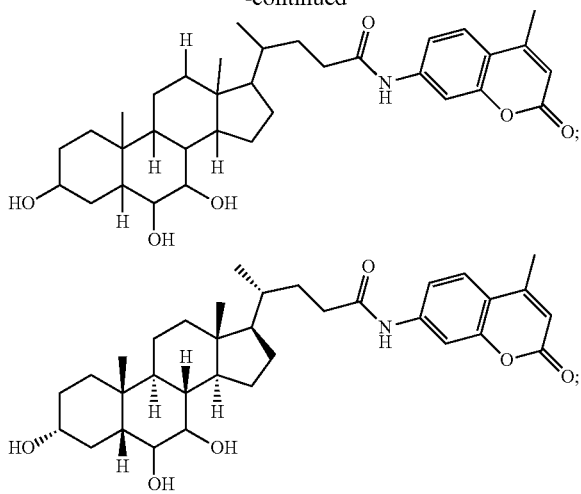
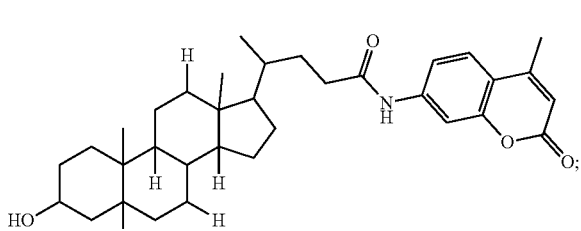
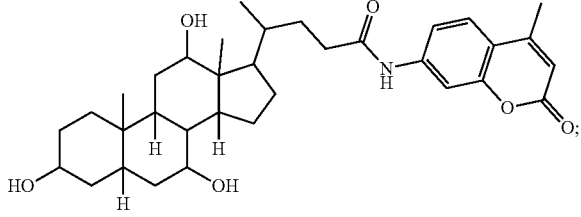
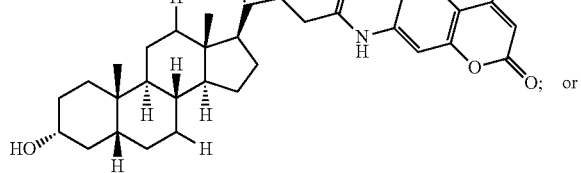
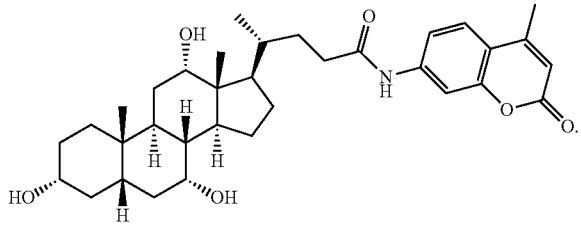
* * * * *